US011771747B2

(12) United States Patent
Jooss et al.

(10) Patent No.: US 11,771,747 B2
(45) Date of Patent: Oct. 3, 2023

(54) MULTIEPITOPE VACCINE CASSETTES

(71) Applicant: Gritstone bio, Inc., Emeryville, CA (US)

(72) Inventors: Karin Jooss, Emeryville, CA (US); Roman Yelensky, Newton, MA (US); James Xin Sun, Newton, MA (US); Amy Rachel Rappaport, Daly City, CA (US); Ciaran Daniel Scallan, San Francisco, CA (US); Leonid Gitlin, Foster City, CA (US); Christine Denise Palmer, Cambridge, MA (US); Monica Lane, Uxbridge, MA (US)

(73) Assignee: Gritstone Bio, Inc., Emeryville, CA (US)

( * ) Notice: Subject to any disclaimer, the term of this patent is extended or adjusted under 35 U.S.C. 154(b) by 0 days.

(21) Appl. No.: 17/727,610

(22) Filed: Apr. 22, 2022

(65) Prior Publication Data

US 2022/0265797 A1 Aug. 25, 2022

Related U.S. Application Data

(63) Continuation of application No. PCT/US2021/045106, filed on Aug. 6, 2021.

(60) Provisional application No. 63/062,268, filed on Aug. 6, 2020.

(51) Int. Cl.

| | |
|---|---|
| ***A61K 39/00*** | (2006.01) |
| ***A61K 39/005*** | (2006.01) |
| ***C12N 15/86*** | (2006.01) |
| ***A61P 35/00*** | (2006.01) |

(52) U.S. Cl.

CPC ....... *A61K 39/001111* (2018.08); *A61P 35/00* (2018.01); *A61K 2039/5256* (2013.01); *A61K 2039/53* (2013.01)

(58) Field of Classification Search

CPC .. A61K 39/00; A61K 39/005; A61K 39/0011; A61K 2039/5256; A61K 2039/53; C12N 15/86

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,656,127 | A | 4/1987 | Mundy |
| 4,722,848 | A | 2/1988 | Paoletti et al. |
| 4,837,028 | A | 6/1989 | Allen |
| 5,019,369 | A | 5/1991 | Presant et al. |
| 5,204,253 | A | 4/1993 | Sanford et al. |
| 5,217,879 | A | 6/1993 | Huang et al. |
| 5,279,833 | A | 1/1994 | Rose |
| 5,505,947 | A | 4/1996 | Johnston et al. |
| 5,580,859 | A | 12/1996 | Felgner et al. |
| 5,589,466 | A | 12/1996 | Felgner et al. |
| 5,622,931 | A | 4/1997 | Edgington et al. |
| 5,643,576 | A | 7/1997 | Johnston et al. |
| 5,662,907 | A | 9/1997 | Kubo et al. |
| 5,814,482 | A | 9/1998 | Dubensky, Jr. et al. |
| 5,843,723 | A | 12/1998 | Dubensky, Jr. et al. |
| 5,849,561 | A | 12/1998 | Falck-Pedersen |
| 5,849,589 | A | 12/1998 | Tedder et al. |
| 5,851,796 | A | 12/1998 | Schatz |
| 6,015,686 | A | 1/2000 | Dubensky, Jr. et al. |
| 6,037,135 | A | 3/2000 | Kubo et al. |
| 6,083,716 | A | 7/2000 | Wilson et al. |
| 6,090,406 | A | 7/2000 | Popescu et al. |
| 6,296,854 | B1 | 10/2001 | Pushko et al. |
| 6,312,946 | B1 | 11/2001 | Yeh et al. |
| 6,365,394 | B1 | 4/2002 | Gao et al. |
| 6,376,236 | B1 | 4/2002 | Dubensky, Jr. et al. |
| 6,413,935 | B1 | 7/2002 | Sette et al. |
| 6,531,135 | B1 | 3/2003 | Johnston et al. |
| 6,610,321 | B2 | 8/2003 | Huang et al. |
| 6,770,283 | B1 | 8/2004 | Garoff et al. |
| 6,783,939 | B2 | 8/2004 | Olmsted et al. |
| 7,078,218 | B2 | 7/2006 | Smith et al. |
| 7,202,351 | B1 | 4/2007 | Sette et al. |
| 7,283,337 | B2 | 10/2007 | Sakai et al. |
| 7,285,265 | B2 | 10/2007 | Vogels et al. |
| 7,291,498 | B2 | 11/2007 | Roy et al. |
| 7,344,872 | B2 | 3/2008 | Gao et al. |
| 7,468,181 | B2 | 12/2008 | Vogels et al. |
| 7,531,180 | B2 | 5/2009 | Polo et al. |
| 7,541,038 | B2 | 6/2009 | Kovacs et al. |
| 7,557,200 | B2 | 7/2009 | Wu et al. |
| 7,572,453 | B2 | 8/2009 | Polo et al. |
| 7,572,628 | B2 | 8/2009 | Dubensky, Jr. et al. |
| 7,605,235 | B2 | 10/2009 | Anderson et al. |
| 7,732,129 | B1 | 6/2010 | Zhang et al. |
| 7,744,900 | B2 | 6/2010 | Dubensky, Jr. et al. |
| 7,771,979 | B2 | 8/2010 | Polo et al. |
| 7,820,440 | B2 | 10/2010 | Vogels et al. |

(Continued)

FOREIGN PATENT DOCUMENTS

| | | | |
|---|---|---|---|
| CA | 2705787 | A1 | 6/2009 |
| CN | 101579528 | A | 11/2009 |

(Continued)

OTHER PUBLICATIONS

Yi et al., Improved efficacy of DNA vaccination against breast cancer by boosting with the repeat beta-hCGC-terminal peptide carried by mycobacterial heat-shock protein HSP65, Vaccine 24: 2575-2584, 2006.*

(Continued)

*Primary Examiner* — Kevin K Hill
(74) *Attorney, Agent, or Firm* — Goodwin Procter LLP

(57) ABSTRACT

Disclosed herein are compositions that include antigen-encoding nucleic acid sequences having multiple iterations of KRAS neoepitope-encoding sequences and/or lacking immunodominant epitopes. Also disclosed are nucleotides, cells, and methods associated with the compositions including their use as vaccines.

23 Claims, 14 Drawing Sheets

Specification includes a Sequence Listing.

(56) References Cited

U.S. PATENT DOCUMENTS 7,820,441 B2 10/2010 Chamberlain et al.
7,838,277 B2 11/2010 Gao et al.
7,850,977 B2 12/2010 Kamrud et al.
7,888,472 B2 2/2011 Sette et al.
8,052,967 B2 11/2011 Vogels et al.
8,093,021 B2 1/2012 Turtado et al.
8,119,336 B2 2/2012 Sampath et al.
8,158,418 B2 4/2012 Polo et al.
8,216,834 B2 7/2012 Colloca et al.
8,252,574 B2 8/2012 Mason et al.
8,426,188 B2 4/2013 Weaver et al.
8,460,913 B2 6/2013 Kamrud et al.
8,614,082 B2 12/2013 Frolov et al.
8,617,533 B2 12/2013 Smith et al.
8,637,313 B2 1/2014 Chamberlain et al.
8,647,864 B2 2/2014 Polo et al.
8,673,319 B2 3/2014 Colloca et al.
8,680,258 B2 3/2014 Coffield et al.
8,691,563 B2 4/2014 Pushko et al.
8,722,044 B2 5/2014 Almagro et al.
8,951,525 B2 2/2015 Almagro et al.
8,961,995 B2 2/2015 Frolov et al.
8,999,333 B2 4/2015 Almagro et al.
9,017,696 B2 4/2015 Draper et al.
9,024,001 B2 5/2015 Tang et al.
9,101,572 B2 8/2015 Pushko et al.
9,115,402 B2 8/2015 Tacohen et al.
9,192,661 B2 11/2015 Jain et al.
9,217,159 B2 12/2015 Roy et al.
9,234,181 B2 1/2016 Tang et al.
9,249,191 B2 2/2016 Ueno et al.
9,254,265 B2 2/2016 Geall et al.
9,255,126 B2 2/2016 Polo et al.
9,273,288 B2 3/2016 Mason et al.
9,295,646 B2 3/2016 Brito et al.
9,340,830 B2 5/2016 Lipson et al.
9,353,353 B2 5/2016 Nabel et al.
9,402,888 B2 8/2016 Ertl et al.
9,416,370 B2 8/2016 Smith et al.
9,453,240 B2 9/2016 Chamberlain et al.
9,486,519 B2 11/2016 Sahin et al.
9,487,563 B2 11/2016 Nabel et al.
9,512,190 B2 12/2016 Ueno et al.
9,580,690 B2 2/2017 Weaver et al.
9,714,435 B2 7/2017 Dicks et al.
9,770,463 B2 9/2017 Geall et al.
9,795,668 B2 10/2017 Jain et al.
9,801,897 B2 10/2017 Geall et al.
10,092,636 B2 10/2018 Binder
10,238,733 B2 3/2019 Brito et al.
10,240,128 B2 3/2019 Thirion et al.
10,487,332 B2 11/2019 Geall
10,532,067 B2 1/2020 Geall et al.
2002/0065241 A1 5/2002 Shankara
2002/0119127 A1 8/2002 Sette et al.
2002/0137081 A1 9/2002 Bandman
2003/0044774 A1 3/2003 Valenzuela et al.
2003/0072767 A1 4/2003 Gaiger et al.
2003/0148262 A1 8/2003 Polo et al.
2003/0232324 A1 12/2003 Polo et al.
2004/0037843 A1 2/2004 Fikes et al.
2004/0115625 A1 6/2004 Ebner
2004/0248113 A1 12/2004 Sette et al.
2005/0003505 A1 1/2005 Marasco et al.
2005/0123555 A1 6/2005 Olmsted et al.
2005/0196754 A1 9/2005 Drmanac et al.
2005/0271676 A1 12/2005 Sette et al.
2006/0051405 A1 3/2006 MacLachlan et al.
2006/0093623 A1 5/2006 Andrieu et al.
2006/0198854 A1 9/2006 Pushko
2006/0252077 A1 11/2006 Buzby
2006/0292175 A1 12/2006 Polo et al.
2007/0031442 A1 2/2007 Sewell
2007/0055049 A1 3/2007 Grey et al.
2007/0224201 A1 9/2007 Wu et al.
2007/0231347 A1 10/2007 Wilson et al.
2008/0050393 A1 2/2008 Tang et al.
2008/0206837 A1 8/2008 Vogels et al.
2008/0241189 A1 10/2008 Wilson
2009/0075384 A1 3/2009 Kamrud et al.
2009/0081200 A1 3/2009 Wang
2009/0093050 A1 4/2009 Wu et al.
2009/0118181 A1 5/2009 Walker et al.
2009/0253184 A1 10/2009 Clarke et al.
2009/0305344 A1 12/2009 Polo et al.
2010/0041737 A1 2/2010 Naldini et al.
2010/0068218 A1 3/2010 Sette et al.
2010/0120897 A1 5/2010 Hurtado et al.
2010/0183665 A1 7/2010 Kamrud et al.
2010/0286070 A1 11/2010 Verheyden et al.
2010/0330121 A1 12/2010 Dubensky, Jr. et al.
2011/0052634 A1 3/2011 Weaver et al.
2011/0091496 A1 4/2011 Graham et al.
2011/0129498 A1 6/2011 Cortese et al.
2011/0142880 A1 6/2011 Lemiale et al.
2011/0217332 A1 9/2011 Colloca et al.
2011/0293637 A1 12/2011 Hacohen et al.
2012/0027788 A1* 2/2012 Colloca ................ C12N 15/861
435/235.1
2012/0258126 A1 10/2012 Scholler et al.
2012/0282290 A1 11/2012 Spencer et al.
2012/0328651 A1 12/2012 Colloca et al.
2013/0011426 A1 1/2013 Tureci et al.
2013/0123199 A1 5/2013 Lee
2013/0149375 A1 6/2013 Geall
2013/0171241 A1 7/2013 Geall
2013/0177639 A1 7/2013 Geall et al.
2013/0177640 A1 7/2013 Geall et al.
2013/0189351 A1 7/2013 Geall
2013/0195968 A1 8/2013 Geall et al.
2013/0195969 A1 8/2013 Geall et al.
2013/0202684 A1 8/2013 Geall et al.
2013/0344097 A1* 12/2013 Guo ........................ A61P 35/00
424/185.1
2014/0010841 A1 1/2014 Weaver et al.
2014/0141070 A1 5/2014 Geall et al.
2014/0178438 A1 6/2014 Sahin et al.
2014/0227346 A1 8/2014 Geall et al.
2014/0234304 A1 8/2014 Almagro et al.
2014/0242152 A1 8/2014 Geall et al.
2014/0248314 A1 9/2014 Swanson et al.
2014/0255472 A1 9/2014 Geall et al.
2014/0271724 A1 9/2014 Ertl et al.
2014/0271829 A1 9/2014 Lilja et al.
2015/0001108 A1 1/2015 Lee et al.
2015/0110831 A1 4/2015 Gilbert et al.
2015/0125465 A1 5/2015 Binder et al.
2015/0125477 A1 5/2015 Kuttruff-Coqui et al.
2015/0140068 A1 5/2015 Barnett et al.
2015/0167003 A1 6/2015 Naldini et al.
2015/0307897 A1 10/2015 Soden et al.
2016/0008447 A1 1/2016 Hlacohen et al.
2016/0074506 A1 3/2016 Jain et al.
2016/0101170 A1 4/2016 Hacohen et al.
2016/0199513 A1 7/2016 Bancel et al.
2016/0289674 A1 10/2016 Bancel et al.
2016/0331822 A1 11/2016 Hacohen et al.
2016/0339090 A1 11/2016 Hacohen et al.
2016/0354409 A1 12/2016 Wang et al.
2017/0028044 A1 2/2017 Soon-Shiong et al.
2017/0212984 A1 7/2017 Yelensky et al.
2017/0340721 A1 11/2017 Volkmann et al.
2018/0000913 A1 1/2018 Hacohen et al.
2018/0050059 A1 2/2018 Geall et al.
2018/0055922 A1 3/2018 Hacohen et al.
2018/0153975 A1 6/2018 Fritsch et al.
2018/0363066 A1 12/2018 Chalmers et al.
2019/0025308 A1 1/2019 Cummings et al.
2019/0060432 A1 2/2019 Hacohen et al.
2019/0134184 A1 5/2019 Yu et al.
2019/0256924 A1 8/2019 Vogelstein et al.
2019/0270766 A1 9/2019 Hogrefe et al.
2020/0010849 A1 1/2020 Blair et al.
2020/0197500 A1 6/2020 Blair et al.

(56) References Cited

U.S. PATENT DOCUMENTS

| | | | |
|---|---|---|---|
| 2021/0213122 A1 | 7/2021 | Blair et al. |
| 2022/0090138 A1 | 3/2022 | Jooss et al. |
| 2022/0125919 A1 | 4/2022 | Jooss et al. |
| 2022/0226453 A1 | 7/2022 | Blair et al. |

FOREIGN PATENT DOCUMENTS

| | | | |
|---|---|---|---|
| CN | 102170900 A | | 8/2011 |
| EP | 1585812 A2 | | 10/2005 |
| EP | 2044947 A1 | | 4/2009 |
| EP | 2370584 A1 | | 10/2011 |
| EP | 2590670 B1 | | 5/2013 |
| EP | 2590676 B1 | | 5/2013 |
| EP | 2917353 A1 | | 9/2015 |
| EP | 2947149 A1 | | 11/2015 |
| FR | 2650840 A1 | | 2/1991 |
| JP | 2007-534295 A | | 11/2007 |
| JP | 2011-504724 A | | 2/2011 |
| JP | 2014-209917 A | | 11/2014 |
| KR | 20060017635 A | | 2/2006 |
| RU | 2206329 C2 | | 6/2003 |
| WO | 1991/02087 A1 | | 2/1991 |
| WO | 1991/06309 A1 | | 5/1991 |
| WO | 1992/15712 A1 | | 9/1992 |
| WO | 1993/24640 A2 | | 12/1993 |
| WO | 1995/007994 A2 | | 3/1995 |
| WO | 1995/13392 A1 | | 5/1995 |
| WO | 1996/13597 A2 | | 5/1996 |
| WO | 1996/18373 A1 | | 6/1996 |
| WO | 1997/41241 A1 | | 11/1997 |
| WO | 2000/018433 A2 | | 4/2000 |
| WO | 2001/055177 A2 | | 8/2001 |
| WO | 2001/073027 A2 | | 10/2001 |
| WO | 2004/023973 A2 | | 3/2004 |
| WO | 2004/055166 A2 | | 7/2004 |
| WO | 2005/016961 A1 | | 2/2005 |
| WO | 2005/033265 A2 | | 4/2005 |
| WO | 2005/071093 A2 | | 8/2005 |
| WO | 2006/078294 A2 | | 7/2006 |
| WO | 2006/090090 A2 | | 8/2006 |
| WO | 2007/024708 A2 | | 3/2007 |
| WO | 2007/047749 A1 | | 4/2007 |
| WO | 2008/122811 A2 | | 10/2008 |
| WO | 2008/145685 A1 | | 12/2008 |
| WO | 2009/079185 A2 | | 6/2009 |
| WO | 2011/128704 A1 | | 10/2011 |
| WO | 2011/143656 A2 | | 11/2011 |
| WO | 2012/006359 A1 | | 1/2012 |
| WO | 2012/006377 A2 | | 1/2012 |
| WO | 2012/006376 A3 | | 4/2012 |
| WO | 2012/172058 A1 | | 12/2012 |
| WO | 2012/172277 A1 | | 12/2012 |
| WO | 2014/072929 A1 | | 5/2014 |
| WO | 2014/168874 A2 | | 10/2014 |
| WO | 2015/085233 A1 | | 6/2015 |
| WO | 2015/095811 A2 | | 6/2015 |
| WO | 2016/085904 A1 | | 6/2016 |
| WO | 2016/100975 A1 | | 6/2016 |
| WO | 2016/100977 A1 | | 6/2016 |
| WO | 2016/122414 A1 | | 8/2016 |
| WO | 2016/124670 A1 | | 8/2016 |
| WO | 2016/154047 A2 | | 9/2016 |
| WO | 2016/154246 A1 | | 9/2016 |
| WO | 2016/187508 A3 | | 1/2017 |
| WO | 2017/106638 A1 | | 6/2017 |
| WO | 2017/151940 A2 | | 9/2017 |
| WO | 2017/173321 A1 | | 10/2017 |
| WO | 2017/184590 A1 | | 10/2017 |
| WO | WO 17/173321 | * | 10/2017 |
| WO | 2017/192924 A1 | | 11/2017 |
| WO | 2017/220463 A1 | | 12/2017 |
| WO | 2018/028438 A1 | | 2/2018 |
| WO | 2018/039131 A1 | | 3/2018 |
| WO | 2018/098362 A1 | | 5/2018 |
| WO | WO 18/098362 | * | 5/2018 |
| WO | 2018/104911 A1 | | 6/2018 |
| WO | 2018/116193 A1 | | 6/2018 |
| WO | 2018/119115 A1 | | 6/2018 |
| WO | 2018102585 A1 | | 6/2018 |
| WO | 2018/187356 A2 | | 10/2018 |
| WO | 2018/208856 A1 | | 11/2018 |
| WO | 2018/227030 A1 | | 12/2018 |
| WO | 2018/232330 A1 | | 12/2018 |
| WO | 2019/090156 A1 | | 5/2019 |
| WO | WO 19/126186 | * | 6/2019 |
| WO | 2019/170773 A1 | | 9/2019 |
| WO | 2019/226939 A1 | | 11/2019 |
| WO | 2019/226941 A1 | | 11/2019 |
| WO | 2020/097393 A1 | | 5/2020 |
| WO | 2020/243719 A1 | | 12/2020 |
| WO | 2021/003348 A1 | | 1/2021 |
| WO | 2021/092095 A1 | | 5/2021 |
| WO | 2021/119545 A1 | | 6/2021 |
| WO | 2021/142437 A1 | | 7/2021 |
| WO | 2021216775 A2 | | 10/2021 |

OTHER PUBLICATIONS

Gupta et al., Engineering, cloning, and expression of genes encoding the multimeric luteinizing-hormone-releasing hormone linked to T cell determinants in *Escherichia coli*, Protein Expression and Purification 37: 1-7, 2004.*

Weng et al., DNA vaccine elicits an efficient antitumor response by targeting the mutant Kras in a transgenic mouse lung cancer model, Gene Therapy 21: 888-896, 2014.*

Abbas et al., "Structure of human IFIT1 with capped RNA reveals adaptable mRNA binding and mechanisms for sensing N1 and N2 ribose 2 ?-O methylations." Proceedings of the National Academy of Sciences 114, No. 11 (2017): E2106-E2115.

Nezafat et al., "A novel multi-epitope peptide vaccine against cancer: an in silico approach." Journal of theoretical biology 349 (2014): 121-134.

Mohammed et al., "Phosphorylation-dependent interaction between antigenic peptides and MHC class I: a molecular basis for the presentation of transformed self." Nature immunology 9, No. 11 (2008): 1236-1243.

Toes et al., "Protective anti-tumor immunity induced by vaccination with recombinant adenoviruses encoding multiple tumor-associated cytotoxic T lymphocyte epitopes in a string of-beads fashion." Proceedings of the National Academy of Sciences 94, No. 26 (1997): 14660-14665.

Wei et al., "Dendritic cells expressing a combined PADRE/MUC4-derived polyepitope DNA vaccine induce multiple cytotoxic T-cell responses." Cancer biotherapy & radiopharmaceuticals 23, No. 1 (2008): 121-128.

Meko'o et al., "Immunopreventive effects against murine H22 hepatocellular carcinoma in vivo by a DNA vaccine targeting a gastrin-releasing peptide." Asian Pacific Journal of Cancer Prevention 15, No. 20 (2014): 9039-9043.

Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," Molecular Pharmaceutics 12 (11) (): 3986-3998, Nov. 2, 2015.

Koizume et al., "Tissue Factor—Factor VII Complex As a Key Regulator of Ovarian Cancer Phenotypes," Biomarkers in Cancer vol. 7, pp. 1-13, Aug. 5, 2015.

Schumacher et al., "Neoantigens in cancer immunotherapy," Science vol. 348, Issue 6230, pp. 69-74, Apr. 3, 2015.

Rivas et al., "Effect of predicted protein-truncating genetic variants on the human transcriptome," Science vol. 348, No. 6235, pp. 666-669, May 8, 2015.

Lundstrom, Kenneth. "Alphavirus-based vaccines." Current opinion in molecular therapeutics 4, No. 1 (Feb. 2002): 28-34.

Alexander et al., "Linear Padre T helper epitope and carbohydrate B cell epitope conjugates induce specific high titer IgG antibody responses." The Journal of Immunology 164, No. 3 (Feb. 2000): 1625-1633.

(56) References Cited

OTHER PUBLICATIONS

Kim et al., "Neopepsee: accurate genome-level prediction of neoantigens by harnessing sequence and amino acid immunogenicity information." Annals of Oncology 29, No. 4 (Apr. 2018): 1030-1036.
Ott et al., "An immunogenic personal neoantigen vaccine for patients with melanoma." Nature 547, No. 7662 (Jul. 2017): 217-221.
Gen Bank: AF394196.1—Simian adenovirus 25, complete genome, 15 pages, 2001.
Fluet et al., "Effects of rapid antigen degradation and VEE glycoprotein specificity on immune responses induced by a VEE replicon vaccine." Virology 370, No. 1 (Jan. 2008): 22-32.
Ogawa et al., "An Attempt of Cytokine Gene Therapy Using Adenovirus Vectors," Partial Translation of: Biotherapy, 1998, vol. 12 No. 5, p. 785-787.
Nielsen et al., "An in vitro-transcribed-mRNA polyepitope construct encoding 32 distinct HLA class I-restricted epitopes from CMV, EBV, and Influenza for use as a functional control in human immune monitoring studies." Journal of Immunological methods 360, No. 1-2 (2010): 149-156.
Bergmann et al., "Differential effects of flanking residues on presentation of epitopes from chimeric peptides." Journal of virology 68, No. 8 (1994): 5306-5310.
Carroll et al., "Alphavirus replicon-based adjuvants enhance the immunogenicity and effectiveness of Fluzone in rhesus macaques." Vaccine 29, No. 5 (2011): 931-940.
Thompson et al., "The contribution of type I interferon signaling to immunity induced by alphavirus replicon vaccines." Vaccine 26, No. 39 (2008): 4998-5003.
Ljungberg et al,. "Increased immunogenicity of a DNA-launched Venezuelan equine encephalitis virus-based replicon DNA vaccine." Journal of virology 81, No. 24 (2007): 13412-13423.
Channon et al., "Improved adenoviral vectors: cautious optimism for gene therapy." QJM: monthly journal of the Association of Physicians 90, No. 2 (1997): 105-109.
Gao et al., "Biology of adenovirus vectors with E1 and E4 deletions for liver-directed gene therapy." Journal of virology 70, No. 12 (1996): 8934-8943.
Andrews et al., "Generation and characterization of E1/E2a/E3/E4-deficient adenoviral vectors encoding human factor VIII." Molecular Therapy 3, No. 3 (2001): 329-336.
Farina et al., "Replication-defective vector based on a chimpanzee adenovirus." Journal of virology 75, No. 23 (2001): 11603-11613.
PCT/US2021/045106—Invitiation to Pay Additional Fees, dated Dec. 9, 2021, 4 pages.
PCT/US2021/045106—International Search Report and Wirtten Opinion, datedFeb. 25, 2022.
Ngo et al., "CNTO 859, a humanized anti-tissue factor monoclonal antibody, is a potent inhibitor of breast cancer metastasis and tumor growth in xenograft models," International Journal of Cancer, vol. 120, No. 6, pp. 1261-1267, 2007.
Hong et al., Immuno-PET of Tissue Factor in Pancreatic Cancer, J Nucl Med, vol. 53, No. 11, pp. 1748-1754, 2012.
Trail et al., "Antibody drug conjugates for treatment of breast cancer: Novel targets and diverse approaches in ADC design," Pharmacol. Ther., vol. 181, pp. 126-142, 2018.
De Graaf et al., Beta-Glucuronidase-Mediated Drug Release, Curr Pharm Des., vol. 8, pp. 1391-1403, 2002.
Chari et al., Immunoconjugates Containing Novel Maytansinoids: Promising Anticancer Drugs, Cancer Research, vol. 52, pp. 127-131, 1992.
Kovtun et al., "Antibody-Mytansinoid Conjugates Designed to Bypass Multidrug Resistance," Cancer Research vol. 70, No. 6, pp. 2528-2537, 2010.
Vitetta et al., "Redesigning Nature's Poisons to Create Anti-Tumor Reagents," Science vol. 238, No. 4830, pp. 1098-1104, 1987.
Junutula et al., "Rapid identification of reactive cysteine residues for site-specific labeling of antibody-Fabs," Journal of Immunological Methods 332, No. 1-2 (2008): 41-52.
Hofer et al., "An engineered selenocysteine defines a unique class of antibody derivatives, " Proc. Natl. Acad. Sci. USA, 2008, 105:12451-12456.
Hofer et al., Molecularly defined antibody conjugation through a selenocysteine interface, Biochemistry, vol. 48, No. 50, pp. 12047-12057, 2009.
Hjortoe et al., Tissue factor-factor VIIa-specific up-regulation of IL-8 expression in MDA-MB-231 cells is mediated by PAR-2 and results in increased cell migration, Blood, 2004, vol. 103, No. 8, pp. 3029-3037.
Sakurai et al., "Expression of Tissue Factor in Epithelial Ovarian Carcinoma is Involved in the Development of Venous Thromboembolism," International Journal of Gynecologic Cancer, vol. 27, No. 1, pp. 37-43, 2017.
Yao et al., Tissue Factor and VEGF Expression in Prostate Carcinoma A Tissue Microarray Study, Cancer Invest., vol. 27, pp. 430-434, 2009.
Abdulkadir et al., "Tissue factor expression and angiogenesisin human prostate carcinoma," Human Pathology 31, No. 4 (2000): 443-447.
Zhang et al., "Pathological expression of tissue factor confers promising antitumor response to a novel therapeutic antibody SC1 in triple negative breast cancer and pancreatic adenocarcinoma," Oncotarget vol. 8, No. 35, pp. 59086-59102, 2017.
Guan et al., "Tissue factor expression and angiogenesis in human glioma." Clinical Biochemistry 35, No. 4 (2002): 321-325.
Carneiro-Lobo et al., Ixolaris, a tissue factor inhibitor, blocks primary tumor growth and angiogenesis in a glioblastoma model, J Thromb Haemost, 2009, 7:1855-1864.
Regina et al., "Increased tissue factor expression is associated with reduced survival in non-small cell lung cancer and with mutations of TP53 and PTEN," Clinical Chemistry, vol. 55, No. 10, pp. 1834-1842, 2009.
Lo et al., "Tissue factor expression in the metaplasia-adenoma-carcinoma sequence of gastric cancer in a European population," British Journal of Cancer vol. 107, No. 7, pp. 1125-1130, 2012.
Chen et al., "Immunolocalisation of tissue factor in esophageal cancer is correlated with intratumoral angiogenesis and prognosis of the patient." Acta Histochemica 112, No. 3 (2010): 233-239.
Patry et al., "Tissue factor expression correlates with disease-specific survival in patients with node-negative muscle-invasive bladder cancer," International Journal of Cancer, vol. 122, No. 7, pp. 1592-1597, 2008.
Bromberg et al., Tissue factor promotes melanoma metastasis by a pathway independent of blood coagulation, Proc Natl Acad Sci U S A., 1995, 92:8205-8209.
Silva et al., "Increased Tissue Factor Expression is an Independent Predictor of Mortality in Clear Cell Carcinoma of the Kidney," Int Braz J Urol., 2014, 40:499-506.
Van Den Berg et al., "The relationship between tissue factor and cancer progression: insights from bench and bedside," Blood vol. 119, No. 4, pp. 924-932, 2012.
Tripisciano et al., "Different Potential of Extracellular Vesicles to Support Thrombin Generation: Contributions of Phosphatidylserine, Tissue Factor, and Cellular Origin," Scientific Reports vol. 7, No. 1, pp. 1-11, 2017.
Teplyakov et al., "Crystal structure of tissue factor in complex with antibody 10H10 reveals the signaling epitope," Cellular Signalling vol. 36, pp. 139-144, 2017.
Iepe et al., "A large fraction of HLA class I ligands are proteasome-generated spliced peptides," Science vol. 354, No. 6310, Oct. 21, 2016.
Smith et al., "Comparison of biosequences," Advances in Applied Mathematics vol. 2, No. 4, pp. 482-489, 1981.
Needleman et al., "A General Method Applicable to the Search for Similarities in the Amino Acid Sequence of Two Proteins," Journal of Molecular Biology, vol. 48, No. 3, pp. 443-453, 1970.
Pearson et al., "Improved tools for biological sequence comparison," Proceedings of the National Academy of Sciences, vol. 85, No. 8, pp. 2444-2448, 1988.
Altschul et al., "Basic Local Alignment Search Tool." Journal of Molecular Biology vol. 215, Issue 3 (1990): 403-410.

(56) References Cited

OTHER PUBLICATIONS

Kornher et al., "Mutation detection using nucleotide analogs that alter electrophoretic mobility," Nucleic Acids Research vol. 17, No. 19, pp. 7779-7784, 1989.
Syvänen et al., "A Primer-Guided Nucleotide Incorporation Assay in the Genotyping of Apolipoprotein E," Genomics , No. 4 (1990): 684-692.
Kuppuswamy et al., "Single nucleotide primer extension to detect genetic diseases: experimental application to hemophilia B (factor IX) and cystic fibrosis genes," Proceedings of the National Academy of Sciences vol. 88, No. 4, pp. 1143-1147, 1991.
Prezant et al., "Trapped-Oligonucleotide Nucleotide Incorporation (TONI) Assay, a Simple Method for Screening Point Mutations," Human Mutation 1, No. 2 (1992): 159-164.
Ugozzoli et al., "Detection of specific alleles by using allele-specific primer extension followed by capture on solid support," Genetic Analysis: Biomolecular Engineering 9, No. 4 (1992): 107-112.
Nyrén et al., "Solid phase DNA minisequencing by an enzymatic luminometric inorganic pyrophosphate detection assay." Analytical Biochemistry 208, No. 1 (1993): 171-175.
Merrifield, "Solid phase synthesis." Science 232 (1986): 341-348.
Dupuis et al., "Dendritic cells internalize vaccine adjuvant after intramuscular injection," Cellular Immunology 186, No. 1 (1998), 18-27.
Allison, "The mode of action of immunological adjuvants," Developments in Biological Standardization 92 (1998): 3-11.
Gabrilovich et al., "IL-12 and Mutant P53 Peptide-Pulsed Dendritic Cells for the Specific Immunotherapy of Cancer," Journal of Immunotherapy, vol. 19, No. 6 (1996): 414-418.
Tatsis et al., "Adenoviruses as vaccine vectors," Molecular Therapy vol. 10, No. 4, pp. 616-629, 2004.
Jensen et al., "Improved methods for predicting peptide binding affinity to MHC class II molecules," Immunology vol. 154, Issue 3, pp. 394-406, 2018.
Carter et al., "Absolute quantification of somatic DNA alterations in human cancer," Nature Biotechnology vol. 30, No. 5, 413-421, 2012.
Farina et al., "Replication-Defective Vector Based on a Chimpanzee Adenovirus," Journal of Virology vol. 75, No. 23, pp. 11603-11613, 2001.
Ljungberg et al., "Self-replicating alphavirus RNA vaccines," Expert Review of Vaccines vol. 14, No. 2, pp. 177-194, Feb. 1, 2015.
Lundstrom, "Alphavirus-Based Vaccines," Viruses vol. 6, No. 6, pp. 2392-2415, 2014.
Geall et al., "Nonviral delivery of self-amplifying RNA vaccines," Proceedings of the National Academy of Sciences, vol. 109, Issue 36, pp. 14604-14609, 2012.
Rodriguez et al., "DNA Immunization with Minigenes: Low Frequency of Memory Cytotoxic T Lymphocytes and Inefficient Antiviral Protection Are Rectified by Ubiquitination," Journal of Virology vol. 72, No. 6, pp. 5174-5181, 1998.
Velders et al., "Defined Flanking Spacers and Enhanced Proteolysis Is Essential for Eradication of Established Tumors by an Epitope String DNA Vaccine, " The Journal of Immunology, vol. 166, No. 9, pp. 5366-5373, 2001.
Kreiter et al., "Increased Antigen Presentation Efficiency by Coupling Antigens to MHC Class I Trafficking Signals," The Journal of Immunology, vol. 180, No. 1, pp. 309-318, 2008.
Rodriguez et al., "DNA Immunization: Ubiquitination of a Viral Protein Enhances Cytotoxic T-Lymphocyte Induction and Antiviral Protection but Abrogates Antibody Induction," Journal of Virology vol. 71, No. 11, pp. 8497-8503, 1997.
James et al., "Tetramer-guided epitope mapping reveals broad, individualized repertoires of tetanus toxin-specific CD4+ T cells and suggests HLA-based differences in epitope recognition," International Immunology vol. 19, No. 11, pp. 1291-1301, 2007.
Jayaraman et al., "Maximizing the Potency of siRNA Lipid Nanoparticles for Hepatic Gene Silencing In Vivo," Angewandte Chemie vol. 51, pp. 8529-8533, 2012.
Démoulins et al., "Polyethylenimine-based polyplex delivery of self-replicating RNA vaccines," Nanomedicine: Nanotechnology, Biology and Medicine vol. 12, No. 3, pp. 711-722, Apr. 1, 2016.
Chahal et al., "Dendrimer-RNA nanoparticles generate protective immunity against lethal Ebola, H1N1 influenza, and Toxoplasma gondii challenges with a single dose," Proceedings of the National Academy of Sciences vol. 113, No. 29 E4133-E4142, Jul. 19, 2016.
Vajdy et al., "Mucosal adjuvants and delivery systems for protein-, DNA- and RNA-based vaccines," Immunology and Cell Biology, vol. 82, No. 6, pp. 617-627, 2004.
Fleeton et al., "Self-Replicative RNA Vaccines Elicit Protection against Influenza A Virus, Respiratory Syncytial Virus, and a Tickborne Encephalitis Virus," The Journal of Infectious Diseases vol. 183, No. 9, pp. 1395-1398, 2001.
Strejan et al., "Suppression of chronic-relapsing experimental allergic encephalomyelitis in strain-13 guinea pigs by administration of liposome-associated myelin basic protein." Journal of Neuroimmunology 7 (1984): 27-41.
Johanning et al., "A Sindbis virus mRNA polynucleotide vector achieves prolonged and high level heterologous gene expression in vivo," Nucleic Aids Research vol. 23, Issue 9, pp. 1495-1501, 1995.
Martinon et al., "Induction of virus-specific cytotoxic T lymphocytes in vivo by liposome-entrapped mRNA," European Journal of Immunology 23, No. 7 (1993): 1719-1722.
Eitner et al., "DNA and RNA-based vaccines: principles, progress and prospects," Vaccine vol. 18, No. 9-10, pp. 765-777, 1999.
Del Val et al., "Efficient Processing of an Antigenic Sequence for Presentation by MHC Class I Molecules Depends on Its Neighboring Residues in the Protein," Cell vol. 66, No. 6, pp. 1145-1153, 1991.
Holzhütter et al., "A Theoretical Approach Towards the Identification of Cleavage-Determining Amino Acid Motifs of the 20S Proteasome," Journal of Molecular Biology, vol. 286, Issue 4, pp. 1251-1265, 1999.
Nussbaum et al., "Cleavage motifs of the yeast 20S proteasome βsubunits deduced from digests of enolase 1," Proceedings of the National Academy of Sciences, vol. 95, No. 21, pp. 12504-12509, 1998.
Eggers et al., "The Cleavage Preference of the Proteasome Governs the Yield of Antigenic Peptides," The Journal of Experimental Medicine vol. 182, No. 6, pp. 1865-1870, 1995.
Borthwick et al., "Vaccine-elicited human T cells recognizing conserved protein regions inhibit HIV-1." Molecular therapy 22, No. 2 (2014): 464-475.
Warimwe et al. "Immunogenicity and efficacy of a chimpanzee adenovirus-vectored Rift Valley fever vaccine in mice," Virology Journal vol. 10, No. 1, pp. 1-9, 2013.
Cappuccini et al. "Immunogenicity and efficacy of the novel cancer vaccine based on simian adenovirus and MVA vectors alone and in combination with PD-1 mAb in a mouse model of prostate cancer," Cancer Immunol. Immunother. vol. 65, No. 6, pp. 701-713, Apr. 6, 2016.
Aurisicchio et al., "Immunogenicity and Therapeutic Efficacy of a Dual-Component Genetic Cancer Vaccine Cotargeting Carcinoembryonic Antigen and HER2/neu in Preclinical Models," Human Gene Therapy, vol. 25, Issue 2, pp. 121-131, Feb. 2014.
Morris et al. "Simian adenoviruses as vaccine vectors." Future Virology, vol. 11, No. 9 pp. 649-659, Sep. 15, 2016.
Levy et al. "A melanoma multiepitope polypeptide induces specific CD8+ T-cell response," Cellular Immunology, vol. 250, No. 1-2, pp. 24-30, 2007.
Tatsis et al. "Chimpanzee-origin adenovirus vectors as vaccine carriers," Gene Therapy vol. 13, No. 5, pp. 421-429, 2006.
Zappasodi et al., "Alphavirus-based vaccines in melanoma: rationale and potential improvements in immunotherapeutic combinations." Immunotherapy 7, No. 9 (Sep. 2015): 981-997.
Riabov et al., "Anti-tumor effect of the alphavirus-based virus-like particlevector expressing prostate-specific antigen in a HLA-DR transgenic mouse model of prostate cancer." Vaccine 33, No. 41 (Oct. 5, 2015): 5386-5395.
Fang et al., "Stable antibody expression at therapeutic levels using the 2A peptide." Nature biotechnology 23, No. 5 (2005): 584-590.

(56) References Cited

OTHER PUBLICATIONS

Wu et al., "Targeting genes: delivery and persistent expression of a foreign gene driven by mammalian regulatory elements in vivo." Journal of Biological Chemistry 264, No. 29 (1989): 16985-16987.
Fisher et al., "The transmembrane domain of diphtheria toxin improves molecular conjugate gene transfer." Biochemical Journal 321, No. 1 (1997): 49-58.
Szoka et al., "Comparative properties and methods of preparation of lipid vesicles (liposomes)." Annual review of biophysics and bioengineering 9, No. 1 (1980): 467-508.
Wolff et al., "Direct gene transfer into mouse muscle in vivo." Science 247, No. 4949 (1990): 1465-1468.
Felgner et al., "Lipofection: a highly efficient, lipid-mediated DNA-transfection procedure." Proceedings of the National Academy of Sciences 84, No. 21 (1987): 7413-7417.
Mannino et al., "Liposome mediated gene transfer." Biotechniques 6, No. 7 (1988): 682-690.
Konarska et al., "Recognition of cap structure in splicing in vitro of mRNA precursors." Cell 38, No. 3 (1984): 731-736.
Tuang, "Sindbis virus vectors for expression in animal cells." Current Opinion in Biotechnology 7, No. 5 (1996): 531-535.
Wang et al., "Identification of T Cell Receptors Targeting KRAS-Mutated Human Tumors", Cancer Immunology Research 4(3) Mar. 2016, pp. 204-214.
Hacohen et al., "Getting personal with neoantigen-based therapeutic cancer vaccines." Cancer immunology research 1, No. 1 (2013): 11-15.
Karasaki et al., "Identification of individual cancer-specific somatic mutations for neoantigen-based immunotherapy of lung cancer." Journal of Thoracic Oncology 11, No. 3 (Mar. 2016): 324-333.
Hu et al., "Immunization Delivered by Lentiviral Vectors for Cancer and Infectious Diseases," Immunological Reviews, vol. 239, Issue 1, pp. 45-61, 2011.
Sakuma et al., "Lentiviral vectors: basic to translational," Biochemical Journal 443, No. 3 (2012): 603-618.
Cooper et al., "Rescue of splicing-mediated intron loss maximizes expression in lentiviral vectors containing the human ubiquitin C promoter," Nucleic Acids Research vol. 43, No. 1, pp. 682-690, Dec. 17, 2014.
Zufferey et al., "Self-Inactivating Lentivirus Vector for Safe and Efficient in Vivo Gene Delivery," Journal of Virology vol. 72, No. 12, pp. 9873-9880, 1998.
Gros et al., "Prospective identification of neoantigen-specific lymphocytes in the peripheral blood of melanoma patients," Nature Medicine vol. 22, Issue 4, pp. 433-438, Feb. 22, 2016.
Strønen et al., "Targeting of cancer neoantigens with donor-derived T cell receptor repertoires," Science 352, No. 6291 (May 19, 2016): 1337-1341.
Lu et al., "Efficient identification of mutated cancer antigens recognized by T cells associated with durable tumor regressions," Clinical Cancer Research vol. 20, No. 13, pp. 3401-3410, 2014.
Stover et al., "New use of BCG for recombinant vaccines," Nature vol. 351, No. 6326, pp. 456-460, 1991.
Boshart et al., "A Very Strong Enhancer is Located Upstream of an Immediate Early Gene of Human Cytomegalovirus," Cell vol. 41, No. 2, 521-530, 1985.
Kost et al., "The nucleotide sequence of the chick cytoplasmic b-actin gene," Nucleic Acids Research vol. 11, No. 23, pp. 8287-8301, 1983.
Shukla et al., "Comprehensive analysis of cancer-associated somatic mutations in class I HLA genes," Nature Biotechnology vol. 33, No. 11. pp. 1152-1158, Nov. 2015.
McGranahan et al., "Allele-specific HLA loss and immune escape in lung cancer evolution," Cell vol. 171, No. 6, pp. 1259-1271, 2017.
Van Loo et al., "Allele-specific copy number analysis of tumors," Proceedings of the National Academy of Sciences, vol. 107, No. 39, pp. 16910-16915, 2010.
Desrichard et al., "Cancer neoantigens and applications for immunotherapy," Clinical Cancer Research vol. 22, No. 4, pp. 807-812, Feb. 15, 2016.
Gubin et al., "Tumor neoantigens: Building a framework for personalized cancer immunotherapy," The Journal of Clinical Investigation, vol. 125, No. 9, pp. 3413-3421, Sep. 2015.
Snyder et al., "Genetic Basis for Clinical Response to CTLA-4 Blockade in Melanoma," New England Journal of Medicine, vol. 371, No. 23, pp. 2189-2199, 2014.
Tran et al., "Cancer Immunotherapy Based on Mutation-Specific CD4+ T Cells in a Patient with Epithelial Cancer," Science vol. 344, No. 6184, pp. 641-645, 2014.
Lundegaard et al., "State of the art and challenges in sequence based T-cell epitope prediction," Immunome Research vol. 6, No. 2, pp. 1-14, 2010.
Yadav et al., "Predicting immunogenic tumour mutations by combining mass spectrometry and exome sequencing," Nature, vol. 515, No. 7528, pp. 572-576, 2014.
Bassani-Sternberg et al., "Mass Spectrometry of Human Leukocyte Antigen Class I Peptidomes Reveals Strong Effects of Protein Abundance and Turnover on Antigen Presentation," Molecular & Cellular Proteomics Vo. 14, Issue 3, 658-673, Mar. 1, 2015.
Van Allen et al., "Genomic correlates of response to CTLA-4 blockade in metastatic melanoma," Science vol. 350, No. 6257, pp. 207-211, Nov. 11, 2015.
Yoshida et al., "Splicing factor mutations and cancer," Wiley Interdisciplinary Reviews: RNA 5, No. 4 (2014): 445-459.
Cancer Genome Atlas Research Network, "Comprehensive molecular profiling of lung adenocarcinoma," Nature, vol. 511, pp. 543-550, 2014.
Rajasagi et al., "Systematic identification of personal tumor-specific neoantigens in chronic lymphocytic leukemia," Blood, vol. 124, No. 3, pp. 453-462, 2014.
Cieslik et al., "The use of exome capture RNA-seq for highly degraded RNA with application to clinical cancer sequencing," Genome Research vol. 25, No. 9, 1372-1381, Sep. 1, 2015.
Bodini et al., "The hidden genomic landscape of acute myeloid leukemia: subclonal structure revealed by undetected mutations," Blood, The Journal of the American Society of Hematology vol. 125, No. 4 (Jan. 22, 2015): 600-605.
Saunders et al., Strelka: accurate somatic small-variant calling from sequenced tumor-normal sample pairs, Bioinformatics vol. 28, No. 14, pp. 1811-1817, 2012.
Cibulskis et al., "Sensitive detection of somatic point mutations in impure and heterogeneous cancer samples," Nature Biotechnology vol. 31, No. 3, pp. 213-219, 2013.
Mose et al., "ABRA: improved coding indel detection via assembly-based realignment," Bioinformatics, vol. 30, No. 19, pp. 2813-2815, 2014.
Ye et al., "Pindel: a pattern growth approach to detect break points of large deletions and medium sized insertions from paired-end short reads," Bioinformatics vol. 25, No. 21, pp. 2865-2871, 2009.
Lam et al., "Nucleotide-resolution analysis of structural variants using BreakSeq and a breakpoint library," Nature Biotechnology vol. 28, No. 1, pp. 47-55 2010.
Pertea et al., "StringTie enables improved reconstruction of a transcriptome from RNA-seq reads," Nature Biotechnology vol. 33, No. 3, pp. 290-295, Mar. 2015.
Roberts et al., "Identification of novel transcripts in annotated genomes using RNA-Seq," Bioinformatics vol. 27, No. 17, pp. 2325-2329, 2011.
Vitting-Seerup et al., "spliceR: an R package for classification of alternative splicing and prediction of coding potential from RNA-seq data," BMC Bioinformatics, vol. 15, Issue 1, pp. 1-7, 2014.
Skelly et al., "A powerful and flexible statistical framework for testing hypotheses of allele-specific gene expression from RNA-seq data," Genome Research vol. 21, No. 10, pp. 1728-1737, 2011.
Anders et al., "HTSeq-a Python framework to work with high-throughput sequencing data." Bioinformatics vol. 31, No. 2 (Jan. 15, 2015): 166-169.
Furney et al., "SF3B1 Mutations Are Associated with Alternative Splicing in Uveal Melanoma," Cancer Discovery vol. 3, Issue 10, pp. 1122-1129, 2013.

(56) References Cited

OTHER PUBLICATIONS

Zhou et al., "A Chemical Genetics Approach for the Functional Assessment of Novel Cancer Genes," Cancer Research vol. 75, No. 10, pp. 1949-1958, May 15, 2015.
Maguire et al., "SF3B1 mutations constitute a novel therapeutic target in breast cancer," The Journal of Pathology vol. 235, No. 4 pp. 571-580, Mar. 2015.
Carithers et al., "A Novel Approach to High-Quality Postmortem Tissue Procurement: The GTEx Project," Biopreservation and Biobanking, vol. 13, No. 5, 311-319, Oct. 1, 2015.
Xu et al., "RNA Compass: A Dual Approach for Pathogen and Host Transcriptome Analysis of RNA-Seq Datasets," Plos One, vol. 9, Issue 2, p. e89445, 2014.
Jørgensen et al., "NETMHCSTAB-predicting stability of peptide—MHC-I complexes; impacts for cytotoxic T lymphocyte epitope discovery," Immunology vol. 141, No. 1, pp. 18-26, 2014.
Larsen et al., "An integrative approach to CTL epitope prediction: a combined algorithm integrating MHC class I binding, TAP transport efficiency, and proteasomal cleavage predictions," European Journal of Immunology, vol. 35, No. 8, pp. 2295-2303, 2005.
Nielsen et al., "The role of the proteasome in generating cytotoxic T-cell epitopes: insights obtained from improved predictions of proteasomal cleavage," Immunogenetics vol. 57, No. 1-2, pp. 33-41, 2005.
Calis et al., "Properties of MHC Class I Presented Peptides That enhance immunogenicity." PLoS Comput Biol. vol. 9, Issue 10 (Oct. 24, 2013): e1003266, 13 pages.
Zhang et al., "Intra-tumor Heterogeneity in Localized Lung Adenocarcinomas Delineated by Multi-region Sequencing," Science vol. 346, No. 6206, pp. 256-259, 2014.
Walter et al., "Clonal Architecture of Secondary Acute Myeloid Leukemia," New England Journal of Medicine, vol. 366, Issue 12, pp. 1090-1098, 2012.
Hunt et al., "Characterization of Peptides Bound to the Class I MHC Molecule HLA-A2. 1 by Mass Spectrometry," Science vol. 255, pp. 1261-1263, 1992.
Zarling et al., "Identification of class I MHC-associated phosphopeptides as targets for cancer immunotherapy," Proceedings of the National Academy of Sciences, vol. 103, No. 40, pp. 14889-14894, 2006.
Abelin et al., "Complementary IMAC enrichment methods for HLA-associated phosphopeptide identification by mass spectrometry," Nature Protocols 10(9) (2015): 1308-1318.
Barnstable et al., "Production of Monoclonal Antibodies to Group A Erythrocytes, HLA and Other Human Cell Surface Antigens—New Tools for Genetic Analysis," Cell vol. 14, 9-20, 1978.
Goldman et al., "HLA-DA monoclonal antibodies inhibit the proliferation of normal and chronic granulocytic leukaemia myeloid progenitor cell," British Journal of Haematology 52, No. 3 (1982): 411-420.
Eng et al., "Comet: An open-source MS/MS sequence database search tool," Proteomics vol. 13, No. 1, pp. 22-24, 2013.
Eng et al., "A Deeper Look into Comet—Implementation and Features," Journal of the American Society for Mass Spectrometry vol. 26, No. 11, pp. 1865-1874, 2015.
Käll et al., "Semi-supervised learning for peptide identification from shotgun proteomics datasets," Nature Methods vol. 4, No. 11, pp. 923-925, 2007.
Käll et al., "Assigning Significance to Peptides Identified by Tandem Mass Spectrometry Using Decoy Databases," Journal of Proteome Research vol. 7, No. 01, pp. 29-34, 2008.
Käll et al., "Non-parametric estimation of posterior error probabilities associated with peptides identified by tandem mass spectrometry," Bioinformatics vol. 24, No. 16, pp. i42-i48, 2008.
Kinney et al., "Nucleotide sequence of the 26 S mRNA of the virulent Trinidad donkey strain of Venezuelan equine encephalitis virus and deduced sequence of the encoded structural proteins," Virology 152, No. 2 (1986): 400-413.
Slansky et al., "Enhanced Antigen-Specific Antitumor Immunity with Altered Peptide Ligands that Stabilize the MHC-Peptide-TCR Complex," Immunity vol. 13, No. 4, pp. 529-538, 2000.
Huang et al., "The immunodominant major histocompatibility complex class I-restricted antigen of a murine colon tumor derives from an endogenous retroviral gene product," Proceedings of the National Academy of Sciences vol. 93, No. 18, pp. 9730-9735, 1996.
Johnson et al., "Molecular Determinants of Alphavirus Neurovirulence: Nucleotide and Deduced Protein Sequence Changes during Attenuation of Venezuelan Equine Encephalitis Virus," Journal of General Virology vol. 67, Issue 9, pp. 1951-1960, 1986.
Alexander et al., "Development of High Potency Universal DR-Restricted Helper Epitopes by Modification of High Affinity DR-Blocking Peptides." Immunity vol. 1, Issue 9 (1994): 751-761.
Cornet et al., "Optimal organization of a polypeptide-based candidate cancer vaccine composed of cryptic tumor peptides with enhanced immunogenicity," Vaccine vol. 24, No. 12, pp. 2102-2109, 2006.
Depla et al., "Rational Design of a Multiepitope Vaccine Encoding T-Lymphocyte Epitopes for Treatment of Chronic Hepatitis B Virus Infections," Journal of Virology vol. 82, No. 1, pp. 435-450, 2008.
Ishioka et al., "Utilization of MHC Class I Transgenic Mice for Development of Minigene DNA Vaccines Encoding Multiple HLA-Restricted CTL Epitopes," The Journal of Immunology vol. 162, No. 7, pp. 3915-3925, 1999.
Janetzki et al., "Guidelines for the automated evaluation of Elispot assays," Nature Protocols vol. 10, No. 7, pp. 1098-1115, Jul. 2015.
Lyons et al., "Influence of Human CD8 on Antigen Recognition by T-Cell Receptor-Transduced Cells," Cancer Research vol. 66, No. 23, pp. 11455-11461, 2006.
Nagai et al., "Aurora kinase A-specific T-cell receptor gene transfer redirects T lymphocytes to display effective antileukemia reactivity," Blood, The Journal of the American Society of Hematology, vol. 119, No. 2, pp. 368-376, 2012.
Panina-Bordignon et al., "Universally immunogenic T cell epitopes: promiscuous binding to human MHC class II and promiscuous recognition by T cells," European Journal of Immunology 19, No. 12 (1989): 2237-2242.
Vitiello et al., "Analysis of the HLA-restricted Influenza-specific Cytotoxic T Lymphocyte Response in Transgenic Mice Carrying a Chimeric Human-Mouse Class I Major Histocompatibility Complex," The Journal of Experimental Medicine, vol. 173, No. 4, pp. 1007-1015, 1991.
Yachi et al., "Altered Peptide Ligands Induce Delayed CD8-T Cell Receptor Interaction—a Role for CD8 in Distinguishing Antigen Quality," Immunity vol. 25, No. 2, pp. 203-211, 2006.
Pushko et al., "Replicon-Helper Systems from Attenuated Venezuelan Equine Encephalitis Virus: Expression of Heterologous Genes in Vitro and Immunization against Heterologous Pathogens in Vivo," Virology vol. 239, No. 2, pp. 389-401, 1997.
Strauss et al., "The Alphaviruses: Gene Expression, Replication, and Evolution," Microbiological Reviews, vol. 58, No. 3, pp. 491-562, 1994.
Rhême et al., "Alphaviral cytotoxicity and its implication in vector development," Experimental Physiology vol. 90, No. 1, pp. 45-52, 2005.
Frolov et al., "Cis-acting RNA elements at the 5' end of Sindbis virus genome RNA regulate minus- and plus-strand RNA synthesis," RNA vol. 7, No. 11, pp. 1638-1651, 2001.
Jose et al., "A structural and functional perspective of alphavirus replication and assembly," Future Microbiology, vol. 4, No. 7, pp. 837-856, 2009.
Li et al., "RSEM: accurate transcript quantification from RNA-Seq data with or without a reference genome." BMC bioinformatics 12, No. 1 (2011): 323, 16 pages.
Pearson et al., "MHC class I-associated peptides derive from selective regions of the human genome," The Journal of Clinical Investigation, vol. 126, No. 12, pp. 4690-4701, Dec. 1, 2016.
Mommen et al., "Sampling from the Proteome to the Human Leukocyte Antigen-DR (HLA-DR) Ligandome ProceedsVia High Specificity," Molecular & Cellular Proteomics, vol. 15, No. 4, pp. 1412-1423, Apr. 1, 2016.
Kreiter et al., "Mutant MHC class II epitopes drive therapeutic immune responses to cancer," Nature, vol. 520, No. 7549, pp. 692-696, Apr. 2015.

(56) References Cited

OTHER PUBLICATIONS

Andreatta et al., "Accurate pan-specific prediction of peptide-MHC class II binding affinity with improved binding core identification." Immunogenetics 67, No. 11-12 (Nov. 2015): 641-650.
Aarnoudse et al., "TCR reconstitution in Jurkat reporter cells facilitates the identification of novel tumor antigens by cDNA expression clonin," International Journal of Vancer, May 1, 2002;99(1):7-13.
Ager et al., "31st Annual Meeting and Associated Programs of the Society for Immunotherapy of Cancer (SITC 2016): part two," in Journal for Immuno Therapy of Cancer, vol. 4, Supplement 1, 2016:107-221.
Andreatta et al., "Gapped sequence alignment using artificial neural networks: application to the MHC class I system," Bioinformatics, Feb. 15, 2016;32(4):511-7.
Banu et al., "Building and Optimizing a Virus-specific T Cell Receptor Library for Targeted Immunotherapy in Viral Infections." Scientific Reports, Feb. 25, 2014;4:1-10.
Boegel et al., "HLA typing from RNA-Seq sequence reads," Genome Medicine, Dec. 22, 2012;4(12):1-12.
Boisvert et al., "A Quantitative Spatial Proteomics Analysis of Proteome Turnover in Human Cells," Molecular & Cellular Proteomics, Mar. 2012;11(3):1-15.
Carreno et al., "A dendritic cell vaccine increases the breadth and diversity of melanoma neoantigen-specific T cells." Science, May 15, 2015;348(6236):803-8.
Christensen et al., "Urokinase-type plasminogen activator receptor (uPAR), tissue factor (TF) and epidermal growth factor receptor (EGFR): tumor expression patterns and prognostic value in oral cancer," BMC Cancer, Aug. 25, 2017;17(1):1-12.
Cocco et al., "Expression of Tissue factor in Adenocarcinoma and Squamous Cell Carcinoma of the Uterine Cervix: Implications for immunotherapy with hl-con1, a factor VII-IgGFc chimeric protein targeting tissue factor," BMC Cancer, Jun. 22, 2011;11:1-10.
Colloca et al., "Vaccine Vectors Derived from a Large Collection of Simian Adenoviruses Induce Potent Cellular Immunity Across Multiple Species," Science Translational Medicine, Jan. 4, 2012;4(115):1-24.
Duan et al., "Genomic and bioinformatic profiling of mutational neoepitopes reveals new rules to predict anticancer immunogenicity," Journal of Experimental Medicine, Oct. 20, 2014;211(11):2231-48.
Frampton et al., "Development and validation of a clinical cancer genomic profiling test based on massively parallel DNA sequencing," Nature Biotechnology Nov. 2013;31(11):1023-31.
Huang et al., "DNA vaccines for cervical cancer," American Journal of Translational Research, Jan. 2, 2010;2(1):75-87.
Junutula et al., "Site-specific conjugation of a cytotoxic drug to an antibody improves the therapeutic index." Aug. 2008;26(8):925-32.
Letourneau et al. "Design and Pre-Clinical Evaluation of a Universal HIV-1 Vaccine," PloS ONE, Oct. 3, 2007;2(10):1-11.
Liu et al., "ATHLATES: accurate typing of human leukocyte antigen through exome sequencing," Nucleic Acids Research Aug. 2013:41(14):1-8.
Maretty et al. "Bayesian transcriptome assembly," Genome Biology, 2014;15(10):1-11.
Mayor et al., "HLA typing for the next generation," PLoS One, May 27, 2015;10(5):1-12.
Nielsen et al., "NN-align. An artificial neural network-based alignment algorithm for MHC class II peptide binding prediction," BMC Bioinformatics, Sep. 18, 2009;10:1-10.
Nielsen et al., "Prediction of MHC class II binding affinity using SMM-align, a novel stabilization matrix alignment method," BMC Bioinformatics, Jul. 4, 2007;8:1-12.
Qiu et al., "Reviving virus based cancer vaccines by using cytomegalovirus vectors expressing modified tumor antigens," OncoImmunology Jun. 5, 2015;5(1):1-4.
Riley et al., "Recent advances in nanomaterials for gene delivery—a review," Nanomaterials, Apr. 28, 2017;7(5):1-19.
Rizvi et al., "Mutational landscape determines sensitivity to PD-1 blockade in non-small cell lung cancer," Science, Apr. 3, 2015;348(6230):1-12.
Roy et al., "Assessing long-distance RNA sequence connectivity via RNA-templated DNA-DNA ligation," Elife. Apr. 13, 2015;4:1-21.
Sokolov, "Primer extension technique for the detection of single nucleotide in genomic DNA," Nucleic Acids Research, Jun. 25, 1990;18(12):3671.
Song et al., "CLASS: constrained transcript assembly of RNA-seq reads," BMC Bioinformatics, BioMed Central, 2013;14 Suppl 5(Suppl 5):1-8.
Syvänen et al., "Identification of Individuals by Analysis of Biallelic DNA Markers, Using PCR and Solid-Phase Minisequencing," American Journal of Human Genetics Jan. 1993;52(1):46-59.
Wan et al., "High-sensitivity monitoring of ctDNA by patient-specific sequencing panels and integration of variant reads." bioRxiv, Sep. 2019:1-37.
Wilkerson et al., "Integrated RNA and DNA sequencing improves mutation detection in low purity tumors," Nucleic Acids Research, Jul. 2014;42(13):1-12.
Yeh et al., "Upregulation of Tissue Factor by Activated Stat3 Contributes to Malignant Pleural Effusion Generation via Enhancing Tumor Metastasis and Vascular Permeability in Lung Adenocarcinoma," PLoS One, Sep. 27, 2013;8(9):1-14.
Zhang, et al., "Peaks DB: De Novo Sequencing Assisted Database Search for Sensitive and Accurate Peptide Identification," Molecular & Cellular Proteomics, Apr. 2012;11(4):1-8.

* cited by examiner

HLA-A01 mice

MULTIEPITOPE VACCINE CASSETTES

CROSS REFERENCE TO RELATED APPLICATIONS

This application is a Continuation of International Application No. PCT/US2021/045106, filed Aug. 6, 2021, which application claims the benefit of U.S. Provisional Application No. 63/062,268 filed Aug. 6, 2020, each of which are hereby incorporated in their entirety by reference for all purposes.

SEQUENCE LISTING

The instant application contains a Sequence Listing which has been submitted electronically in ASCII format and is hereby incorporated by reference in its entirety. Said ASCII copy, created on Jun. 5, 223, is named GSO-095WOC1_SL_Replacement_06_05_2023.txt and is 456,934 bytes in size.

BACKGROUND

Therapeutic vaccines based on tumor-specific antigens hold great promise as a next-generation of personalized cancer immunotherapy. [1-3] For example, cancers with a high mutational burden, such as non-small cell lung cancer (NSCLC) and melanoma, are particularly attractive targets of such therapy given the relatively greater likelihood of neoantigen generation. [4,5] Early evidence shows that neoantigen-based vaccination can elicit T-cell responses[6] and that neoantigen targeted cell-therapy can cause tumor regression under certain circumstances in selected patients.[7]

One question for antigen vaccine design in both cancer and infectious disease settings is which of the many coding mutations present generate the "best" therapeutic antigens, e.g., antigens that can elicit immunity.

In addition to the challenges of current antigen prediction methods certain challenges also exist with the available vector systems that can be used for antigen delivery in humans, many of which are derived from humans. For example, many humans have pre-existing immunity to human viruses as a result of previous natural exposure, and this immunity can be a major obstacle to the use of recombinant human viruses for antigen delivery in vaccination strategies, such as in cancer treatment or vaccinations against infectious diseases. While some progress has been made in vaccinations strategies addressing the above problems, improvements are still needed, particularly for clinical applications, such as improved vaccine potency and efficacy.

SUMMARY

Disclosed herein is: an antigen-encoding cassette, or a polypeptide sequence encoded by the cassette, wherein the antigen-encoding cassette comprises at least one antigen-encoding nucleic acid sequence described, from 5' to 3', by the formula:

$$(E_x-(E^N{}_n)_y)_z$$

wherein E represents a nucleotide sequence comprising a distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof, and at least one of the distinct epitope-encoding nucleic acid sequences comprising the at least two iterations encodes a distinct KRAS-associated MHC class I neoepitope.

In some aspects, the antigen-encoding cassette encodes at least 4 iterations of each of the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82). In some aspects, the KRAS-associated MHC class I neoepitope or the KRAS mutation comprises a KRAS G12C mutation, a KRAS G12V mutation, a KRAS G12D mutation, or a KRAS Q61H mutation. In some aspects, the KRAS-associated MHC class I neoepitope or the KRAS mutation comprises any one of the amino acid sequence shown in SEQ ID NOs: 75-82. In some aspects, the antigen-encoding cassette comprises each of the amino acid sequence shown in SEQ ID NOs: 75-82.In some aspects, the antigen-encoding cassette comprises two or more iterations of each of the amino acid sequence shown in SEQ ID NOs: 75-82. In some aspects, the antigen-encoding cassette comprises 4 iterations of each of the amino acid sequence shown in SEQ ID NOs: 75-82. In some aspects, the KRAS-associated MHC class I neoepitope or the KRAS mutation comprises the amino acid sequence shown in SEQ ID NO: 57, SEQ ID NO: 58, SEQ ID NO: 59, or SEQ ID NO: 60. In some aspects, the epitope-encoding nucleic acid sequences comprises two or more distinct epitope-encoding nucleic acid sequences independently encoding a distinct KRAS-associated MHC class I neoepitope or a distinct KRAS mutation. In some aspects, each of the epitope-encoding nucleic acid sequences independently encodes a distinct KRAS-associated MHC class I neoepitope or a distinct KRAS mutation. In some aspects, the epitope-encoding nucleic acid sequences comprises two or more distinct epitope-encoding nucleic acid sequences independently encoding a KRAS G12C mutation, a KRAS G12V mutation, a KRAS G12D mutation, or a KRAS Q61H mutation. In some aspects, the epitope-encoding nucleic acid sequences independently encodes each of a KRAS G12C mutation, a KRAS G12V mutation, and a KRAS G12D mutation, and optionally a KRAS Q61H mutation. In some aspects, the antigen-encoding nucleic acid sequence encodes a peptide comprising the amino acid sequence shown in SEQ ID NO: 64 or SEQ ID NO: 65. In some aspects, the antigen-encoding nucleic acid sequence encodes a peptide comprising the amino acid sequence shown in SEQ ID NO: 65.

In some aspects, at least two of the distinct epitope-encoding nucleic acid sequences comprising the at least two iterations encode distinct KRAS-associated MHC class I neoepitopes. In some aspects, at least 3, at least 4, at least 5, at least 6, at least 7, or at least 8 of the distinct epitope-encoding nucleic acid sequences comprising the at least two iterations encode distinct KRAS-associated MHC class I neoepitopes. In some aspects, each of the distinct epitope-encoding nucleic acid sequences comprising the at least two iterations encode distinct KRAS-associated MHC class I neoepitopes. In some aspects, one or more of the nucleic acid sequences encoding the KRAS-associated MHC class I neoepitopes comprises at least 2, at least 3, at least 4, at least 5, at least 6, at least 7, or at least 8 iterations. In some aspects, each of the nucleic acid sequences encoding the KRAS-associated MHC class I neoepitopes comprises at least 2, at least 3, at least 4, at least 5, at least 6, at least 7, or at least 8 iterations. In some aspects, one or more of the nucleic acid sequences encoding the distinct KRAS-associated MHC class I neoepitopes comprises at least 4 iterations. In some aspects, each of the nucleic acid sequences encoding the distinct KRAS-associated MHC class I neoepitopes comprises at least 4 iterations. In some aspects, one or more of the distinct KRAS-associated MHC class I neoepitopes independently comprises a KRAS G12C mutation, a KRAS G12V mutation, a KRAS G12D mutation, or a KRAS Q61H mutation.

In some aspects, each E or $E^N$ independently comprises a nucleotide sequence described, from 5' to 3', by the formula ($L5_b$-$N_c$-$L3_d$), wherein N comprises the distinct epitope-encoding nucleic acid sequence associated with each E or $E^N$, where c=1, L5 comprises a 5' linker sequence, where b=0 or 1, and L3 comprises a 3' linker sequence, where d=0 or 1. In some aspects, each N encodes an epitope 7-15 amino acids in length, L5 is a native 5' linker sequence that encodes a native N-terminal amino acid sequence of the epitope, and wherein the 5' linker sequence encodes a peptide that is at least 2 amino acids in length, and L3 is a native 3' linker sequence that encodes a native C-terminal amino acid sequence of the epitope, and wherein the 3' linker sequence encodes a peptide that is at least 32 amino acids in length. In some aspects, the 5' and/or 3' linker sequence encodes a peptide that is at least 3 amino acids in length. In some aspects, the 5' and/or 3' linker sequence encodes a peptide that is at least 4 amino acids in length. In some aspects, the 5' and/or 3' linker sequence encodes a peptide that is at least 5 amino acids in length. In some aspects, the 5' and/or 3' linker sequence encodes a peptide that is at least 8 amino acids in length. In some aspects, the 5' and/or 3' linker sequence encodes a peptide that is at least 2-8 amino acids in length. In some aspects, the 5' and/or 3' linker sequence encodes a peptide that is at least 2-10 amino acids in length.

In some aspects, each E and $E^N$ encodes an epitope at least 7 amino acids in length. In some aspects, each E and $E^N$ encodes an epitope 7-15 amino acids in length. In some aspects, each E and $E^N$ is a nucleotide sequence at least 21 nucleotides in length. In some aspects, each E and $E^N$ is a nucleotide sequence 75 nucleotides in length.

Also disclosed herein is a composition for delivery of an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) an epitope-encoding nucleic acid sequence encoding a KRAS-associated MHC class I neoepitope, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the at least one antigen-encoding nucleic acid sequence comprises at least two iterations of the epitope-encoding nucleic acid sequence encoding the KRAS-associated MHC class I neoepitope.

Also disclosed herein is a composition for delivery of an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) at least one polyadenylation (poly(A)) sequence; and (b) a cassette, wherein the cassette comprises: (i) at least one antigen-encoding nucleic acid sequence, comprising: (I) at least 2, 3, 4, 5, 6, 7, 8, 9, or 10 distinct epitope-encoding nucleic acid sequences linearly linked to each other wherein at least one of the distinct epitope-encoding nucleic acid sequences encodes a KRAS-associated MHC class I neoepitope, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the at least one antigen-encoding nucleic acid sequence comprises at least two iterations of at least one of the distinct epitope-encoding nucleic acid sequences encoding the KRAS-associated MHC class I neoepitope.

In some aspects, the at least one antigen-encoding nucleic acid sequence comprises at least 3 distinct epitope-encoding nucleic acid sequences.

Also disclosed herein is a composition for delivery of an antigen expression system, comprising: the antigen expression system, wherein the antigen expression system comprises one or more vectors, the one or more vectors comprising: (a) a vector backbone, wherein the vector backbone comprises a chimpanzee adenovirus vector, optionally wherein the chimpanzee adenovirus vector is a ChAdV68 vector, or an alphavirus vector, optionally wherein the alphavirus vector is a Venezuelan equine encephalitis virus vector; and (b) a cassette, optionally wherein the cassette is integrated between a native promoter nucleotide sequence native to the vector backbone and a poly(A) sequence, optionally wherein the poly(A) sequence is native to the vector backbone, wherein the cassette comprises: (i) at least one antigen-encoding nucleic acid sequence, comprising: (I) an epitope-encoding nucleic acid sequence encoding a KRAS-associated MHC class I neoepitope, optionally comprising at least two distinct epitope-encoding nucleic acid sequences linearly linked to each other, each epitope-encoding nucleic acid sequence optionally comprising: (A) a MHC class I epitope encoding nucleic acid sequence, wherein the MHC class I epitope encoding nucleic acid sequence encodes a MHC class I epitope 7-15 amino acids in length, (B) a 5' linker sequence, wherein the 5' linker sequence encodes a native N-terminal amino acid sequence of the MHC class I epitope, and wherein the 5' linker sequence encodes a peptide that is at least 2 amino acids in length, (C) a 3' linker sequence, wherein the 3' linker sequence encodes a native C-terminal acid sequence of the MHC class I epitope, and wherein the 3' linker sequence encodes a peptide that is at least 2 amino acids in length, and wherein the cassette is operably linked to the native promoter nucleotide sequence, wherein each of the epitope-encoding nucleic acid sequences encodes a polypeptide that is between 13 and 25 amino acids in length, and wherein each 3' end of each epitope-encoding nucleic acid sequence is linked to the 5' end of the following epitope-encoding nucleic acid sequence with the exception of the final epitope-encoding nucleic acid sequence in the cassette; and (ii) at least two MHC class II epitope-encoding nucleic acid sequences comprising: (I) a PADRE MHC class II sequence (SEQ ID NO:48), (II) a Tetanus toxoid MHC class II sequence (SEQ ID NO:46), (III) a first nucleic acid sequence encoding a GPGPG amino acid linker sequence linking the PADRE MHC class II sequence and the Tetanus toxoid MHC class II sequence, (IV) a second nucleic acid sequence encoding a GPGPG amino acid linker sequence linking the 5' end of the at least two MHC class II epitope-encoding nucleic acid sequences to the epitope-encoding nucleic acid sequences, (V) optionally, a third nucleic acid sequence encoding a GPGPG amino acid linker sequence at the 3' end of the at least two MHC class II epitope-encoding nucleic acid sequences; (iii) optionally, a second promoter nucleotide sequence operably linked to the antigen-encoding nucleic acid sequence; and wherein if the second promoter nucleotide sequence is absent, the antigen-encoding nucleic acid sequence is operably linked to the native promoter nucleotide sequence, and wherein the at least one antigen-encoding nucleic acid sequence comprises at least two iterations of the epitope-encoding nucleic acid sequence encoding the KRAS-associated MHC class I neoepitope.

In some aspects, an ordered sequence of each element of the cassette is described in the formula, from 5' to 3', comprising:

$$P_a\text{-}(L5_b\text{-}N_c\text{-}L3_d)_X\text{-}(G5_e\text{-}U_f)_Y\text{-}G3_g$$

wherein, P comprises the second promoter nucleotide sequence, where a=0 or 1, N comprises one of the distinct epitope-encoding nucleic acid sequences, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker, where e=0 or 1, G3 comprises one of the at least one nucleic acid sequences encoding a GPGPG amino acid linker, where g=0 or 1, U comprises one of the at least one MHC class II epitope-encoding nucleic acid sequence, where f=1, X=1 to 400, where for each X the corresponding $N_c$ is an epitope-encoding nucleic acid sequence, and Y=0, 1, or 2, where for each Y the corresponding $U_f$ is an MHC class II epitope-encoding nucleic acid sequence.

In some aspects, for each X the corresponding $N_c$ is a distinct epitope-encoding nucleic acid sequence, except for the $N_c$ corresponding to the at least two iterations of the distinct epitope-encoding nucleic acid sequence. In some aspects, for each Y the corresponding $U_f$ is a distinct MHC class II epitope-encoding nucleic acid sequence. In some aspects, a=0, b=1, d=1, e=1, g=1, h=1, X=16, Y=2, the at least one promoter nucleotide sequence is a single native promoter nucleotide sequence native to the vector backbone, the at least one polyadenylation poly(A) sequence is a poly(A) sequence of at least 80 consecutive A nucleotides provided by the vector backbone, each N encodes an epitope 7-15 amino acids in length, L5 is a native 5' linker sequence that encodes a native N-terminal amino acid sequence of the epitope, and wherein the 5' linker sequence encodes a peptide that is at least 2 amino acids in length, L3 is a native 3' linker sequence that encodes a native C-terminal amino acid sequence of the epitope, and wherein the 3' linker sequence encodes a peptide that is at least 2 amino acids in length, U is each of a PADRE class II sequence and a Tetanus toxoid MHC class II sequence, the vector backbone comprises a chimpanzee adenovirus vector, optionally wherein the chimpanzee adenovirus vector is a ChAdV68 vector, or an alphavirus vector, optionally wherein the alphavirus vector is a Venezuelan equine encephalitis virus vector, optionally wherein the native promoter nucleotide sequence is a subgenomic (e.g., 26S) promoter when the vector backbone comprises an alphavirus vector, and each of the MHC class II epitope-encoding nucleic acid sequences encodes a polypeptide that is between 13 and 25 amino acids in length.

In some aspects, the antigen-encoding cassette encodes at least 4 iterations of each of the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82). In some aspects, the KRAS-associated MHC class I neoepitope or the KRAS mutation comprises a KRAS G12C mutation, a KRAS G12V mutation, a KRAS G12D mutation, or a KRAS Q61H mutation. In some aspects, the KRAS-associated MHC class I neoepitope or the KRAS mutation comprises any one of the amino acid sequence shown in SEQ ID NOs: 75-82. In some aspects, the antigen-encoding cassette comprises each of the amino acid sequence shown in SEQ ID NOs: 75-82.In some aspects, the antigen-encoding cassette comprises two or more iterations of each of the amino acid sequence shown in SEQ ID NOs: 75-82. In some aspects, the antigen-encoding cassette comprises 4 iterations of each of the amino acid sequence shown in SEQ ID NOs: 75-82. In some aspects, the KRAS-associated MHC class I neoepitope or the KRAS mutation comprises the amino acid sequence shown in SEQ ID NO: 57, SEQ ID NO: 58, SEQ ID NO: 59, or SEQ ID NO: 60. In some aspects, the epitope-encoding nucleic acid sequences comprises two or more distinct epitope-encoding nucleic acid sequences independently encoding a distinct KRAS-associated MHC class I neoepitope or a distinct KRAS mutation. In some aspects, each of the epitope-encoding nucleic acid sequences independently encodes a distinct KRAS-associated MHC class I neoepitope or a distinct KRAS mutation. In some aspects, the epitope-encoding nucleic acid sequences comprises two or more distinct epitope-encoding nucleic acid sequences independently encoding a KRAS G12C mutation, a KRAS G12V mutation, a KRAS G12D mutation, or a KRAS Q61H mutation. In some aspects, the epitope-encoding nucleic acid sequences independently encodes each of a KRAS G12C mutation, a KRAS G12V mutation, and a KRAS G12D mutation, and optionally a KRAS Q61H mutation. In some aspects, the antigen-encoding nucleic acid sequence encodes a peptide comprising the amino acid sequence shown in SEQ ID NO: 64 or SEQ ID NO: 65. In some aspects, the antigen-encoding nucleic acid sequence encodes a peptide comprising the amino acid sequence shown in SEQ ID NO: 65.

In some aspects, the at least two iterations is at least 3, at least 4, at least 5, at least 6, at least 7, or at least 8 iterations. In some aspects, the at least two iterations is at least 8 iterations. In some aspects, the at least two iterations is at least 8, at least 9, at least 10, at least 11, at least 12, at least 13, 1 at least 4, at least 15, at least 16, at least 17, at least 18, at least 19, or at least 20 iterations. In some aspects, the at least two iterations is between 2-3, between 2-4, between 2-5, between 2-6, between 2-7 iterations, or between 2-8 iterations. In some aspects, the at least two iterations is 7 iterations or less, 6 iterations or less, 5 iterations or less, 4 iterations or less, or 3 iterations or less.

In some aspects, the at least one antigen-encoding nucleic acid sequence comprises at least two iterations of at least two distinct epitope-encoding nucleic acid sequences. In some aspects, the at least one antigen-encoding nucleic acid sequence comprises at least two iterations of at least 3, at least 4, at least 5, at least 6, at least 7, at least 8, at least 9, or at least 10 distinct epitope-encoding nucleic acid sequences. In some aspects, the at least two iterations are separated by at least one separate distinct epitope-encoding nucleic acid sequence. In some aspects, the at least two iterations are separated by at least 2 separate distinct epitope-encoding nucleic acid sequences. In some aspects, the at least two iterations, inclusive of the optional 5' linker sequence and/or the optional 3' linker sequence, are separated by at least 75 nucleotides. In some aspects, the at least two iterations, inclusive of the optional 5' linker sequence and/or the optional 3' linker sequence, are separated by at least 150 nucleotides, at least 300 nucleotides, or at least 675 nucleotides. In some aspects, the at least two iterations, inclusive of the optional 5' linker sequence and/or the optional 3' linker sequence, are separated by at least 50 nucleotides, at least 100 nucleotides, at least 200 nucleotides, at least 250 nucleotides, at least 350 nucleotides, at least 400 nucleotides, at least 450 nucleotides, at least 500 nucleotides, at least 700 nucleotides, at least 700 nucleotides, at least 750 nucleotides, at least 800 nucleotides, at least 900 nucleotides, or at least 1000 nucleotides. In some aspects, the at least two iterations, inclusive of the optional 5' linker sequence and/or the optional 3' linker sequence, are separated by at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, or at least 70 nucleotides.

In some aspects, the at least one antigen-encoding nucleic acid sequence is described, from 5' to 3', by the formula:

$$(E_x\text{-}(E^N{}_n)_y)_z$$

wherein, E represents a nucleotide sequence comprising at least one of the distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof.

In some aspects, the antigen-encoding cassette encodes at least 4 iterations of each of the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82).

In some aspects, the distinct epitope-encoding nucleic acid sequences comprises at least two distinct epitope-encoding nucleic acid sequences each encoding distinct KRAS-associated MHC class I neoepitopes. In some aspects, the distinct epitope-encoding nucleic acid sequences comprises at least 3, at least 4, at least 5, at least 6, at least 7, or at least 8 distinct epitope-encoding nucleic acid sequences each encoding distinct KRAS-associated MHC class I neoepitopes. In some aspects, each of the epitope-encoding nucleic acid sequences of the at least one antigen-encoding nucleic acid sequence encodes a distinct KRAS-associated MHC class I neoepitope. In some aspects, one or more of the nucleic acid sequences encoding the distinct KRAS-associated MHC class I neoepitopes comprises at least 2, at least 3, at least 4, at least 5, at least 6, at least 7, or at least 8 iterations. In some aspects, each of the nucleic acid sequences encoding the distinct KRAS-associated MHC class I neoepitopes comprises at least 2, at least 3, at least 4, at least 5, at least 6, at least 7, or at least 8 iterations. In some aspects, one or more of the nucleic acid sequences encoding the distinct KRAS-associated MHC class I neoepitopes comprises at least 4 iterations. In some aspects, each of the nucleic acid sequences encoding the distinct KRAS-associated MHC class I neoepitopes comprises at least 4 iterations. In some aspects, one or more of the distinct KRAS-associated MHC class I neoepitopes independently comprises a KRAS G12C mutation, a KRAS G12V mutation, a KRAS G12D mutation, or a KRAS Q61H mutation.

In some aspects, the at least two iterations comprises a number of iterations, or z comprises a number, sufficient to stimulate a greater immune response relative to an antigen-encoding nucleic acid sequence comprising a single iteration of the epitope-encoding nucleic acid sequence. In some aspects, the at least two iterations comprises a number of iterations, or z comprises a number, sufficient to stimulate an immune response, and a single iteration of the epitope-encoding nucleic acid sequence is insufficient to stimulate the immune response or insufficient to stimulate a detectable immune response. In some aspects, the immune response is an expansion of epitope-specific T cells following in vivo immunization with the composition for delivery of the antigen expression system. In some aspects, the immune response is increased activation of epitope-specific T cells and/or increased epitope-specific killing by epitope-specific T cells following in vivo immunization with the composition for delivery of the antigen expression system.

Also provided for herein is a composition for delivery of an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) at least two distinct epitope-encoding nucleic acid sequences, optionally comprising: (1) at least one alteration that makes the encoded epitope sequence distinct from the corresponding peptide sequence encoded by a wild-type nucleic acid sequence, optionally wherein the at least one alteration is a KRAS mutation, or (2) a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A)

sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response.

Also provided for herein is a composition for delivery of an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) at least 2, 3, 4, 5, 6, 7, 8, 9, or 10 distinct epitope-encoding nucleic acid sequences linearly linked to each other, optionally comprising: (1) at least one alteration that makes the encoded epitope sequence distinct from the corresponding peptide sequence encoded by a wild-type nucleic acid sequence, optionally wherein the at least one alteration is a KRAS mutation, or (2) a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, and wherein if the second promoter nucleotide sequence is absent, the antigen-encoding nucleic acid sequence is operably linked to the at least one promoter nucleotide sequence, and wherein the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response.

In some aspects, at least one of the distinct epitope-encoding nucleic acid sequences encodes a KRAS-associated MHC class I neoepitope.

Also provided for herein is a composition for delivery of an antigen expression system, comprising: the antigen expression system, wherein the antigen expression system comprises one or more vectors, the one or more vectors comprising: (a) a vector backbone, wherein the vector backbone comprises a chimpanzee adenovirus vector, optionally wherein the chimpanzee adenovirus vector is a ChAdV68 vector, or an alphavirus vector, optionally wherein the alphavirus vector is a Venezuelan equine encephalitis virus vector; and (b) a cassette, optionally wherein the cassette is integrated between a native promoter nucleotide sequence native to the vector backbone and a poly(A) sequence, optionally wherein the poly(A) sequence is native to the vector backbone, wherein the cassette comprises: (i) at least one antigen-encoding nucleic acid sequence, comprising: (I) at least one epitope-encoding nucleic acid sequence, optionally comprising at least two distinct epitope-encoding nucleic acid sequences linearly linked to each other, each epitope-encoding nucleic acid sequence optionally comprising: (A) a MHC class I epitope encoding nucleic acid sequence, wherein the MHC class I epitope encoding nucleic acid sequence encodes a MHC class I epitope 7-15 amino acids in length, (B) a 5' linker sequence, wherein the 5' linker sequence encodes a native N-terminal amino acid sequence of the MHC class I epitope, and wherein the 5' linker sequence encodes a peptide that is at least 2 amino acids in length, (C) a 3' linker sequence, wherein the 3' linker sequence encodes a native C-terminal acid sequence of the MHC class I epitope, and wherein the 3' linker sequence encodes a peptide that is at least 2 amino acids in length, and wherein the cassette is operably linked to the native promoter nucleotide sequence, wherein each of the epitope-encoding nucleic acid sequences encodes a polypeptide that is between 13 and 25 amino acids in length, and wherein each 3' end of each epitope-encoding nucleic acid sequence is linked to the 5' end of the following epitope-encoding nucleic acid sequence with the exception of the final epitope-encoding nucleic acid sequence in the cassette; and (ii) at least two MHC class II epitope-encoding nucleic acid sequences comprising: (I) a PADRE MHC class II sequence (SEQ ID NO:48), (II) a Tetanus toxoid MHC class II sequence (SEQ ID NO:46), (III) a first nucleic acid sequence encoding a GPGPG amino acid linker sequence linking the PADRE MHC class II sequence and the Tetanus toxoid MHC class II sequence, (IV) a second nucleic acid sequence encoding a GPGPG amino acid linker sequence linking the 5' end of the at least two MHC class II epitope-encoding nucleic acid sequences to the epitope-encoding nucleic acid sequences, (V) optionally, a third nucleic acid sequence encoding a GPGPG amino acid linker sequence at the 3' end of the at least two MHC class II epitope-encoding nucleic acid sequences, and (iii) optionally, a second promoter nucleotide sequence operably linked to the antigen-encoding nucleic acid sequence; and wherein if the second promoter nucleotide sequence is absent, the antigen-encoding nucleic acid sequence is operably linked to the native promoter nucleotide sequence, and wherein the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response.

In some aspects, the immunodominant MHC class I epitope stimulates a 10-fold, 20-fold, 30-fold, 40-fold, 50-fold, 100-fold, 200-fold, 300-fold, 400-fold, 500-fold, 1000-fold, 2000-fold, 3000-fold, 4000-fold, 5000-fold, or 10,000-fold or greater immune response when administered in a vaccine composition to a subject relative to another MHC class I epitope encoded in the cassette and capable of stimulating an immune response in the subject. In some aspects, the immunodominant MHC class I epitope reduces the immune response of the other MHC class I epitope to below a limit of detection and/or does not stimulate a therapeutically effective response. In some aspects, the subject expresses at least one HLA allele known or predicted to present both the immunodominant MHC class I epitope and the other MHC class I epitope encoded in the cassette.

In some aspects, one or more of the epitope-encoding nucleic acid sequences are derived from a tumor, an infection, or an infected cell of a subject. In some aspects, each of the epitope-encoding nucleic acid sequences are derived from a tumor, an infection, or an infected cell of a subject. In some aspects, one or more of the epitope-encoding nucleic acid sequences are not derived from a tumor, an infection, or an infected cell of a subject. In some aspects, each of the epitope-encoding nucleic acid sequences are not derived from a tumor, an infection, or an infected cell of a subject.

In some aspects, the epitope-encoding nucleic acid sequence encodes an epitope known or suspected to be presented by MHC class I on a surface of a cell, optionally wherein the surface of the cell is a tumor cell surface or an infected cell surface, and optionally wherein the cell is a subject's cell. In some aspects, the cell is a tumor cell selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, T cell lymphocytic leukemia, non-small cell lung cancer, and small cell lung cancer, or wherein the cell is an infected cell selected from the group consisting of: a pathogen infected cell, a virally infected cell, a bacterially infected cell, a fungally infected cell, and a parasitically infected cell. In some aspects, the virally infected cell is selected from the group consisting of: an HIV infected cell, a Severe acute respiratory syndrome-related coronavirus (SARS) infected cell, a severe acute respiratory syndrome coronavirus 2 (SARS-CoV-2) infected cell, a Ebola infected cell, a Hepatitis B virus (HBV) infected cell, an influenza infected cell, an orthymyxoviridae family virus infected cell, a Human papillomavirus (HPV) infected cell, a Cytomegalovirus (CMV) infected cell, a Chikungunya virus infected cell, a Respiratory syncytial virus (RSV) infected cell, a Dengue virus infected cell, and a Hepatitis C virus (HCV) infected cell.

In some aspects, the composition further comprises a nanoparticulate delivery vehicle. In some aspects, the nanoparticulate delivery vehicle is a lipid nanoparticle (LNP). In some aspects, the LNP comprises ionizable amino lipids. In some aspects, the ionizable amino lipids comprise MC3-like (dilinoleylmethyl-4-dimethylaminobutyrate) molecules. In some aspects, the nanoparticulate delivery vehicle encapsulates the antigen expression system.

In some aspects, the cassette is integrated between the at least one promoter nucleotide sequence and the at least one poly(A) sequence. In some aspects, the second promoter is absent and the at least one promoter nucleotide sequence is operably linked to the antigen-encoding nucleic acid sequence.

In some aspects, the one or more vectors comprise one or more +-stranded RNA vectors. In some aspects, the one or more +-stranded RNA vectors comprise a 5' 7-methylguanosine (m7g) cap. In some aspects, the one or more +-stranded RNA vectors are produced by in vitro transcription. In some aspects, the one or more vectors are self-replicating within a mammalian cell. In some aspects, the backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus. In some aspects, the backbone comprises at least one nucleotide sequence of a Venezuelan equine encephalitis virus. In some aspects, the backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the backbone comprises at least sequences for nonstructural protein-mediated amplification, a 26S promoter sequence, and a poly(A) sequence encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, sequences for nonstructural protein-mediated amplification are selected from the group consisting of an alphavirus 5' UTR, a 51-nt CSE, a 24-nt CSE, a 26S subgenomic promoter sequence, a 19-nt CSE, an alphavirus 3' UTR, or combinations thereof. In some aspects, the backbone does not encode structural virion proteins capsid, E2 and E1. In some aspects, the cassette is inserted in place of structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus.

In some aspects, the Venezuelan equine encephalitis virus comprises the sequence of SEQ ID NO:3 or SEQ ID NO:5. In some aspects, the Venezuelan equine encephalitis virus comprises the sequence of SEQ ID NO:3 or SEQ ID NO:5 further comprising a deletion between base pair 7544 and 11175. In some aspects, the backbone comprises the sequence set forth in SEQ ID NO:6 or SEQ ID NO:7. In some aspects, the cassette is inserted at position 7544 to replace the deletion between base pairs 7544 and 11175 as set forth in the sequence of SEQ ID NO:3 or SEQ ID NO:5.

In some aspects, the insertion of the cassette provides for transcription of a polycistronic RNA comprising the nsP1-4 genes and the at least one antigen-encoding nucleic acid sequence, wherein the nsP1-4 genes and the at least one antigen-encoding nucleic acid sequence are in separate open reading frames.

In some aspects, the backbone comprises at least one nucleotide sequence of a chimpanzee adenovirus vector. In some aspects, the chimpanzee adenovirus vector is a ChAdV68 vector. In some aspects, the ChAdV68 vector comprises a ChAdV68 vector backbone comprising the sequence set forth in SEQ ID NO:1. In some aspects, the ChAdV68 vector comprises a ChAdV68 vector backbone comprising the sequence set forth in SEQ ID NO:1, except that the sequence is fully deleted or functionally deleted in at least one gene selected from the group consisting of the chimpanzee adenovirus E1A, E1B, E2A, E2B, E3, E4, L1, L2, L3, L4, and L5 genes of the sequence set forth in SEQ ID NO:1, optionally wherein the sequence is fully deleted or functionally deleted in: (1) E1A and E1B; (2) E1A, E1B, and E3; or (3) E1A, E1B, E3, and E4 of the sequence set forth in SEQ ID NO:1. In some aspects, the ChAdV68 vector comprises a ChAdV68 vector backbone comprising a gene or regulatory sequence obtained from the sequence of SEQ ID NO:1, optionally wherein the gene is selected from the group consisting of the chimpanzee adenovirus inverted terminal repeat (ITR), E1A, E1B, E2A, E2B, E3, E4, L1, L2, L3, L4, and L5 genes of the sequence set forth in SEQ ID NO:1. In some aspects, the ChAdV68 vector comprises a ChAdV68 vector backbone comprising a partially deleted E4 gene comprising a deleted or partially-deleted E4orf2 region and a deleted or partially-deleted E4orf3 region, and optionally a deleted or partially-deleted E4orf4 region. In some aspects, the ChAdV68 vector comprises a ChAdV68 vector backbone comprising at least nucleotides 2 to 36,518 of the sequence set forth in SEQ ID NO:1 and further comprising: (1) an E1 deletion of at least nucleotides 577 to 3403 of the sequence shown in SEQ ID NO: 1, (2) an E3 deletion of at least nucleotides 27,125 to 31,825 of the sequence shown in SEQ ID NO:1, and (3) an E4 deletion of at least nucleotides 34,916 to 35,642 of the sequence shown in SEQ ID NO:1; optionally wherein the antigen cassette is inserted within the E1 deletion. In some aspects, the ChAdV68 vector comprises a ChAdV68 vector backbone comprising the sequence set forth in SEQ ID NO:68, optionally wherein the antigen cassette is inserted within the E1 deletion. In some aspects, the ChAdV68 vector comprises a ChAdV68 vector backbone comprising one or more deletions between base pair number 577 and 3403 or between base pair 456 and 3014, and optionally wherein the vector further comprises one or more deletions between base pair 27,125 and 31,825 or between base pair 27,816 and 31,333 of the sequence set forth in SEQ ID NO:1. In some aspects, the ChAdV68 vector comprises a ChAdV68 vector backbone comprising one or more deletions between base pair number 3957 and 10346, base pair number 21787 and 23370, and base pair number 33486 and 36193 of the sequence set forth in SEQ ID NO:1. In some aspects, the cassette is inserted in the ChAdV vector backbone at the E1 region, E3 region, and/or any deleted AdV region that allows incorporation of the cassette.

In some aspects, the at least one promoter nucleotide sequence is the native 26S promoter nucleotide sequence encoded by the backbone. In some aspects, the at least one promoter nucleotide sequence is an exogenous RNA promoter. In some aspects, the second promoter nucleotide sequence is a 26S promoter nucleotide sequence. In some aspects, the second promoter nucleotide sequence comprises multiple 26S promoter nucleotide sequences, wherein each 26S promoter nucleotide sequence provides for transcription of one or more of the separate open reading frames.

In some aspects, the one or more vectors are each at least 300nt in size. In some aspects, the one or more vectors are each at least 1kb in size. In some aspects, the one or more vectors are each 2kb in size. In some aspects, the one or more vectors are each less than 5kb in size.

In some aspects, at least one of the at least one antigen-encoding nucleic acid sequences encodes a polypeptide sequence or portion thereof that is presented by MHC class I on a cell surface, optionally a tumor cell surface or an infected cell surface.

In some aspects, each epitope-encoding nucleic acid sequence is linked directly to one another. In some aspects, at least one of the epitope-encoding nucleic acid sequences is linked to a distinct epitope-encoding nucleic acid sequence with a nucleic acid sequence encoding a linker. In some aspects, the linker links two MHC class I sequences or an MHC class I sequence to an MHC class II sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II sequences or an MHC class II sequence to an MHC class I sequence. In some aspects, the linker comprises the sequence GPGPG. In some aspects, at least one sequence of the epitope-encoding nucleic acid sequences is linked, operably or directly, to a separate or contiguous sequence that enhances the expression, stability, cell trafficking, processing and presentation, and/or immunogenicity of the epitope-encoding nucleic acid sequences of epitope encoded therefrom. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, at least one of the epitope-encoding nucleic acid sequences encodes a polypeptide sequence or portion thereof that has increased binding affinity to its corresponding MHC allele relative to the translated, corresponding wild-type nucleic acid sequence. In some aspects, at least one of the epitope-encoding nucleic acid sequences encodes a polypeptide sequence or portion thereof that has increased binding stability to its corresponding MHC allele relative to the translated, corresponding wild-type nucleic acid sequence. In some aspects, at least one of the epitope-encoding nucleic acid sequences encodes a polypeptide sequence or portion thereof that has an increased likelihood of presentation on its corresponding MHC allele relative to the translated, corresponding wild-type nucleic acid sequence. In some aspects, the at least one alteration comprises a point mutation, a frameshift mutation, a non-frameshift mutation, a deletion mutation, an insertion mutation, a splice variant, a genomic rearrangement, or a proteasome-generated spliced antigen.

In some aspects, the tumor is selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer, or the infectious disease organism is selected from the group consisting of: Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, an orthymyxoviridae family virus, and tuberculosis.

In some aspects, the at least one antigen-encoding nucleic acid sequence comprises at least 2-10, 2, 3, 4, 5, 6, 7, 8, 9, or 10 epitope-encoding nucleic acid sequences. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 epitope-encoding nucleic acid sequences. In some aspects, the at least one antigen-encoding nucleic acid sequence comprises at least 2-400 epitope-encoding nucleic acid sequences and wherein at least two of the epitope-encoding nucleic acid sequences encode polypeptide sequences or portions thereof that are presented by MHC class I on a cell surface, optionally a tumor cell surface or an infected cell surface. In some aspects, the at least one antigen-encoding nucleic acid sequence comprises at least 2-10, 2, 3, 4, 5, 6, 7, 8, 9, or 10 antigen-encoding nucleic acid sequences. In some aspects, the at least one antigen-encoding nucleic acid sequence comprises at least 11-20, 15-20, 11-100, 11-200, 11-300, 11-400, 11, 12, 13, 14, 15, 16, 17, 18, 19, 20 or up to 400 antigen-encoding nucleic acid sequences. In some aspects, the at least one antigen-encoding nucleic acid sequence comprises at least 2-400 antigen-encoding nucleic acid sequences and wherein at least two of the antigen-encoding nucleic acid sequences encode polypeptide sequences or portions thereof that are presented by MHC class I on a cell surface, optionally a tumor cell surface or an infected cell surface. In some aspects, at least two of the epitope-encoding nucleic acid sequences encode polypeptide sequences or portions thereof that are presented by MHC class I on a cell surface, optionally a tumor cell surface or an infected cell surface.

In some aspects, when administered to the subject and translated, at least one of the epitopes encoded by the epitope-encoding nucleic acid sequences are presented on antigen presenting cells resulting in an immune response targeting at least one of the antigens on the tumor cell surface or the infected cell surface. In some aspects, the at least one antigen-encoding nucleic acid sequences when administered to the subject and translated, at least one of the MHC class I or class II epitopes are presented on antigen presenting cells resulting in an immune response targeting at least one of the epitopes on a tumor cell surface or the infected cell surface, and optionally wherein the expression of each of the at least one antigen-encoding nucleic acid sequences is driven by the at least one promoter nucleotide sequence.

In some aspects, each epitope-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, the at least one MHC class II epitope-encoding nucleic acid sequence is present. In some aspects, the at least one MHC class II epitope-encoding nucleic acid sequence is present and comprises at least one MHC class II epitope-encoding nucleic acid sequence that comprises at least one alteration that makes the encoded peptide sequence distinct from the corresponding peptide sequence encoded by a wild-type nucleic acid sequence. In some aspects, the at least one MHC class II epitope-encoding nucleic acid sequence is 12-20, 12, 13, 14, 15, 16, 17, 18, 19, 20, or 20-40 amino acids in length. In some aspects, the at least one MHC class II epitope-encoding nucleic acid sequence is present and comprises at least one universal MHC class II antigen-encoding nucleic acid sequence, optionally wherein the at least one universal sequence comprises at least one of Tetanus toxoid and PADRE.

In some aspects, the at least one promoter nucleotide sequence or the second promoter nucleotide sequence is inducible. In some aspects, the at least one promoter nucleotide sequence or the second promoter nucleotide sequence is non-inducible.

In some aspects, the at least one poly(A) sequence comprises a poly(A) sequence native to the backbone. In some aspects, the at least one poly(A) sequence comprises a poly(A) sequence exogenous to the backbone. In some aspects, the at least one poly(A) sequence is operably linked to at least one of the at least one antigen-encoding nucleic acid sequences. In some aspects, the at least one poly(A) sequence is at least 20, at least 30, at least 40, at least 50, at least 60, at least 70, at least 80, at least 90, or at least 100 consecutive A nucleotides. In some aspects, the at least one poly(A) sequence is at least 80 consecutive A nucleotides.

In some aspects, the cassette further comprises at least one of: an intron sequence, a woodchuck hepatitis virus post-transcriptional regulatory element (WPRE) sequence, an internal ribosome entry sequence (IRES) sequence, a nucleotide sequence encoding a 2A self-cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one antigen-encoding nucleic acid sequences. In some aspects, the cassette further comprises a reporter gene, including but not limited to, green fluorescent protein (GFP), a GFP variant, secreted alkaline phosphatase, luciferase, a luciferase variant, or a detectable peptide or epitope. In some aspects, the detectable peptide or epitope is selected from the group consisting of an HA tag, a Flag tag, a His-tag, or a V5 tag.

In some aspects, the one or more vectors further comprises one or more nucleic acid sequences encoding at least one immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A or IRES; or the heavy and light chain sequences of the antibody are linked by a flexible linker such as consecutive glycine residues. In some aspects, the immune modulator is a cytokine. In some aspects, the cytokine is at least one of IL-2, IL-7, IL-12, IL-15, or IL-21 or variants thereof of each.

In some aspects, at least one epitope-encoding nucleic acid sequence is selected by performing the steps of: (a) obtaining at least one of exome, transcriptome, or whole genome nucleotide sequencing data from a tumor, an infected cell, or an infectious disease organism, wherein the nucleotide sequencing data is used to obtain data representing peptide sequences of each of a set of antigens; (b) inputting the peptide sequence of each antigen into a presentation model to generate a set of numerical likelihoods that each of the antigens is presented by one or more of the MHC alleles on a cell surface, optionally a tumor cell surface or an infected cell surface, the set of numerical likelihoods having been identified at least based on received mass spectrometry data; and (c) selecting a subset of the set of antigens based on the set of numerical likelihoods to generate a set of selected antigens which are used to generate the epitope-encoding nucleic acid sequences.

In some aspects, each of the epitope-encoding nucleic acid sequences is selected by performing the steps of: (a) obtaining at least one of exome, transcriptome, or whole genome nucleotide sequencing data from a tumor, an infected cell, or an infectious disease organism, wherein the nucleotide sequencing data is used to obtain data representing peptide sequences of each of a set of antigens; (b) inputting the peptide sequence of each antigen into a presentation model to generate a set of numerical likelihoods that each of the antigens is presented by one or more of the MHC alleles on a cell surface, optionally a tumor cell surface or an infected cell surface, the set of numerical likelihoods having been identified at least based on received mass spectrometry data; and (c) selecting a subset of the set of antigens based on the set of numerical likelihoods to generate a set of selected antigens which are used to generate the at least 20 epitope-encoding nucleic acid sequences. In some aspects, a number of the set of selected antigens is 2-20. In some aspects, the presentation model represents dependence between: (a) presence of a pair of a particular one of the MHC alleles and a particular amino acid at a particular position of a peptide sequence; and (b) likelihood of presentation on a cell surface, optionally a tumor cell surface or an infected cell surface, by the particular one of the MHC alleles of the pair, of such a peptide sequence comprising the particular amino acid at the particular position. In some aspects, selecting the set of selected antigens comprises selecting antigens that have an increased likelihood of being presented on the cell surface relative to unselected antigens based on the presentation model, optionally wherein the selected antigens have been validated as being presented by one or more specific HLA alleles. In some aspects, selecting the set of selected antigens comprises selecting antigens that have an increased likelihood of being capable of inducing a tumor-specific or infectious disease-specific immune response in the subject relative to unselected antigens based on the presentation model. In some aspects, selecting the set of selected antigens comprises selecting antigens that have an increased likelihood of being capable of being presented to naïve T cells by professional antigen presenting cells (APCs) relative to unselected antigens based on the presentation model, optionally wherein the APC is a dendritic cell (DC). In some aspects, selecting the set of selected antigens comprises selecting antigens that have a decreased likelihood of being subject to inhibition via central or peripheral tolerance relative to unselected antigens based on the presentation model. In some aspects, selecting the set of selected antigens comprises selecting antigens that have a decreased likelihood of being capable of inducing an autoimmune response to normal tissue in the subject relative to unselected antigens based on the presentation model. In some aspects, exome or transcriptome nucleotide sequencing data is obtained by performing sequencing on a tumor cell or tissue, an infected cell, or an infectious disease organism. In some aspects, the sequencing is next generation sequencing (NGS) or any massively parallel sequencing approach.

In some aspects, the cassette comprises junctional epitope sequences formed by adjacent sequences in the cassette. In some aspects, at least one or each junctional epitope sequence has an affinity of greater than 500 nM for MHC. In some aspects, each junctional epitope sequence is non-self.

In some aspects, each of the MHC class I epitopes is predicted or validated to be capable of presentation by at least one HLA allele present in at least 5% of a population. In some aspects, each of the MHC class I epitopes is predicted or validated to be capable of presentation by at least one HLA allele, wherein each antigen/HLA pair has an antigen/HLA prevalence of at least 0.01% in a population. In some aspects, each of the MHC class I epitopes is predicted or validated to be capable of presentation by at least one HLA allele, wherein each antigen/HLA pair has an antigen/HLA prevalence of at least 0.1% in a population.

In some aspects, the cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject. In some aspects, the non-therapeutic predicted MHC class I or class II epitope sequence is a junctional epitope sequence formed by adjacent sequences in the cassette.

In some aspects, the prediction is based on presentation likelihoods generated by inputting sequences of the non-therapeutic epitopes into a presentation model.

In some aspects, an order of the at least one antigen-encoding nucleic acid sequences in the cassette is determined by a series of steps comprising: (a) generating a set of candidate cassette sequences corresponding to different orders of the at least one antigen-encoding nucleic acid sequences; (b) determining, for each candidate cassette sequence, a presentation score based on presentation of non-therapeutic epitopes in the candidate cassette sequence; and (c) selecting a candidate cassette sequence associated with a presentation score below a predetermined threshold as the cassette sequence for an antigen vaccine.

Also provided for herein is a pharmaceutical composition comprising any of the compositions described herein and a pharmaceutically acceptable carrier. In some aspects, the composition further comprises an adjuvant. In some aspects, the composition further comprises an immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

Also provided for herein is an isolated nucleotide sequence or set of isolated nucleotide sequences comprising the cassette of any of the compositions described herein and one or more elements obtained from the sequence of SEQ ID NO:3 or SEQ ID NO:5,optionally wherein the one or more elements are selected from the group consisting of the sequences necessary for nonstructural protein-mediated amplification, the 26S promoter nucleotide sequence, the poly(A) sequence, and the nsP1-4 genes of the sequence set forth in SEQ ID NO:3 or SEQ ID NO:5, and optionally wherein the nucleotide sequence is cDNA. In some aspects, the sequence or set of isolated nucleotide sequences comprises the cassette of any of the above composition claims inserted at position 7544 of the sequence set forth in SEQ ID NO:6 or SEQ ID NO:7. In some aspects, the composition further comprises: a) a T7 or SP6 RNA polymerase promoter nucleotide sequence 5' of the one or more elements obtained from the sequence of SEQ ID NO:3 or SEQ ID NO:5; and b) optionally, one or more restriction sites 3' of the poly(A) sequence. In some aspects, the cassette of any of the above composition claims is inserted at position 7563 of SEQ ID NO:8 or SEQ ID NO:9.

Also provided for herein is a vector or set of vectors comprising any of the nucleotide sequence described herein.

Also provided for herein is an isolated cell comprising any of the nucleotide sequences or set of isolated nucleotide sequences described herein, optionally wherein the cell is a BHK-21, CHO, HEK293 or variants thereof, 911, HeLa, A549, LP-293, PER.C6, or AE1-2a cell.

Also provided for herein is a kit comprising any of the compositions described herein and instructions for use.

In some aspects, any of the above compositions further comprise a nanoparticulate delivery vehicle. The nanoparticulate delivery vehicle, in some aspects, may be a lipid nanoparticle (LNP). In some aspects, the LNP comprises ionizable amino lipids. In some aspects, the ionizable amino lipids comprise MC3-like (dilinoleylmethyl-4-dimethylaminobutyrate) molecules. In some aspects, the nanoparticulate delivery vehicle encapsulates the antigen expression system.

In some aspects, any of the above compositions further comprise a plurality of LNPs, wherein the LNPs comprise: the antigen expression system; a cationic lipid; a non-cationic lipid; and a conjugated lipid that inhibits aggregation of the LNPs, wherein at least about 95% of the LNPs in the plurality of LNPs either: have a non-lamellar morphology; or are electron-dense.

In some aspects, the non-cationic lipid is a mixture of (1) a phospholipid and (2) cholesterol or a cholesterol derivative.

In some aspects, the conjugated lipid that inhibits aggregation of the LNPs is a polyethyleneglycol (PEG)-lipid conjugate. In some aspects, the PEG-lipid conjugate is selected from the group consisting of a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof. In some aspects the PEG-DAA conjugate is a member selected from the group consisting of: a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

In some aspects, the antigen expression system is fully encapsulated in the LNPs.

In some aspects, the non-lamellar morphology of the LNPs comprises an inverse hexagonal ($H_{II}$) or cubic phase structure.

In some aspects, the cationic lipid comprises from about 10 mol % to about 50 mol % of the total lipid present in the LNPs. In some aspects, the cationic lipid comprises from about 20 mol % to about 50 mol % of the total lipid present in the LNPs. In some aspects, the cationic lipid comprises from about 20 mol % to about 40 mol % of the total lipid present in the LNPs.

In some aspects, the non-cationic lipid comprises from about 10 mol % to about 60 mol % of the total lipid present in the LNPs. In some aspects, the non-cationic lipid comprises from about 20 mol % to about 55 mol % of the total lipid present in the LNPs. In some aspects, the non-cationic lipid comprises from about 25 mol % to about 50 mol % of the total lipid present in the LNPs.

In some aspects, the conjugated lipid comprises from about 0.5 mol % to about 20 mol % of the total lipid present in the LNPs. In some aspects, the conjugated lipid comprises from about 2 mol % to about 20 mol % of the total lipid present in the LNPs. In some aspects, the conjugated lipid comprises from about 1.5 mol % to about 18 mol % of the total lipid present in the LNPs.

In some aspects, greater than 95% of the LNPs have a non-lamellar morphology. In some aspects, greater than 95% of the LNPs are electron dense.

In some aspects, any of the above compositions further comprise a plurality of LNPs, wherein the LNPs comprise: a cationic lipid comprising from 50 mol % to 65 mol % of the total lipid present in the LNPs; a conjugated lipid that inhibits aggregation of LNPs comprising from 0.5 mol % to 2 mol % of the total lipid present in the LNPs; and a non-cationic lipid comprising either: a mixture of a phospholipid and cholesterol or a derivative thereof, wherein the phospholipid comprises from 4 mol % to 10 mol % of the total lipid present in the LNPs and the cholesterol or derivative thereof comprises from 30 mol % to 40 mol % of the total lipid present in the LNPs; a mixture of a phospholipid and cholesterol or a derivative thereof, wherein the phospholipid comprises from 3 mol % to 15 mol % of the total lipid present in the LNPs and the cholesterol or derivative thereof comprises from 30 mol % to 40 mol % of the total lipid present in the LNPs; or up to 49.5 mol % of the total lipid present in the LNPs and comprising a mixture of a phospholipid and cholesterol or a derivative thereof, wherein the cholesterol or derivative thereof comprises from 30 mol % to 40 mol % of the total lipid present in the LNPs.

In some aspects, any of the above compositions further comprise a plurality of LNPs, wherein the LNPs comprise: a cationic lipid comprising from 50 mol % to 85 mol % of the total lipid present in the LNPs; a conjugated lipid that inhibits aggregation of LNPs comprising from 0.5 mol % to 2 mol % of the total lipid present in the LNPs; and a non-cationic lipid comprising from 13 mol % to 49.5 mol % of the total lipid present in the LNPs.

In some aspects, the phospholipid comprises dipalmitoylphosphatidylcholine (DPPC), distearoylphosphatidylcholine (DSPC), or a mixture thereof.

In some aspects, the conjugated lipid comprises a polyethyleneglycol (PEG)-lipid conjugate. In some aspects, the PEG-lipid conjugate comprises a PEG-diacylglycerol (PEG-DAG) conjugate, a PEG-dialkyloxypropyl (PEG-DAA) conjugate, or a mixture thereof. In some aspects, the PEG-DAA conjugate comprises a PEG-dimyristyloxypropyl (PEG-DMA) conjugate, a PEG-distearyloxypropyl (PEG-DSA) conjugate, or a mixture thereof. In some aspects, the PEG portion of the conjugate has an average molecular weight of about 2,000 daltons.

In some aspects, the conjugated lipid comprises from 1 mol % to 2 mol % of the total lipid present in the LNPs.

In some aspects, the LNP comprises a compound having a structure of Formula I:

I

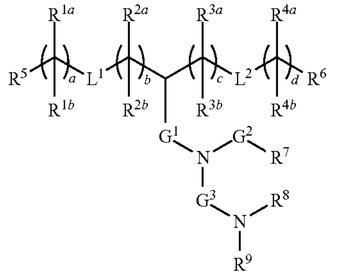

or a pharmaceutically acceptable salt, tautomer, prodrug or stereoisomer thereof, wherein: $L^1$ and L2 are each independently —O(C═O)—, —(C═O)O—, —C(═O)—, —O—, —$S(O)_X$—, —S—S—, —C(═O)S—, —SC(═O)—, —$R^a$C(═O)—, —C(═O) $R^a$—, —$R^a$C(═O) $R^a$—, —OC(═O) $R^a$—, —$R^a$C(═O)O— or a direct bond; $G^1$ is Ci-$C_2$ alkylene, —(C═O)—, —O(C═O)—, —SC(═O)—, —$R^a$C(═O)— or a direct bond: —C(═O)—, —(C═O)O—, —C(═O)S—, —C(═O) $R^a$— or a direct bond; G is Ci-C6 alkylene; $R^a$ is H or C1-C12 alkyl; $R^{1a}$ and $R^{1b}$ are, at each occurrence, independently either: (a) H or C1-C12 alkyl; or (b) $R^{1a}$ is H or C1-$C_{12}$ alkyl, and $R^{1b}$ together with the carbon atom to which it is bound is taken together with an adjacent $R^{1b}$ and the carbon atom to which it is bound to form a carbon-carbon double bond; $R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond; $R^{4a}$ and $R^{4b}$ are, at each occurrence, independently either: (a) H or $C_1$-$C_{12}$ alkyl; or (b) $R^{4a}$ is H or C1-C12 alkyl, and $R^{4b}$ together with the carbon atom to which it is bound is taken together with an adjacent $R^{4b}$ and the carbon atom to which it is bound to form a carbon-carbon double bond; $R^5$ and $R^6$ are each independently H or methyl; $R^7$ is C4-C20 alkyl; $R^8$ and $R^9$ are each independently C1-C12 alkyl; or $R^8$ and R9, together with the nitrogen atom to which they are attached, form a 5, 6 or 7-membered heterocyclic ring; a, b, c and d are each independently an integer from 1 to 24; and x is 0, 1 or 2.

In some aspects, the LNP comprises a compound having a structure of Formula II:

II

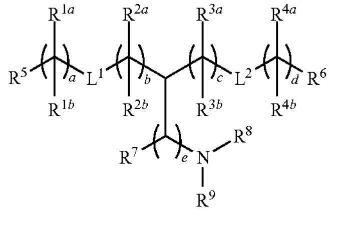

or a pharmaceutically acceptable salt, tautomer, prodrug or stereoisomer thereof, wherein: $L^1$ and L2 are each independently —O(C═O)—, —(C═O)O— or a carbon-carbon double bond; $R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond; $R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond; $R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond; $R^5$ and $R^6$ are each independently methyl or cycloalkyl; $R^7$ is, at each occurrence, independently H or $C_1$-$C_{12}$ alkyl; $R^8$ and $R^9$ are each independently unsubstituted C1-C12 alkyl; or $R^8$ and $R^9$, together with the nitrogen atom to which they are attached, form a 5, 6 or 7-membered heterocyclic ring comprising one nitrogen atom; a and d are each independently an integer from 0 to 24; b and c are each independently an integer from 1 to 24; and e is 1 or 2, provided that: at least one of $R^{1a}$, $R^{2a}$, $R^{3a}$ or $R^{4a}$ is C1-C12 alkyl, or at least one of $L^1$ or $L^2$ is —O(C═O)— or —(C═O)O—; and $R^{1a}$ and $R^{1b}$ are not isopropyl when a is 6 or n-butyl when a is 8.

In some aspects, any of the above compositions further comprise one or more excipients comprising a neutral lipid, a steroid, and a polymer conjugated lipid. In some aspects, the neutral lipid comprises at least one of 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), and 1,2-Dioleoyl-sn-glycero-3-phosphoethanolamine (DOPE). In some aspects, the neutral lipid is DSPC.

In some aspects, the molar ratio of the compound to the neutral lipid ranges from about 2:1 to about 8:1.

In some aspects, the steroid is cholesterol. In some aspects, the molar ratio of the compound to cholesterol ranges from about 2:1 to 1:1.

In some aspects, the polymer conjugated lipid is a pegylated lipid. In some aspects, the molar ratio of the compound to the pegylated lipid ranges from about 100:1 to about 25:1. In some aspects, the pegylated lipid is PEG-DAG, a PEG polyethylene (PEG-PE), a PEG-succinoyl-diacylglycerol (PEG-S-DAG), PEG-cer or a PEG dialkyoxypropylcarbamate. In some aspects, the pegylated lipid has the following structure III:

III

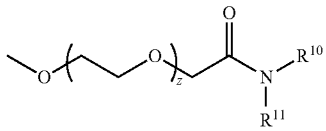

or a pharmaceutically acceptable salt, tautomer or stereoisomer thereof, wherein: $R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60. In some aspects, $R^{10}$ and $R^{11}$ are each independently straight, saturated alkyl chains having 12 to 16 carbon atoms. In some aspects, the average z is about 45.

Start Here

In some aspects, the LNP self-assembles into non-bilayer structures when mixed with polyanionic nucleic acid. In some aspects, the non-bilayer structures have a diameter between 60 nm and 120 nm. In some aspects, the non-bilayer structures have a diameter of about 70 nm, about 80 nm, about 90 nm, or about 100 nm. In some aspects, wherein the nanoparticulate delivery vehicle has a diameter of about 100 nm.

Also provided for herein is a method for treating a subject with cancer, the method comprising administering to the subject any of the compositions or any of the pharmaceutical compositions described herein. In some aspects, the epitope-encoding nucleic acid sequence is derived from the tumor of the subject with cancer or from a cell or sample of the infected subject. In some aspects, the epitope-encoding nucleic acid sequence are not derived from the tumor of the subject with cancer or from a cell or sample of the infected subject.

Also provided for herein is a method for stimulating an immune response in a subject, the method comprising administering to the subject any of the compositions or any of the pharmaceutical compositions described herein.

In some aspects, the subject expresses at least one HLA allele predicted or known to present the MHC class I epitope. In some aspects, HLA allele predicted or known to present the MHC class I epitope is A*03:01, A*11:01, A*02:01, C*01:02, and/or A*01:01. In some aspects, HLA allele predicted or known to present the MHC class I epitope is A*03:01. In some aspects, HLA allele predicted or known to present the MHC class I epitope is A*11:01. In some aspects, HLA allele predicted or known to present the MHC class I epitope is A*02:01. In some aspects, HLA allele predicted or known to present the MHC class I epitope is C*01:02. In some aspects, HLA allele predicted or known to present the MHC class I epitope is A*01:01. In some aspects, the composition is administered intramuscularly (IM), intradermally (ID), subcutaneously (SC), or intravenously (IV). In some aspects, the composition is administered intramuscularly. In some aspects, the method further comprising administration of one or more immune modulators, optionally wherein the immune modulator is administered before, concurrently with, or after administration of the composition or pharmaceutical composition. In some aspects, the one or more immune modulators are selected from the group consisting of: an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the immune modulator is administered intravenously (IV), intramuscularly (IM), intradermally (ID), or subcutaneously (SC). In some aspects, the subcutaneous administration is near the site of the composition or pharmaceutical composition administration or in close proximity to one or more vector or composition draining lymph nodes.

In some aspects, the method further comprises administering to the subject a second vaccine composition. In some aspects, the second vaccine composition is administered prior to the administration of any of the compositions or the pharmaceutical compositions described herein. In some aspects, the second vaccine composition is administered subsequent to the administration of any of the compositions or the pharmaceutical compositions described herein. In some aspects, the second vaccine composition is the same as any of the compositions or the pharmaceutical compositions described herein. In some aspects, the second vaccine composition is different any of the compositions or the pharmaceutical compositions described herein. In some aspects, the second vaccine composition comprises a chimpanzee adenovirus vector encoding at least one antigen-encoding nucleic acid sequence. In some aspects, the at least one antigen-encoding nucleic acid sequence encoded by the chimpanzee adenovirus vector is the same as the at least one antigen-encoding nucleic acid sequence of any of the above composition claims.

Also provided for herein is a method of manufacturing the one or more vectors of any of the above composition claims, the method comprising: (a) obtaining a linearized DNA sequence comprising the backbone and the cassette; (b) in vitro transcribing the linearized DNA sequence by addition of the linearized DNA sequence to an in vitro transcription reaction containing all the necessary components to transcribe the linearized DNA sequence into RNA, optionally further comprising in vitro addition of the m7g cap to the resulting RNA; and (c) isolating the one or more vectors from the in vitro transcription reaction. In some aspects, the linearized DNA sequence is generated by linearizing a DNA plasmid sequence or by amplification using PCR. In some aspects, the DNA plasmid sequence is generated using one of bacterial recombination or full genome DNA synthesis or full genome DNA synthesis with amplification of synthesized DNA in bacterial cells. In some aspects, isolating the one or more vectors from the in vitro transcription reaction involves one or more of phenol chloroform extraction, silica column based purification, or similar RNA purification methods.

Also provided for herein is a method of manufacturing the composition of any of the above composition claims for delivery of the antigen expression system, the method comprising: (a) providing components for the nanoparticulate delivery vehicle; (b) providing the antigen expression system; and (c) providing conditions sufficient for the nanoparticulate delivery vehicle and the antigen expression system to produce the composition for delivery of the antigen expression system. In some aspects, the conditions are provided by microfluidic mixing.

Also provided for herein is a method for treating a subject with a disease, optionally wherein the disease is cancer or an infection, the method comprising administering to the subject an antigen-based vaccine to the subject, wherein the antigen-based vaccine comprises an antigen-encoding cassette, or a polypeptide sequence encoded by the cassette, wherein the antigen-encoding cassette comprises at least one antigen-encoding nucleic acid sequence described, from 5' to 3', by the formula:

$$(E_x-(E^N{}_n)_y)_z$$

wherein E represents a nucleotide sequence comprising a distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof, and at least one of the distinct epitope-encoding nucleic acid sequences comprising the at least two iterations encodes a distinct KRAS-associated MHC class I neoepitope.

Also provided for herein is a method for treating a subject with a disease, optionally wherein the disease is cancer, the method comprising administering to the subject an antigen-based vaccine to the subject, wherein the antigen-based vaccine comprises an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) an epitope-encoding nucleic acid sequence encoding a KRAS-associated MHC class I neoepitope, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the at least one antigen-encoding nucleic acid sequence comprises at least two iterations of the epitope-encoding nucleic acid sequence encoding the KRAS-associated MHC class I neoepitope.

Also provided for herein is a method for treating a subject with a disease, optionally wherein the disease is cancer, the method comprising administering to the subject an antigen-based vaccine to the subject, wherein the antigen-based vaccine comprises an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) at least two distinct epitope-encoding nucleic acid sequences, optionally comprising: (1) at least one alteration that makes the encoded epitope sequence distinct from the corresponding peptide sequence encoded by a wild-type nucleic acid sequence, optionally wherein the at least one alteration is a KRAS mutation, or (2) a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response.

In some aspects, the antigen-encoding cassette encodes at least 4 iterations of each of the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82).

In some aspects, the epitope-encoding nucleic acid sequence is derived from a tumor of the subject with cancer or from a cell or sample of the infected subject. In some aspects, the epitope-encoding nucleic acid sequence are not derived from a tumor of the subject with cancer or from a cell or sample of the infected subject.

Also provided for herein is a method for stimulating an immune response in a subject, the method comprising the method comprising administering to the subject an antigen-based vaccine to the subject, wherein the antigen-based vaccine comprises an antigen-encoding cassette, or a polypeptide sequence encoded by the cassette, wherein the antigen-encoding cassette comprises at least one antigen-encoding nucleic acid sequence described, from 5' to 3', by the formula:

$$(E_x-(E^N{}_n)_y)_z$$

wherein E represents a nucleotide sequence comprising a distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof, and at least one of the distinct epitope-encoding nucleic acid sequences comprising the at least two iterations encodes a distinct KRAS-associated MHC class I neoepitope.

Also provided for herein is a method for stimulating an immune response in a subject, the method comprising the method comprising administering to the subject an antigen-based vaccine to the subject, wherein the antigen-based vaccine comprises: an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) an epitope-encoding nucleic acid sequence encoding a KRAS-associated MHC class I neoepitope, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the at least one antigen-encoding nucleic acid sequence comprises at least two iterations of at least one of the epitope-encoding nucleic acid sequences encoding the KRAS-associated MHC class I neoepitope.

Also provided for herein is a method for treating a subject with a disease, optionally wherein the disease is cancer of an infection, the method comprising administering to the subject an antigen-based vaccine to the subject, wherein the antigen-based vaccine comprises an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) at least two distinct epitope-encoding nucleic acid sequences, optionally comprising: (1) at least one alteration that makes the encoded epitope sequence distinct from the corresponding peptide sequence encoded by a wild-type nucleic acid sequence, optionally wherein the at least one alteration is a KRAS mutation, or (2) a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response.

In some aspects, the antigen-encoding cassette encodes at least 4 iterations of each of the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82).

In some aspects, the subject expresses at least one HLA allele predicted or known to present the at least one epitope sequence, optionally wherein the at least one epitope sequence predicted or known to be presented comprises (1) the KRAS-associated MHC class I neoepitope, and/or (2) the immunodominant MHC class I epitope and the other MHC class I epitope encoded in the cassette. In some aspects, the subject expresses at least one HLA allele predicted or known to present the at least one epitope sequence, and wherein the at least one epitope sequence comprises an epitope known or suspected to be presented by MHC class I on a surface of a cell, optionally wherein the at least one epitope sequence predicted or known to be presented comprises (1) the KRAS-associated MHC class I neoepitope, and/or (2) the immunodominant MHC class I epitope and the other MHC class I epitope encoded in the cassette. In some aspects, the surface of the cell is a tumor cell surface. In some aspects, the cell is a tumor cell selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, T cell lymphocytic leukemia, non-small cell lung cancer, and small cell lung cancer. In some aspects, the surface of the cell is an infected cell surface. In some aspects, the cell is an infected cell selected from the group consisting of: a pathogen infected cell, a virally infected cell, a bacterially infected cell, a fungally infected cell, and a parasitically infected cell. In some aspects, the virally infected cell is selected from the group consisting of: an HIV infected cell, a Severe acute respiratory syndrome-related coronavirus (SARS) infected cell, a severe acute respiratory syndrome coronavirus 2 (SARS-CoV-2) infected cell, a Ebola infected cell, a Hepatitis B virus (HBV) infected cell, an influenza infected cell, an orthymyxoviridae family virus infected cell, a Human papillomavirus (HPV) infected cell, a Cytomegalovirus (CMV) infected cell, a Chikungunya virus infected cell, a Respiratory syncytial virus (RSV) infected cell, a Dengue virus infected cell, and a Hepatitis C virus (HCV) infected cell.

Also provided for herein is a method for inducing an immune response in a subject, the method comprising administering to the subject an antigen-based vaccine to the subject, wherein the antigen-based vaccine comprises an antigen-encoding cassette, or a polypeptide sequence encoded by the cassette, wherein the antigen-encoding cassette comprises at least one antigen-encoding nucleic acid sequence described, from 5' to 3', by the formula:

$$(E_x-(E^N{}_n)_y)_z$$

wherein E represents a nucleotide sequence comprising a distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof, and at least one of the distinct epitope-encoding nucleic acid sequences comprising the at least two iterations encodes a distinct KRAS-associated MHC class I neoepitope.

Also provided for herein is a method for inducing an immune response in a subject, the method comprising administering to the subject an antigen-based vaccine to the subject, wherein the antigen-based vaccine comprises: an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) an epitope-encoding nucleic acid sequence encoding a KRAS-associated MHC class I neoepitope, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, wherein the at least one antigen-encoding nucleic acid sequence comprises at least two iterations of the epitope-encoding nucleic acid sequence encoding the KRAS-associated MHC class I neoepitope, and wherein the subject expresses at least one HLA allele predicted or known to present the at least one KRAS-associated MHC class I neoepitope.

Also provided for herein is a method for inducing an immune response in a subject, the method comprising administering to the subject an antigen-based vaccine to the subject, wherein the antigen-based vaccine comprises: an antigen expression system, comprising: the antigen expression system, wherein the antigen expression system comprises one or more vectors, the one or more vectors comprising: (a) a vector backbone, wherein the backbone comprises: (i) at least one promoter nucleotide sequence, and (ii) optionally, at least one polyadenylation (poly(A)) sequence; and (b) a cassette, wherein the cassette comprises: (i) at least one antigen-encoding nucleic acid sequence, comprising: (I) at least two epitope-encoding nucleic acid sequence, optionally comprising: (1) at least one alteration that makes the encoded epitope sequence distinct from the corresponding peptide sequence encoded by a wild-type nucleic acid sequence, optionally wherein the at least one alteration is a KRAS mutation, or (2) a nucleic acid sequence encoding an infectious disease organism peptide selected from the group consisting of: a pathogen-derived peptide, a virus-derived peptide, a bacteria-derived peptide, a fungus-derived peptide, and a parasite-derived peptide, and optionally wherein the epitope-encoding nucleic acid sequence encodes a MHC class I epitope, and wherein each of the epitope-encoding nucleic acid sequences comprises; (A) optionally, a 5' linker sequence, and (B) optionally, a 3' linker sequence; (ii) optionally, a second promoter nucleotide sequence operably linked to the antigen-encoding nucleic acid sequence; and (iii) optionally, at least one MHC class II epitope-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the vector backbone, wherein if the second promoter nucleotide sequence is absent, the antigen-encoding nucleic acid sequence is operably linked to the at least one promoter nucleotide sequence, and wherein the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response, and wherein the subject expresses at least one HLA allele predicted or known to present both the immunodominant MHC class I epitope and the other MHC class I epitope encoded in the cassette.

In some aspects, the antigen-encoding cassette encodes at least 4 iterations of each of the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82). In some aspects, the KRAS-associated MHC class I neoepitope or the KRAS mutation comprises a KRAS G12C mutation, a KRAS G12V mutation, a KRAS G12D mutation, or a KRAS Q61H mutation. In some aspects, the KRAS-associated MHC class I neoepitope or the KRAS mutation comprises any one of the amino acid sequence shown in SEQ ID NOs: 75-82. In some aspects, the antigen-encoding cassette comprises each of the amino acid sequence shown in SEQ ID NOs: 75-82.In some aspects, the antigen-encoding cassette comprises two or more iterations of each of the amino acid sequence shown in SEQ ID NOs: 75-82. In some aspects, the antigen-encoding cassette comprises 4 iterations of each of the amino acid sequence shown in SEQ ID NOs: 75-82. In some aspects, the KRAS-associated MHC class I neoepitope or the KRAS mutation comprises the amino acid sequence shown in SEQ ID NO: 57, SEQ ID NO: 58, SEQ ID NO: 59, or SEQ ID NO: 60. In some aspects, the epitope-encoding nucleic acid sequences comprises two or more distinct epitope-encoding nucleic acid sequences independently encoding a distinct KRAS-associated MHC class I neoepitope or a distinct KRAS mutation. In some aspects, each of the epitope-encoding nucleic acid sequences independently encodes a distinct KRAS-associated MHC class I neoepitope or a distinct KRAS mutation. In some aspects, the epitope-encoding nucleic acid sequences comprises two or more distinct epitope-encoding nucleic acid sequences independently encoding a KRAS G12C mutation, a KRAS G12V mutation, a KRAS G12D mutation, or a KRAS Q61H mutation. In some aspects, the epitope-encoding nucleic acid sequences independently encodes each of a KRAS G12C mutation, a KRAS G12V mutation, and a KRAS G12D mutation, and optionally a KRAS Q61H mutation. In some aspects, the antigen-encoding nucleic acid sequence encodes a peptide comprising the amino acid sequence shown in SEQ ID NO: 64 or SEQ ID NO: 65. In some aspects, the antigen-encoding nucleic acid sequence encodes a peptide comprising the amino acid sequence shown in SEQ ID NO: 65.

In some aspects, the cassette does not encode an immunodominant MHC class I epitope that: (1) stimulates a 5-fold or greater immune response when administered in a vaccine composition to a subject relative to another MHC class I epitope encoded in the cassette and capable of stimulating an immune response in the subject, and/or (2) reduces an immune response to another MHC class I epitope encoded in the cassette when administered in a vaccine composition to a subject relative to an immune response when the other MHC class I epitope is administered in the absence of the immunodominant MHC class I epitope, optionally wherein the immune response is reduced to below a limit of detection and/or wherein the immune response is not a therapeutically effective response. In some aspects, the cassette does not encode an immunodominant MHC class I epitope that stimulates a 5-fold or greater immune response when administered in a vaccine composition to a subject relative to a KRAS-associated neoepitope encoded in the cassette and capable of stimulating an immune response in the subject. In some aspects, the cassette does not encode an immunodominant MHC class I epitope that reduces an immune response to another MHC class I epitope encoded in the cassette when administered in a vaccine composition to a subject relative to an immune response when the other MHC class I epitope is administered in the absence of the immunodominant MHC class I epitope. In some aspects, the cassette does not encode an immunodominant MHC class I epitope that reduces an immune response to another MHC class I epitope encoded in the cassette to below a limit of detection when administered in a vaccine composition to a subject relative to an immune response when the other MHC class I epitope is administered in the absence of the immunodominant MHC class I epitope. In some aspects, the cassette does not encode an immunodominant MHC class I epitope that reduces an immune response to another MHC class I epitope encoded in the cassette when administered in a vaccine composition to a subject relative to an immune response when the other MHC class I epitope is administered in the absence of the immunodominant MHC class I epitope, wherein the immune response to the other MHC class I epitope is not a therapeutically effective response.

In some aspects, the immunodominant epitope is a TP53-associated MHC class I neoepitope, optionally wherein the TP53-associated MHC class I neoepitope comprises a S127Y mutation.

In some aspects, the antigen expression system comprises any one of the antigen expression systems described herein. In some aspects, the antigen-based vaccine comprises any one of the pharmaceutical compositions described herein.

In some aspects, the antigen-based vaccine is administered as a priming dose. In some aspects, the antigen-based vaccine is administered as one or more boosting doses. In some aspects, the boosting dose is different than the priming dose. In some aspects, a) the priming dose comprises a chimpanzee adenovirus vector and the boosting dose comprises an alphavirus vector; or b) the priming dose comprises an alphavirus vector vector and the boosting dose comprises a chimpanzee adenovirus vector. In some aspects, the boosting dose is the same as the priming dose. In some aspects, the injection site of the one or more boosting doses is as close as possible to the injection site of the priming dose.

In some aspects, the method further comprises determining or having determined the HLA-haplotype of the subject.

In some aspects, the antigen-based vaccine is administered intramuscularly (IM), intradermally (ID), subcutaneously (SC), or intravenously (IV). In some aspects, the antigen-based vaccine is administered intramuscularly (IM). In some aspects, the IM administration is administered at separate injection sites. In some aspects, the separate injection sites are in opposing deltoid muscles. In some aspects, the separate injection sites are in gluteus or rectus femoris sites on each side.

Also disclosed herein is a pharmaceutical composition comprising any of the compositions disclosed herein (such as an alphavirus-based or ChAd-based vector disclosed herein) and a pharmaceutically acceptable carrier. In some aspects, the pharmaceutical composition further comprises an adjuvant. In some aspects, the pharmaceutical composition further comprises an immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

Also disclosed herein is a vector comprising an isolated nucleotide sequence disclosed herein.

Also disclosed herein is a kit comprising a vector or a composition disclosed herein and instructions for use.

Also disclosed herein is a method for treating a subject, the method comprising administering to the subject a vector disclosed herein or a pharmaceutical composition disclosed herein. Also disclosed herein is a method for inducing an immune response in a subject, the method comprising administering to the subject any of the compositions, vectors, or pharmaceutical compositions described herein. In some aspects, the subject expresses at least one HLA allele predicted or known to present the MHC class I epitope. In some aspects, HLA allele predicted or known to present the MHC class I epitope is A*03:01, A*11:01, A*02:01, C*01:02, and/or A*01:01. In some aspects, HLA allele predicted or known to present the MHC class I epitope is A*03:01. In some aspects, HLA allele predicted or known to present the MHC class I epitope is A*11:01. In some aspects, HLA allele predicted or known to present the MHC class I epitope is A*02:01. In some aspects, HLA allele predicted or known to present the MHC class I epitope is C*01:02. In some aspects, HLA allele predicted or known to present the MHC class I epitope is A*01:01. In some aspects, the vector or composition is administered intramuscularly (IM), intradermally (ID), or subcutaneously (SC), or intravenously (IV).

Also disclosed herein is a method of manufacturing the one or more vectors of any of the above compositions, the method comprising: obtaining a linearized DNA sequence comprising the backbone and the antigen cassette; in vitro transcribing the linearized DNA sequence by addition of the linearized DNA sequence to a in vitro transcription reaction containing all the necessary components to transcribe the linearized DNA sequence into RNA, optionally further comprising in vitro addition of the m7g cap to the resulting RNA; and isolating the one or more vectors from the in vitro transcription reaction. In some aspects, the linearized DNA sequence is generated by linearizing a DNA plasmid sequence or by amplification using PCR. In some aspects, the DNA plasmid sequence is generated using one of bacterial recombination or full genome DNA synthesis or full genome DNA synthesis with amplification of synthesized DNA in bacterial cells. In some aspects, the isolating the one or more vectors from the in vitro transcription reaction involves one or more of phenol chloroform extraction, silica column based purification, or similar RNA purification methods.

Also disclosed herein is a method of manufacturing any of the compositions disclosed herein, the method comprising: providing components for the nanoparticulate delivery vehicle; providing the antigen expression system; and providing conditions sufficient for the nanoparticulate delivery vehicle and the antigen expression system to produce the composition for delivery of the antigen expression system. In some aspects, the conditions are provided by microfluidic mixing.

Also disclosed herein is a method of manufacturing a adenovirus vector disclosed herein, the method comprising: obtaining a plasmid sequence comprising the at least one promoter sequence and the antigen cassette; transfecting the plasmid sequence into one or more host cells; and isolating the adenovirus vector from the one or more host cells.

In some aspects, isolating comprises: lysing the host cell to obtain a cell lysate comprising the adenovirus vector; and purifying the adenovirus vector from the cell lysate.

In some aspects, the plasmid sequence is generated using one of bacterial recombination or full genome DNA synthesis or full genome DNA synthesis with amplification of synthesized DNA in bacterial cells. In some aspects, the one or more host cells are at least one of CHO, HEK293 or variants thereof, 911, HeLa, A549, LP-293, PER.C6, and AE1-2a cells. In some aspects, purifying the adenovirus vector from the cell lysate involves one or more of chromatographic separation, centrifugation, virus precipitation, and filtration.

BRIEF DESCRIPTION OF THE SEVERAL VIEWS OF THE DRAWINGS

These and other features, aspects, and advantages of the present invention will become better understood with regard to the following description, and accompanying drawings, where.

81). Data presented as spot forming colonies (SFC) per $1\times10^6$ splenocytes for each animal. Bar represents the median.

Figure 2A:
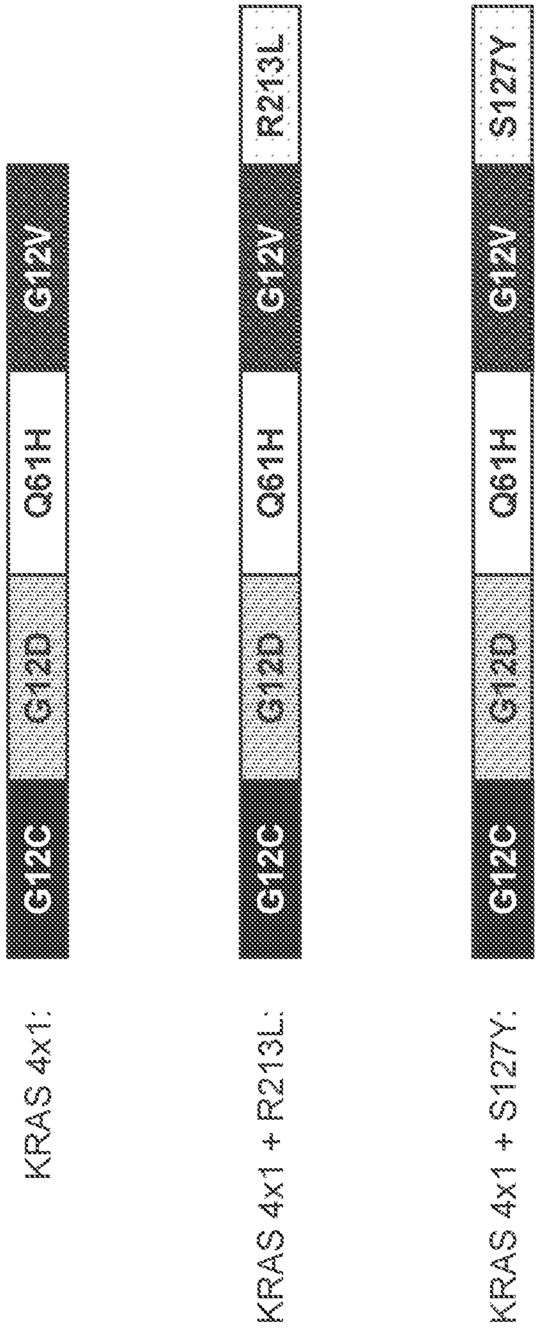
FIG. 2A presents an illustration of ChAdV68 delivery vectors designed to assess immunodominance of a TP53 epitope, specifically vectors containing only KRAS neoepitopes G12C, G12V, G12D, and Q61H ("KRAS 4×1"; cassette=SEQ ID NO: 66), KRAS neoepitopes in combination with a TP53 R213L neoepitope ("KRAS 4×1+R213L"; cassette=SEQ ID NO: 67), and KRAS neoepitopes in combination with a TP53 S127Y neoepitope ("KRAS 4×1+S127Y"; cassette=SEQ ID NO: 68).
Figure 2B:
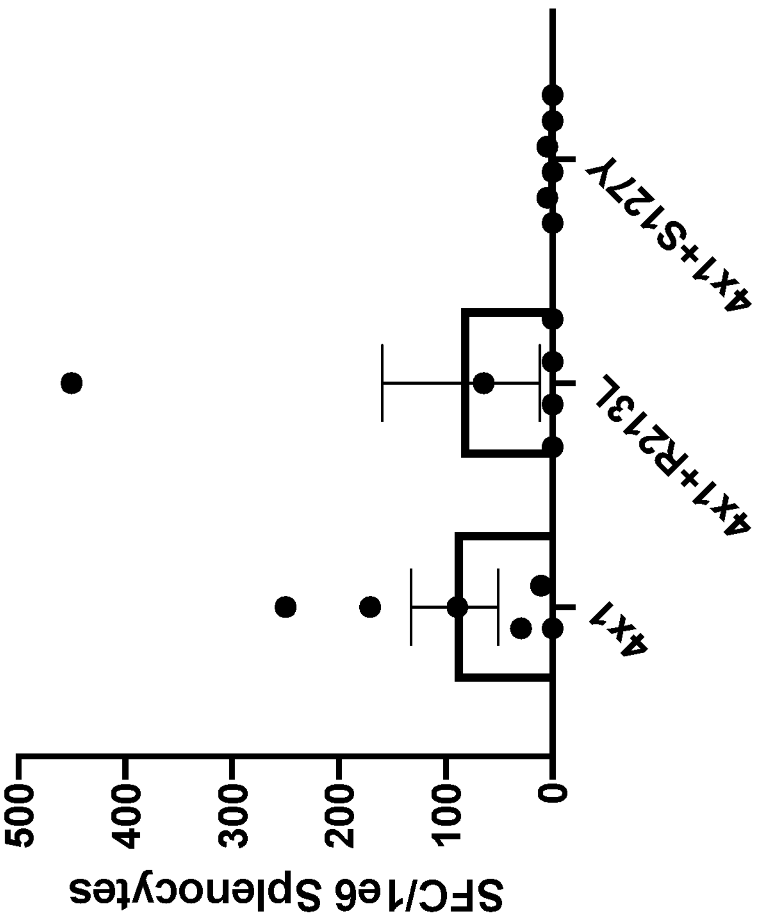
FIG. 2B demonstrates removal of an immunodominant epitope increases vaccine induced antigen-specific T-cell response to KRAS neoepitopes. Shown are ELISpot results for the neoepitope KRAS G12C. Mice engineered to express human HLA-A11:01 were immunized with $5\times10^{10}$ VP using the ChAdV68 delivery vectors indicated and splenocytes isolated 14 days post-immunization. The number of antigen-specific T-cells were measured by IFNg ELISpot following overnight stimulation with VVVGACGVGK (SEQ ID NO: 75). Data presented as spot forming colonies (SFC) per $1\times10^6$ splenocytes for each animal. Bar represents the median.
Figure 2C:
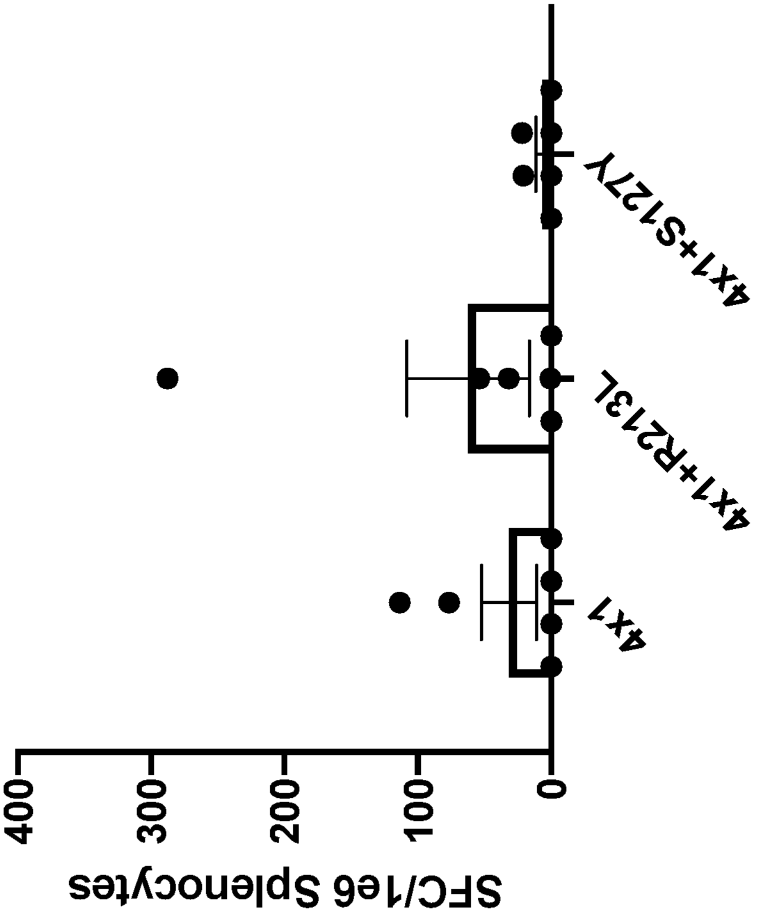
FIG. 2C demonstrates removal of an immunodominant epitope increases vaccine induced antigen-specific T-cell response to KRAS neoepitopes. Shown are ELISpot results for the neoepitope KRAS G12D. Mice engineered to express human HLA-A11:01 were immunized with $5\times10^{10}$ VP using the ChAdV68 delivery vectors indicated and splenocytes isolated 14 days post-immunization. The number of antigen-specific T-cells were measured by IFNg ELISpot following overnight stimulation with VVVGADGVGK (SEQ ID NO: 78). Data presented as spot forming colonies (SFC) per $1\times10^6$ splenocytes for each animal. Bar represents the median.
Figure 2D:
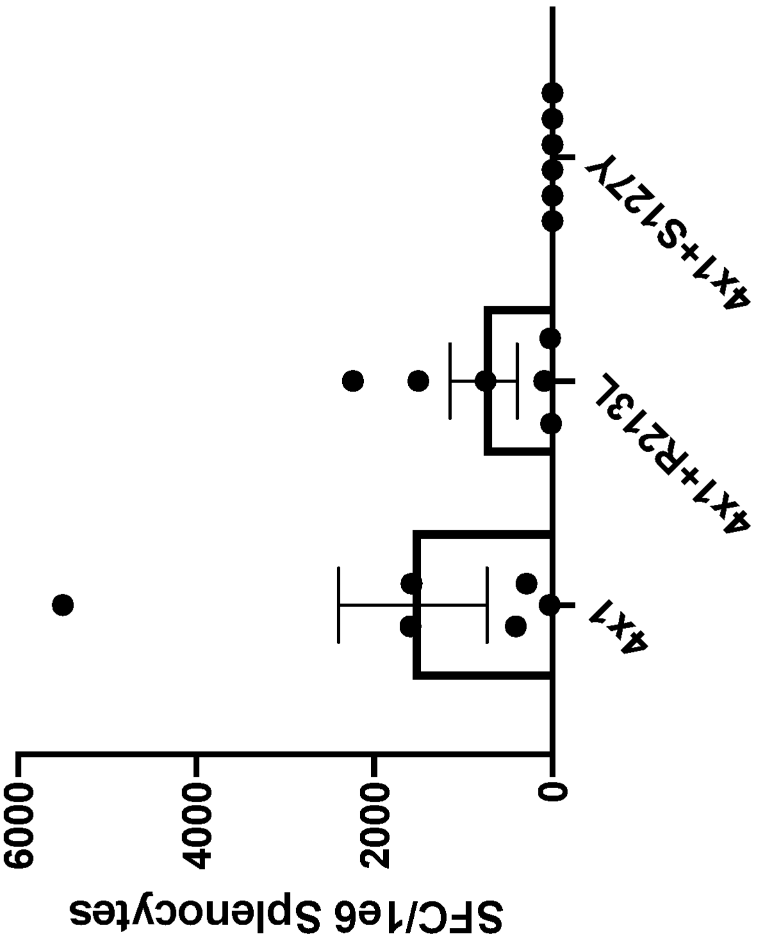
FIG. 2D demonstrates removal of an immunodominant epitope increases vaccine induced antigen-specific T-cell response to KRAS neoepitopes. Shown are ELISpot results for the neoepitope KRAS G12V. Mice engineered to express human HLA-A11:01 were immunized with $5\times10^{10}$ VP using the ChAdV68 delivery vectors indicated and splenocytes isolated 14 days post-immunization. The number of antigen-specific T-cells were measured by IFNg ELISpot following overnight stimulation with VVVGAVGVGK (SEQ ID NO.
Figure 2E:
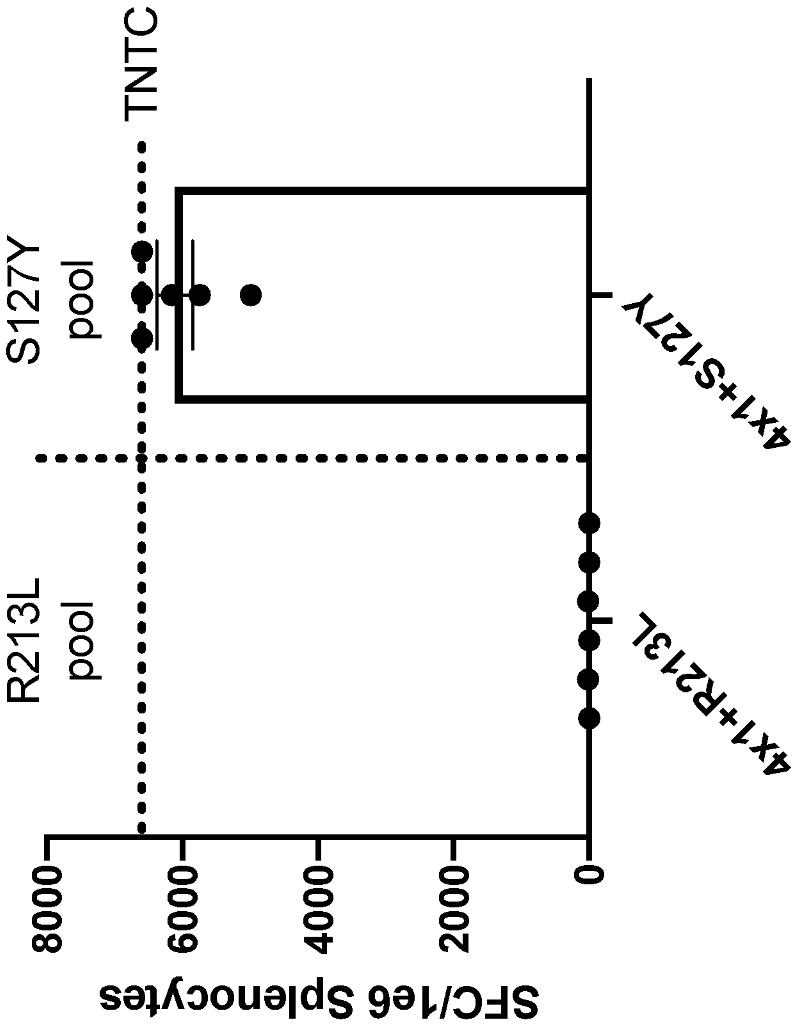

FIG. 2E demonstrates the immune response of an immunodominant epitope and related control epitope. Shown are ELISpot results for the TP53 neoepitope pools for R213L and S127Y neoepitopes. Mice engineered to express human HLA-A11:01 were immunized with $5\times10^{10}$ VP using the ChAdV68 delivery vectors indicated and splenocytes isolated 14 days post-immunization. The number of antigen-specific T-cells were measured by IFNg ELISpot following overnight stimulation. Data presented as spot forming colonies (SFC) per $1\times10^6$ splenocytes for each animal. Bar represents the median. Dashed line represent samples that were too numerous to count (TNTC).

Figure 3:
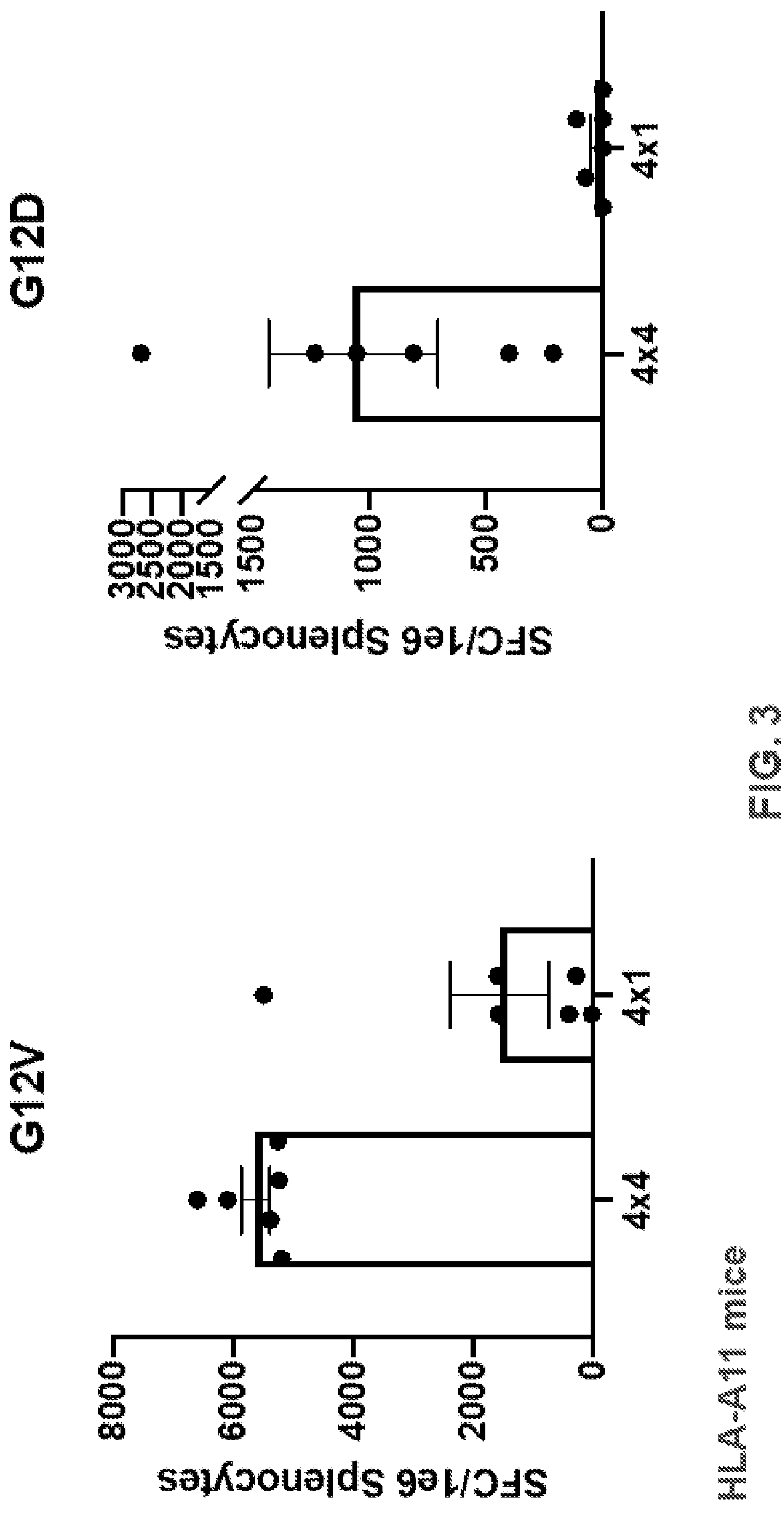

FIG. 3 demonstrates repeating epitopes increases vaccine induced antigen-specific T-cell response. Shown are ELISpot results for the repeated neoepitope KRAS G12V (left panel) or KRAS G12D (right panel). Mice engineered to express human HLA-A11:01 were immunized with $5\times10^{10}$ VP using the ChAdV68 delivery vectors indicated and splenocytes isolated 14 days post-immunization. The number of antigen-specific T-cells were measured by IFNg ELISpot following overnight stimulation with VVVGAVGVGK (SEQ ID NO: 81) or VVVGADGVGK (SEQ ID NO: 78), respectively. Data presented as spot forming colonies (SFC) per $1\times10^6$ splenocytes for each animal. Bar represents the median.

Figure 4:
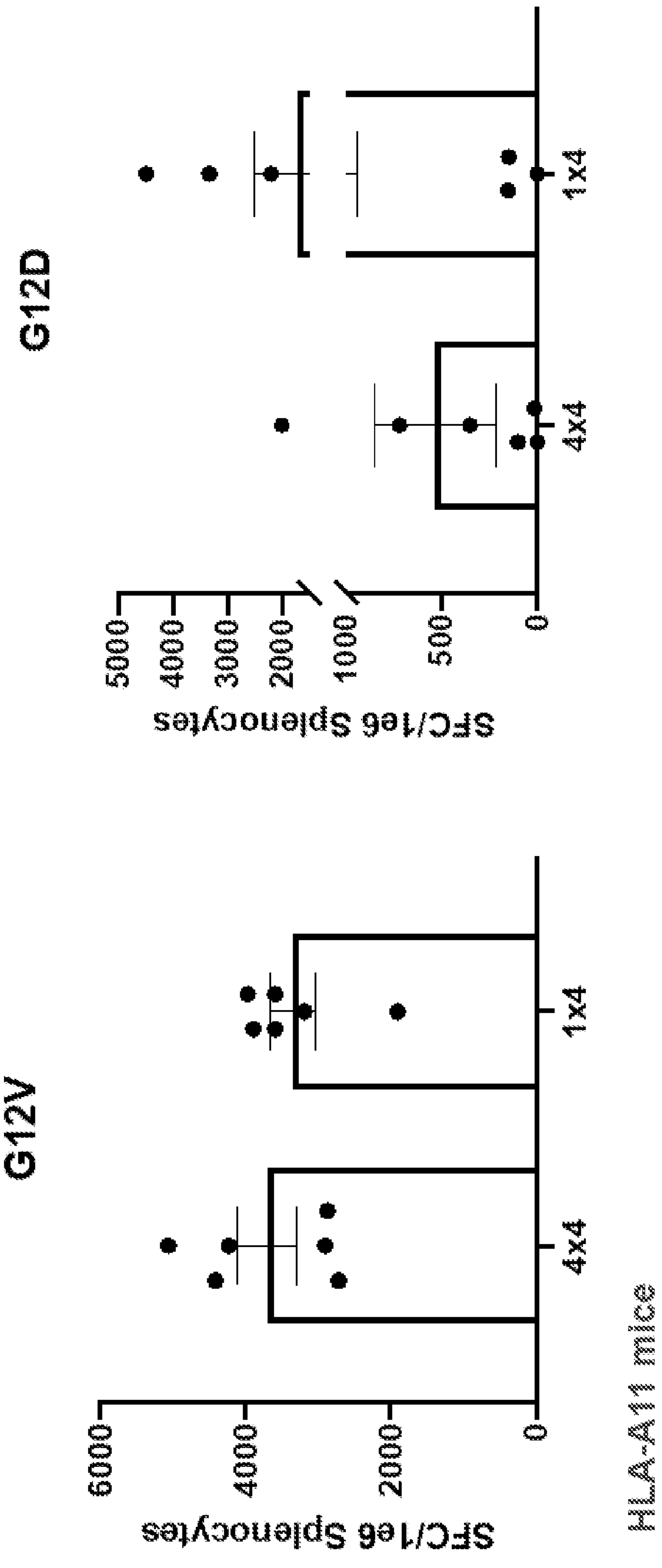

FIG. 4 demonstrates repeating epitopes increases vaccine induced antigen-specific T-cell response. Shown are ELISpot results for the repeated neoepitope KRAS G12V (left panel) or KRAS G12D (right panel). Mice engineered to express human HLA-A11:01 were immunized with $7\times10^{10}$ VP using the ChAdV68 delivery vectors indicated and splenocytes isolated 14 days post-immunization. The number of antigen-specific T-cells were measured by IFNg ELISpot following overnight stimulation with VVVGAVGVGK (SEQ ID NO: 81) or VVVGADGVGK (SEQ ID NO: 78), respectively. Data presented as spot forming colonies (SFC) per $1\times10^6$ splenocytes for each animal. Bar represents the median.

Figure 5:
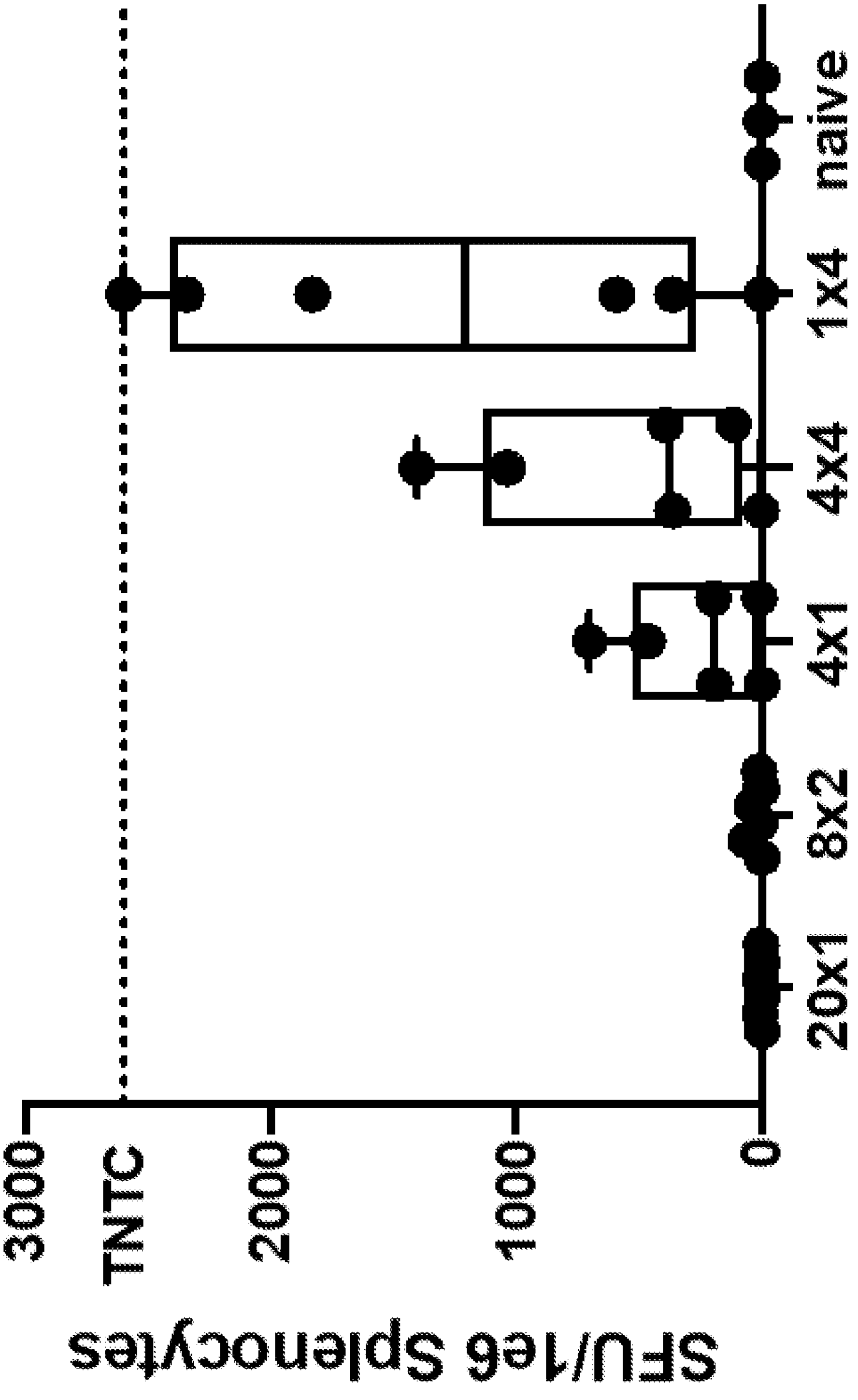

FIG. 5 demonstrates repeating epitopes increases vaccine induced antigen-specific T-cell response for KRAS Q61H. Shown are ELISpot results for the repeated neoepitope KRAS Q61H for the indicated cassette formats. Mice engineered to express human HLA-A01:01 were immunized with $5\times10^{10}$ VP using the ChAdV68 delivery vectors indicated and splenocytes isolated 12 days post-immunization. The number of antigen-specific T-cells were measured by IFNg ELISpot following overnight stimulation with ILDTAGHEEY (SEQ ID NO: 82). Data presented as spot forming colonies (SFC) per $1\times10^6$ splenocytes for each animal. Bar represents the median. Dashed line represent samples that were too numerous to count (TNTC).

Figure 6:
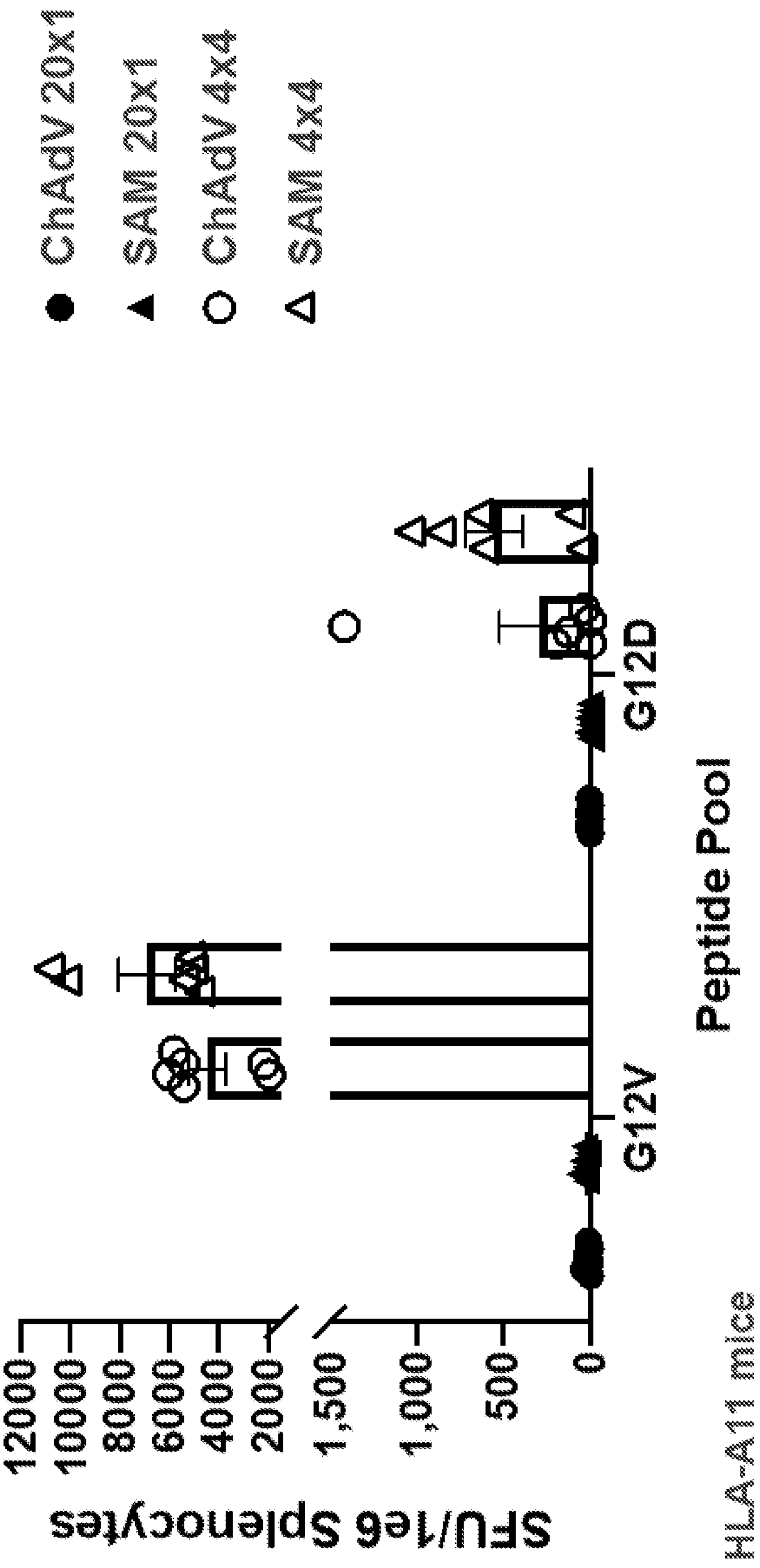

FIG. 6 demonstrates repeating epitopes increases vaccine induced antigen-specific T-cell response for both ChAdV68 and SAM vector formats. Shown are ELISpot results for the repeated neoepitope KRAS G12V (left panel) or KRAS G12D (right panel). Mice engineered to express human HLA-A11:01 were immunized with $5\times10^{10}$ VP using the ChAdV68 delivery vectors indicated or 10 μg the SAM vectors indicated and splenocytes isolated 14 days post-immunization. The number of antigen-specific T-cells were measured by IFNg ELISpot following overnight stimulation with respective peptide pools that contained all possible 38 minimal epitopes that span the 25mer. Data presented as spot forming colonies (SFC) per $1\times10^6$ splenocytes for each animal. Bar represents the median. Columns from left to right are ChAdV68 20×1, SAM 20×1, ChAdV68 4×4, and SAM 4×4.

Figure 7:
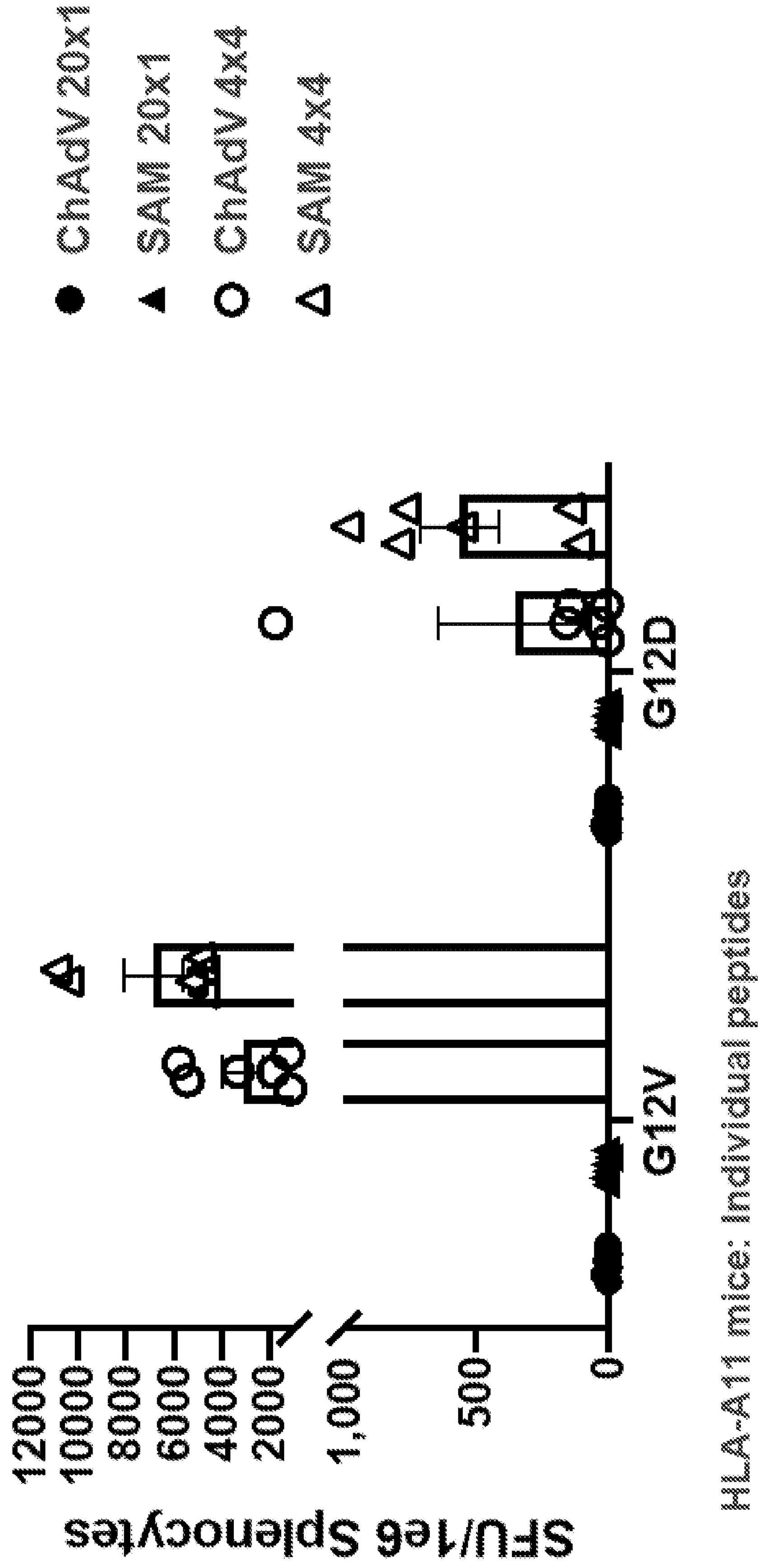

FIG. 7 demonstrates repeating epitopes increases vaccine induced antigen-specific T-cell response for both ChAdV68 and SAM vector formats. Shown are ELISpot results for the repeated neoepitope KRAS G12V (left panel) or KRAS G12D (right panel). Mice engineered to express human HLA-A11:01 were immunized with $5\times10^{10}$ VP using the ChAdV68 delivery vectors indicated or 10 μg the SAM vectors indicated and splenocytes isolated 14 days post-immunization. The number of antigen-specific T-cells were measured by IFNg ELISpot following overnight stimulation with VVGAVGVGK (SEQ ID NO: 79) or VVVGADGVGK (SEQ ID NO: 78). Data presented as spot forming colonies (SFC) per $1\times10^6$ splenocytes for each animal. Bar represents the median. Columns from left to right are ChAdV68 20×1, SAM 20×1, ChAdV68 4×4, and SAM 4×4.

DETAILED DESCRIPTION

I. Definitions

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that stimulates an immune response. An antigen can be a neoantigen. An antigen can be a "shared antigen" that is an antigen found among a specific population, e.g., a specific population of cancer patients.

As used herein the term "neoantigen" is an antigen that has at least one alteration that makes it distinct from the corresponding wild-type antigen, e.g., via mutation in a tumor cell or post-translational modification specific to a tumor cell. A neoantigen can include a polypeptide sequence or a nucleotide sequence. A mutation can include a frameshift or non-frameshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354(6310):354-358. The subject can be identified for administration through the use of various diagnostic methods, e.g., patient selection methods described further below.

As used herein the term "tumor antigen" is an antigen present in a subject's tumor cell or tissue but not in the subject's corresponding normal cell or tissue, or derived from a polypeptide known to or have been found to have altered expression in a tumor cell or cancerous tissue in comparison to a normal cell or tissue.

As used herein the term "antigen-based vaccine" is a vaccine composition based on one or more antigens, e.g., a plurality of antigens. The vaccines can be nucleotide-based (e.g., virally based, RNA based, or DNA based), protein-based (e.g., peptide based), or a combination thereof.

As used herein the term "candidate antigen" is a mutation or other aberration giving rise to a sequence that may represent an antigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon or causing removal of a canonical start codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to stimulate an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor, or the infectious disease peptidome, meaning the union of the peptidomes of all cells that are infected by the infectious disease).

As used herein the term "ELISPOT" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to, humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, infection type, infection sub-type, and smoking history.

The term "antigen-encoding nucleic acid sequences derived from a tumor" refers to nucleic acid sequences obtained from the tumor, e.g. via RT-PCR; or sequence data obtained by sequencing the tumor and then synthesizing the nucleic acid sequences using the sequencing data, e.g., via various synthetic or PCR-based methods known in the art. Derived sequences can include nucleic acid sequence variants, such as sequence-optimized nucleic acid sequence variants (e.g., codon-optimized and/or otherwise optimized for expression), that encode the same polypeptide sequence as the corresponding native nucleic acid sequence obtained from a tumor.

The term "antigen-encoding nucleic acid sequences derived from an infection" refers to nucleic acid sequences obtained from infected cells or an infectious disease organism, e.g. via RT-PCR; or sequence data obtained by sequencing the infected cell or infectious disease organism and then synthesizing the nucleic acid sequences using the sequencing data, e.g., via various synthetic or PCR-based methods known in the art. Derived sequences can include nucleic acid sequence variants, such as sequence-optimized nucleic acid sequence variants (e.g., codon-optimized and/or otherwise optimized for expression), that encode the same polypeptide sequence as the corresponding native infectious disease organism nucleic acid sequence. Derived sequences can include nucleic acid sequence variants that encode a modified infectious disease organism polypeptide sequence having one or more (e.g., 1, 2, 3, 4, or 5) mutations relative to a native infectious disease organism polypeptide sequence. For example, a modified polypeptide sequence can have one or more missense mutations relative to the native polypeptide sequence of an infectious disease organism protein.

The term "alphavirus" refers to members of the family Togaviridae, and are positive-sense single-stranded RNA viruses. Alphaviruses are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis and its derivative strain TC-83. Alphaviruses are typically self-replicating RNA viruses.

The term "alphavirus backbone" refers to minimal sequence(s) of an alphavirus that allow for self-replication of the viral genome. Minimal sequences can include conserved sequences for nonstructural protein-mediated amplification, a nonstructural protein 1 (nsP1) gene, a nsP2 gene, a nsP3 gene, a nsP4 gene, and a polyA sequence, as well as sequences for expression of subgenomic viral RNA including a subgenomic (e.g., a 26S) promoter element.

The term "sequences for nonstructural protein-mediated amplification" includes alphavirus conserved sequence elements (CSE) well known to those in the art. CSEs include, but are not limited to, an alphavirus 5' UTR, a 51-nt CSE, a 24-nt CSE, a subgenomic promoter sequence (e.g., a 26S subgenomic promoter sequence), a 19-nt CSE, and an alphavirus 3' UTR.

The term "RNA polymerase" includes polymerases that catalyze the production of RNA polynucleotides from a DNA template. RNA polymerases include, but are not limited to, bacteriophage derived polymerases including T3, T7, and SP6.

The term "lipid" includes hydrophobic and/or amphiphilic molecules. Lipids can be cationic, anionic, or neutral. Lipids can be synthetic or naturally derived, and in some instances biodegradable. Lipids can include cholesterol, phospholipids, lipid conjugates including, but not limited to, polyethyleneglycol (PEG) conjugates (PEGylated lipids), waxes, oils, glycerides, fats, and fat-soluble vitamins. Lipids can also include dilinoleylmethyl-4-dimethylaminobutyrate (MC3) and MC3-like molecules.

The term "lipid nanoparticle" or "LNP" includes vesicle like structures formed using a lipid containing membrane surrounding an aqueous interior, also referred to as liposomes. Lipid nanoparticles includes lipid-based compositions with a solid lipid core stabilized by a surfactant. The core lipids can be fatty acids, acylglycerols, waxes, and mixtures of these surfactants. Biological membrane lipids such as phospholipids, sphingomyelins, bile salts (sodium taurocholate), and sterols (cholesterol) can be utilized as stabilizers. Lipid nanoparticles can be formed using defined ratios of different lipid molecules, including, but not limited to, defined ratios of one or more cationic, anionic, or neutral lipids. Lipid nanoparticles can encapsulate molecules within an outer-membrane shell and subsequently can be contacted with target cells to deliver the encapsulated molecules to the host cell cytosol. Lipid nanoparticles can be modified or functionalized with non-lipid molecules, including on their surface. Lipid nanoparticles can be single-layered (unilamellar) or multi-layered (multilamellar). Lipid nanoparticles can be complexed with nucleic acid. Unilamellar lipid nanoparticles can be complexed with nucleic acid, wherein the nucleic acid is in the aqueous interior. Multilamellar lipid nanoparticles can be complexed with nucleic acid, wherein the nucleic acid is in the aqueous interior, or to form or sandwiched between Abbreviations: MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Antigen Identification

Research methods for NGS analysis of tumor and normal exome and transcriptomes have been described and applied in the antigen identification space. [6,14,15]Certain optimizations for greater sensitivity and specificity for antigen identification in the clinical setting can be considered. These optimizations can be grouped into two areas, those related to laboratory processes and those related to the NGS data analysis. The research methods described can also be applied to identification of antigens in other settings, such as identification of identifying antigens from an infectious disease organism, an infection in a subject, or an infected cell of a subject. Examples of optimizations are known to those skilled in the art, for example the methods described in more detail in U.S. Pat. No. 10,055,540, US Application Pub. No. US20200010849A1, U.S. application Ser. No. 16/606,577, and international patent application publications WO2020181240A1, WO/2018/195357 and WO/2018/208856, each herein incorporated by reference, in their entirety, for all purposes.

Methods for identifying antigens (e.g., antigens derived from a tumor or an infectious disease organism) include identifying antigens that are likely to be presented on a cell surface (e.g., presented by MHC on a tumor cell, an infected cell, or an immune cell, including professional antigen presenting cells such as dendritic cells), and/or are likely to be immunogenic. As an example, one such method may comprise the steps of: obtaining at least one of exome, transcriptome or whole genome nucleotide sequencing and/or expression data from a tumor, an infected cell, or an infectious disease organism, wherein the nucleotide sequencing data and/or expression data is used to obtain data representing peptide sequences of each of a set of antigens (e.g., antigens derived from a tumor or an infectious disease organism); inputting the peptide sequence of each antigen into one or more presentation models to generate a set of numerical likelihoods that each of the antigens is presented by one or more MHC alleles on a cell surface, such as a tumor cell or an infected cell of the subject, the set of numerical likelihoods having been identified at least based on received mass spectrometry data; and selecting a subset of the set of antigens based on the set of numerical likelihoods to generate a set of selected antigens.

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject. Specific methods for identifying neoantigens, including shared neoantigens, that are specific to tumors are known to those skilled in the art, for example the methods described in more detail in U.S. Pat. No. 10,055,540, US Application Pub. No. US20200010849A1, and international patent application publications WO/2018/195357 and WO/2018/208856, each herein incorporated by reference, in their entirety, for all purposes. Examples of shared neoantigens that are specific to tumors are described in more detail in international patent application publication WO2019226941A1, herein incorporated by reference in its entirety, for all purposes. Shared neoantigens include, but are not limited to, KRAS-associated mutations (e.g., KRAS G12C, KRAS G12V, KRAS G12D, and/or KRAS Q61H mutations). For example, KRAS-associated MHC class I neoepitope can include those mutations with reference to wild-type (WT) human KRAS, such as with reference to the following exemplary amino acid sequence:

(SEQ ID NO: 84)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

RVEDAFYTLVREIRQYRLKKISKEEKTPGCVKIKKCIIM.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of non-frameshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., Genetic Analysis: Biomolecular Engineering 9, no. 4 (1992): 107-112; Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle includes adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Antigens

Antigens can include nucleotides or polypeptides. For example, an antigen can be an RNA sequence that encodes for a polypeptide sequence. Antigens useful in vaccines can therefore include nucleotide sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleotide sequence (e.g., DNA or RNA) that codes for the related polypeptide sequence.

Specifically, disclosed herein cassettes including iterations of KRAS-associated MHC class I neoepitopes. KRAS-associated MHC class I neoepitopes include, but are not limited to, neoepitopes having KRAS G12 mutations and/or KRAS Q61 mutations. Cassettes can include iterations of KRAS-associated MHC class I neoepitopes having a KRAS G12 mutation. Cassettes can include iterations of KRAS-associated MHC class I neoepitopes having a KRAS Q61 mutation. Cassettes can include iterations of KRAS-associated MHC class I neoepitopes having KRAS GT2C, KRAS GT2V, KRAS GT2D, and/or KRAS Q61H mutations. Cassettes can include iterations of KRAS-associated MHC class I neoepitopes having a KRAS G12C mutation. Cassettes can include iterations of KRAS-associated MHC class I neoepitopes having a KRAS G12V mutation. Cassettes can include iterations of KRAS-associated MHC class I neoepitopes having a KRAS G12D mutation. Cassettes can include iterations of KRAS-associated MHC class I neoepitopes having a KRAS Q61H mutation. Cassettes can include iterations of each of KRAS-associated MHC class I neoepitopes having a KRAS G12C, KRAS G12V, KRAS G12D, and KRAS Q61H mutation. Cassettes can include iterations of at least two distinct KRAS-associated MHC class I neoepitopes selected from the group consisting of: a KRAS G12C, KRAS G12V, KRAS G12D, and KRAS Q61H mutation. Cassettes can include iterations of at least three distinct KRAS-associated MHC class I neoepitopes selected from the group consisting of: a KRAS G12C, KRAS G12V, KRAS G12D, and KRAS Q61H mutation. Cassettes can include iterations only of a single distinct KRAS-associated MHC class I neoepitope. Cassettes can include iterations only of a single distinct KRAS-associated MHC class I neoepitope having a KRAS G12C mutation. Cassettes can include iterations only of a single distinct KRAS-associated MHC class I neoepitope having a KRAS G12D mutation. Cassettes can include iterations only of a single distinct KRAS-associated MHC class I neoepitope having a KRAS G12V mutation. Cassettes can include iterations only of a single distinct KRAS-associated MHC class I neoepitope having a KRAS Q61H mutation.

KRAS-associated MHC class I neoepitopes having a KRAS G12C mutation include VVVGACGVGK (SEQ ID NO: 75) or KLVVVGACGV (SEQ ID NO: 76). KRAS-associated MHC class I neoepitopes having a KRAS G12D mutation include VVGADGVGK (SEQ ID NO: 77) or VVVGADGVGK (SEQ ID NO: 78), KRAS-associated MHC class I neoepitopes having a KRAS G12V mutation include VVGAVGVGK (SEQ ID NO: 79), VVVGAVGVGK (SEQ ID NO: 81), or AVGVGKSAL (SEQ ID NO: 80).

Cassettes can include iterations of each of KRAS-associated MHC class I neoepitopes having the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82). Cassettes can include iterations of at least two distinct KRAS-associated MHC class I neoepitopes having the amino acid sequences selected from the group consisting of: VVVGACGVGK (SEQ ID NO: 75), VVVGADGVGK (SEQ ID NO: 78), VVGAVGVGK (SEQ ID NO: 79), and ILDTAGHEEY (SEQ ID NO: 82). Cassettes can include iterations of at least three distinct KRAS-associated MHC class I neoepitopes having the amino acid sequences selected from the group consisting of: VVVGACGVGK (SEQ ID NO: 75), VVVGADGVGK (SEQ ID NO: 78), VVGAVGVGK (SEQ ID NO: 79), and ILDTAGHEEY (SEQ ID NO: 82). Cassettes can include iterations of at least one of KRAS-associated MHC class I neoepitopes having the amino acid sequences VVVGACGVGK (SEQ ID NO: 75), VVVGADGVGK (SEQ ID NO: 78), VVGAVGVGK (SEQ ID NO: 79), and ILDTAGHEEY (SEQ ID NO: 82).

KRAS-associated MHC class I neoepitopes can include native N- and/or C-terminal flanking sequences of the therapeutic vaccine epitope in the context of the native KRAS protein. Illustrative non-limiting examples of KRAS-associated MHC class I neoepitopes are the 25mers MTEYKLVVVGACGVGKSALTIQLIQ (SEQ ID NO: 57) for KRAS G12C, MTEYKLVVVGADGVGKSALTIQLIQ (SEQ ID NO: 58) for KRAS G12D, MTEYKLVVVGAVGVGKSALTIQLIQ (SEQ ID NO: 59) for KRAS G12V, and ETCLLDILDTAGHEEYSAMRDQYMR (SEQ ID NO: 60) for KRAS Q61H. KRAS-associated MHC class I neoepitopes that include native flanking sequences can be linked (concatenated) to other neoepitopes encoded in a cassette, including other neoepitopes (e.g., other KRAS-associated MHC class I neoepitopes) that include their respective native flanking sequences. An illustrative non-limiting cassette of concantenated KRAS-associated MHC class I neoepitopes that are linked through their native flanking sequences and that includes 4 iterations for each of the KRAS neoepitopes having the mutations KRAS G12C, KRAS G12D, KRAS G12V, and KRAS Q61H is represented by the amino acid sequence shown in SEQ ID NO: 65.

Epitope-encoding nucleic acid sequences that encode KRAS-associated MHC class I neoepitopes, such as those that include native N- and/or C-terminal flanking sequences, can encode multiple known and/or predicted KRAS-associated MHC class I neoepitopes. As an illustrative example, the KRAS G12V 25mer MTEYKLVVVGAVGVGKSALTIQLIQ (SEQ ID NO: 59) encodes each of the known and/or predicted KRAS-associated MHC class I neoepitopes VVGAVGVGK (SEQ ID NO: 79), VVVGAVGVGK (SEQ ID NO: 81), and AVGVGKSAL (SEQ ID NO: 80).

Epitope-encoding nucleic acid sequences, including those that encode KRAS-associated MHC class I neoepitopes, can be in any order in a cassette. Epitope-encoding nucleic acid sequences, including those that encode KRAS-associated MHC class I neoepitopes, can be in an order that minimizes junctional epitopes, as described further herein. As an illustrative non-limiting example, concantenated KRAS-associated MHC class I neoepitopes linked together to minimize junctional epitopes is represented by the amino acid sequence shown in SEQ ID NO: 65 and has the order: G12C G12D Q61H G12D G12V G12C Q61H G12D G12V G12C Q61H G12D G12V Q61H G12V G12C.

Also disclosed herein are peptides derived from any polypeptide known to or have been found to have altered expression in a tumor cell or cancerous tissue in comparison to a normal cell or tissue, for example any polypeptide known to or have been found to be aberrantly expressed in a tumor cell or cancerous tissue in comparison to a normal cell or tissue. Suitable polypeptides from which the antigenic peptides can be derived can be found for example in the COSMIC database. COSMIC curates comprehensive information on somatic mutations in human cancer. The peptide contains the tumor specific mutation. Tumor antigens (e.g., shared tumor antigens and tumor neoantigens) can include, but are not limited to, those described in U.S. application Ser. No. 17/058,128, herein incorporated by reference for all purposes. Antigen peptides can be described in the context of their coding sequence where an antigen includes the nucleotide sequence (e.g., DNA or RNA) that codes for the related polypeptide sequence.

Also disclosed herein are peptides derived from any polypeptide associated with an infectious disease organism, an infection in a subject, or an infected cell of a subject. Antigens can be derived from nucleotide sequences or polypeptide sequences of an infectious disease organism. Polypeptide sequences of an infectious disease organism include, but are not limited to, a pathogen-derived peptide, a virus-derived peptide, a bacteria-derived peptide, a fungus-derived peptide, and/or a parasite-derived peptide. Infectious disease organism include, but are not limited to, Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, an orthymyxoviridae family virus, and tuberculosis.

Disclosed herein are isolated peptides that comprise infectious disease organism specific antigens or epitopes identified by the methods disclosed herein, peptides that comprise known infectious disease organism specific antigens or epitopes, and mutant polypeptides or fragments thereof identified by methods disclosed herein. Antigen peptides can be described in the context of their coding sequence where an antigen includes the nucleotide sequence (e.g., DNA or RNA) that codes for the related polypeptide sequence.

Vectors and associated compositions described herein can be used to deliver antigens from any organism, including their toxins or other by-products, to prevent and/or treat infection or other adverse reactions associated with the organism or its by-product.

Antigens that can be incorporated into a vaccine (e.g., encoded in a cassette) include immunogens which are useful to immunize a human or non-human animal against viruses, such as pathogenic viruses which infect human and non-human vertebrates. Antigens may be selected from a variety of viral families. Example of desirable viral families against which an immune response would be desirable include, the picomavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for stimulating immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The Flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus (e.g., the glyco-(G) protein and the fusion (F) protein, for which sequences are available from GenBank). Influenza virus is classified within the family orthomyxovirus and can be suitable source of antigens (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. Nos. 5,891,994 and 6,193,981.] See, also, the HIV and SIV proteins described in D. H. Barouch et al, J. Virol., 75(5):2462-2467 (March 2001), and R. R. Amara, et al, *Science*, 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (Human CMV), muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxyirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxyirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Antigens that can be incorporated into a vaccine (e.g., encoded in a cassette) also include immunogens which are useful to immunize a human or non-human animal against pathogens including bacteria, fungi, parasitic microorganisms or multicellular parasites which infect human and non-human vertebrates. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; *pseudomonas*, acinetobacteria and *eikenella;* melioidosis; *salmonella; shigella; haemophilus* (*Haemophilus influenzae, Haemophilus somnus*); *moraxella; H. ducreyi* (which causes chancroid); *brucella*; Franisella *tularensis* (which causes tularemia); *yersinia* (*pasteurella*); *streptobacillus* monilformis and spirillum. Gram-positive bacilli include *Listeria monocytogenes; erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Examples of specific bacterium species are, without limitation, *Streptococcus pneumoniae, Streptococcus pyogenes, Streptococcus agalactiae, Streptococcus faecalis, Moraxella catarrhalis, Helicobacter pylori, Neisseria meningitidis, Neisseria gonorrhoeae, Chlamydia trachomatis, Chlamydia pneumoniae, Chlamydia psittaci, Bordetella pertussis, Sal-*

*monella typhi, Salmonella typhimurium, Salmonella choleraesuis, Escherichia coli, Shigella, Vibrio cholerae, Corynebacterium diphtheriae, Mycobacterium tuberculosis, Mycobacterium avium, Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis (*Cryptococcus*), blastomycosis (*Blastomyces*), histoplasmosis (*Histoplasma*) and coccidioidomycosis (Coccidiodes); candidiasis (*Candida*), aspergillosis (Aspergillis), and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and chlamydial infections include: *Mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis (e.g., caused by *Leishmania major*); trypanosomiasis; toxoplasmosis (e.g., caused by *Toxoplasma gondii*); *Pneumocystis carinii*; Trichans; *Toxoplasma gondii*; babesiosis; giardiasis (e.g., caused by Giardia); trichinosis (e.g., caused by *Trichomonas*); filariasis; schistosomiasis (e.g., caused by *Schistosoma*); nematodes; trematodes or flukes; and cestode (tapeworm) infections. Other parasitic infections may be caused by *Ascaris, Trichuris, Cryptosporidium*, and *Pneumocystis carinii*, among others.

Also disclosed herein are peptides derived from any polypeptide associated with an infectious disease organism, an infection in a subject, or an infected cell of a subject. Antigens can be derived from nucleic acid sequences or polypeptide sequences of an infectious disease organism. Polypeptide sequences of an infectious disease organism include, but are not limited to, a pathogen-derived peptide, a virus-derived peptide, a bacteria-derived peptide, a fungus-derived peptide, and/or a parasite-derived peptide. Infectious disease organism include, but are not limited to, Severe acute respiratory syndrome-related coronavirus (SARS), severe acute respiratory syndrome coronavirus 2 (SARS-CoV-2), Ebola, HIV, Hepatitis B virus (HBV), influenza, Hepatitis C virus (HCV), Human papillomavirus (HPV), Cytomegalovirus (CMV), Chikungunya virus, Respiratory syncytial virus (RSV), Dengue virus, an orthymyxoviridae family virus, and tuberculosis.

Antigens can be selected that are predeicted to be presented on the cell surface of a cell, such as a tumor cell, an infected cell, or an immune cell, including professional antigen presenting cells such as dendritic cells. Antigens can be selected that are predicted to be immunogenic.

One or more polypeptides encoded by an antigen nucleotide sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more antigens can be presented on the surface of a tumor. One or more antigens can be presented on the surface of an infected cell.

One or more antigens can be immunogenic in a subject having a tumor, e.g., capable of stimulating a T cell response and/or a B cell response in the subject. One or more antigens can be immunogenic in a subject having or suspected to have an infection, e.g., capable of stimulating a T cell response and/or a B cell response in the subject. One or more antigens can be immunogenic in a subject at risk of an infection, e.g., capable of stimulating a T cell response and/or a B cell response in the subject that provides immunological protection (i.e., immunity) against the infection, e.g., such as stimulating the production of memory T cells, memory B cells, and/or antibodies specific to the infection.

One or more antigens can be capable of stimulating a B cell response, such as the production of antibodies that recognize the one or more antigens (e.g., antibodies that recognize a tumor or an infectious disease antigen). Antibodies can recognize linear polypeptide sequences or recognize secondary and tertiary structures. Accordingly, B cell antigens can include linear polypeptide sequences or polypeptides having secondary and tertiary structures, including, but not limited to, full-length proteins, protein subunits, protein domains, or any polypeptide sequence known or predicted to have secondary and tertiary structures. Antigens capable of stimulating a B cell response to a tumor or an infectious disease antigen can be an antigen found on the surface of tumor cell or an infectious disease organism, respectively. Antigens capable of eliciting a B cell response to a tumor or an infectious disease antigen can be an intracellular neoantigen expressed in a tumor or an infectious disease organism, respectively.

One or more antigens can include a combination of antigens capable of stimulating a T cell response (e.g., peptides including predicted T cell epitope sequences) and distinct antigens capable of stimulating a B cell response (e.g., full-length proteins, protein subunits, protein domains).

One or more antigens that stimulate an autoimmune response in a subject can be excluded from consideration in the context of vaccine generation for a subject.

The size of at least one antigenic peptide molecule (e.g., an epitope sequence) can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the antigenic peptide molecules are equal to or less than 50 amino acids.

Antigenic peptides and polypeptides can be: for MHC Class 115 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific or infectious disease-specific amino acids—thus bypassing the need for computational or in vitro test-based selection of the strongest HLA-presented shorter peptide. In both cases, use of a longer peptide allows endogenous processing by patient cells and may lead to more effective antigen presentation and stimulation of T cell responses. Longer peptides can also include a full-length protein, a protein subunit, a protein domain, and combinations thereof of a peptide, such as those expressed in a tumor or an infectious disease organism, respectively. Longer peptides (e.g., full-length protein, protein subunit, or protein domain) and combinations thereof can be included to stimulate a B cell response.

Antigenic peptides and polypeptides can be presented on an HLA protein. In some aspects antigenic peptides and polypeptides are presented on an HLA protein with greater affinity than a wild-type peptide. In some aspects, an antigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, antigenic peptides and polypeptides do not stimulate an autoimmune response and/or invoke immunological tolerance when administered to a subject.

Also provided are compositions comprising at least two or more antigenic peptides. In some embodiments the composition contains at least two distinct peptides. At least two distinct peptides can be derived from the same polypeptide. By distinct polypeptides is meant that the peptide vary by length, amino acid sequence, or both. A peptide can include a tumor-specific mutation. Tumor-specific peptides can be derived from any polypeptide known to or have been found to contain a tumor specific mutation or peptides derived from any polypeptide known to or have been found to have altered expression in a tumor cell or cancerous tissue in comparison to a normal cell or tissue, for example any polypeptide known to or have been found to be aberrantly expressed in a tumor cell or cancerous tissue in comparison to a normal cell or tissue. The peptides can be derived from any polypeptide known to or suspected to be associated with an infectious disease organism, or peptides derived from any polypeptide known to or have been found to have altered expression in an infected cell in comparison to a normal cell or tissue (e.g., an infectious disease polynucleotide or polypeptide, including infectious disease polynucleotides or polypeptides with expression restricted to a host cell). Suitable polypeptides from which the antigenic peptides can be derived can be found for example in the COSMIC database or the AACR Genomics Evidence Neoplasia Information Exchange (GENIE) database. COSMIC curates comprehensive information on somatic mutations in human cancer. AACR GENIE aggregates and links clinical-grade cancer genomic data with clinical outcomes from tens of thousands of cancer patients. In some aspects the tumor specific mutation is a driver mutation for a particular cancer type. A peptide can include a KRAS mutation (e.g., KRAS G12C, KRAS G12V, KRAS G12D, and/or KRAS Q61H mutations).

Antigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, antigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to stimulate CTL activity can be enhanced by linkage to a sequence which contains at least one epitope that is capable of stimulating a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

An antigenic peptide can be linked to the T helper peptide either directly or via a spacer either at the amino or carboxy terminus of the peptide. The amino terminus of either the antigenic peptide or the T helper peptide can be acylated.

Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect an antigen includes a nucleic acid (e.g. polynucleotide) that encodes an antigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothioate backbone, or combinations thereof and it may or may not contain introns. A polynucleotide sequence encoding an antigen can be sequence-optimized to improve expression, such as through improving transcription, translation, post-transcriptional processing, and/or RNA stability. For example, polynucleotide sequence encoding an antigen can be codon-optimized. "Codon-optimization" herein refers to replacing infrequently used codons, with respect to codon bias of a given organism, with frequently used synonymous codons. Polynucleotide sequences can be optimized to improve post-transcriptional processing, for example optimized to reduce unintended splicing, such as through removal of splicing motifs (e.g., canonical and/or cryptic/non-canonical splice donor, branch, and/or acceptor sequences) and/or introduction of exogenous splicing motifs (e.g., splice donor, branch, and/or acceptor sequences) to bias favored splicing events. Exogenous intron sequences include, but are not limited to, those derived from SV40 (e.g., an SV40 mini-intron) and derived from immunoglobulins (e.g., human β-globin gene). Exogenous intron sequences can be incorporated between a promoter/enhancer sequence and the antigen(s) sequence. Exogenous intron sequences for use in expression vectors are described in more detail in Callendret et al. (Virology. 2007 Jul. 5; 363(2): 288-302), herein incorporated by reference for all purposes. Polynucleotide sequences can be optimized to improve transcript stability, for example through removal of RNA instability motifs (e.g., AU-rich elements and 3' UTR motifs) and/or repetitive nucleotide sequences. Polynucleotide sequences can be optimized to improve accurate transcription, for example through removal of cryptic transcriptional initiators and/or terminators. Polynucleotide sequences can be optimized to improve translation and translational accuracy, for example through removal of cryptic AUG start codons, premature polyA sequences, and/or secondary structure motifs. Polynucleotide sequences can be optimized to improve nuclear export of transcripts, such as through addition of a Constitutive Transport Element (CTE), RNA Transport Element (RTE), or Woodchuck Posttranscriptional Regulatory Element (WPRE). Nuclear export signals for use in expression vectors are described in more detail in Callendret et al. (Virology. 2007 Jul. 5; 363(2): 288-302), herein incorporated by reference for all purposes. Polynucleotide sequences can be optimized with respect to GC content, for example to reflect the average GC content of a given organism. Sequence optimization can balance one or more sequence properties, such as transcription, translation, post-transcriptional processing, and/or RNA stability. Sequence optimization can generate an optimal sequence balancing each of transcription, translation, post-transcriptional processing, and RNA stability. Sequence optimization algorithms are known to those of skill in the art, such as GeneArt (Thermo Fisher), Codon Optimization Tool (IDT), Cool Tool (University of Singapore), SGI-DNA (La Jolla Calif.). One or more regions of an antigen-encoding protein can be sequence-optimized separately.

A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

V. Vaccine Compositions

Also disclosed herein is an immunogenic composition, e.g., a vaccine composition, capable of raising a specific immune response, e.g., a tumor-specific immune response or an infectious disease organism-specific immune response. Vaccine compositions typically comprise one or a plurality of antigens, e.g., selected using a method described herein, or selected from a pathogen-derived peptide, a virus-derived peptide, a bacteria-derived peptide, a fungus-derived peptide, and/or a parasite-derived peptide. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 antigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen sequences, 6, 7, 8, 9, 10 11, 12, 13, or 14 different antigen sequences, or 12, 13 or 14 different antigen sequences.

A vaccine can contain between 1 and 30 antigen-encoding nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different antigen-encoding nucleic acid sequences, 6, 7, 8, 9, 10 11, 12, 13, or 14 different antigen-encoding nucleic acid sequences, or 12, 13 or 14 different antigen-encoding nucleic acid sequences. Antigen-encoding nucleic acid sequences can refer to the antigen encoding portion of an "antigen cassette." Features of an antigen cassette are described in greater detail herein. An antigen-encoding nucleic acid sequence can contain one or more epitope-encoding nucleic acid sequences (e.g., an antigen-encoding nucleic acid sequence encoding concatenated T cell epitopes).

A vaccine can contain between 1 and 30 distinct epitope-encoding nucleic acid sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more distinct epitope-encoding nucleic acid sequences, 6, 7, 8, 9, 10 11, 12, 13, or 14 distinct epitope-encoding nucleic acid sequences, or 12, 13 or 14 distinct epitope-encoding nucleic acid sequences. Epitope-encoding nucleic acid sequences can refer to sequences for individual epitope sequences, such as each of the T cell epitopes in an antigen-encoding nucleic acid sequence encoding concatenated T cell epitopes.

A vaccine can contain at least two iterations of an epitope-encoding nucleic acid sequence. A used herein, an "iteration" (or interchangeably a "repeat") refers to two or more identical nucleic acid epitope-encoding nucleic acid sequences (inclusive of the optional 5' linker sequence and/or the optional 3' linker sequences described herein) within an antigen-encoding nucleic acid sequence. In one example, the antigen-encoding nucleic acid sequence portion of a cassette encodes at least two iterations of an epitope-encoding nucleic acid sequence. In further non-limiting examples, the antigen-encoding nucleic acid sequence portion of a cassette encodes more than one distinct epitope, and at least one of the distinct epitopes is encoded by at least two iterations of the nucleic acid sequence encoding the distinct epitope (i.e., at least two distinct epitope-encoding nucleic acid sequences). In illustrative non-limiting examples, an antigen-encoding nucleic acid sequence encodes epitopes A, B, and C encoded by epitope-encoding nucleic acid sequences epitope-encoding sequence A ($E_A$), epitope-encoding sequence B ($E_B$), and epitope-encoding sequence C ($E_C$), and exemplary antigen-encoding nucleic acid sequences having iterations of at least one of the distinct epitopes are illustrated by, but is not limited to, the formulas below:

Iteration of one distinct epitope (iteration of epitope A):

$E_A$-$E_B$-$E_C$-$E_A$; or $E_A$-$E_A$-$E_B$-$E_C$

Iteration of multiple distinct epitopes (iterations of epitopes A, B, and C):

$E_A$-$E_B$-$E_C$-$E_A$-$E_B$-$E_C$; or $E_A$-$E_A$-$E_B$-$E_B$-$E_C$-$E_C$

Multiple iterations of multiple distinct epitopes (iterations of epitopes A, B, and C):

$E_A$-$E_B$-$E_C$-$E_A$-$E_B$-$E_C$-$E_A$-$E_B$-$E_C$; or $E_A$-$E_A$-$E_A$-$E_B$-$E_B$-$E_B$-$E_C$-$E_C$-$E_C$

The above examples are not limiting and the antigen-encoding nucleic acid sequences having iterations of at least one of the distinct epitopes can encode each of the distinct epitopes in any order or frequency. For example, the order and frequency can be a random arrangement of the distinct epitopes, e.g., in an example with epitopes A, B, and C, by the formula $E_A$-$E_B$-$E_C$-$E_C$-$E_A$-$E_B$-$E_A$-$E_C$-$E_A$-$E_C$-$E_C$-$E_B$.

Also provided for herein is an antigen-encoding cassette, the antigen-encoding cassette having at least one antigen-encoding nucleic acid sequence described, from 5' to 3', by the formula:

$$(E_x\text{-}(E^N{}_n)_y)_z$$

where E represents a nucleotide sequence including a distinct epitope-encoding nucleic acid sequences, n represents the number of separate distinct epitope-encoding nucleic acid sequences and is any integer including 0, $E^N$ represents a nucleotide sequence comprising the separate distinct epitope-encoding nucleic acid sequence for each corresponding n, for each iteration of z: x=0 or 1, y=0 or 1 for each n, and at least one of x or y=1, and z=2 or greater, wherein the antigen-encoding nucleic acid sequence comprises at least two iterations of E, a given $E^N$, or a combination thereof. In some aspects, at least one of the distinct epitope-encoding nucleic acid sequences with the at least two iterations encodes a KRAS-associated MHC class I neoepitope.

Each E or $E^N$ can independently comprise any epitope-encoding nucleic acid sequence described herein (e.g., a peptide encoding an infectious disease T cell epitope and/or a neoantigen epitope). For example, Each E or $E^N$ can independently comprises a nucleotide sequence described, from 5' to 3', by the formula ($L5_b$-$N_c$-$L3_d$), where N comprises the distinct epitope-encoding nucleic acid sequence associated with each E or $E^N$, where c=1, L5 comprises a 5' linker sequence, where b=0 or 1, and L3 comprises a 3' linker sequence, where d=0 or 1. Epitopes and linkers that can be used are further described herein.

Iterations of an epitope-encoding nucleic acid sequences (inclusive of optional 5' linker sequence and/or the optional 3' linker sequences) can be linearly linked directly to one another (e.g., $E_A$-$E_A$- . . . as illustrated above). Iterations of an epitope-encoding nucleic acid sequences can be separated by one or more additional nucleotides sequences. In general, iterations of an epitope-encoding nucleic acid sequences can be separated by any size nucleotide sequence applicable for the compositions described herein. In one example, iterations of an epitope-encoding nucleic acid sequences can be separated by a separate distinct epitope-encoding nucleic acid sequence (e.g., $E_A$-$E_B$-$E_C$-$E_A$ . . . , as illustrated above). In examples where iterations are separated by a single separate distinct epitope-encoding nucleic acid sequence, and each epitope-encoding nucleic acid sequences (inclusive of optional 5' linker sequence and/or the optional 3' linker sequences) encodes a peptide 25 amino acids in length, the iterations can be separated by 75 nucleotides, such as in antigen-encoding nucleic acid represented by $E_A$-$E_B$-$E_A$ . . . , $E_A$ is separated by 75 nucleotides. In an illustrative example, an antigen-encoding nucleic acid having the sequence VTNTEMFVTAPDNLGYMY-EVQWPGQTQPQIANCSVYDFFVWLHYYSVRDTVT- NTEMFVTAPDNLGYMYEVQWPGQTQPQIANCSVYDFFVWLHYYSVRDT encoding iterations of 25mer antigens Trp1 (VTNTEMFVTAPDNLGYMYEVQWPGQ) and Trp2 (TQPQIANCSVYDFFVWLHYYSVRDT), the iterations of Trp1 are separated by the 25mer Trp2 and thus the repeats of the Trp1 epitope-encoding nucleic acid sequences are separated the 75 nucleotide Trp2 epitope-encoding nucleic acid sequence. In examples where iterations are separated by 2, 3, 4, 5, 6, 7, 8, or 9 separate distinct epitope-encoding nucleic acid sequence, and each epitope-encoding nucleic acid sequences (inclusive of optional 5′ linker sequence and/or the optional 3′ linker sequences) encodes a peptide 25 amino acids in length, the iterations can be separated by 150, 225, 300, 375, 450, 525, 600, or 675 nucleotides, respectively.

In one embodiment, different peptides and/or polypeptides or nucleotide sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or different MHC class II molecules. Hence, vaccine compositions can comprise different fragments capable of associating with at least 2 preferred, at least 3 preferred, or at least 4 preferred MHC class I molecules and/or different MHC class II molecules.

The vaccine composition can be capable of stimulating a specific cytotoxic T-cell response and/or a specific helper T-cell response. The vaccine composition can be capable of stimulating a specific cytotoxic T-cell response and a specific helper T-cell response.

The vaccine composition can be capable of stimulating a specific B-cell response (e.g., an antibody response).

The vaccine composition can be capable of stimulating a specific cytotoxic T-cell response, a specific helper T-cell response, and/or a specific B-cell response. The vaccine composition can be capable of stimulating a specific cytotoxic T-cell response and a specific B-cell response. The vaccine composition can be capable of stimulating a specific helper T-cell response and a specific B-cell response. The vaccine composition can be capable of stimulating a specific cytotoxic T-cell response, a specific helper T-cell response, and a specific B-cell response.

A vaccine composition can further comprise an adjuvant and/or a carrier. Examples of useful adjuvants and carriers are given herein below. A composition can be associated with a carrier such as e.g. a protein or an antigen-presenting cell such as, e.g., a dendritic cell (DC) capable of presenting the peptide to a T-cell.

Adjuvants are any substance whose admixture into a vaccine composition increases or otherwise modifies the immune response to an antigen. Carriers can be scaffold structures, for example a polypeptide or a polysaccharide, to which an antigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diphtheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more antigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41, Lu et al., Efficient identification of mutated cancer antigens recognized by T cells associated with durable tumor regressions, *Clin Cancer Res.* (2014) 20(13): 3401-10). Upon introduction into a host, infected cells express the antigens, and thereby stimulate a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

V.A. Antigen Cassette

The methods employed for the selection of one or more antigens, the cloning and construction of an "antigen cassette" and its insertion into a viral vector are within the skill in the art given the teachings provided herein. By "antigen cassette" or "cassette" is meant the combination of a selected antigen or plurality of antigens (e.g., antigen-encoding nucleic acid sequences) and the other regulatory elements necessary to transcribe the antigen(s) and express the transcribed product. The selected antigen or plurality of antigens can refer to distinct epitope sequences, e.g., an antigen-encoding nucleic acid sequence in the cassette can encode an epitope-encoding nucleic acid sequence (or plurality of epitope-encoding nucleic acid sequences) such that the epitopes are transcribed and expressed. An antigen or plurality of antigens can be operatively linked to regulatory components in a manner which permits transcription. Such components include conventional regulatory elements that can drive expression of the antigen(s) in a cell transfected with the viral vector. Thus the antigen cassette can also contain a selected promoter which is linked to the antigen(s) and located, with other, optional regulatory elements, within the selected viral sequences of the recombinant vector. A cassette can include one or more antigens, such as one or more pathogen-derived peptides, virus-derived peptides, bacteria-derived peptides, fungus-derived peptides, parasite-derived peptides, and/or tumor-derived peptides. A cassette can have one or more antigen-encoding nucleic acid sequences, such as a cassette containing multiple antigen-encoding nucleic acid sequences each independently operably linked to separate promoters and/or linked together using other multicistonic systems, such as 2A ribosome skipping sequence elements (e.g., E2A, P2A, F2A, or T2A sequences) or Internal Ribosome Entry Site (IRES) sequence elements. A linker can also have a cleavage site, such as a TEV or furin cleavage site. Linkers with cleavage sites can be used in combination with other elements, such as those in a multicistronic system. In a non-limiting illustrative example, a furin protease cleavage site can be used in conjunction with a 2A ribosome skipping sequence element such that the furin protease cleavage site is configured to facilitate removal of the 2A sequence following translation. In a cassette containing more than one antigen-encoding nucleic acid sequences, each antigen-encoding nucleic acid sequence can contain one or more epitope-encoding nucleic acid sequences (e.g., an antigen-encoding nucleic acid sequence encoding concatenated T cell epitopes).

Useful promoters can be constitutive promoters or regulated (inducible) promoters, which will enable control of the amount of antigen(s) to be expressed. For example, a desirable promoter is that of the cytomegalovirus immediate early promoter/enhancer [see, e.g., Boshart et al, Cell, 41:521-530 (1985)]. Another desirable promoter includes the Rous sarcoma virus LTR promoter/enhancer. Still another promoter/enhancer sequence is the chicken cytoplasmic beta-actin promoter [T. A. Kost et al, Nucl. Acids Res., 11(23):8287 (1983)]. Other suitable or desirable promoters can be selected by one of skill in the art.

Also disclosed herein is a viral vector comprising a cassette with at least one payload sequence operably linked to a regulatable promoter that is a TET promoter system, such as a TET-On system or TET-Off system. Without wishing to be bound by theory, a TET promoter system can be used to minimize transcription of payload nucleic acids encoded in a cassette, such as antigens encoded in a vaccine cassette, during viral production. TET promoter systems are described in detail in international patent application publication WO2020/243719, herein incorporated by reference for all purposes.

A TET promoter system can include a tetracycline (TET) repressor protein (TETr) controlled promoter. Accordingly, also disclosed herein is a viral vector comprising a cassette with at least one payload sequence operably linked to a tetracycline (TET) repressor protein (TETr) controlled promoter. A TETr controlled promoter can include the 19 bp TET operator (TETo) sequence TCCCTATCAGTGA- TAGAGA (SEQ ID NO:83). A TETr controlled promoter can include 2, 3, 4, 5, 6, 7, 8, 9, or 10 or more TETo nucleic acid sequences. In TETr controlled promoter have 2 or more TETo nucleic acid sequences, the TETo sequences can be linked together. In TETr controlled promoter have 2 or more TETo nucleic acid sequences, the TETo sequences can be directly linked together. In TETr controlled promoter have 2 or more TETo nucleic acid sequences, the TETo sequences can be linked together with a linker sequence, such as a linker sequence having 1, 2, 3, 4, 5, 6, 7, 8, 9, 10, 11, 12, 13, 14, 15, 16, 17, 18, 19, or 20 or more nucleotides. In general, a TETr controlled promoter can use any promoter sequence desired, such as a SV40, EF-1, RSV, PGK, HSA, MCK or EBV promoter sequence. A TETr controlled promoter can use a CMV promoter sequence. A TETr controlled promoter can use a minimal CMV promoter sequence. TETo sequences can be upstream (5') of a promoter sequence region where RNA polymerase binds. In an illustrative example, 7 TETo sequences are upstream (5') of a promoter sequence. A TETr controlled promoter operably linked to the at least one payload nucleic acid sequence with TETo sequence upstream of the promoter sequence region can have an ordered sequence described in the formula, from 5' to 3':

$$(T\text{-}L_Y)_X\text{-}P\text{-}N$$

where N is a payload nucleic acid sequence, P is a RNA polymerase binding sequence of the promoter sequence operably linked to payload nucleic acid sequence, T is a TETo nucleic acid sequences comprising the nucleotide sequence shown in SEQ ID NO:66, L is a linker sequence, where Y=0 or 1 for each X, and wherein X=1, 2, 3, 4, 5, 6, 7, 8, 9, 10, 11, 12, 13, 14, 15, 16, 17, 18, 19, or 20. In an illustrative example, X=7 and Y=1 for each X describes where 7 TETo sequences are upstream (5') of the promoter sequence and each TETo sequence is separated by a linker.

A TETo sequences can be downstream (3') of a promoter sequence region where RNA polymerase binds. In another illustrative example, 2 TETo sequences are downstream (3') of a promoter sequence. A TETr controlled promoter operably linked to the at least one payload nucleic acid sequence with TETo sequence downstream of the promoter sequence region can have an ordered sequence described in the formula, from 5' to 3':

$$P\text{-}(T\text{-}L_Y)_X\text{-}N$$

where N is a payload nucleic acid sequence, P is a RNA polymerase binding sequence of the promoter sequence operably linked to payload nucleic acid sequence, T is a TETo nucleic acid sequences comprising the nucleotide sequence shown in SEQ ID NO:66, L is a linker sequence, where Y=0 or 1 for each X, and wherein X=1, 2, 3, 4, 5, 6, 7, 8, 9, 10, 11, 12, 13, 14, 15, 16, 17, 18, 19, or 20. In an illustrative example, X=2 and Y=1 for each X describes where 2 TETo sequences are downstream (3') of the promoter sequence and each TETo sequence is separated by a linker.

Viral production of vectors with TETr controlled promoters can use any viral production cell line engineered to express a TETr sequence (tTS), such as a 293 cell line or its derivatives (e.g., a 293F cell line) engineered to express tTS. Viral production of vectors with TETr controlled promoters in tTS-expressing cell can improve viral production. Viral production of vectors with TETr controlled promoters in tTS-expressing cell can improve viral infectivity defined as viral particles (VP) per infectious unit (IU). Viral production of vectors with TETr controlled promoters in tTS-expressing cell can improve viral production and/or viral infectivity by at least 1.5, at least 2, at least 2.5, at least 3, at least 3.5, at least 4, at least 4.5, at least 5, at least 6, at least 7, at least 8, at least 9, or at least 10-fold relative to production in a non-tTS-expressing cell. Viral production of vectors with TETr controlled promoters in tTS-expressing cell can improve viral production and/or viral infectivity by at least 15, at least 20, at least 25, at least 30, at least 35, at least 40, at least 45, at least 50, at least 60, at least 70, at least 80, at least 90, or at least 100-fold relative to production in a non-tTS-expressing cell. Viral production of vectors with TETr controlled promoters in tTS-expressing cell can improve viral production and/or viral infectivity by at least 1.5, at least 2, at least 2.5, at least 3, at least 3.5, at least 4, at least 4.5, at least 5, at least 6, at least 7, at least 8, at least 9, or at least 10-fold relative to production of a vector not having a TETr controlled promoter. Viral production of vectors with TETr controlled promoters in tTS-expressing cell can improve viral production and/or viral infectivity by at least 15, at least 20, at least 25, at least 30, at least 35, at least 40, at least 45, at least 50, at least 60, at least 70, at least 80, at least 90, or at least 100-fold relative to production of a vector not having a TETr controlled promoter.

The antigen cassette can also include nucleic acid sequences heterologous to the viral vector sequences including sequences providing signals for efficient polyadenylation of the transcript (poly(A), poly-A or pA) and introns with functional splice donor and acceptor sites. A common poly-A sequence which is employed in the exemplary vectors of this invention is that derived from the papovavirus SV-40. The poly-A sequence generally can be inserted in the cassette following the antigen-based sequences and before the viral vector sequences. A common intron sequence can also be derived from SV-40, and is referred to as the SV-40 T intron sequence. An antigen cassette can also contain such an intron, located between the promoter/enhancer sequence and the antigen(s). Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

An antigen cassette can have one or more antigens. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more antigens. Antigens can be linked directly to one another. Antigens can also be linked to one another with linkers. Antigens can be in any orientation relative to one another including N to C or C to N.

As described elsewhere herein, the antigen cassette can be located in the site of any selected deletion in a viral vector, such as the deleted structural proteins of a VEE backbone or the site of the E1 gene region deletion or E3 gene region deletion of a ChAd-based vector, among others which may be selected.

The antigen cassette can be described using the following formula to describe the ordered sequence of each element, from 5' to 3':

$$(P_a\text{-}(L5_b\text{-}N_c\text{-}L3_d)_X)_Z\text{-}(P2_h\text{-}(G5_e\text{-}U_f)_Y)_W\text{-}G3_g$$

wherein P and P2 comprise promoter nucleotide sequences, N comprises an MHC class I epitope-encoding nucleic acid sequence, L5 comprises a 5' linker sequence, L3 comprises a 3' linker sequence, G5 comprises a nucleic acid sequences encoding an amino acid linker, G3 comprises one of the at least one nucleic acid sequences encoding an amino acid linker, U comprises an MHC class II antigen-encoding nucleic acid sequence, where for each X the corresponding $N_c$ is an epitope encoding nucleic acid sequence, where for each Y the corresponding Uf is a MHC class II epitope-encoding nucleic acid sequence (e.g., universal MHC class II epitope-encoding nucleic acid sequence). A universal sequence can comprise at least one of Tetanus toxoid and PADRE. A universal sequence can comprise a Tetanus toxoid peptide. A universal sequence can comprise a PADRE peptide. A universal sequence can comprise a Tetanus toxoid and PADRE peptides. The composition and ordered sequence can be further defined by selecting the number of elements present, for example where a=0 or 1, where b=0 or 1, where c=1, where d=0 or 1, where e=0 or 1, where f=1, where g=0 or 1, where h=0 or 1, X=1 to 400, Y=0, 1, 2, 3, 4 or 5, Z=1 to 400, and W=0, 1, 2, 3, 4 or 5.

In one example, elements present include where a=0, b=1, d=1, e=1, g=1, h=0, X=10, Y=2, Z=1, and W=1, describing where no additional promoter is present (e.g. only the promoter nucleotide sequence provided by a vector backbone, such as an RNA alphavirus backbone is present), 10 MHC class I epitopes are present, a 5' linker is present for each N, a 3' linker is present for each N, 2 MHC class II epitopes are present, a linker is present linking the two MHC class II epitopes, a linker is present linking the 5' end of the two MHC class II epitopes to the 3' linker of the final MHC class I epitope, and a linker is present linking the 3' end of the two MHC class II epitopes to the to a vector backbone (e.g., an RNA alphavirus backbone). Examples of linking the 3' end of the antigen cassette to a vector backbone (e.g., an RNA alphavirus backbone) include linking directly to the 3' UTR elements provided by the vector backbone, such as a 3' 19-nt CSE. Examples of linking the 5' end of the antigen cassette to a vector backbone (e.g., an RNA alphavirus backbone) include linking directly to a promoter or 5' UTR element of the vector backbone, such as a subgenomic promoter sequence (e.g., a 26S subgenomic promoter sequence), an alphavirus 5' UTR, a 51-nt CSE, or a 24-nt CSE.

Other examples include: where a=1 describing where a promoter other than the promoter nucleotide sequence provided by a vector backbone (e.g., an RNA alphavirus backbone) is present; where a=1 and Z is greater than 1 where multiple promoters other than the promoter nucleotide sequence provided by the vector backbone are present each driving expression of 1 or more distinct MHC class I epitope encoding nucleic acid sequences; where h=1 describing where a separate promoter is present to drive expression of the MHC class II epitope-encoding nucleic acid sequences; and where g=0 describing the MHC class II epitope-encoding nucleic acid sequence, if present, is directly linked to a vector backbone (e.g., an RNA alphavirus backbone).

Other examples include where each MHC class I epitope that is present can have a 5' linker, a 3' linker, neither, or both. In examples where more than one MHC class I epitope is present in the same antigen cassette, some MHC class I epitopes may have both a 5' linker and a 3' linker, while other MHC class I epitopes may have either a 5' linker, a 3' linker, or neither. In other examples where more than one MHC class I epitope is present in the same antigen cassette, some MHC class I epitopes may have either a 5' linker or a 3' linker, while other MHC class I epitopes may have either a 5' linker, a 3' linker, or neither.

In examples where more than one MHC class II epitope is present in the same antigen cassette, some MHC class II epitopes may have both a 5' linker and a 3' linker, while other MHC class II epitopes may have either a 5' linker, a 3' linker, or neither. In other examples where more than one MHC class II epitope is present in the same antigen cassette, some MHC class II epitopes may have either a 5' linker or a 3' linker, while other MHC class II epitopes may have either a 5' linker, a 3' linker, or neither.

Other examples include where each antigen that is present can have a 5' linker, a 3' linker, neither, or both. In examples where more than one antigen is present in the same antigen cassette, some antigens may have both a 5' linker and a 3' linker, while other antigens may have either a 5' linker, a 3' linker, or neither. In other examples where more than one antigen is present in the same antigen cassette, some antigens may have either a 5' linker or a 3' linker, while other antigens may have either a 5' linker, a 3' linker, or neither.

The promoter nucleotide sequences P and/or P2 can be the same as a promoter nucleotide sequence provided by a vector backbone, such as an RNA alphavirus backbone. For example, the promoter sequence provided by the vector backbone, Pn and P2, can each comprise a subgenomic promoter sequence (e.g., a 26S subgenomic promoter sequence) or a CMV promoter. The promoter nucleotide sequences P and/or P2 can be different from the promoter nucleotide sequence provided by a vector backbone (e.g., an RNA alphavirus backbone), as well as can be different from each other.

The 5' linker L5 can be a native sequence or a non-natural sequence. Non-natural sequence include, but are not limited to, AAY, RR, and DPP. The 3' linker L3 can also be a native sequence or a non-natural sequence. Additionally, L5 and L3 can both be native sequences, both be non-natural sequences, or one can be native and the other non-natural. For each X, the amino acid linkers can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each X, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G5, for each Y, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each Y, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G3 can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. G3 can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

For each X, each N can encode a MHC class I epitope, a MHC class II epitope, an epitope/antigen capable of stimulating a B cell response, or a combination thereof. For each X, each N can encode a combination of a MHC class I epitope, a MHC class II epitope, and an epitope/antigen capable of stimulating a B cell response. For each X, each N can encode a combination of a MHC class I epitope and a MHC class II epitope. For each X, each N can encode a combination of a MHC class I epitope and an epitope/antigen capable of stimulating a B cell response. For each X, each N can encode a combination of a MHC class II epitope and an epitope/antigen capable of stimulating a B cell response. For each X, each N can encode a MHC class II epitope. For each X, each N can encode an epitope/antigen capable of stimulating a B cell response. For each X, each N can encode a MHC class I epitope 7-15 amino acids in length. For each X, each N can also encodes a MHC class I epitope 5, 6, 7, 8, 9, 10, 11, 12, 13, 14, 15, 16, 17, 18, 19, 20, 21, 22, 23, 24, 25, 26, 27, 28, 29, or 30 amino acids in length. For each X, each N can also encodes a MHC class I epitope at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The cassette encoding the one or more antigens can be 700 nucleotides or less. The cassette encoding the one or more antigens can be 700 nucleotides or less and encode 2 distinct epitope-encoding nucleic acid sequences (e.g., encode 2 distinct infectious disease or tumor derived nucleic acid sequences encoding an immunogenic polypeptide). The cassette encoding the one or more antigens can be 700 nucleotides or less and encode at least 2 distinct epitope-encoding nucleic acid sequences. The cassette encoding the one or more antigens can be 700 nucleotides or less and encode 3 distinct epitope-encoding nucleic acid sequences. The cassette encoding the one or more antigens can be 700 nucleotides or less and encode at least 3 distinct epitope-encoding nucleic acid sequences. The cassette encoding the one or more antigens can be 700 nucleotides or less and include 1-10, 1-5, 1, 2, 3, 4, 5, 6, 7, 8, 9, 10, or more antigens.

The cassette encoding the one or more antigens can be between 375-700 nucleotides in length. The cassette encoding the one or more antigens can be between 375-700 nucleotides in length and encode 2 distinct epitope-encoding nucleic acid sequences (e.g., encode 2 distinct infectious disease or tumor derived nucleic acid sequences encoding an immunogenic polypeptide). The cassette encoding the one or more antigens can be between 375-700 nucleotides in length and encode at least 2 distinct epitope-encoding nucleic acid sequences. The cassette encoding the one or more antigens can be between 375-700 nucleotides in length and encode 3 distinct epitope-encoding nucleic acid sequences. The cassette encoding the one or more antigens be between 375-700 nucleotides in length and encode at least 3 distinct epitope-encoding nucleic acid sequences. The cassette encoding the one or more antigens can be between 375-700 nucleotides in length and include 1-10, 1-5, 1, 2, 3, 4, 5, 6, 7, 8, 9, 10, or more antigens.

The cassette encoding the one or more antigens can be 600, 500, 400, 300, 200, or 100 nucleotides in length or less. The cassette encoding the one or more antigens can be 600, 500, 400, 300, 200, or 100 nucleotides in length or less and encode 2 distinct epitope-encoding nucleic acid sequences. The cassette encoding the one or more antigens can be 600, 500, 400, 300, 200, or 100 nucleotides in length or less and encode at least 2 distinct epitope-encoding nucleic acid sequences. The cassette encoding the one or more antigens can be 600, 500, 400, 300, 200, or 100 nucleotides in length or less and encode 3 distinct epitope-encoding nucleic acid sequences. The cassette encoding the one or more antigens can be 600, 500, 400, 300, 200, or 100 nucleotides in length or less and encode at least 3 distinct epitope-encoding nucleic acid sequences. The cassette encoding the one or more antigens can be 600, 500, 400, 300, 200, or 100 nucleotides in length or less and include 1-10, 1-5, 1, 2, 3, 4, 5, 6, 7, 8, 9, 10, or more antigens.

The cassette encoding the one or more antigens can be between 375-600, between 375-500, or between 375-400 nucleotides in length. The cassette encoding the one or more antigens can be between 375-600, between 375-500, or between 375-400 nucleotides in length and encode 2 distinct epitope-encoding nucleic acid sequences. The cassette encoding the one or more antigens can be between 375-600, between 375-500, or between 375-400 nucleotides in length and encode at least 2 distinct epitope-encoding nucleic acid sequences. The cassette encoding the one or more antigens can be between 375-600, between 375-500, or between 375-400 nucleotides in length and encode 3 distinct epitope-encoding nucleic acid sequences. The cassette encoding the one or more antigens can be between 375-600, between 375-500, or between 375-400 nucleotides in length and encode at least 3 distinct epitope-encoding nucleic acid sequences. The cassette encoding the one or more antigens can be between 375-600, between 375-500, or between 375-400 nucleotides in length and include 1-10, 1-5, 1, 2, 3, 4, 5, 6, 7, 8, 9, 10, or more antigens.

In some instances, an antigen or epitope in a cassette encoding additional antigens and/or epitopes may be an immunodominant epitope relative to the others encoded. Immunodominance, in general, is the skewing of an immune response towards only one or a few specific immunogenic peptides. Immunodominance can be assessed as part of an immune monitoring protocol. For example, immunodominance can be assessed through evaluating T cell and/or B cell responses to the encoded antigens.

Immunodominance can be assessed as the impact of an immunodominant antigen's presence on the immune response to one or more other antigens. For example, an immunodominant antigen and its respective immune response (e.g., an immunodominant MHC class I epitope) can reduce the immune response of another antigen relative to the immune response in the absence of the immunodominant antigen. This reduction can be such that the immune response in the presence of the immunodominant antigen is not considered a therapeutically effective response. For example, an MHC class I epitope would generally be considered immunodominant if T cell responses to other antigens are no longer considered therapeutically effective responses compared to responses elicited in the absence of the immunodominant MHC class I epitope. An immune response can also be reduced to below a limit of detection or near the limit of detection. relative to the response in the absence of the immunodominant antigen. For example, an MHC class I epitope would generally be considered immunodominant if T cell responses to other antigens are at or below the limit of detection compared to responses elicited in the absence of the immunodominant MHC class I epitope. In general, the assessment of immunodominance is between two antigens both capable of stimulating an immune response, e.g., between two T cell epitopes in a vaccine composition administered to a subject possessing a cognate MHC allele known or predicted to present each epitope, respectively. Immunodominance can be assessed through evaluating relative immune responses to other antigens in the presence and absence of the suspected immunodominant antigen.

Immunodominance can be assessed as a relative difference in the immune responses between two or more antigens. Immunodominance can refer to a 5-fold, 10-fold, 20-fold, 30-fold, 40-fold, or 50-fold immune response of a specific antigen relative to another antigen encoded in the same cassette. Immunodominance can refer to a 100-fold, 200-fold, 300-fold, 400-fold, or 500-fold immune response of a specific antigen relative to another antigen encoded in the same cassette. Immunodominance can refer to a 1000-fold, 2000-fold, 3000-fold, 4000-fold, or 5000-fold immune response of a specific antigen relative to another antigen encoded in the same cassette. Immunodominance can refer to a 10,000-fold immune response of a specific antigen relative to another antigen encoded in the same cassette.

In some instances, it may be desired to avoid vaccine compositions containing an immunodominant epitope. For example, it may be desired to avoid designing a vaccine cassette encoding an immunodominant epitope. Without wishing to be bound by theory, administering and/or encoding an immunodominant epitope together with additional epitope may reduce the immune response to the additional epitopes, including potentially ultimately reducing vaccine efficacy against the additional epitopes. As an illustrative non-limiting example, vaccine compositions including TP53-associated neoepitopes may have the immune response, e.g., a T cell response, skewed towards the TP53-associated neoepitope negatively impacting (e.g., reducing the immune response to where the immune response is not a therapeutically effective response and/or to below a limit of detection) the immune response to other antigens or epitopes in the vaccine composition (e.g., one or more KRAS-associated neoepitopes in the vaccine composition, such as any of the KRAS-associated neoepitopes shown in SEQ ID NOs. 75-82). Accordingly, vaccine compositions can be designed to not contain an immunodominant epitope, such as designing a vaccine cassette (e.g., a (neo)antigen-encoding cassette) to not encode an immunodominant epitope. For example, the cassette does not encode an epitope that reduces an immune response to another epitope encoded in the cassette when administered in a vaccine composition to a subject relative to an immune response when the other epitope is administered in the absence of the immunodominant MHC class I epitope. In another example, the cassette does not encode an epitope that reduces an immune response to another epitope encoded in the cassette to below a limit of detection when administered in a vaccine composition to a subject relative to an immune response when the other epitope is administered in the absence of the immunodominant MHC class I epitope. In another example, the cassette does not encode an epitope that reduces an immune response to another epitope encoded in the cassette, wherein the immune response is not a therapeutically effective response, when administered in a vaccine composition to a subject relative to an immune response when the other epitope is administered in the absence of the immunodominant MHC class I epitope. In another example, the cassette does not encode an epitope that stimulates a 5-fold, 10-fold, 20-fold, 30-fold, 40-fold, or 50-fold or greater immune response relative to another epitope encoded in the same cassette in a vaccine composition administered to a subject, where each antigen is capable of stimulating an immune response in the subject. In another example, the cassette does not encode an epitope that stimulates a 100-fold, 200-fold, 300-fold, 400-fold, or 500-fold or greater immune response relative to another epitope encoded in the same cassette in a vaccine composition administered to a subject, where each antigen is capable of stimulating an immune response in the subject. In another example, the cassette does not encode an epitope that stimulates a 1000-fold, 2000-fold, 3000-fold, 4000-fold, or 5000-fold or greater immune response relative to another epitope encoded in the same cassette in a vaccine composition administered to a subject, where each antigen is capable of stimulating an immune response in the subject. In another example, the cassette does not encode an epitope that results in a 10,000-fold or greater immune response relative to another epitope encoded in the same cassette in a vaccine composition administered to a subject, where each antigen is capable of stimulating an immune response in the subject.

V.B. Immune Modulators

Vectors described herein, such as C68 vectors described herein or alphavirus vectors described herein, can comprise a nucleic acid which encodes at least one antigen and the same or a separate vector can comprise a nucleic acid which encodes at least one immune modulator. An immune modulator can include a binding molecule (e.g., an antibody such as an scFv) which binds to and blocks the activity of an immune checkpoint molecule. An immune modulator can include a cytokine, such as IL-2, IL-7, IL-12 (including IL-12 p35, p40, p70, and/or p70-fusion constructs), IL-15, or IL-21. An immune modulator can include a modified cytokine (e.g., pegIL-2). Vectors can comprise an antigen cassette and one or more nucleic acid molecules encoding an immune modulator.

Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, $\gamma\delta$, and memory CD8+($\alpha\beta$) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal Antibody (Anti-B7-H1; MEDI4736), ipilimumab, MK-3475 (PD-1 blocker), Nivolumamb (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Antibody-encoding sequences can be engineered into vectors such as C68 using ordinary skill in the art. An exemplary method is described in Fang et al., Stable antibody expression at therapeutic levels using the 2A peptide. *Nat Biotechnol.* 2005 May; 23(5):584-90. Epub 2005 Apr. 17; herein incorporated by reference for all purposes.

V.C. Additional Considerations for Vaccine Design and Manufacture

V.C.1. Determination of a Set of Peptides that Cover all Tumor Subclones

Truncal peptides, meaning those presented by all or most tumor subclones, can be prioritized for inclusion into a vaccine. Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by a vaccine.

V.C.2. Antigen Prioritization

After all of the above antigen filters are applied, more candidate antigens may still be available for vaccine inclusion than the vaccine technology can support. Additionally, uncertainty about various aspects of the antigen analysis may remain and tradeoffs may exist between different properties of candidate vaccine antigens. Thus, in place of predetermined filters at each step of the selection process, an integrated multi-dimensional model can be considered that places candidate antigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of antigens may lower the probability that a tumor, an infectious disease, and/or an infected cell will escape immune attack via downregulation or mutation of HLA molecules)
7. Coverage of HLA classes (covering both HLA-I and HLA-II may increase the probability of therapeutic response and decrease the probability of tumor or infectious disease escape)

Additionally, optionally, antigens can be deprioritized (e.g., excluded) from the vaccination if they are predicted to be presented by HLA alleles lost or inactivated in either all or part of the patient's tumor or infected cell. HLA allele loss can occur by either somatic mutation, loss of heterozygosity, or homozygous deletion of the locus. Methods for detection of HLA allele somatic mutation are well known in the art, e.g. (Shukla et al., 2015). Methods for detection of somatic LOH and homozygous deletion (including for HLA locus) are likewise well described. (Carter et al., 2012; McGranahan et al., 2017; Van Loo et al., 2010). Antigens can also be deprioritized if mass-spectrometry data indicates a predicted antigen is not presented by a predicted HLA allele.

V.D. Alphavirus

V.D.1. Alphavirus Biology

Alphaviruses are members of the family Togaviridae, and are positive-sense single stranded RNA viruses. Members are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis virus and its derivative strain TC-83 (Strauss Microbial Review 1994). A natural alphavirus genome is typically around 12kb in length, the first two-thirds of which contain genes encoding non-structural proteins (nsPs) that form RNA replication complexes for self-replication of the viral genome, and the last third of which contains a subgenomic expression cassette encoding structural proteins for virion production (Frolov RNA 2001).

A model lifecycle of an alphavirus involves several distinct steps (Strauss Microbial Review 1994, Jose Future Microbiol 2009). Following virus attachment to a host cell, the virion fuses with membranes within endocytic compartments resulting in the eventual release of genomic RNA into the cytosol. The genomic RNA, which is in a plus-strand orientation and comprises a 5' methylguanylate cap and 3' polyA tail, is translated to produce non-structural proteins nsP1-4 that form the replication complex. Early in infection, the plus-strand is then replicated by the complex into a minus-stand template. In the current model, the replication complex is further processed as infection progresses, with the resulting processed complex switching to transcription of the minus-strand into both full-length positive-strand genomic RNA, as well as the 26S subgenomic positive-strand RNA containing the structural genes. Several conserved sequence elements (CSEs) of alphavirus have been identified to potentially play a role in the various RNA replication steps including; a complement of the 5' UTR in the replication of plus-strand RNAs from a minus-strand template, a 51-nt CSE in the replication of minus-strand synthesis from the genomic template, a 24-nt CSE in the junction region between the nsPs and the 26S RNA in the transcription of the subgenomic RNA from the minus-strand, and a 3' 19-nt CSE in minus-strand synthesis from the plus-strand template.

Following the replication of the various RNA species, virus particles are then typically assembled in the natural lifecycle of the virus. The 26S RNA is translated and the resulting proteins further processed to produce the structural proteins including capsid protein, glycoproteins E1 and E2, and two small polypeptides E3 and 6K (Strauss 1994). Encapsidation of viral RNA occurs, with capsid proteins normally specific for only genomic RNA being packaged, followed by virion assembly and budding at the membrane surface.

V.D.2. Alphavirus as a Delivery Vector

Alphaviruses (including alphavirus sequences, features, and other elements) can be used to generate alphavirus-based delivery vectors (also be referred to as alphavirus vectors, alphavirus viral vectors, alphavirus vaccine vectors, self-replicating RNA (srRNA) vectors, or self-amplifying mRNA (SAM) vectors). Alphaviruses have previously been engineered for use as expression vector systems (Pushko 1997, Rheme 2004). Alphaviruses offer several advantages, particularly in a vaccine setting where heterologous antigen expression can be desired. Due to its ability to self-replicate in the host cytosol, alphavirus vectors are generally able to produce high copy numbers of the expression cassette within a cell resulting in a high level of heterologous antigen production. Additionally, the vectors are generally transient, resulting in improved biosafety as well as reduced induction of immunological tolerance to the vector. The public, in general, also lacks pre-existing immunity to alphavirus vectors as compared to other standard viral vectors, such as human adenovirus. Alphavirus based vectors also generally result in cytotoxic responses to infected cells. Cytotoxicity, to a certain degree, can be important in a vaccine setting to properly stimulate an immune response to the heterologous antigen expressed. However, the degree of desired cytotoxicity can be a balancing act, and thus several attenuated alphaviruses have been developed, including the TC-83 strain of VEE. Thus, an example of an antigen expression vector described herein can utilize an alphavirus backbone that allows for a high level of antigen expression, stimulates a robust immune response to antigen, does not stimulate an immune response to the vector itself, and can be used in a safe manner. Furthermore, the antigen expression cassette can be designed to stimulate different levels of an immune response through optimization of which alphavirus sequences the vector uses, including, but not limited to, sequences derived from VEE or its attenuated derivative TC-83.

Several expression vector design strategies have been engineered using alphavirus sequences (Pushko 1997). In one strategy, a alphavirus vector design includes inserting a second copy of the 26S promoter sequence elements downstream of the structural protein genes, followed by a heterologous gene (Frolov 1993). Thus, in addition to the natural non-structural and structural proteins, an additional subgenomic RNA is produced that expresses the heterologous protein. In this system, all the elements for production of infectious virions are present and, therefore, repeated rounds of infection of the expression vector in non-infected cells can occur.

Another expression vector design makes use of helper virus systems (Pushko 1997). In this strategy, the structural proteins are replaced by a heterologous gene. Thus, following self-replication of viral RNA mediated by still intact non-structural genes, the 26S subgenomic RNA provides for expression of the heterologous protein. Traditionally, additional vectors that expresses the structural proteins are then supplied in trans, such as by co-transfection of a cell line, to produce infectious virus. A system is described in detail in U.S. Pat. No. 8,093,021, which is herein incorporated by reference in its entirety, for all purposes. The helper vector system provides the benefit of limiting the possibility of forming infectious particles and, therefore, improves biosafety. In addition, the helper vector system reduces the total vector length, potentially improving the replication and expression efficiency. Thus, an example of an antigen expression vector described herein can utilize an alphavirus backbone wherein the structural proteins are replaced by an antigen cassette, the resulting vector both reducing biosafety concerns, while at the same time promoting efficient expression due to the reduction in overall expression vector size.

V.D.3. Alphavirus Production In Vitro

Alphavirus delivery vectors are generally positive-sense RNA polynucleotides. A convenient technique well-known in the art for RNA production is in vitro transcription IVT. In this technique, a DNA template of the desired vector is first produced by techniques well-known to those in the art, including standard molecular biology techniques such as cloning, restriction digestion, ligation, gene synthesis (e.g., chemical and/or enzymatic synthesis), and polymerase chain reaction (PCR). The DNA template contains a RNA polymerase promoter at the 5' end of the sequence desired to be transcribed into RNA. Promoters include, but are not limited to, bacteriophage polymerase promoters such as T3, T7, or SP6. The DNA template is then incubated with the appropriate RNA polymerase enzyme, buffer agents, and nucleotides (NTPs). The resulting RNA polynucleotide can optionally be further modified including, but limited to, addition of a 5' cap structure such as 7-methylguanosine or a related structure, and optionally modifying the 3' end to include a polyadenylate (polyA) tail. The RNA can then be purified using techniques well-known in the field, such as phenol-chloroform extraction or column purification (e.g., chromatography-based purification).

V.D.4. Delivery Via Lipid Nanoparticle

An important aspect to consider in vaccine vector design is immunity against the vector itself (Riley 2017). This may be in the form of preexisting immunity to the vector itself, such as with certain human adenovirus systems, or in the form of developing immunity to the vector following administration of the vaccine. The latter is an important consideration if multiple administrations of the same vaccine are performed, such as separate priming and boosting doses, or if the same vaccine vector system is to be used to deliver different antigen cassettes.

In the case of alphavirus vectors, the standard delivery method is the previously discussed helper virus system that provides capsid, E1, and E2 proteins in trans to produce infectious viral particles. However, it is important to note that the E1 and E2 proteins are often major targets of neutralizing antibodies (Strauss 1994). Thus, the efficacy of using alphavirus vectors to deliver antigens of interest to target cells may be reduced if infectious particles are targeted by neutralizing antibodies.

An alternative to viral particle mediated gene delivery is the use of nanomaterials to deliver expression vectors (Riley 2017). Nanomaterial vehicles, importantly, can be made of non-immunogenic materials and generally avoid eliciting immunity to the delivery vector itself. These materials can include, but are not limited to, lipids, inorganic nanomaterials, and other polymeric materials. Lipids can be cationic, anionic, or neutral. The materials can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soluble vitamins.

Lipid nanoparticles (LNPs) are an attractive delivery system due to the amphiphilic nature of lipids enabling formation of membranes and vesicle like structures (Riley 2017). In general, these vesicles deliver the expression vector by absorbing into the membrane of target cells and releasing nucleic acid into the cytosol. In addition, LNPs can be further modified or functionalized to facilitate targeting of specific cell types. Another consideration in LNP design is the balance between targeting efficiency and cytotoxicity. Lipid compositions generally include defined mixtures of cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids.

Nucleic-acid vectors, such as expression vectors, exposed directly to serum can have several undesirable consequences, including degradation of the nucleic acid by serum nucleases or off-target stimulation of the immune system by the free nucleic acids. Therefore, encapsulation of the alphavirus vector can be used to avoid degradation, while also avoiding potential off-target affects. In certain examples, an alphavirus vector is fully encapsulated within the delivery vehicle, such as within the aqueous interior of an LNP. Encapsulation of the alphavirus vector within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with the alphavirus delivery vector and other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the expression vectors can be further treated or modified to prepare them for administration.

V.E. Chimpanzee Adenovirus (ChAd)

V.E.1. Viral Delivery with Chimpanzee Adenovirus

Vaccine compositions for delivery of one or more antigens (e.g., via an antigen cassette) can be created by providing adenovirus nucleotide sequences of chimpanzee origin, a variety of novel vectors, and cell lines expressing chimpanzee adenovirus genes. A nucleotide sequence of a chimpanzee C68 adenovirus (also referred to herein as ChAdV68) can be used in a vaccine composition for antigen delivery (See SEQ ID NO: 1). Use of C68 adenovirus derived vectors is described in further detail in U.S. Pat. No. 6,083,716, which is herein incorporated by reference in its entirety, for all purposes. ChAdV68-based vectors and delivery systems are described in detail in US App. Pub. No. US20200197500A1 and international patent application publication WO2020243719A1, each of which is herein incorporated by reference for all purposes.

In a further aspect, provided herein is a recombinant adenovirus comprising the DNA sequence of a chimpanzee adenovirus such as C68 and an antigen cassette operatively linked to regulatory sequences directing its expression. The recombinant virus is capable of infecting a mammalian, preferably a human, cell and capable of expressing the antigen cassette product in the cell. In this vector, the native chimpanzee E1 gene, and/or E3 gene, and/or E4 gene can be deleted. An antigen cassette can be inserted into any of these sites of gene deletion. The antigen cassette can include an antigen against which a primed immune response is desired.

In another aspect, provided herein is a mammalian cell infected with a chimpanzee adenovirus such as C68.

In still a further aspect, a novel mammalian cell line is provided which expresses a chimpanzee adenovirus gene (e.g., from C68) or functional fragment thereof.

In still a further aspect, provided herein is a method for delivering an antigen cassette into a mammalian cell comprising the step of introducing into the cell an effective amount of a chimpanzee adenovirus, such as C68, that has been engineered to express the antigen cassette.

Still another aspect provides a method for stimulating an immune response in a mammalian host to treat cancer. The method can comprise the step of administering to the host an effective amount of a recombinant chimpanzee adenovirus, such as C68, comprising an antigen cassette that encodes one or more antigens from the tumor against which the immune response is targeted.

Still another aspect provides a method for stimulating an immune response in a mammalian host to treat or prevent a disease in a subject, such as an infectious disease. The method can comprise the step of administering to the host an effective amount of a recombinant chimpanzee adenovirus, such as C68, comprising an antigen cassette that encodes one or more antigens, such as from the infectious disease against which the immune response is targeted.

Also disclosed is a non-simian mammalian cell that expresses a chimpanzee adenovirus gene obtained from the sequence of SEQ ID NO: 1. The gene can be selected from the group consisting of the adenovirus E1A, E1B, E2A, E2B, E3, E4, L1, L2, L3, L4 and L5 of SEQ ID NO: 1.

Also disclosed is a nucleic acid molecule comprising a chimpanzee adenovirus DNA sequence comprising a gene obtained from the sequence of SEQ ID NO: 1. The gene can be selected from the group consisting of said chimpanzee adenovirus E1A, E1B, E2A, E2B, E3, E4, L1, L2, L3, L4 and L5 genes of SEQ ID NO: 1. In some aspects the nucleic acid molecule comprises SEQ ID NO: 1. In some aspects the nucleic acid molecule comprises the sequence of SEQ ID NO: 1, lacking at least one gene selected from the group consisting of E1A, E1B, E2A, E2B, E3, E4, L1, L2, L3, L4 and L5 genes of SEQ ID NO: 1.

Also disclosed is a vector comprising a chimpanzee adenovirus DNA sequence obtained from SEQ ID NO: 1 and an antigen cassette operatively linked to one or more regulatory sequences which direct expression of the cassette in a heterologous host cell, optionally wherein the chimpanzee adenovirus DNA sequence comprises at least the cis-elements necessary for replication and virion encapsidation, the cis-elements flanking the antigen cassette and regulatory sequences. In some aspects, the chimpanzee adenovirus DNA sequence comprises a gene selected from the group consisting of E1A, E1B, E2A, E2B, E3, E4, L1, L2, L3, L4 and L5 gene sequences of SEQ ID NO: 1. In some aspects the vector can lack the E1A and/or E1B gene.

Also disclosed herein is a adenovirus vector comprising: a partially deleted E4 gene comprising a deleted or partially-deleted E4orf2 region and a deleted or partially-deleted E4orf3 region, and optionally a deleted or partially-deleted E4orf4 region. The partially deleted E4 can comprise an E4 deletion of at least nucleotides 34,916 to 35,642 of the sequence shown in SEQ ID NO:1, and wherein the vector comprises at least nucleotides 2 to 36,518 of the sequence set forth in SEQ ID NO:1. The partially deleted E4 can comprise an E4 deletion of at least a partial deletion of nucleotides 34,916 to 34,942 of the sequence shown in SEQ ID NO:1, at least a partial deletion of nucleotides 34,952 to 35,305 of the sequence shown in SEQ ID NO:1, and at least a partial deletion of nucleotides 35,302 to 35,642 of the sequence shown in SEQ ID NO:1, and wherein the vector comprises at least nucleotides 2 to 36,518 of the sequence set forth in SEQ ID NO:1 The partially deleted E4 can comprise an E4 deletion of at least nucleotides 34,980 to 36,516 of the sequence shown in SEQ ID NO:1, and wherein the vector comprises at least nucleotides 2 to 36,518 of the sequence set forth in SEQ ID NO:1. The partially deleted E4 can comprise an E4 deletion of at least nucleotides 34,979 to 35,642 of the sequence shown in SEQ ID NO: 1, and wherein the vector comprises at least nucleotides 2 to 36,518 of the sequence set forth in SEQ ID NO:1. The partially deleted E4 can comprise an E4 deletion of at least a partial deletion of E4Orf2, a fully deleted E4Orf3, and at least a partial deletion of E4Orf4. The partially deleted E4 can comprise an E4 deletion of at least a partial deletion of E4Orf2, at least a partial deletion of E4Orf3, and at least a partial deletion of E4Orf4. The partially deleted E4 can comprise an E4 deletion of at least a partial deletion of E4Orf1, a fully deleted E4Orf2, and at least a partial deletion of E4Orf3. The partially deleted E4 can comprise an E4 deletion of at least a partial deletion of E4Orf2 and at least a partial deletion of E4Orf3. The partially deleted E4 can comprise an E4 deletion between the start site of E4Orf1 to the start site of E4Orf5. The partially deleted E4 can be an E4 deletion adjacent to the start site of E4Orf1. The partially deleted E4 can be an E4 deletion adjacent to the start site of E4Orf2. The partially deleted E4 can be an E4 deletion adjacent to the start site of E4Orf3. The partially deleted E4 can be an E4 deletion adjacent to the start site of E4Orf4. The E4 deletion can be at least 50, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, or at least 2000 nucleotides. The E4 deletion can be at least 700 nucleotides. The E4 deletion can be at least 1500 nucleotides. The E4 deletion can be 50 or less, 100 or less, 200 or less, 300 or less, 400 or less, 500 or less, 600 or less, 700 or less, 800 or less, 900 or less, 1000 or less, 1100 or less, 1200 or less, 1300 or less, 1400 or less, 1500 or less, 1600 or less, 1700 or less, 1800 or less, 1900 or less, or 2000 or less nucleotides. The E4 deletion can be 750 nucleotides or less. The E4 deletion can be at least 1550 nucleotides or less.

The partially deleted E4 gene can be the E4 gene sequence shown in SEQ ID NO:1 that lacks at least nucleotides 34,916 to 35,642 of the sequence shown in SEQ ID NO: 1. The partially deleted E4 gene can be the E4 gene sequence shown in SEQ ID NO:1 that lacks the E4 gene sequence shown in SEQ ID NO:1 and that lacks at least nucleotides 34,916 to 34,942, nucleotides 34,952 to 35,305 of the sequence shown in SEQ ID NO:1, and nucleotides 35,302 to 35,642 of the sequence shown in SEQ ID NO:1. The partially deleted E4 gene can be the E4 gene sequence shown in SEQ ID NO:1 and that lacks at least nucleotides 34,980 to 36,516 of the sequence shown in SEQ ID NO:1. The partially deleted E4 gene can be the E4 gene sequence shown in SEQ ID NO:1 and that lacks at least nucleotides 34,979 to 35,642 of the sequence shown in SEQ ID NO:1. The adenovirus vector having the partially deleted E4 gene can have a cassette, wherein the cassette comprises at least one payload nucleic acid sequence, and wherein the cassette comprises at least one promoter sequence operably linked to the at least one payload nucleic acid sequence. The adenovirus vector having the partially deleted E4 gene can have one or more genes or regulatory sequences of the ChAdV68 sequence shown in SEQ ID NO: 1, optionally wherein the one or more genes or regulatory sequences comprise at least one of the chimpanzee adenovirus inverted terminal repeat (ITR), E1A, E1B, E2A, E2B, E3, E4, L1, L2, L3, L4, and L5 genes of the sequence shown in SEQ ID NO: 1. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, and optionally the nucleotides 2 to 34,916 additionally lack nucleotides 577 to 3403 of the sequence shown in SEQ ID NO:1 corresponding to an E1 deletion and/or lack nucleotides 27,125 to 31,825 of the sequence shown in SEQ ID NO:1 corresponding to an E3 deletion. The adenovirus vector having the partially deleted E4 gene can have nucleotides 35,643 to 36,518 of the sequence shown in SEQ ID NO:1, and wherein the partially deleted E4 gene is 5' of the nucleotides 35,643 to 36,518. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion. The adenovirus vector having the partially deleted E4 gene can have nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion, and have nucleotides 35,643 to 36,518 of the sequence shown in SEQ ID NO:1, and wherein the partially deleted E4 gene is 5' of the nucleotides 35,643 to 36,518.

The partially deleted E4 gene can be the E4 gene sequence shown in SEQ ID NO:1 that lacks at least nucleotides 34,916 to 35,642 of the sequence shown in SEQ ID NO: 1, nucleotides 2 to 34,916 of the sequence shown in SEQ ID NO:1, wherein the partially deleted E4 gene is 3' of the nucleotides 2 to 34,916, the nucleotides 2 to 34,916 additionally lack nucleotides 577 to 3403 of the sequence shown in SEQ ID NO:1 corresponding to an E1 deletion and lack nucleotides 27,125 to 31,825 of the sequence shown in SEQ ID NO:1 corresponding to an E3 deletion, and have nucleotides 35,643 to 36,518 of the sequence shown in SEQ ID NO:1, and wherein the partially deleted E4 gene is 5' of the nucleotides 35,643 to 36,518.

Also disclosed herein is a host cell transfected with a vector disclosed herein such as a C68 vector engineered to expression an antigen cassette. Also disclosed herein is a human cell that expresses a selected gene introduced therein through introduction of a vector disclosed herein into the cell.

Also disclosed herein is a method for delivering an antigen cassette to a mammalian cell comprising introducing into said cell an effective amount of a vector disclosed herein such as a C68 vector engineered to expression the antigen cassette.

Also disclosed herein is a method for producing an antigen comprising introducing a vector disclosed herein into a mammalian cell, culturing the cell under suitable conditions and producing the antigen.

V.E.2. E1-Expressing Complementation Cell Lines

To generate recombinant chimpanzee adenoviruses (Ad) deleted in any of the genes described herein, the function of the deleted gene region, if essential to the replication and infectivity of the virus, can be supplied to the recombinant virus by a helper virus or cell line, i.e., a complementation or packaging cell line. For example, to generate a replication-defective chimpanzee adenovirus vector, a cell line can be used which expresses the E1 gene products of the human or chimpanzee adenovirus; such a cell line can include HEK293 or variants thereof. The protocol for the generation of the cell lines expressing the chimpanzee E1 gene products (Examples 3 and 4 of U.S. Pat. No. 6,083,716) can be followed to generate a cell line which expresses any selected chimpanzee adenovirus gene.

An AAV augmentation assay can be used to identify a chimpanzee adenovirus E1-expressing cell line. This assay is useful to identify E1 function in cell lines made by using the E1 genes of other uncharacterized adenoviruses, e.g., from other species. That assay is described in Example 4B of U.S. Pat. No. 6,083,716.

A selected chimpanzee adenovirus gene, e.g., E1, can be under the transcriptional control of a promoter for expression in a selected parent cell line. Inducible or constitutive promoters can be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, incorporated by reference herein can also be used in the production of packaging cell lines. Constitutive promoters in control of the expression of the chimpanzee adenovirus gene can be employed also.

A parent cell can be selected for the generation of a novel cell line expressing any desired C68 gene. Without limitation, such a parent cell line can be HeLa [ATCC Accession No. CCL 2], A549 [ATCC Accession No. CCL 185], KB [CCL 17], Detroit [e.g., Detroit 510, CCL 72] and WI-38 [CCL 75] cells. Other suitable parent cell lines can be obtained from other sources. Parent cell lines can include CHO, HEK293 or variants thereof, 911, HeLa, A549, LP-293, PER.C6, or AE1-2a.

An E1-expressing cell line can be useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products. Further, cell lines which express other human Ad E1 gene products are also useful in generating chimpanzee recombinant Ads.

V.E.3. Recombinant Viral Particles as Vectors

The compositions disclosed herein can comprise viral vectors, that deliver at least one antigen to cells. Such vectors comprise a chimpanzee adenovirus DNA sequence such as C68 and an antigen cassette operatively linked to regulatory sequences which direct expression of the cassette. The C68 vector is capable of expressing the cassette in an infected mammalian cell. The C68 vector can be functionally deleted in one or more viral genes. An antigen cassette comprises at least one antigen under the control of one or more regulatory sequences such as a promoter. Optional helper viruses and/or packaging cell lines can supply to the chimpanzee viral vector any necessary products of deleted adenoviral genes.

The term "functionally deleted" means that a sufficient amount of the gene region is removed or otherwise altered, e.g., by mutation or modification, so that the gene region is no longer capable of producing one or more functional products of gene expression. Mutations or modifications that can result in functional deletions include, but are not limited to, nonsense mutations such as introduction of premature stop codons and removal of canonical and non-canonical start codons, mutations that alter mRNA splicing or other transcriptional processing, or combinations thereof. If desired, the entire gene region can be removed.

Modifications of the nucleic acid sequences forming the vectors disclosed herein, including sequence deletions, insertions, and other mutations may be generated using standard molecular biological techniques and are within the scope of this invention.

V.E.4. Construction of the Viral Plasmid Vector

The chimpanzee adenovirus C68 vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus C68 vectors for delivery of an antigen cassette to a human (or other mammalian) cell, a range of adenovirus nucleic acid sequences can be employed in the vectors. A vector comprising minimal chimpanzee C68 adenovirus sequences can be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

V.E.5. Recombinant Minimal Adenovirus

A minimal chimpanzee Ad C68 virus is a viral particle containing just the adenovirus cis-elements necessary for replication and virion encapsidation. That is, the vector contains the cis-acting 5' and 3' inverted terminal repeat (ITR) sequences of the adenoviruses (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597 and incorporated herein by reference.

V.E.6. Other Defective Adenoviruses

Recombinant, replication-deficient adenoviruses can also contain more than the minimal chimpanzee adenovirus sequences. These other Ad vectors can be characterized by deletions of various portions of gene regions of the virus, and infectious virus particles formed by the optional use of helper viruses and/or packaging cell lines.

As one example, suitable vectors may be formed by deleting all or a sufficient portion of the C68 adenoviral immediate early gene E1a and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus E1a and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express antigen(s), but cannot replicate in most cells that do not carry the chimpanzee E1 region DNA unless the cell is infected at a very high multiplicity of infection.

As another example, all or a portion of the C68 adenovirus delayed early gene E3 can be eliminated from the chimpanzee adenovirus sequence which forms a part of the recombinant virus.

Chimpanzee adenovirus C68 vectors can also be constructed having a deletion of the E4 gene. Still another vector can contain a deletion in the delayed early gene E2a.

Deletions can also be made in any of the late genes L1 through L5 of the chimpanzee C68 adenovirus genome. Similarly, deletions in the intermediate genes IX and IVa2 can be useful for some purposes. Other deletions may be made in the other structural or non-structural adenovirus genes.

The above discussed deletions can be used individually, i.e., an adenovirus sequence can contain deletions of E1 only. Alternatively, deletions of entire genes or portions thereof effective to destroy or reduce their biological activity can be used in any combination. For example, in one exemplary vector, the adenovirus C68 sequence can have deletions of the E1 genes and the E4 gene, or of the E1, E2a and E3 genes, or of the E1 and E3 genes, or of E1, E2a and E4 genes, with or without deletion of E3, and so on. As discussed above, such deletions can be used in combination with other mutations, such as temperature-sensitive mutations, to achieve a desired result.

The cassette comprising antigen(s) be inserted optionally into any deleted region of the chimpanzee C68 Ad virus. Alternatively, the cassette can be inserted into an existing gene region to disrupt the function of that region, if desired.

V.E.7. Helper Viruses

Depending upon the chimpanzee adenovirus gene content of the viral vectors employed to carry the antigen cassette, a helper adenovirus or non-replicating virus fragment can be used to provide sufficient chimpanzee adenovirus gene sequences to produce an infective recombinant viral particle containing the cassette.

Useful helper viruses contain selected adenovirus gene sequences not present in the adenovirus vector construct and/or not expressed by the packaging cell line in which the vector is transfected. A helper virus can be replication-defective and contain a variety of adenovirus genes in addition to the sequences described above. The helper virus can be used in combination with the E1-expressing cell lines described herein.

For C68, the “helper” virus can be a fragment formed by clipping the C terminal end of the C68 genome with SspI, which removes about 1300 bp from the left end of the virus. This clipped virus is then co-transfected into an E1-expressing cell line with the plasmid DNA, thereby forming the recombinant virus by homologous recombination with the C68 sequences in the plasmid.

Helper viruses can also be formed into poly-cation conjugates as described in Wu et al, J. Biol. Chem., 264:16985-16987 (1989); K. J. Fisher and J. M. Wilson, Biochem. J., 299:49 (Apr. 1, 1994). Helper virus can optionally contain a reporter gene. A number of such reporter genes are known to the art. The presence of a reporter gene on the helper virus which is different from the antigen cassette on the adenovirus vector allows both the Ad vector and the helper virus to be independently monitored. This second reporter is used to enable separation between the resulting recombinant virus and the helper virus upon purification.

V.E.8. Assembly of Viral Particle and Infection of a Cell Line

Assembly of the selected DNA sequences of the adenovirus, the antigen cassette, and other vector elements into various intermediate plasmids and shuttle vectors, and the use of the plasmids and vectors to produce a recombinant viral particle can all be achieved using conventional techniques. Such techniques include conventional cloning techniques of cDNA, in vitro recombination techniques (e.g., Gibson assembly), use of overlapping oligonucleotide sequences of the adenovirus genomes, polymerase chain reaction, and any suitable method which provides the desired nucleotide sequence. Standard transfection and co-transfection techniques are employed, e.g., CaPO4 precipitation techniques or liposome-mediated transfection methods such as lipofectamine. Other conventional methods employed include homologous recombination of the viral genomes, plaquing of viruses in agar overlay, methods of measuring signal generation, and the like.

For example, following the construction and assembly of the desired antigen cassette-containing viral vector, the vector can be transfected in vitro in the presence of a helper virus into the packaging cell line. Homologous recombination occurs between the helper and the vector sequences, which permits the adenovirus-antigen sequences in the vector to be replicated and packaged into virion capsids, resulting in the recombinant viral vector particles.

The resulting recombinant chimpanzee C68 adenoviruses are useful in transferring an antigen cassette to a selected cell. In in vivo experiments with the recombinant virus grown in the packaging cell lines, the E1-deleted recombinant chimpanzee adenovirus demonstrates utility in transferring a cassette to a non-chimpanzee, preferably a human, cell.

V.E.9. Use of the Recombinant Virus Vectors

The resulting recombinant chimpanzee C68 adenovirus containing the antigen cassette (produced by cooperation of the adenovirus vector and helper virus or adenoviral vector and packaging cell line, as described above) thus provides an efficient gene transfer vehicle which can deliver antigen(s) to a subject in vivo or ex vivo.

The above-described recombinant vectors are administered to humans according to published methods for gene therapy. A chimpanzee viral vector bearing an antigen cassette can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of antigen transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. The dosage will be adjusted to balance the therapeutic benefit against any side effects and such dosages may vary depending upon the therapeutic application for which the recombinant vector is employed. The levels of expression of antigen(s) can be monitored to determine the frequency of dosage administration.

Recombinant, replication defective adenoviruses can be administered in a “pharmaceutically effective amount”, that is, an amount of recombinant adenovirus that is effective in a route of administration to transfect the desired cells and provide sufficient levels of expression of the selected gene to provide a vaccinal benefit, i.e., some measurable level of protective immunity. C68 vectors comprising an antigen cassette can be co-administered with adjuvant. Adjuvant can be separate from the vector (e.g., alum) or encoded within the vector, in particular if the adjuvant is a protein. Adjuvants are well known in the art.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

The levels of immunity to antigen(s) can be monitored to determine the need, if any, for boosters. Following an assessment of antibody titers in the serum, for example, optional booster immunizations may be desired

VI. Therapeutic and Manufacturing Methods

Also provided is a method of stimulating a tumor specific immune response in a subject, vaccinating against a tumor, treating and/or alleviating a symptom of cancer in a subject by administering to the subject one or more antigens such as a plurality of antigens identified using methods disclosed herein.

Also provided is a method of stimulating an infectious disease organism-specific immune response in a subject, vaccinating against an infectious disease organism, treating and/or alleviating a symptom of an infection associated with an infectious disease organism in a subject by administering to the subject one or more antigens such as a plurality of antigens identified using methods disclosed herein.

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

In some aspects, a subject has been diagnosed with an infection or is at risk of an infection (e.g., age, geographical/travel, and/or work-related increased risk of or predisposition to an infection, or at risk to a seasonal and/or novel disease infection).

An antigen can be administered in an amount sufficient to stimulate a CTL response. An antigen can be administered in an amount sufficient to stimulate a T cell response. An antigen can be administered in an amount sufficient to stimulate a B cell response. An antigen can be administered in an amount sufficient to stimulate both a T cell response and a B cell response An antigen can be administered alone or in combination with other therapeutic agents. Therapeutic agents can include those that target an infectious disease organism, such as an anti-viral or antibiotic agent.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each antigen to be included in a vaccine composition and the optimum dosing regimen can be determined. For example, an antigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of antigens present in the composition is/are tissue, cancer, infectious disease, and/or patient-specific. For instance, the exact selection of peptides can be guided by expression patterns of the parent proteins in a given tissue or guided by mutation or disease status of a patient. The selection can be dependent on the specific type of cancer, the specific infectious disease (e.g. a specific infectious disease isolate/strain the subject is infected with or at risk for infection by), the status of the disease, the goal of the vaccination (e.g., preventative or targeting an ongoing disease), earlier treatment regimens, the immune status of the patient, and, of course, the HLA-haplotype of the patient. Furthermore, a vaccine can contain individualized components, according to personal needs of the particular patient. Examples include varying the selection of antigens according to the expression of the antigen in the particular patient or adjustments for secondary treatments following a first round or scheme of treatment.

A patient can be identified for administration of an antigen vaccine through the use of various diagnostic methods, e.g., patient selection methods described further below. Patient selection can involve identifying mutations in, or expression patterns of, one or more genes. Patient selection can involve identifying the infectious disease of an ongoing infection. Patient selection can involve identifying risk of an infection by an infectious disease. In some cases, patient selection involves identifying the haplotype of the patient. The various patient selection methods can be performed in parallel, e.g., a sequencing diagnostic can identify both the mutations and the haplotype of a patient. The various patient selection methods can be performed sequentially, e.g., one diagnostic test identifies the mutations and separate diagnostic test identifies the haplotype of a patient, and where each test can be the same (e.g., both high-throughput sequencing) or different (e.g., one high-throughput sequencing and the other Sanger sequencing) diagnostic methods.

For a composition to be used as a vaccine for cancer or an infectious disease, antigens with similar normal self-peptides that are expressed in high amounts in normal tissues can be avoided or be present in low amounts in a composition described herein. On the other hand, if it is known that the tumor or infected cell of a patient expresses high amounts of a certain antigen, the respective pharmaceutical composition for treatment of this cancer or infection can be present in high amounts and/or more than one antigen specific for this particularly antigen or pathway of this antigen can be included.

Compositions comprising an antigen can be administered to an individual already suffering from cancer or an infection. In therapeutic applications, compositions are administered to a subject in an amount sufficient to stimulate an effective CTL response to the tumor antigen or infectious disease organism antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when a cancer has metastasized or an infectious disease organism has induced organ damage and/or other immune pathology. In such cases, in view of the minimization of extraneous substances and the relative nontoxic nature of an antigen, it is possible and can be felt desirable by the treating physician to administer substantial excesses of these compositions.

For therapeutic use, administration can begin at the detection or surgical removal of tumors, or begin at the detection or treatment of an infection. This can be followed by boosting doses until at least symptoms are substantially abated and for a period thereafter, or immunity is considered to be provided (e.g., a memory B cell or T cell population, or antigen specific B cells or antibodies are produced).

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered at a site of surgical excision to stimulate a local immune response to a tumor. The compositions can be administered to target specific infected tissues and/or cells of a subject. Disclosed herein are compositions for parenteral administration which comprise a solution of the antigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Antigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the antigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired antigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); U.S. Pat. No. 5,279,833 Rose U.S. Pat. Nos. 5,279,833; 9,106,309WOAWO 91/06309; and Felgner et al., Proc. Natl. Acad. Sci. USA 84: 7413-7414 (1987).

Antigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more antigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41, Lu et al., Efficient identification of mutated cancer antigens recognized by T cells associated with durable tumor regressions, *Clin Cancer Res.* (2014) 20(13): 3401-10). Upon introduction into a host, infected cells express the antigens, and thereby stimulate a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vaccine vectors useful for therapeutic administration or immunization of antigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a vaccine, comprising performing the steps of a method disclosed herein; and producing a vaccine comprising a plurality of antigens or a subset of the plurality of antigens.

Antigens disclosed herein can be manufactured using methods known in the art. For example, a method of producing an antigen or a vector (e.g., a vector including at least one sequence encoding one or more antigens) disclosed herein can include culturing a host cell under conditions suitable for expressing the antigen or vector wherein the host cell comprises at least one polynucleotide encoding the antigen or vector, and purifying the antigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NSO cell, yeast, or a HEK293 cell. Host cells can be transformed with one or more polynucleotides comprising at least one nucleic acid sequence that encodes an antigen or vector disclosed herein, optionally wherein the isolated polynucleotide further comprises a promoter sequence operably linked to the at least one nucleic acid sequence that encodes the antigen or vector. In certain embodiments the isolated polynucleotide can be cDNA.

VII. Antigen Use and Administration

A vaccination protocol can be used to dose a subject with one or more antigens. A priming vaccine and a boosting vaccine can be used to dose the subject. Vaccination methods, protocols, and schedules that can be used include, but are not limited to, those described in international application publication WO2021092095, herein incorporated by reference for all purposes.

A priming vaccine, can be based on C68 (e.g., the sequences shown in SEQ ID NO:1 or 2) or SAM (e.g., the sequences shown in SEQ ID NO:3 or 4). A boosting vaccine can also be based on C68 (e.g., the sequences shown in SEQ ID NO:1 or 2) or SAM (e.g., the sequences shown in SEQ ID NO:3 or 4).

Each vector in a prime/boost strategy typically includes a cassette that includes antigens. Cassettes can include about 1-50 antigens, separated by spacers such as the natural sequence that normally surrounds each antigen or other non-natural spacer sequences such as AAY. Cassettes can also include MHCII antigens such a tetanus toxoid antigen and PADRE antigen, which can be considered universal class II antigens. Cassettes can also include a targeting sequence such as a ubiquitin targeting sequence. In addition, each vaccine dose can be administered to the subject in conjunction with (e.g., concurrently, before, or after) an immune modulator. Each vaccine dose can be administered to the subject in conjunction with (e.g., concurrently, before, or after) a checkpoint inhibitor (CPI). CPI's can include those that inhibit CTLA4, PD1, and/or PDL1 such as antibodies or antigen-binding portions thereof. Such antibodies can include tremelimumab or durvalumab. Each vaccine dose can be administered to the subject in conjunction with (e.g., concurrently, before, or after) a cytokine, such as IL-2, IL-7, IL-12 (including IL-12 p35, p40, p70, and/or p70-fusion constructs), IL-15, or IL-21. Each vaccine dose can be administered to the subject in conjunction with (e.g., concurrently, before, or after) a modified cytokine (e.g., pegIL-2).

A priming vaccine can be injected (e.g., intramuscularly) in a subject. Bilateral injections per dose can be used. For example, one or more injections of ChAdV68 (C68) can be used (e.g., total dose $1\times10^{12}$ viral particles); one or more injections of SAM vectors at low vaccine dose selected from the range 0.001 to 1 ug RNA, in particular 0.1 or 1 ug can be used; or one or more injections of SAM vectors at high vaccine dose selected from the range 1 to 100 ug RNA, in particular 10 or 100 ug can be used.

A vaccine boost (boosting vaccine) can be injected (e.g., intramuscularly) after prime vaccination. A boosting vaccine can be administered about every 1, 2, 3, 4, 5, 6, 7, 8, 9, or 10 weeks, e.g., every 4 weeks and/or 8 weeks after the prime. Bilateral injections per dose can be used. For example, one or more injections of ChAdV68 (C68) can be used (e.g., total dose $1\times10^{12}$ viral particles); one or more injections of SAM vectors at low vaccine dose selected from the range 0.001 to 1 ug RNA, in particular 0.1 or 1 ug can be used; or one or more injections of SAM vectors at high vaccine dose selected from the range 1 to 100 ug RNA, in particular 10 or 100 ug can be used.

Anti-CTLA-4 (e.g., tremelimumab) can also be administered to the subject. For example, anti-CTLA4 can be administered subcutaneously near the site of the intramuscular vaccine injection (ChAdV68 prime or SAM low doses) to ensure drainage into the same lymph node. Tremelimumab is a selective human IgG2 mAb inhibitor of CTLA-4. Target Anti-CTLA-4 (tremelimumab) subcutaneous dose is typically 70-75 mg (in particular 75 mg) with a dose range of, e.g., 1-100 mg or 5-420 mg.

In certain instances an anti-PD-L1 antibody can be used such as durvalumab (MEDI 4736). Durvalumab is a selective, high affinity human IgG1 mAb that blocks PD-L1 binding to PD-1 and CD80. Durvalumab is generally administered at 20 mg/kg i.v. every 4 weeks.

Immune monitoring can be performed before, during, and/or after vaccine administration. Such monitoring can inform safety and efficacy, among other parameters.

To perform immune monitoring, PBMCs are commonly used. PBMCs can be isolated before prime vaccination, and after prime vaccination (e.g. 4 weeks and 8 weeks). PBMCs can be harvested just prior to boost vaccinations and after each boost vaccination (e.g. 4 weeks and 8 weeks).

Immune responses, such as T cell responses and B cell responses, can be assessed as part of an immune monitoring protocol. For example, the ability of a vaccine composition described herein to stimulate an immune response can be monitored and/or assessed. As used herein, “stimulate an immune response” refers to any increase in a immune response, such as initiating an immune response (e.g., a priming vaccine stimulating the initiation of an immune response in a naïve subject) or enhancement of an immune response (e.g., a boosting vaccine stimulating the enhancement of an immune response in a subject having a pre-existing immune response to an antigen, such as a pre-existing immune response initiated by a priming vaccine). T cell responses can be measured using one or more methods known in the art such as ELISpot, intracellular cytokine staining, cytokine secretion and cell surface capture, T cell proliferation, MHC multimer staining, or by cytotoxicity assay. T cell responses to epitopes encoded in vaccines can be monitored from PBMCs by measuring induction of cytokines, such as IFN-gamma, using an ELISpot assay. Specific CD4 or CD8 T cell responses to epitopes encoded in vaccines can be monitored from PBMCs by measuring induction of cytokines captured intracellularly or extracellularly, such as IFN-gamma, using flow cytometry. Specific CD4 or CD8 T cell responses to epitopes encoded in the vaccines can be monitored from PBMCs by measuring T cell populations expressing T cell receptors specific for epitope/MHC class I complexes using MHC multimer staining. Specific CD4 or CD8 T cell responses to epitopes encoded in the vaccines can be monitored from PBMCs by measuring the ex vivo expansion of T cell populations following 3H-thymidine, bromodeoxyuridine and carboxyfluoresceine-diacetate-succinimidylester (CFSE) incorporation. The antigen recognition capacity and lytic activity of PBMC-derived T cells that are specific for epitopes encoded in vaccines can be assessed functionally by chromium release assay or alternative colorimetric cytotoxicity assays.

B cell responses can be measured using one or more methods known in the art such as assays used to determine B cell differentiation (e.g., differentiation into plasma cells), B cell or plasma cell proliferation, B cell or plasma cell activation (e.g., upregulation of costimulatory markers such as CD80 or CD86), antibody class switching, and/or antibody production (e.g., an ELISA). Antibodies can also be assessed for function, such as assessed for neutralizing ability.

Disease status of a subject can be monitored following administration of any of the vaccine compositions described herein. For example, disease status may be monitored using isolated cell-free DNA (cfDNA) from a subject. In addition, the efficacy of a vaccine therapy may be monitored using isolated cfDNA from a subject. cfDNA minotoring can include the steps of: a. isolating or having isolated cfDNA from a subject; b. sequencing or having sequenced the isolated cfDNA; c. determining or having determined a frequency of one or more mutations in the cfDNA relative to a wild-type germline nucleic acid sequence of the subject, and d. assessing or having assessed from step (c) the status of a disease in the subject. The method can also include, following step (c) above, d. performing more than one iteration of steps (a)-(c) for the given subject and comparing the frequency of the one or more mutations determined in the more than one iterations; and f. assessing or having assessed from step (d) the status of a disease in the subject. The more than one iterations can be performed at different time points, such as a first iteration of steps (a)-(c) performed prior to administration of the vaccine composition and a second iteration of steps (a)-(c) is performed subsequent to administration of the vaccine composition. Step (c) can include comparing: the frequency of the one or more mutations determined in the more than one iterations, or the frequency of the one or more mutations determined in the first iteration to the frequency of the one or more mutations determined in the second iteration. An increase in the frequency of the one or more mutations determined in subsequent iterations or the second iteration can be assessed as disease progression. A decrease in the frequency of the one or more mutations determined in subsequent iterations or the second iteration can be assessed as a response. In some aspects, the response is a Complete Response (CR) or a Partial Response (PR). A therapy can be administered to a subject following an assessment step, such as where assessment of the frequency of the one or more mutations in the cfDNA indicates the subject has the disease. The cfDNA isolation step can use centrifugation to separate cfDNA from cells or cellular debris. cfDNA can be isolated from whole blood, such as by separating the plasma layer, buffy coat, and red bloods. cfDNA sequencing can use next generation sequencing (NGS), Sanger sequencing, duplex sequencing, whole-exome sequencing, whole-genome sequencing, de novo sequencing, phased sequencing, targeted amplicon sequencing, shotgun sequencing, or combinations thereof, and may include enriching the cfDNA for one or more polynucleotide regions of interest prior to sequencing (e.g., polynucleotides known or suspected to encode the one or more mutations, coding regions, and/or tumor exome polynucleotides). Enriching the cfDNA may include hybridizing one or more polynucleotide probes, which may be modified (e.g., biotinylated), to the one or more polynucleotide regions of interest. In general, any number of mutations may be monitored simultaneously or in parallel.

VIII. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60) Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
|---|---|
| W6/32 | Class I HLA-A, B, C |
| L243 | Class II-HLA-DR |
| Tu36 | Class II-HLA-DR |
| LN3 | Class II-HLA-DR |
| Tu39 | Class II-HLA-DR, DP, DQ |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20C prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector with targeted method known as parallel reaction monitoring. In targeted PRM, specific peptide precursor ions are isolated in the Orbitrap detector and all resulting HCD fragmentation ions are scanned across the elution of the peptide peak. This enables both peptide identification and quantitation of endogenous peptide in the presence of a co-injected stabile isotopically labeled peptide standard.

MS2 spectra from each analysis are searched against a protein database using Comet (61, 62) and the peptide identification are scored using Percolator (63-65). Additional sequencing is performed using PEAKS studio (Bioinformatics Solutions Inc.) and other search engines or sequencing methods can be used including spectral matching and de novo sequencing (97). Targeted MS1 and MS2 spectra are processed through Skyline (104).

VIIIB.1. MS Limit of Detection Studies in Support of Comprehensive HLA Peptide Sequencing Using the peptide YVYVADVAAK it was determined what the limits of detection are using different amounts of peptide loaded onto the LC column. The amounts of peptide tested were 1 pmol, 100fmol, 10 fmol, 1 fmol, and 100amol. (Table 1) These results indicate that the lowest limit of detection (LoD) is in the attomol range ($10^{-18}$), that the dynamic range spans five orders of magnitude, and that the signal to noise appears sufficient for sequencing at low femtomol ranges ($10^{-15}$).

TABLE 1

| Peptide m/z | Loaded on Column | Copies/Cell in 1e9cells |
|---|---|---|
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

IX. Presentation Model

Presentation models can be used to identify likelihoods of peptide presentation in patients. Various presentation models are known to those skilled in the art, for example the presentation models described in more detail in U.S. Pat. No. 10,055,540, US Application Pub. No. US20200010849A1 and US20110293637, and international patent application publications WO/2018/195357, WO/2018/208856, and WO2016187508, each herein incorporated by reference, in their entirety, for all purposes.

X. Training Module

Training modules can be used to construct one or more presentation models based on training data sets that generate likelihoods of whether peptide sequences will be presented by MHC alleles associated with the peptide sequences. Various training modules are known to those skilled in the art, for example the presentation models described in more detail in U.S. Pat. No. 10,055,540, US Application Pub. No. US20200010849A1, and international patent application publications WO/2018/195357 and WO/2018/208856, each herein incorporated by reference, in their entirety, for all purposes. A training module can construct a presentation model to predict presentation likelihoods of peptides on a per-allele basis. A training module can also construct a presentation model to predict presentation likelihoods of peptides in a multiple-allele setting where two or more MHC alleles are present.

XI. Prediction Module

A prediction module can be used to receive sequence data and select candidate antigens in the sequence data using a presentation model. Specifically, the sequence data may be DNA sequences, RNA sequences, and/or protein sequences extracted from tumor tissue cells of patients, infected cells patients, or infectious disease organisms themselves. A prediction module may identify candidate neoantigens that are mutated peptide sequences by comparing sequence data extracted from normal tissue cells of a patient with the sequence data extracted from tumor tissue cells of the patient to identify portions containing one or more mutations. A prediction module may identify candidate antigens that are pathogen-derived peptides, virally-derived peptides, bacterially-derived peptides, fungally-derived peptides, and parasitically-derived peptides, such as by comparing sequence data extracted from normal tissue cells of a patient with the sequence data extracted from infected cells of the patient to identify portions containing one or more infectious disease organism associated antigens. A prediction module may identify candidate antigens that have altered expression in a tumor cell or cancerous tissue in comparison to a normal cell or tissue by comparing sequence data extracted from normal tissue cells of a patient with the sequence data extracted from tumor tissue cells of the patient to identify improperly expressed candidate antigens. A prediction module may identify candidate antigens that are expressed in an infected cell or infected tissue in comparison to a normal cell or tissue by comparing sequence data extracted from normal tissue cells of a patient with the sequence data extracted from infected tissue cells of the patient to identify expressed candidate antigens (e.g., identifying expressed polynucleotides and/or polypeptides specific to an infectious disease).

A presentation module can apply one or more presentation model to processed peptide sequences to estimate presentation likelihoods of the peptide sequences. Specifically, the prediction module may select one or more candidate antigen peptide sequences that are likely to be presented on tumor HLA molecules or infected cell HLA molecules by applying presentation models to the candidate antigens. In one implementation, the presentation module selects candidate antigen sequences that have estimated presentation likelihoods above a predetermined threshold. In another implementation, the presentation model selects the N candidate antigen sequences that have the highest estimated presentation likelihoods (where N is generally the maximum number of epitopes that can be delivered in a vaccine). A vaccine including the selected candidate antigens for a given patient can be injected into a subject to stimulate immune responses.

XI.B.Cassette Design Module

XI.B.1 Overview

A cassette design module can be used to generate a vaccine cassette sequence based on selected candidate peptides for injection into a patient. Various cassette design modules are known to those skilled in the art, for example the cassette design modules described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

A set of therapeutic epitopes may be generated based on the selected peptides determined by a prediction module associated with presentation likelihoods above a predetermined threshold, where the presentation likelihoods are determined by the presentation models. However it is appreciated that in other embodiments, the set of therapeutic epitopes may be generated based on any one or more of a number of methods (alone or in combination), for example, based on binding affinity or predicted binding affinity to HLA class I or class II alleles of the patient, binding stability or predicted binding stability to HLA class I or class II alleles of the patient, random sampling, and the like.

Therapeutic epitopes may correspond to selected peptides themselves. Therapeutic epitopes may also include C- and/or N-terminal flanking sequences in addition to the selected peptides. N- and C-terminal flanking sequences can be the native N- and C-terminal flanking sequences of the therapeutic vaccine epitope in the context of its source protein. Therapeutic epitopes can represent a fixed-length epitope Therapeutic epitopes can represent a variable-length epitope, in which the length of the epitope can be varied depending on, for example, the length of the C- or N-flanking sequence. For example, the C-terminal flanking sequence and the N-terminal flanking sequence can each have varying lengths of 2-5 residues, resulting in 16 possible choices for the epitope.

A cassette design module can also generate cassette sequences by taking into account presentation of junction epitopes that span the junction between a pair of therapeutic epitopes in the cassette. Junction epitopes are novel non-self but irrelevant epitope sequences that arise in the cassette due to the process of concatenating therapeutic epitopes and linker sequences in the cassette. The novel sequences of junction epitopes are different from the therapeutic epitopes of the cassette themselves.

A cassette design module can generate a cassette sequence that reduces the likelihood that junction epitopes are presented in the patient. Specifically, when the cassette is injected into the patient, junction epitopes have the potential to be presented by HLA class I or HLA class II alleles of the patient, and stimulate a CD8 or CD4 T-cell response, respectively. Such reactions are often times undesirable because T-cells reactive to the junction epitopes have no therapeutic benefit, and may diminish the immune response to the selected therapeutic epitopes in the cassette by antigenic competition.[76]

A cassette design module can iterate through one or more candidate cassettes, and determine a cassette sequence for which a presentation score of junction epitopes associated with that cassette sequence is below a numerical threshold. The junction epitope presentation score is a quantity associated with presentation likelihoods of the junction epitopes in the cassette, and a higher value of the junction epitope presentation score indicates a higher likelihood that junction epitopes of the cassette will be presented by HLA class I or HLA class II or both.

In one embodiment, a cassette design module may determine a cassette sequence associated with the lowest junction epitope presentation score among the candidate cassette sequences.

A cassette design module may iterate through one or more candidate cassette sequences, determine the junction epitope presentation score for the candidate cassettes, and identify an optimal cassette sequence associated with a junction epitope presentation score below the threshold.

A cassette design module may further check the one or more candidate cassette sequences to identify if any of the junction epitopes in the candidate cassette sequences are self-epitopes for a given patient for whom the vaccine is being designed. To accomplish this, the cassette design module checks the junction epitopes against a known database such as BLAST. In one embodiment, the cassette design module may be configured to design cassettes that avoid junction self-epitopes.

A cassette design module can perform a brute force approach and iterate through all or most possible candidate cassette sequences to select the sequence with the smallest junction epitope presentation score. However, the number of such candidate cassettes can be prohibitively large as the capacity of the vaccine increases. For example, for a vaccine capacity of 20 epitopes, the cassette design module has to iterate through ~$10^{18}$ possible candidate cassettes to determine the cassette with the lowest junction epitope presentation score. This determination may be computationally burdensome (in terms of computational processing resources required), and sometimes intractable, for the cassette design module to complete within a reasonable amount of time to generate the vaccine for the patient. Moreover, accounting for the possible junction epitopes for each candidate cassette can be even more burdensome. Thus, a cassette design module may select a cassette sequence based on ways of iterating through a number of candidate cassette sequences that are significantly smaller than the number of candidate cassette sequences for the brute force approach.

A cassette design module can generate a subset of randomly or at least pseudo-randomly generated candidate cassettes, and selects the candidate cassette associated with a junction epitope presentation score below a predetermined threshold as the cassette sequence. Additionally, the cassette design module may select the candidate cassette from the subset with the lowest junction epitope presentation score as the cassette sequence. For example, the cassette design module may generate a subset of ~1 million candidate cassettes for a set of 20 selected epitopes, and select the candidate cassette with the smallest junction epitope presentation score. Although generating a subset of random cassette sequences and selecting a cassette sequence with a low junction epitope presentation score out of the subset may be sub-optimal relative to the brute force approach, it requires significantly less computational resources thereby making its implementation technically feasible. Further, performing the brute force method as opposed to this more efficient technique may only result in a minor or even negligible improvement in junction epitope presentation score, thus making it not worthwhile from a resource allocation perspective. A cassette design module can determine an improved cassette configuration by formulating the epitope sequence for the cassette as an asymmetric traveling salesman problem (TSP). Given a list of nodes and distances between each pair of nodes, the TSP determines a sequence of nodes associated with the shortest total distance to visit each node exactly once and return to the original node. For example, given cities A, B, and C with known distances between each other, the solution of the TSP generates a closed sequence of cities, for which the total distance traveled to visit each city exactly once is the smallest among possible routes. The asymmetric version of the TSP determines the optimal sequence of nodes when the distance between a pair of nodes are asymmetric. For example, the “distance” for traveling from node A to node B may be different from the “distance” for traveling from node B to node A. By solving for an improved optimal cassette using an asymmetric TSP, the cassette design module can find a cassette sequence that results in a reduced presentation score across the junctions between epitopes of the cassette. The solution of the asymmetric TSP indicates a sequence of therapeutic epitopes that correspond to the order in which the epitopes should be concatenated in a cassette to minimize the junction epitope presentation score across the junctions of the cassette. A cassette sequence determined through this approach can result in a sequence with significantly less presentation of junction epitopes while potentially requiring significantly less computational resources than the random sampling approach, especially when the number of generated candidate cassette sequences is large. Illustrative examples of different computational approaches and comparisons for optimizing cassette design are described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

An illustrative non-limiting cassette of concantenated KRAS-associated MHC class I neoepitopes that are linked through their native flanking sequences, includes 4 iterations for each of the KRAS neoepitopes having the mutations KRAS G12C, KRAS G12D, KRAS G12V, and KRAS Q61H, and has been ordered to minimize potential junctional epitopes is represented by the amino acid sequence shown in SEQ ID NO: 65 and having the order of KRAS-associated neoepitopes: G12C G12D Q61H G12D G12V G12C Q61H G12D G12V G12C Q61H G12D G12V Q61H G12V G12C.

Shared (neo)antigen sequences for inclusion in a shared antigen vaccine and appropriate patients for treatment with such vaccine can be chosen by one of skill in the art, e.g., as described in U.S. application Ser. No. 17/058,128, herein incorporated by reference for all purposes. Mass spectrometry (MS) validation of candidate shared (neo)antigens can performed as part of the selection process.

XIII. Example Computer

A computer can be used for any of the computational methods described herein. One skilled in the art will recognize a computer can have different architectures. Examples of computers are known to those skilled in the art, for example the computers described in more detail in U.S. Pat. No. 10,055,540, US Application Pub. No. US20200010849A1, and international patent application publications WO/2018/195357 and WO/2018/208856, each herein incorporated by reference, in their entirety, for all purposes.

XIV. Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* 3rd *Ed.* (Plenum Press) Vols A and B(1992).

XIV.A. Evaluation of Cassettes with Repeated Neoepitopess and/or Removal of Immunodominant Neoepitopes Overview Through vaccination, multiple class I MHC restricted neoantigens that stimulate the corresponding cellular immune response(s) can be delivered. Several vaccine cassettes were engineered to encode multiple neoepitopes, specifically multiple distinct KRAS-associated neoepitopes, as a single gene product where the epitopes were embedded within their natural, surrounding peptide sequence. Various cassettes designs feature multiple copies (i.e., iterations) of one or more neoepitopes. Various cassettes designs also feature removing immunodominant neoepitopes.

XIV.B. Repeated Neoepitopes and/or Removal of Immunodominant Neoepitopes Evaluation Materials and Methods Antigens The epitope-containing 25mer amino acid sequences (i.e., epitope flanked by native N and C terminal amino acid linkers) used in the examples below are presented in Table 2A were used as described below. The antigen-encoding sequences of the cassettes for the various constructs were constructed by directly linking each 25mer sequence to each other (i.e., no additional amino acids in between consecutive 25mer sequences) in the order and number described in the examples below, e.g., see FIGS. 1A, 2A, 3A, and 4A. The cassettes containing the full-length antigen-encoding sequences containing the multiple distinct epitopes linked together, as well as universal MHC class II antigens tetanus toxoid and PADRE (bolded sequence), are presented in Table 2B. The complete exogenous nucleotide insertions into the vectors include from 5' to 3': a Kozak sequence (GCCACC), nucleotides encoding three amino acids MAG (ATGGCCGGG), one of the cassette sequences of Table 2B, and two stop codons (TAATGA). Further cassettes were generated with 4 iterations of individual KRAS mutations G12V, G12C, and G12D (i.e., separate concatemers of SEQ ID NOs 57, 58, or 59).

TABLE 2A

25mer Neoepitope Containing Sequences

| Antigen Name | 25mer Sequence | SEQ ID NO: |
|---|---|---|
| KRAS G12C | MTEYKLVVVGACGVGKSALTIQLIQ | 57 |
| KRAS G12D | MTEYKLVVVGADGVGKSALTIQLIQ | 58 |
| KRAS G12V | MTEYKLVVVGAVGVGKSALTIQLIQ | 59 |
| KRAS Q61H | ETCLLDILDTAGHEEYSAMRDQYMR | 60 |
| TP53 R213L | LRVEYLDDRNTFLHSVVVPYEPPEV | 61 |
| TP53 S127Y | HSGTAKSVTCTYYPALNKMFCQLAK | 62 |

TABLE 2B

Full-Length Multi-Neoepitope Sequences in Cassettes 1x (20 × 1) Cassette (SEQ ID NO: 63)

MTEYKLVVVGAGDVGKSALTIQLIQETCLLDILDTAGKEEYSAMRDQYMR
MCNSSCMGGMNRMPILTIITLEDSSSGIHSGATTTAPPLSGKGNPEEEDV
SGIHSGATTTAPFLSGKGNPEEEDVEILDEAYVMAYVMAGVGSPYVSRLL
MTEYKLVVVGADGVGKSALTIQLIQETCLLDILDTAGREEYSAMRDQYMR
SYLDSGIHSGATATAPSLSGKGNPEKSVTCTYSPALNNMFCQLAKTCPVQ
MTEYKLVVVGAAGVGKSALTIQLIQETCLLDILDTAGLEEYSAMRDQYMR
LRVEYLDDRNTFLHSVVVPYEPPEVDGQITVGQRIGSVSFGTVYKGKWHG
MTEYKLVVVGAVGVGKSALTIQLIQETCLLDILDTAGHEEYSAMRDQYMR
WQQQSYLDSGIHFGATTTAPSLSGKHSGTAKSVTCTYYPALNKMFCQLAK
KSVTCTYSPALNEMFCQLAKTCPVQMTEYKLVVVGACGVGKSALTIQLIQ
GPGPGAKFVAAWTLKAAAGPGPGQYIKANSKFIGITELGPGPG

ERAS 2X (8 × 2) Cassette (SEQ ID NO: 64)

MTEYKLVVVGACGVGKSALTIQLIQETCLLDILDTAGHEEYSAMRDQYMR
MTEYKLVVVGAGDVGKSALTIQLIQETCLLDILDTAGREEYSAMRDQYMR
MTEYKLVVVGADGVGKSALTIQLIQETCLLDILDTAGLEEYSAMRDQYMR
MTEYKLVVVGAVGVGKSALTIQLIQETCLLDILDTAGKEEYSAMRDQYMR
MTEYKLVVVGACGVGKSALTIQLIQETCLLDILDTAGKEEYSAMRDQYMR
MTEYKLVVVGAGDVGKSALTIQLIQETCLLDILDTAGHEEYSAMRDQYMR
MTEYKLVVVGAVGVGKSALTIQLIQETCLLDILDTAGREEYSAMRDQYMR
MTEYKLVVVGADGVGKSALTIQLIQETCLLDILDTAGLEEYSAMRDQYMR
GPGPGAKFVAAWTLKAAAGPGPGQYIKANSKFIGITELGPGPG

ERAS 4X (4 × 4) Cassette (SEQ ID NO: 65)

MTEYKLVVVGACGVGKSALTIQLIQMTEYKLVVVGADGVGKSALTIQLIQ
ETCLLDILDTAGHEEYSAMRDQYMRMTEYKLVVVGADGVGKSALTIQLIQ
MTEYKLVVVGAVGVGKSALTIQLIQMTEYKLVVVGACGVGKSALTIQLIQ
ETCLLDILDTAGHEEYSAMRDQYMRMTEYKLVVVGADGVGKSALTIQLIQ
MTEYKLVVVGAVGVGKSALTIQLIQMTEYKLVVVGACGVGKSALTIQLIQ
ETCLLDILDTAGHEEYSAMRDQYMRMTEYKLVVVGADGVGKSALTIQLIQ
MTEYKLVVVGAVGVGKSALTIQLIQETCLLDILDTAGHEEYSAMRDQYMR
MTEYKLVVVGAVGVGKSALTIQLIQMTEYKLVVVGACGVGKSALTIQLIQ
GPGPGAKFVAAWTLKAAAGPGPGQYIKANSKFIGITELGPGPG

TABLE 2B-continued

Full-Length Multi-Neoepitope Sequences in Cassettes

ERAS 4 × 1 Cassette (SEQ ID NO: 66)

MTEYKLVVVGACGVGKSALTIQLIQMTEYKLVVVGADGVGKSALTIQLIQ
ETCLLDILDTAGHEEYSAMRDQYMRMTEYKLVVVGAVGVGKSALTIQLIQ
GPGPGAKFVAAWTLKAAAGPGPGQYIKANSKFIGITELGPGPG

ERAS 4 × 1 + R213L Cassette (SEQ ID NO: 67)

MTEYKLVVVGACGVGKSALTIQLIQMTEYKLVVVGADGVGKSALTIQLIQ
ETCLLDILDTAGHEEYSAMRDQYMRMTEYKLVVVGAVGVGKSALTIQLIQ
LRVEYLDDRNTFLHSVVVPYEPPEVGPGPGAKFVAA
WTLKAAAGPGPGQYIKANSKFIGITELGPGPG

KRAS 4 × 1 + S127Y Cassette (SEQ ID NO: 68)

MTEYKLVVVGACGVGKSALTIQLIQMTEYKLVVVGADGVGKSALTIQLIQ
ETCLLDILDTAGHEEYSAMRDQYMRMTEYKLVVVGAVGVGKSALTIQLIQ
HSGTAKSVTCTYYPALNKMFCQLAKGPGPGAKFVAA
WTLKAAAGPGPGQYIKANSKFIGITELGPGPG

Adenoviral Vectors

A modified ChAdV68 vector for the antigen expression system was generated based on AC_000011.1 with E1 (nt 577 to 3403) and E3 (nt 27,125-31,825) sequences deleted and the corresponding ATCC VR-594 (Independently sequenced Full-Length VR-594 C68 SEQ ID NO:10) nucleotides substituted at five positions. The full-length ChAdVC68 AC_000011.1 sequence with corresponding ATCC VR-594 nucleotides substituted at five positions is referred to as "ChAdV68.5WTnt" (SEQ ID NO:1). Antigen cassettes under the control of the CMV promoter/enhancer were inserted in place of deleted E1 sequences. A representative ChAdV68 vector containing 20 model antigens in an antigen cassette is "ChAdV68.5WTnt.MAG25mer" (SEQ ID NO:2). The vectors featuring antigen cassettes described below having the MAG25mer cassette can be replaced by the antigen cassettes described above, e.g., in Table 2B.

Adenoviral Production in 293F Cells

ChAdV68 virus production was performed in 293F cells grown in 293 FreeStyle™ (ThermoFisher) media in an incubator at 8% C02. On the day of infection cells were diluted to $10^6$ cells per mL, with 98% viability and 400 mL were used per production run in 1 L Shake flasks (Corning). 4 mL of the tertiary viral stock with a target MOI of >3.3 was used per infection. The cells were incubated for 48-72 h until the viability was <70% as measured by Trypan blue. The infected cells were then harvested by centrifugation, full speed bench top centrifuge and washed in 1×PBS, re-centrifuged and then re-suspended in 20 mL of 10 mM Tris pH7.4. The cell pellet was lysed by freeze thawing 3× and clarified by centrifugation at 4,300×g for 5 minutes.

Adenoviral Purification by CsCl Centrifugation

Viral DNA was purified by CsCl centrifugation. Two discontinuous gradient runs were performed. The first to purify virus from cellular components and the second to further refine separation from cellular components and separate defective from infectious particles.

10 mL of 1.2 (26.8 g CsCl dissolved in 92 mL of 10 mM Tris pH 8.0) CsCl was added to polyallomer tubes. Then 8 mL of 1.4 CsCl (53 g CsCl dissolved in 87 mL of 10 mM Tris pH 8.0) was carefully added using a pipette delivering to the bottom of the tube. The clarified virus was carefully layered on top of the 1.2 layer. If needed more 10 mM Tris was added to balance the tubes. The tubes were then placed in a SW-32Ti rotor and centrifuged for 2 h 30 min at 10° C. The tube was then removed to a laminar flow cabinet and the virus band pulled using an 18 gauge needle and a 10 mL syringe. Care was taken not to remove contaminating host cell DNA and protein. The band was then diluted at least 2× with 10 mM Tris pH 8.0 and layered as before on a discontinuous gradient as described above. The run was performed as described before except that this time the run was performed overnight. The next day the band was pulled with care to avoid pulling any of the defective particle band. The virus was then dialyzed using a Slide-a-Lyzer™ Cassette (Pierce) against ARM buffer (20 mM Tris pH 8.0, 25 mM NaCl, 2.5% Glycerol). This was performed 3×, 1 h per buffer exchange. The virus was then aliquoted for storage at −80° C.

Adenoviral Viral Assays

VP concentration was performed by using an OD 260 assay based on the extinction coefficient of $1.1\times10^{12}$ viral particles (VP) is equivalent to an Absorbance value of 1 at OD260 nm. Two dilutions (1:5 and 1:10) of adenovirus were made in a viral lysis buffer (0.1% SDS, 10 mM Tris pH 7.4, 1 mM EDTA). OD was measured in duplicate at both dilutions and the VP concentration/mL was measured by multiplying the OD260 value X dilution factor X $1.1\times10^{12}$VP.

An infectious unit (IU) titer was calculated by a limiting dilution assay of the viral stock. The virus was initially diluted 100× in DMEM/5% NS/1× PS and then subsequently diluted using 10-fold dilutions down to $1\times10^{-7}$. 100 µL of these dilutions were then added to 293A cells that were seeded at least an hour before at 3e5 cells/well of a 24 well plate. This was performed in duplicate. Plates were incubated for 48 h in a CO2 (5%) incubator at 37° C. The cells were then washed with 1×PBS and were then fixed with 100% cold methanol (−20° C.). The plates were then incubated at −20° C. for a minimum of 20 minutes. The wells were washed with 1×PBS then blocked in 1×PBS/0.1% BSA for 1 h at room temperature. A rabbit anti-Ad antibody (Abcam, Cambridge, Mass.) was added at 1:8,000 dilution in blocking buffer (0.25 ml per well) and incubated for 1 h at room temperature. The wells were washed 4× with 0.5 mL PBS per well. A HRP conjugated Goat anti-Rabbit antibody (Bethyl Labs, Montgomery Texas) diluted 1000× was added per well and incubated for 1 h prior to a final round of washing. 5 PBS washes were performed and the plates were developed using DAB (Diaminobenzidine tetrahydrochloride) substrate in Tris buffered saline (0.67 mg/mL DAB in 50 mM Tris pH 7.5, 150 mM NaCl) with 0.01% $H_2O_2$. Wells were developed for 5 min prior to counting. Cells were counted under a 10× objective using a dilution that gave between 4-40 stained cells per field of view. The field of view that was used was a 0.32 $mm^2$ grid of which there are equivalent to 625 per field of view on a 24 well plate. The number of infectious viruses/mL can be determined by the number of stained cells per grid multiplied by the number of grids per field of view multiplied by a dilution factor 10. Similarly, when working with GFP expressing cells florescent can be used rather than capsid staining to determine the number of GFP expressing virions per mL.

SAM Vectors

A RNA alphavirus backbone for the antigen expression system was generated from a self-replicating Venezuelan Equine Encephalitis (VEE) virus (Kinney, 1986, Virology 152: 400-413) by deleting the structural proteins of VEE located 3' of the 26S sub-genomic promoter (VEE sequences 7544 to 11,175 deleted; numbering based on Kinney et al 1986; SEQ ID NO:6). To generate the self-amplifying mRNA ("SAM") vector, the deleted sequences are replaced by antigen sequences. A representative SAM vector containing 20 model antigens is "VEE-MAG25mer" (SEQ ID NO:4). The vectors featuring the antigen cassettes described having the MAG25mer cassette can be replaced by the SARS-CoV-2 cassettes and/or full-length proteins described herein.

In Vitro Transcription to Generate SAM

For in vivo studies: SAM vectors were generated as "AU-SAM" vectors. A modified T7 RNA polymerase promoter (TAATACGACTCACTATA), which lacks the canonical 3' dinucleotide GG, was added to the 5' end of the SAM vector to generate the in vitro transcription template DNA (e.g., the sequence set forth in SEQ ID NO:6; SAM with 7544 to 11,175 deleted without an inserted antigen cassette). Reaction conditions are described below:

1× transcription buffer (40 mM Tris-HCL [pH7.9], 10 mM dithiothreitol, 2 mM spermidine, 0.002% Triton X-100, and 27 mM magnesium chloride) using final concentrations of 1× T7 RNA polymerase mix (E2040S); 0.025 mg/mL DNA transcription template (linearized by restriction digest); 8 mM CleanCap Reagent AU (Cat. No. N-7114) and 10 mM each of ATP, cytidine triphosphate (CTP), GTP, and uridine triphosphate (UTP)

Transcription reactions were incubated at 37° C. for 2 hr and treated with final 2 U DNase I (AM2239)/0.001 mg DNA transcription template in DNase I buffer for 1 hr at 37° C.

SAM was purified by RNeasy Maxi (QIAGEN, 75162)

Alternatively to co-transcriptional addition of a 5' cap structure, a 7-methylguanosine or a related 5' cap structure can be enzymatically added following transcription using a vaccinia capping system (NEB Cat. No. M2080) containing mRNA 2'-O-methyltransferase and S-Adenosyl methionine.

Immunizations

For ChAdV68 vaccines, transgenic mice expressing a chimeric HLA-A11:01 (Taconic Model #9660-[CB6F1-Tg (HLA-A*1101/H2-Kb)A11.01]) were injected with $8\times10^{10}$ viral particles (VP) or $5\times10^{10}$ VP, as indicated, in 100 µL volume, bilateral intramuscular injection (50 µL per leg).

For SAM vaccines, 10 µg of RNA-LNP complexes in 100 µL volume were administered as a bilateral intramuscular injection (50 µL per leg).

Splenocyte Dissociation

Splenocytes were isolated 14 days post-immunization. Spleens for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM NH4Cl, 10 mM $KHCO_3$, 0.1 mM Na2EDTA). Cells were filtered again through a 30 micron filter and then resuspended in complete RPMI. Cells were counted on the Cytoflex LX (Beckman Coulter) using propidium iodide staining to exclude dead and apoptotic cells. Cell were then adjusted to the appropriate concentration of live cells for subsequent analysis.

Ex Vivo Enzyme-Linked Immunospot (ELISpot) Analysis

ELISPOT analysis was performed according to ELISPOT harmonization guidelines {DOI: 10.1038/nprot.2015.068} with the mouse IFNg ELISpotPLUS kit (MABTECH). $1\times10^5$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XIV.C. Repeated Neopitope Evaluation Results

Vaccine efficacy with cassettes having repeated (i.e., iterated) neoepitopes was compared against cassettes having only a single copy of a given neoepitope. Mice engineered to express human HLA-A11:01 were immunized with $8\times10^{10}$ VP using the ChAdV68 delivery vectors described below and efficacy was assessed by IFNγ ELISpot.

Figure 1A:
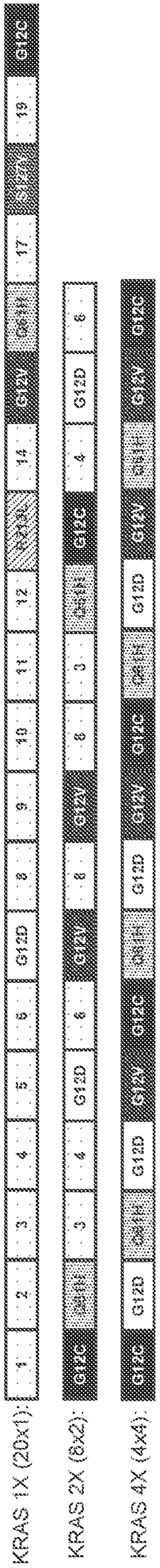
FIG. 1A presents an illustration of cassettes featuring either a single copy of KRAS neoepitopes G12C, G12V, G12D, and Q61H ("KRAS 1× (20×1)"; cassette=SEQ ID NO: 63), 2 repeats of the KRAS G12C, G12V, G12D, and Q61H neoepitopes and 2 repeats of additional KRAS neoepitopes ("KRAS 2× (8×2)"; cassette=SEQ ID NO: 64), or 4 repeats of the KRAS neoepitopes ("KRAS 4× (4×4)"; cassette=SEQ ID NO: 65). Numerical identifiers are in reference to the epitope "slot" relative to each cassette respectively and not across cassette designs (e.g., the slot "3" epitope in the 20×1 cassette is not the same as the epitope in slot 3 of the 8×2 cassette).

As illustrated in FIG. 1A, a series of ChAdV68 delivery vectors were designed to assess efficacy of cassettes featuring either a single copy of KRAS neoepitopes G12C, G12V, G12D, and Q61H ("KRAS 1× (20×1)"; cassette=SEQ ID NO: 63), 2 repeats of the KRAS G12C, G12V, G12D, and Q61H neoepitopes and 2 repeats of additional KRAS neoepitopes ("KRAS 2× (8×2)"; cassette=SEQ ID NO: 64), or 4 repeats of the KRAS neoepitopes ("KRAS 4× (4×4)"; cassette=SEQ ID NO: 65). HLA-A11:01 was previously predicted to present KRAS G12C, G12V, and G12D neoepitopes (data not shown).

Figure 1B:
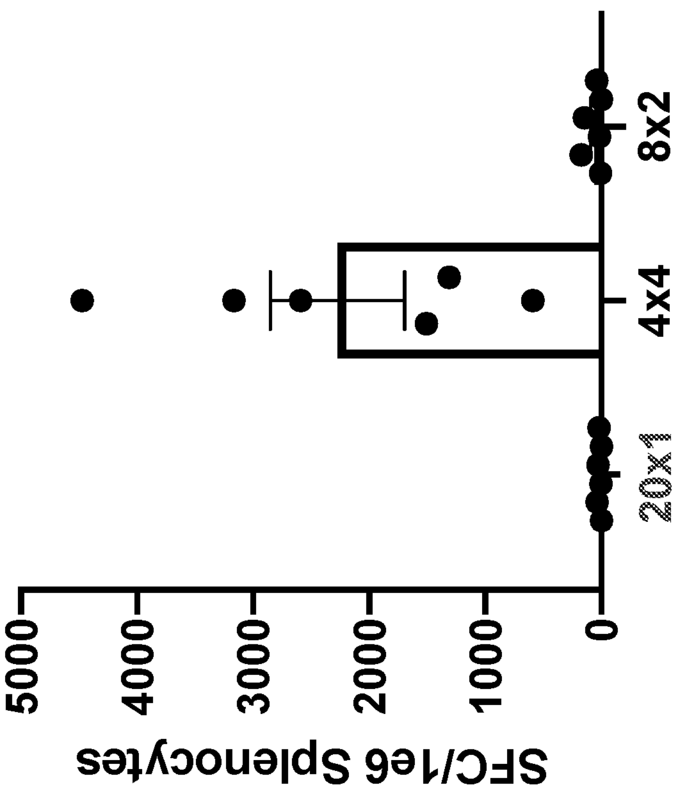
FIG. 1B demonstrates repeating epitopes increases vaccine induced antigen-specific T-cell response. Shown are ELISpot results for the repeated neoepitope KRAS G12C. Mice engineered to express human HLA-A11:01 were immunized with $8\times10^{10}$ VP using the ChAdV68 delivery vectors indicated and splenocytes isolated 14 days post-immunization. The number of antigen-specific T-cells were measured by IFNg ELISpot following overnight stimulation with VVVGACGVGK (SEQ ID NO: 75). Data presented as spot forming colonies (SFC) per $1\times10^6$ splenocytes for each animal. Bar represents the median.

As shown in FIG. 1B and presented in Table 3, vaccination with vectors featuring multiple repeats of the neoepitopes demonstrated increased spot forming colonies (SFC), indicating repetition of epitope-encoding sequences in a cassette led to an increased antigen-specific immune response against KRAS neoepitope G12C. However, upon further observation that there was a response to the G12C peptide with the G12V 1×4 cassette (only expressing G12V) and none with the G12C 1×4 cassette (only expressing G12C), the observed response to the G12C peptide with the 4×4 cassette was likely driven by the G12V epitope. Mass spec analysis confirmed that the G12C peptide was contaminated with G12V peptide.

Figure 1C:
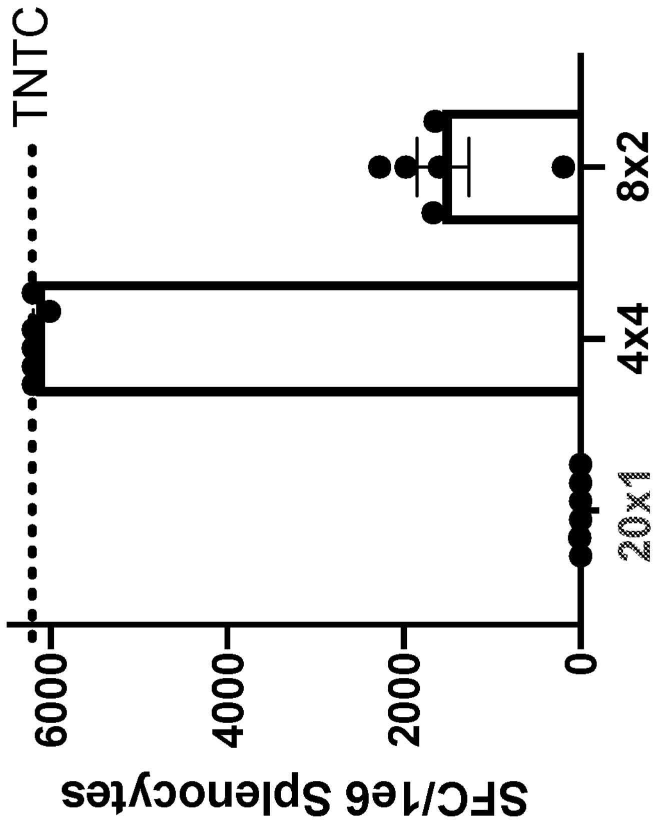
FIG. 1C demonstrates repeating epitopes increases vaccine induced antigen-specific T-cell response. Shown are ELISpot results for the repeated neoepitope KRAS G12V. Mice engineered to express human HLA-A11:01 were immunized with $8\times10^{10}$ VP using the ChAdV68 delivery vectors indicated and splenocytes isolated 14 days post-immunization. The number of antigen-specific T-cells were measured by IFNg ELISpot following overnight stimulation with VVVGAVGVGK (SEQ ID NO: 81). Data presented as spot forming colonies (SFC) per $1\times10^6$ splenocytes for each animal. Bar represents the median. Dashed line represent samples that were too numerous to count (TNTC).
Figure 1D:
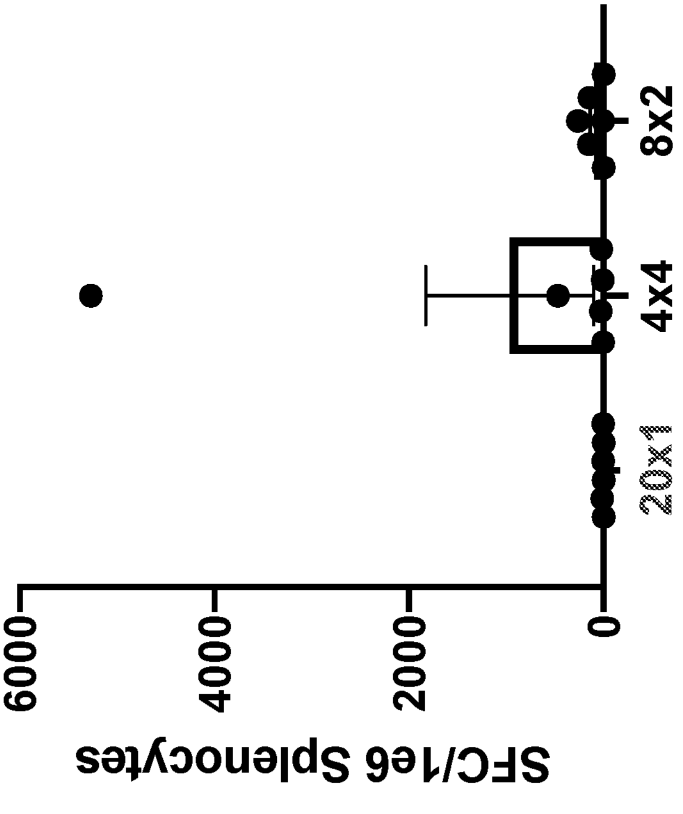
FIG. 1D demonstrates repeating epitopes increases vaccine induced antigen-specific T-cell response. Shown are ELISpot results for the repeated neoepitope KRAS G12D. Mice engineered to express human HLA-A11:01 were immunized with $8\times10^{10}$ VP using the ChAdV68 delivery vectors indicated and splenocytes isolated 14 days post-immunization. The number of antigen-specific T-cells were measured by IFNg ELISpot following overnight stimulation with VVVGADGVGK (SEQ ID NO: 78). Data presented as spot forming colonies (SFC) per $1\times10^6$ splenocytes for each animal. Bar represents the median.

As shown in FIG. 1C and FIG. 1D and presented in Table 3A, vaccination with vectors featuring multiple repeats of the neoepitopes demonstrated increased spot forming colonies (SFC), indicating repetition of epitope-encoding sequences in a cassette led to an increased antigen-specific immune response against KRAS neoepitopes, specifically G12V and G12D neoepitopes, using a ChAdV68 delivery system.

TABLE 3

ELISpot data for KRAS Neoepitopes G12C, G12V, and G12D +/− Repetition

| Antigen | G12C | | G12V | | G12D | |
|---|---|---|---|---|---|---|
| Cassette | Mean | +/− SE | Mean | +/− SE | Mean | +/− SE |
| 20x1 | 17 | 7 | 3 | 2 | 5 | 3 |
| 4x4 | 2277+ | 580 | 6169* | 31 | 970 | 864 |
| 8x2 | 66 | 31 | 1563 | 293 | 97 | 45 |

*5/6 samples were too numerous to count (max value 6200)
+likely due to contamination with G12V XIV.D. Immunodominant Epitope Removal Evaluation Results Vaccine efficacy with cassettes having a potentially immunodominant TP53 neoepitope capable of stimulating an immune response was compared against cassettes without a TP53 neoepitope capable of stimulating an immune response. Mice engineered to express human HLA-A11:01 were immunized with $5\times10^{10}$ VP using the ChAdV68 delivery vectors described below and efficacy was assessed by ELISpot. HLA-A11:01 was previously predicted to present KRAS G12C, G12V, G12D, and TP53 S127Y neoepitopes (data not shown).

As illustrated in FIG. 2A, a series of ChAdV68 delivery vectors were designed to assess immunodominance of a TP53 epitope. Vector containing only KRAS neoepitopes G12C, G12V, G12D, and Q61H ("KRAS 4×1"; cassette=SEQ ID NO: 66), KRAS neoepitopes in combination with a TP53 R213L neoepitope considered unable to stimulate an immune response in the HLA-A11:01 mouse model as it is predicted to be presented by human HLA-A02:01 and not HLA-A11:01 ("KRAS 4×1+R213L"; cassette=SEQ ID NO: 67), or KRAS neoepitopes in combination with a TP53 S127Y neoepitope predicted to be presented by HLA-A11:01 ("KRAS 4×1+S127Y"; cassette=SEQ ID NO: 68).

As shown in FIG. 2B and presented in Table 4, vaccination with vectors including the immunogenic TP53 S127Y epitope demonstrated reduced spot forming colonies (SFC) for KRAS epitope G12C relative to vectors not including a TP53 neoepitope ("4×1") or including a non-immunogenic TP53 neoepitope ("4×1+R213L"), indicating presence of the TP53 S127Y neoepitope in the vaccine cassette acts as an immunodominant neoepitope decreasing KRAS-specific T cell responses. However, upon further observation that there was a response to the G12C peptide with the G12V 1×4 cassette (only expressing G12V) and none with the G12C 1×4 cassette (only expressing G12C), the observed response to the G12C peptide with the 4×4 cassette was likely driven by the G12V epitope. Mass spec analysis confirmed that the G12C peptide was contaminated with G12V peptide.

As shown in FIGS. 2C-E and presented in Table 4, vaccination with vectors including the immunogenic TP53 S127Y epitope demonstrated reduced spot forming colonies (SFC) for KRAS epitopes G12V and G12D relative to vectors not including a TP53 neoepitope ("4×1") or including a non-immunogenic TP53 neoepitope ("4×1+R213L"), indicating presence of the TP53 S127Y neoepitope in the vaccine cassette acts as an immunodominant neoepitope decreasing KRAS-specific T cell responses.

TABLE 4

ELISpot data for KRAS and TP53 Neoepitopes

| Antigen | G12C | | G12D | | G12V | | R213L | | S127Y | |
|---|---|---|---|---|---|---|---|---|---|---|
| Cassette | Mean | +/−SE | Mean | +/−SE | Mean | +/−SE | Mean | +/−SE | Mean | +/−SE |
| 4x1 | 92 | 41 | 32 | 21 | 1570 | 833 | ND | ND | ND | ND |
| 4x1 + R213L | 86 | 74 | 62 | 46 | 773 | 378 | 5 | 3 | ND | ND |
| 4x1 + S127Y | 2 | 1 | 7 | 5 | 0 | 0 | ND | ND | 6118* | 264 |

ND = Not Determined; *3/6 samples were too numerous to count (max value 6200)

XIV.E. Evaluation of Presentation of KRAS Neoepitopes by Mass Spectrometry

Mass spectrometry (MS) validation of candidate KRAS epitopes was performed using targeted mass spectrometry methods. Either donor tumor resections (multi-allelic; allele assignment from EDGE prediction) or single allelic K562 lines engineered to express the indicated cassettes were assessed. Mass spectrometry analysis methods are described in more detail in Gillete et al. (*Nat Methods.* 2013 January; 10(1):28-34), herein incorporated by reference in its entirety for all purposes. Targeted mass spectrometry analysis, including use of K562 single allelic in vitro systems, is described in international application publication WO2021092095, herein incorporated by reference for all purposes. Results are shown in Table 5 demonstrating confirmation of HLA-specific presentation by various KRAS neoepitopes.

TABLE 5

KRAS Neoepitope Mass Spectrometry

| Mutation | HLA | Sequence | Tumors | 20 × 1 K562 Cell Lines | 4 × 4 K562 Cell Lines | 8 × 2 K562 Cell Lines |
|---|---|---|---|---|---|---|
| G12C | A*03:01 | VVVGACGVGK | No | Yes | NA | NA |
| G12C | A*11:01 | VVVGACGVGK | No | Yes | Yes | No |
| G12D | A*03:01 | VVGADGVGK | No | Yes | NA | NA |
| G12D | A*03:01 | VVVGADGVGK | No | Yes | NA | NA |
| G12D | A*11:01 | VVGADGVGK | Yes | Yes | Yes | No |
| G12D | A*11:01 | VVVGADGVGK | Yes | Yes | Yes | Yes |
| G12V | A*02:01 | KLVVVGAVGV | No | No | Yes | No |
| G12V | A*03:01 | VVGAVGVGK | No | Yes | NA | NA |
| G12V | A*03:01 | VVVGAVGVGK | Yes | Yes | NA | NA |
| G12V | A*11:01 | VVGAVGVGK | Yes | Yes | Yes | Yes |
| G12V | A*11:01 | VVVGAVGVGK | Yes | Yes | Yes | Yes |
| G12V | C*01:02 | AVGVGKSAL | Yes | NA | NA | NA |
| Q61H | A*01:01 | ILDTAGHEEY | NA | Yes | Yes | Yes |

NA = not applicable (either tumor or cell line not available/generated to test)

XIV.F. Iterated KRAS Neoepitope Cassette Evaluation Results

Vaccine efficacy with various cassettes having repeated (i.e., iterated) neoepitopes or a single copy of a given neoepitope were evaluated. Mice engineered to express human HLA-A11:01 for KRAS G12 mutations or human HLA-A01:01 for KRAS Q61H were immunized with $5\times10^{10}$ VP using the ChAdV68 delivery vectors described below and efficacy was assessed by IFNγ ELISpot.

A series of ChAdV68 delivery vectors were designed to assess efficacy of cassettes featuring either a single copy of KRAS neoepitopes G12C, G12V, G12D, and Q61H ("KRAS 4×1"; cassette=SEQ ID NO: 66), 4 iterations of each of the KRAS neoepitopes G12C, G12V, G12D, and Q61H ("KRAS 4× (4×4)"; cassette=SEQ ID NO: 65), or 4 iterations of only one of the KRAS neoepitopes G12C, G12V, G12D, or Q61H ("KRAS 1×4").

Cassettes featuring either a single copy of KRAS neoepitopes ("4×1") or 4 iterations of each of the KRAS neoepitopes ("4×4") were compared. As shown in FIG. 3 and quantified in Table 6, vaccination with vectors featuring multiple iterations of the neoepitopes demonstrated increased spot forming colonies (SFC), indicating repetition of epitope-encoding sequences in a cassette led to an increased antigen-specific immune response against KRAS neoepitopes, specifically G12V and G12D neoepitopes, using a ChAdV68 delivery system.

Cassettes featuring either 4 iterations of each of the KRAS neoepitopes ("4×4") or 4 iterations of only one of the KRAS ("1×4") were compared. As shown in FIG. 4 and quantified in Table 7, vaccination with vectors featuring multiple iterations of the neoepitopes in either the 4×4 or 1×4 formats generated immune responses by spot forming colonies (SFC) and were comparable across formats, indicating repetition of epitope-encoding sequences in a cassette led to an increased antigen-specific immune response against KRAS neoepitopes, specifically G12V and G12D neoepitopes, using a ChAdV68 delivery system.

Immune responses for cassette formats for KRAS Q61H were compared, including cassettes featuring either a single copy of KRAS Q61H with 19 other distinct neoepitopes ("20×1"), 2 iterations of the KRAS Q61H ("8×2"), a single copy of KRAS Q61H together with single copies of KRAS G12 neoepitopes ("4×1"), 4 iterations of the KRAS Q61H together with KRAS G12 neoepitope iterations ("4×4"); or 4 iterations of only KRAS Q61H ("1×4"). As shown in FIG. 5 and quantified in Table 8, while vaccination with a vector a single copy of KRAS Q61H together with single copies of KRAS G12 neoepitopes demonstrated a small improvement over larger cassettes (4×1 vs 20×1 or 8×2), vaccination with vectors featuring multiple iterations of the neoepitopes in either the 4×4 or 1×4 formats generated immune responses by spot forming colonies (SFC) with the 1×4 format demonstrating the most robust response, indicating repetition of epitope-encoding sequences in a cassette as well as shorter formats and/or removal of additional distinct neoepitopes led to an increased antigen-specific immune response against the KRAS neoepitopes Q61H, using a ChAdV68 delivery system.

Responses following immunization with either a ChAdV68 delivery system or a SAM delivery system we compared. Cassettes featuring either a single copy of KRAS neoepitopes as well as other neoepitopes ("20×1") or 4 iterations of each of the KRAS neoepitopes ("4×4") were assessed. As shown in FIG. 6 and FIG. 7 and quantified in Table 9, vaccination with vectors featuring multiple iterations of the neoepitopes demonstrated increased spot forming colonies (SFC) for both ChAdV68 and SAM formats, indicating repetition of epitope-encoding sequences in a cassette led to an increased antigen-specific immune response against KRAS neoepitopes, specifically G12V and G12D neoepitopes, using either a ChAdV68 or SAM delivery system suggesting the improved response with cassettes featuring iterations of neoepitopes is agnostic of the vector platform used.

TABLE 6

ELISpot data for KRAS Neoepitopes G12V and G12D +/- Repetition

| Antigen | G12V (VVVGAVGGK) | | G12D (VVVGADGVGK) | |
|---|---|---|---|---|
| Cassette | Mean | +/- SE | Mean | +/- SE |
| 4 × 4 | 5632 | 237.9 | 1069 | 361.4 |
| 4 × 1 | 1570 | 833.2 | 32 | 20.6 |

TABLE 7

| ELISpot data for KRAS Neoepitopes G12V and G12D +/- Repetition | | | | |
|---|---|---|---|---|
| Antigen | G12V (VVVGAVGGK) | | G12D (VVVGADGVGK)* | |
| Cassette | Mean | +/- SE | Mean | +/- SE |
| 4 × 4 | 3700 | 404.9 | 536 | 316.1 |
| 1 × 4 | 3358 | 310.8 | 1726 | 784.7 |

*Results were not significantly different between formats (p = 0.1896)

TABLE 8

| ELISpot data for KRAS Neoepitope Q61H +/- Repetition | | |
|---|---|---|
| Antigen | Q61H (ILDTAGHEEY) | |
| Cassette | Mean | +/- SE |
| 20 × 1 | 3 | 1.3 |
| 4 × 4 | 554 | 225 |
| 8 × 2 | 20 | 10.8 |
| 4 × 1 | 262 | 112.2 |
| 1 × 4 | 1289 | 451.7 |
| Naive | 1 | 0.6 |

TABLE 9

| ELISpot for KRAS G12V and G12D +/- Repetition in Chad/SAM Formats | | | | | | | | | | | | |
|---|---|---|---|---|---|---|---|---|---|---|---|---|
| | ChAdV68 20 × 1 | | | SAM 20 × 1 | | | ChAdV68 4 × 4 | | | SAM 4 × 4 | | |
| | Mean | SEM | N | Mean | SEM | N | Mean | SEM | N | Mean | SEM | N |
| G12V pool | 13 | 6 | 6 | 33 | 6 | 6 | 4483 | 767 | 6 | 6939 | 1149 | 6 |
| G12D pool | 5 | 2 | 6 | 6 | 3 | 6 | 297 | 227 | 6 | 560 | 163 | 6 |
| G12V (VVGAVGVGK) | 4 | 2 | 6 | 12 | 3 | 6 | 3167 | 846 | 6 | 6878 | 1216 | 6 |
| G12D (VVVGAD-GVGK) | 4 | 3 | 6 | 8 | 3 | 6 | 356 | 288 | 6 | 564 | 148 | 6 |

Certain Sequences

Vectors, cassettes, and antibodies referred to herein are described below and referred to by SEQ ID NO.

Tremelimumab VL (SEQ ID NO: 16)

Tremelimumab VH (SEQ ID NO: 17)

Tremelimumab VH CDR1 (SEQ ID NO: 18)

Tremelimumab VH CDR2 (SEQ ID NO: 19)

Tremelimumab VH CDR3 (SEQ ID NO: 20)

Tremelimumab VL CDR1 (SEQ ID NO: 21)

Tremelimumab VL CDR2 (SEQ ID NO: 22)

Tremelimumab VL CDR3 (SEQ ID NO: 23)

Durvalumab (MEDI4736) VL (SEQ ID NO: 24)

MEDI4736 VH (SEQ ID NO: 25)

MEDI4736 VH CDR1 (SEQ ID NO: 26)

MEDI4736 VH CDR2 (SEQ ID NO: 27)

MEDI4736 VH CDR3 (SEQ ID NO: 28)

MEDI4736 VL CDR1 (SEQ ID NO: 29)

MEDI4736 VL CDR2 (SEQ ID NO: 30)

MEDI4736 VL CDR3 (SEQ ID NO: 31)

UbA76-25merPDTT nucleotide (SEQ ID NO: 32)

UbA76-25merPDTT polypeptide (SEQ ID NO: 33)

MAG-25merPDTT nucleotide (SEQ ID NO: 34)

MAG-25merPDTT polypeptide (SEQ ID NO: 35)

-continued

Ub7625merPDTT NoSFL nucleotide (SEQ ID NO: 36)

Ub7625merPDTT NoSFL polypeptide (SEQ ID NO: 37)

ChAdV68.5WTnt.MAG25mer (SEQ ID NO: 2); AC_000011.1 with E1 (nt 577 to 3403) and E3 (nt 27,125-31,825) sequences deleted; corresponding ATCC VR-594 nucleotides substituted at five positions; model neoantigen cassette under the control of the CMV promoter/enhancer inserted in place of deleted E1; SV40 polyA 3' of cassette Venezuelan equine encephalitis virus [VEE] (SEQ ID NO: 3) GenBank: L01442.2

VEE-MAG25mer (SEQ ID NO: 4); contains MAG-25merPDTT nucleotide (bases 30-1755)

Venezuelan equine encephalitis virus strain TC-83 [TC-83](SEQ ID NO: 5) GenBank: L01443.1

VEE Delivery Vector (SEQ ID NO: 6); VEE genome with nucleotides 7544-11175 deleted [alphavirus structural proteins removed]

TC-83 Delivery Vector(SEQ ID NO: 7); TC-83 genome with nucleotides 7544-11175 deleted [alphavirus structural proteins removed]

VEE Production Vector (SEQ ID NO: 8); VEE genome with nucleotides 7544-11175 deleted, plus 5' T7-promoter, plus 3' restriction sites TC-83 Production Vector(SEQ ID NO: 9); TC-83 genome with nucleotides 7544-11175 deleted, plus 5' T7-promoter, plus 3' restriction sites VEE-UbAAY (SEQ ID NO: 14); VEE delivery vector with MHC class I mouse tumor epitopes SIINFEKL and AH1-A5 inserted VEE-Luciferase (SEQ ID NO: 15); VEE delivery vector with luciferase gene inserted at 7545 ubiquitin (SEQ ID NO: 38)>UbG76 0-228

Ubiquitin A76 (SEQ ID NO: 39)>UbA76 0-228

HLA-A2 (MHC class I) signal peptide (SEQ ID NO: 40)>MHC SignalPep 0-78

HLA-A2 (MHC class I) Trans Membrane domain (SEQ ID NO: 41)>HLA A2 TM Domain 0-201

IgK Leader Seq (SEQ ID NO: 42)>IgK Leader Seq 0-60

Human DC-Lamp (SEQ ID NO: 43)>HumanDCLAMP 0-3178

Mouse LAMP1 (SEQ ID NO: 44)>MouseLamp1 0-1858

Human Lamp1 cDNA (SEQ ID NO: 45)>Human Lamp1 0-2339

Tetanus toxoid nulceic acid sequence (SEQ ID NO: 46)

Tetanus toxoid amino acid sequence (SEQ ID NO: 47)

PADRE nulceotide sequence (SEQ ID NO: 48)

PADRE amino acid sequence (SEQ ID NO: 49)

WPRE (SEQ ID NO: 50)>WPRE 0-593

IRES (SEQ ID NO: 51)>eGFP_IRES_SEAP_Insert 1746-2335

GFP (SEQ ID NO: 52)

SEAP (SEQ ID NO: 53)

Firefly Luciferase (SEQ ID NO: 54)

FMDV 2A (SEQ ID NO: 55)

GPGPG linker (SEQ ID NO: 56)

1x (20 x 1) Cassette Nucleotide Sequence (SEQ ID NO: 69)

ATGGCTGGCATGACCGAGTACAAACTTGTGGTGGTTGGTGCTGGAGACGTGGGGAAAAGCGCCCTG

ACAATTCAGCTTATTCAGGAAACTTGCTTATTAGACATATTAGATACTGCCGGAAAAGAAGAGTATT

CTGCTATGAGAGATCAGTACATGCGGATGTGCAACAGCAGCTGCATGGGCGGCATGAACCGCATGC

-continued

CCATCTTGACTATTATCACCCTGGAGGATTCCTCCAGTGGAATACATTCGGGAGCCACCACCACTGC

TCCTCCCCTGTCAGGTAAGGGAAATCCTGAAGAAGAAGATGTTAGCGGCATTCATTCCGGTGCTAC

GACAACTGCACCATTTCTGTCTGGTAAAGGTAATCCAGAGGAGGAGGATGTGGAAATTCTGGATGA

GGCCTACGTCATGGCCTATGTGATGGCTGGCGTTGGAAGCCCATACGTGAGTAGACTGCTGATGAC

AGAATATAAATTAGTGGTAGTAGGAGCAGATGGGGTAGGAAAGAGTGCCTTAACAATCCAACTCAT

TCAGGAGACCTGTTTGTTGGATATTCTGGATACAGCTGGCCGGGAAGAGTATTCGGCAATGAGGGA

CCAATATATGCGATCTTACCTCGACAGCGGAATCCACTCCGGTGCCACTGCAACAGCGCCGAGCCT

GAGTGGTAAGGGGAACCCTGAGAAGTCAGTAACGTGTACATACAGCCCTGCTTTAAACAACATGTT

TTGCCAACTTGCAAAAACATGTCCTGTACAGATGACAGAGTATAAACTTGTAGTGGTGGGGGCAGC

TGGTGTAGGTAAAAGTGCACTTACCATCCAGCTGATTCAAGAGACATGTCTGTTAGACATCTTGGAC

ACAGCCGGGCTCGAGGAATATAGCGCCATGAGAGACCAGTACATGCGACTGCGCGTGGAGTATCTG

GATGACAGGAACACCTTCCTGCATTCTGTTGTGGTGCCCTATGAGCCCCCGGAGGTGGATGGACAG

ATCACAGTGGGCCAGAGAATTGGCAGCGTGTCCTTCGGGACTGTGTACAAGGGCAAGTGGCACGGA

ATGACGGAATATAAGCTGGTGGTGGTAGGAGCAGTAGGTGTCGGTAAATCAGCCCTCACCATTCAG

CTTATACAGGAGACTTGTTTGCTGGACATCCTAGACACTGCTGGCCATGAGGAGTACTCCGCCATGC

GCGATCAATACATGAGGTGGCAGCAGCAGAGCTACCTGGACTCAGGGATCCACTTTGGAGCTACCA

CAACTGCGCCATCACTAAGTGGGAAACACAGCGGCACCGCCAAATCTGTCACGTGTACTTACTACC

CAGCCTTGAACAAGATGTTCTGTCAATTAGCAAAGAAAAGTGTCACCTGCACATATTCACCGGCAC

TGAATGAGATGTTCTGCCAGCTGGCTAAGACCTGTCCTGTGCAGATGACTGAGTACAAACTGGTCGT

TGTGGGGGCCTGTGGGGTTGGGAAGAGCGCTCTGACCATCCAGCTCATCCAGGGACCCGGACCAGG

CGCCAAATTTGTTGCTGCTTGGACACTGAAAGCTGCTGCTGGGCCCGGACCAGGCCAGTACATCAA

GGCCAACTCTAAGTTTATCGGCATCACCGAATTGGGACCTGGACCCGGCTAGTAGTGA

KRAS 2X (8 x 2) Cassette Nucleotide Sequence (SEQ ID NO: 70)

ATGGCTGGCATGACTGAATACAAATTAGTTGTCGTCGGTGCATGCGGGGTAGGCAAGTCGGCCTTA

ACGATACAACTTATTCAAGAGACATGTCTACTGGATATCCTTGACACTGCCGGTCACGAAGAATAT

AGTGCAATGAGGGACCAGTACATGCGTATGACGGAATATAAGTTAGTAGTAGTTGGCGCAGGCGAC

GTAGGGAAATCCGCTCTAACTATCCAACTAATTCAAGAAACGTGCCTACTAGATATATTAGACACA

GCGGGACGTGAGGAGTATAGCGCCATGCGTGACCAGTATATGCGGATGACCGAGTATAAGCTAGTC

GTAGTCGGCGCGGATGGGGTTGGTAAGAGCGCCTTGACCATCCAGCTCATACAAGAAACTTGCCTT

CTGGACATCCTAGACACCGCGGGTCTCGAAGAGTACAGTGCGATGAGAGATCAGTACATGAGGATG

ACAGAATACAAGCTCGTTGTTGTTGGTGCGGTCGGTGTTGGAAAGAGTGCGCTAACCATTCAGCTTA

TCCAGGAAACCTGTCTGTTAGACATCTTAGATACCGCAGGTAAAGAGGAATATTCGGCCATGAGGG

ATCAATATATGCGAATGACAGAGTATAAATTGGTAGTGGTAGGGGCTTGCGGAGTGGGGAAAAGC

GCATTGACTATACAATTGATTCAGGAAACATGCCTATTGGACATACTCGACACGGCCGGGAAAGAA

GAGTATTCCGCGATGCGAGATCAATACATGCGCATGACCGAATATAAACTTGTCGTTGTCGGAGCG

GGTGATGTAGGTAAATCGGCGCTCACAATCCAATTAATCCAAGAGACGTGCTTGCTAGACATTCTG

GATACAGCTGGGCACGAGGAGTACTCAGCTATGCGCGATCAGTATATGAGGATGACTGAGTACAAG

TTGGTCGTCGTAGGAGCGGTTGGTGTCGGAAAATCTGCGTTGACAATTCAACTGATACAAGAGACT

TGTTTGTTAGATATTCTCGATACTGCGGGTCGGGAAGAATACTCGGCTATGAGAGACCAATATATGA

GAATGACGGAGTACAAACTCGTAGTTGTAGGTGCGGACGGTGTAGGAAAGTCTGCGCTTACGATTC

AGTTGATACAGGAGACCTGTTTGCTCGATATCTTGGATACGGCGGGTTTGGAGGAATACAGCGCAA

-continued

TGCGGGACCAATACATGAGAGGACCCGGACCAGGCGCCAAATTTGTTGCTGCTTGGACACTGAAAG
CTGCTGCTGGGCCCGGACCAGGCCAGTACATCAAGGCCAACTCTAAGTTTATCGGCATCACCGAAT
TGGGACCTGGACCCGGCTAG

KRAS 4X (4 × 4) Cassette Nucleotide Sequence (SEQ ID NO: 71)

ATGGCTGGCATGACCGAGTATAAACTAGTAGTTGTGGGAGCGTGTGGTGTAGGCAAGTCGGCACTT
ACAATTCAGTTGATACAAATGACGGAATATAAGCTCGTAGTAGTCGGAGCAGACGGCGTGGGGAA
ATCAGCGTTGACTATCCAGTTAATACAGGAAACTTGCCTATTAGACATCTTGGATACGGCAGGTCAT
GAGGAATATTCCGCTATGAGAGATCAGTATATGCGCATGACGGAGTATAAGCTTGTGGTTGTCGGG
GCCGACGGGGTAGGTAAGTCAGCGCTCACGATACAATTAATTCAAATGACCGAATACAAGTTGGTC
GTGGTGGGGGCAGTTGGGGTCGGTAAATCCGCGTTAACGATCCAACTTATCCAAATGACAGAATAT
AAACTCGTTGTTGTAGGTGCATGTGGCGTAGGAAAAAGCGCATTGACCATCCAGCTAATTCAGGAG
ACGTGTCTCCTTGATATCCTAGACACGGCGGGGCACGAAGAATACTCGGCTATGCGCGACCAGTAC
ATGAGAATGACGGAATACAAACTTGTTGTCGTGGGTGCGGATGGAGTAGGGAAAAGTGCTCTAACA
ATACAACTCATTCAGATGACAGAGTACAAATTGGTAGTCGTCGGTGCGGTAGGAGTTGGGAAGTCT
GCACTAACTATTCAGCTCATACAGATGACCGAGTACAAGCTGGTGGTGGTAGGCGCTTGCGGTGTG
GGTAAGAGTGCATTAACCATACAGCTTATACAAGAGACATGTCTGCTAGATATATTAGATACCGCC
GGGCATGAAGAGTACTCTGCCATGCGAGACCAATACATGCGTATGACAGAGTATAAATTAGTAGTG
GTTGGGGCGGACGGTGTTGGCAAGAGCGCCTTAACTATACAGTTGATCCAGATGACGGAGTACAAA
CTGGTCGTCGTTGGTGCAGTGGGAGTGGGAAAATCTGCGCTGACGATTCAACTAATCCAAGAAACA
TGTTTACTTGACATCCTCGACACTGCGGGTCACGAGGAGTATTCGGCGATGCGTGATCAATATATGA
GGATGACTGAGTATAAGTTAGTCGTAGTTGGAGCGGTCGGTGTCGGAAAGTCCGCGCTAACCATTC
AATTGATTCAAATGACTGAATACAAGCTAGTGGTAGTAGGAGCATGCGGCGTCGGCAAATCGGCTT
TAACAATCCAACTGATACAGGGACCCGGACCAGGCGCCAAATTTGTTGCTGCTTGGACACTGAAAG
CTGCTGCTGGGCCCGGACCAGGCCAGTACATCAAGGCCAACTCTAAGTTTATCGGCATCACCGAAT
TGGGACCTGGACCCGGCTAG

KRAS 4 × 1 Cassette Nucleotide Sequence (SEQ ID NO: 72)

ATGGCTGGCATGACCGAGTATAAACTAGTAGTTGTGGGAGCGTGTGGTGTAGGCAAGTCGGCACTT
ACAATTCAGTTGATACAAATGACGGAATATAAGCTCGTAGTAGTCGGAGCAGACGGCGTGGGGAA
ATCAGCGTTGACTATCCAGTTAATACAGGAAACTTGCCTATTAGACATCTTGGATACGGCAGGTCAT
GAGGAATATTCCGCTATGAGAGATCAGTATATGCGCATGACCGAATACAAGTTGGTCGTGGTGGGG
GCAGTTGGGGTCGGTAAATCCGCGTTAACGATCCAACTTATCCAAGGACCCGGACCAGGCGCCAAA
TTTGTTGCTGCTTGGACACTGAAAGCTGCTGCTGGGCCCGGACCAGGCCAGTACATCAAGGCCAAC
TCTAAGTTTATCGGCATCACCGAATTGGGACCTGGACCCGGCTAG

KRAS 4 × 1 + R213L Cassette Nucleotide Sequence (SEQ ID NO: 73)

ATGGCTGGCATGACCGAGTATAAACTAGTAGTTGTGGGAGCGTGTGGTGTAGGCAAGTCGGCACTT
ACAATTCAGTTGATACAAATGACGGAATATAAGCTCGTAGTAGTCGGAGCAGACGGCGTGGGGAA
ATCAGCGTTGACTATCCAGTTAATACAGGAAACTTGCCTATTAGACATCTTGGATACGGCAGGTCAT
GAGGAATATTCCGCTATGAGAGATCAGTATATGCGCATGACCGAATACAAGTTGGTCGTGGTGGGG
GCAGTTGGGGTCGGTAAATCCGCGTTAACGATCCAACTTATCCAACTGCGCGTGGAGTATCTGGAT
GACAGGAACACCTTCCTGCATTCTGTTGTGGTGCCCTATGAGCCCCCGGAGGTGGGACCCGGACCA

-continued

GGCGCCAAATTTGTTGCTGCTTGGACACTGAAAGCTGCTGCTGGGCCCGGACCAGGCCAGTACATC

AAGGCCAACTCTAAGTTTATCGGCATCACCGAATTGGGACCTGGACCCGGCTAG

KRAS 4 × 1 + 5127Y Cassette Nucleotide Sequence (SEQ ID NO: 74)

ATGGCTGGCATGACCGAGTATAAACTAGTAGTTGTGGGAGCGTGTGGTGTAGGCAAGTCGGCACTT

ACAATTCAGTTGATACAAATGACGGAATATAAGCTCGTAGTAGTCGGAGCAGACGGCGTGGGGAA

ATCAGCGTTGACTATCCAGTTAATACAGGAAACTTGCCTATTAGACATCTTGGATACGGCAGGTCAT

GAGGAATATTCCGCTATGAGAGATCAGTATATGCGCATGACCGAATACAAGTTGGTCGTGGTGGGG

GCAGTTGGGGTCGGTAAATCCGCGTTAACGATCCAACTTATCCAACACAGCGGCACCGCCAAATCT

GTCACGTGTACTTACTACCCAGCCTTGAACAAGATGTTCTGTCAATTAGCAAAGGGACCCGGACCA

GGCGCCAAATTTGTTGCTGCTTGGACACTGAAAGCTGCTGCTGGGCCCGGACCAGGCCAGTACATC

AAGGCCAACTCTAAGTTTATCGGCATCACCGAATTGGGACCTGGACCCGGCTAG

KRAS G12C Neoepitope (SEQ ID NO: 75)

VVVGACGVGK

KRAS G12C Neoepitope (SEQ ID NO: 76)

KLVVVGACGV

KRAS G12D Neoepitope (SEQ ID NO: 77)

VVGADGVGK

KRAS G12D Neoepitope (SEQ ID NO: 78)

VVVGADGVGK

KRAS G12V Neoepitope (SEQ ID NO: 79)

VVGAVGVGK

KRAS G12V Neoepitope (SEQ ID NO: 80)

AVGVGKSAL

KRAS G12V Neoepitope (SEQ ID NO: 81)

VVVGAVGVGK

KRAS Q61H Neoepitope (SEQ ID NO: 82)

ILDTAGHEEY

REFERENCES

1. Desrichard, A., Snyder, A. & Chan, T. A. Cancer Neoantigens and Applications for Immunotherapy. *Clin. Cancer Res. Off J. Am. Assoc. Cancer Res.* (2015). doi:10.1158/1078-0432.CCR-14-3175
2. Schumacher, T. N. & Schreiber, R. D. Neoantigens in cancer immunotherapy. *Science* 348, 69-74 (2015).
3. Gubin, M. M., Artyomov, M. N., Mardis, E. R. & Schreiber, R. D. Tumor neoantigens: building a framework for personalized cancer immunotherapy. *J. Clin. Invest.* 125, 3413-3421 (2015).
4. Rizvi, N. A. et al. Cancer immunology. Mutational landscape determines sensitivity to PD-1 blockade in non-small cell lung cancer. *Science* 348, 124-128 (2015).
5. Snyder, A. et al. Genetic basis for clinical response to CTLA-4 blockade in melanoma. *N. Engl. J. Med.* 371, 2189-2199 (2014).
6. Carreno, B. M. et al. Cancer immunotherapy. A dendritic cell vaccine increases the breadth and diversity of melanoma neoantigen-specific T cells. *Science* 348, 803-808 (2015).
7. Tran, E. et al. Cancer immunotherapy based on mutation-specific CD4+ T cells in a patient with epithelial cancer. *Science* 344, 641-645 (2014).
8. Hacohen, N. & Wu, C. J.-Y. United States Patent Application: 20110293637-COMPOSITIONS AND METHODS OF IDENTIFYING TUMOR SPECIFIC NEOANTIGENS. (A1). at <appft1.uspto.gov/netacgi/nph-Parser?Sect1=PTO1&Sect2=HITOFF&d=PG01&p=1&u=/netahtml/PTO/srchnum.html&r=1&f=G&l=50&s1=20110293637.PGNR.>
9. Lundegaard, C., Hoof, I., Lund, O. & Nielsen, M. State of the art and challenges in sequence based T-cell epitope prediction. *Immunome Res.* 6 Suppl 2, S3 (2010).
10. Yadav, M. et al. Predicting immunogenic tumour mutations by combining mass spectrometry and exome sequencing. *Nature* 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics MCP* 14, 658-673 (2015).

12. Van Allen, E. M. et al. Genomic correlates of response to CTLA-4 blockade in metastatic melanoma. *Science* 350, 207-211 (2015).
13. Yoshida, K. & Ogawa, S. Splicing factor mutations and cancer. *Wiley Interdiscip. Rev. RNA* 5, 445-459 (2014).
14. Cancer Genome Atlas Research Network. Comprehensive molecular profiling of lung adenocarcinoma. *Nature* 511, 543-550 (2014).
15. Rajasagi, M. et al. Systematic identification of personal tumor-specific neoantigens in chronic lymphocytic leukemia. *Blood* 124, 453-462 (2014).
16. Downing, S. R. et al. U.S. patent application Ser. No. 01/202,08706-OPTIMIZATION OF MULTIGENE ANALYSIS OF TUMOR SAMPLES. (A1). at <appft1.uspto.gov/netacgi/nph-Parser?Sect1=PTO1&Sect2=HITOFF&d=PG01&p=1&u=/netahtml/PTO/srchnum.html&r=1&f=G&l=50&s1=20120208706.PGNR.>
17. Target Capture for NextGen Sequencing-IDT. at <www.idtdna.com/pages/products/nextgen/target-capture>
18. Shukla, S. A. et al. Comprehensive analysis of cancer-associated somatic mutations in class I HLA genes. *Nat. Biotechnol.* 33, 1152-1158 (2015).
19. Cieslik, M. et al. The use of exome capture RNA-seq for highly degraded RNA with application to clinical cancer sequencing. *Genome Res.* 25, 1372-1381 (2015).
20. Bodini, M. et al. The hidden genomic landscape of acute myeloid leukemia: subclonal structure revealed by undetected mutations. *Blood* 125, 600-605 (2015).
21. Saunders, C. T. et al. Strelka: accurate somatic small-variant calling from sequenced tumor-normal sample pairs. *Bioinforma. Oxf. Engl.* 28, 1811-1817 (2012).
22. Cibulskis, K. et al. Sensitive detection of somatic point mutations in impure and heterogeneous cancer samples. *Nat. Biotechnol.* 31, 213-219 (2013).
23. Wilkerson, M. D. et al. Integrated RNA and DNA sequencing improves mutation detection in low purity tumors. *Nucleic Acids Res.* 42, e107 (2014).
24. Mose, L. E., Wilkerson, M. D., Hayes, D. N., Perou, C. M. & Parker, J. S. ABRA: improved coding indel detection via assembly-based realignment. *Bioinforma. Oxf. Engl.* 30, 2813-2815 (2014).
25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf. Engl.* 25, 2865-2871 (2009).
26. Lam, H. Y. K. et al. Nucleotide-resolution analysis of structural variants using BreakSeq and a breakpoint library. *Nat. Biotechnol.* 28, 47-55 (2010).
27. Frampton, G. M. et al. Development and validation of a clinical cancer genomic profiling test based on massively parallel DNA sequencing. *Nat. Biotechnol.* 31, 1023-1031 (2013).
28. Boegel, S. et al. HLA typing from RNA-Seq sequence reads. *Genome Med.* 4, 102 (2012).
29. Liu, C. et al. ATHLATES: accurate typing of human leukocyte antigen through exome sequencing. *Nucleic Acids Res.* 41, e142 (2013).
30. Mayor, N. P. et al. HLA Typing for the Next Generation. *PloS One* 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).
32. Song, L. & Florea, L. CLASS: constrained transcript assembly of RNA-seq reads. *BMC Bioinformatics* 14 Suppl 5, S14 (2013).
33. Maretty, L., Sibbesen, J. A. & Krogh, A. Bayesian transcriptome assembly. *Genome Biol.* 15, 501 (2014).
34. Pertea, M. et al. StringTie enables improved reconstruction of a transcriptome from RNA-seq reads. *Nat. Biotechnol.* 33, 290-295 (2015).
35. Roberts, A., Pimentel, H., Trapnell, C. & Pachter, L. Identification of novel transcripts in annotated genomes using RNA-Seq. *Bioinforma. Oxf. Engl.* (2011). doi:10.1093/bioinformatics/btr355
36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).
37. Rivas, M. A. et al. Human genomics. Effect of predicted protein-truncating genetic variants on the human transcriptome. *Science* 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).
39. Anders, S., Pyl, P. T. & Huber, W. HTSeq—a Python framework to work with high-throughput sequencing data. *Bioinforma. Oxf. Engl.* 31, 166-169 (2015).
40. Furney, S. J. et al. SF3B1 mutations are associated with alternative splicing in uveal melanoma. *Cancer Discov.* (2013). doi:10.1158/2159-8290.CD-13-0330
41. Zhou, Q. et al. A chemical genetics approach for the functional assessment of novel cancer genes. *Cancer Res.* (2015). doi:10.1158/0008-5472.CAN-14-2930
42. Maguire, S. L. et al. SF3B1 mutations constitute a novel therapeutic target in breast cancer. *J. Pathol.* 235, 571-580 (2015).
43. Carithers, L. J. et al. A Novel Approach to High-Quality Postmortem Tissue Procurement: The GTEx Project. *Biopreservation Biobanking* 13, 311-319 (2015).
44. Xu, G. et al. RNA CoMPASS: a dual approach for pathogen and host transcriptome analysis of RNA-seq datasets. *PloS One* 9, e89445 (2014).
45. Andreatta, M. & Nielsen, M. Gapped sequence alignment using artificial neural networks: application to the MHC class I system. *Bioinforma. Oxf. Engl.* (2015). doi:10.1093/bioinformatics/btv639
46. Jorgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).
47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).
48. Nielsen, M., Lundegaard, C., Lund, O. & Keşmir, C. The role of the proteasome in generating cytotoxic T-cell epitopes: insights obtained from improved predictions of proteasomal cleavage. *Immunogenetics* 57, 33-41 (2005).
49. Boisvert, F.-M. et al. A Quantitative Spatial Proteomics Analysis of Proteome Turnover in Human Cells. *Mol. Cell. Proteomics* 11, M111.011429-M11.011429 (2012).
50. Duan, F. et al. Genomic and bioinformatic profiling of mutational neoepitopes reveals new rules to predict anticancer immunogenicity. *J. Exp. Med.* 211, 2231-2248 (2014).

51. Janeway's Immunobiology: 9780815345312: Medicine & Health Science Books @Amazon.com. at <www.amazon.com/Janeways-Immunobiology-Kenneth-Murphy/dp/0815345313>
52. Calis, J. J. A. et al. Properties of MHC Class I Presented Peptides That Enhance Immunogenicity. *PLoS Comput. Biol.* 9, e1003266 (2013).
53. Zhang, J. et al. Intratumor heterogeneity in localized lung adenocarcinomas delineated by multiregion sequencing. *Science* 346, 256-259 (2014)
54. Walter, M. J. et al. Clonal architecture of secondary acute myeloid leukemia. *N. Engl. J. Med.* 366, 1090-1098 (2012).
55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science 1992. 255: 1261-1263.
56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.
57. Bassani-Stemberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.
58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6
59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.
60. Goldman J M, Hibbin J, Kearney L, Orchard K, Th'ng K H. HLA-DR monoclonal antibodies inhibit the proliferation of normal and chronic granulocytic leukaemia myeloid progenitor cells. Br J Haematol. 1982 November; 52(3):411-20.
61. Eng J K, Jahan T A, Hoopmann M R. Comet: an open-source MS/MS sequence database search tool. Proteomics. 2013 January; 13(1):22-4. doi: 10.1002/pmic.201200439. Epub 2012 Dec. 4.
62. Eng J K, Hoopmann M R, Jahan T A, Egertson J D, Noble W S, MacCoss M J. A deeper look into Comet—implementation and features. J Am Soc Mass Spectrom. 2015 November; 26(11):1865-74. doi: 10.1007/s13361-015-1179-x. Epub 2015 Jun. 27.
63. Lukas Käll, Jesse Canterbury, Jason Weston, William Stafford Noble and Michael J. MacCoss. Semi-supervised learning for peptide identification from shotgun proteomics datasets. Nature Methods 4:923-925, November 2007
64. Lukas Käll, John D. Storey, Michael J. MacCoss and William Stafford Noble. Assigning confidence measures to peptides identified by tandem mass spectrometry. Journal of Proteome Research, 7(1):29-34, January 2008
65. Lukas Käll, John D. Storey and William Stafford Noble. Nonparametric estimation of posterior error probabilities associated with peptides identified by tandem mass spectrometry. Bioinformatics, 24(16):i42-i48, August 2008
66. Kinney R M, B J Johnson, V L Brown, D W Trent. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. 1986 Jul. 30.
67. Jill E Slansky, Frédérique M Rattis, Lisa F Boyd, Tarek Fahmy, Elizabeth M Jaffee, Jonathan P Schneck, David H Margulies, Drew M Pardoll. Enhanced Antigen-Specific Antitumor Immunity with Altered Peptide Ligands that Stabilize the MHC-Peptide-TCR Complex. Immunity, Volume 13, Issue 4, 1 Oct. 2000, Pages 529-538.
68. A Y Huang, P H Gulden, A S Woods, M C Thomas, C D Tong, W Wang, V H Engelhard, G Pasternack, R Cotter, D Hunt, D M Pardoll, and E M Jaffee. The immunodominant major histocompatibility complex class I-restricted antigen of a murine colon tumor derives from an endogenous retroviral gene product. Proc Natl Acad Sci USA; 93(18): 9730-9735, 1996 Sep. 3.
69. JOHNSON, BARBARA J. B., RICHARD M. KINNEY, CRYSTLE L. KOST AND DENNIS W. TRENT. Molecular Determinants of Alphavirus Neurovirulence: Nucleotide and Deduced Protein Sequence Changes during Attenuation of Venezuelan Equine Encephalitis Virus. J Gen Virol 67:1951-1960, 1986.
70. Aarnoudse, C. A., Krüse, M., Konopitzky, R., Brouwenstijn, N., and Schrier, P. I. (2002). TCR reconstitution in Jurkat reporter cells facilitates the identification of novel tumor antigens by cDNA expression cloning. Int J Cancer 99, 7-13.
71. Alexander, J., Sidney, J., Southwood, S., Ruppert, J., Oseroff, C., Maewal, A., Snoke, K., Serra, H. M., Kubo, R. T., and Sette, A. (1994). Development of high potency universal DR-restricted helper epitopes by modification of high affinity DR-blocking peptides. Immunity 1, 751-761.
72. Banu, N., Chia, A., Ho, Z. Z., Garcia, A. T., Paravasivam, K., Grotenbreg, G. M., Bertoletti, A., and Gehring, A. J. (2014). Building and optimizing a virus-specific T cell receptor library for targeted immunotherapy in viral infections. Scientific Reports 4, 4166.
73. Cornet, S., Miconnet, I., Menez, J., Lemonnier, F., and Kosmatopoulos, K. (2006). Optimal organization of a polypeptide-based candidate cancer vaccine composed of cryptic tumor peptides with enhanced immunogenicity. Vaccine 24, 2102-2109.
74. Depla, E., van der Aa, A., Livingston, B. D., Crimi, C., Allosery, K., de Brabandere, V., Krakover, J., Murthy, S., Huang, M., Power, S., et al. (2008). Rational design of a multiepitope vaccine encoding T-lymphocyte epitopes for treatment of chronic hepatitis B virus infections. Journal of Virology 82, 435-450.
75. Ishioka, G. Y., Fikes, J., Hermanson, G., Livingston, B., Crimi, C., Qin, M., del Guercio, M. F., Oseroff, C., Dahlberg, C., Alexander, J., et al. (1999). Utilization of MHC class I transgenic mice for development of minigene DNA vaccines encoding multiple HLA-restricted CTL epitopes. J Immunol 162, 3915-3925.
76. Janetzki, S., Price, L., Schroeder, H., Britten, C. M., Welters, M. J. P., and Hoos, A. (2015). Guidelines for the automated evaluation of Elispot assays. Nat Protoc 10, 1098-1115.
77. Lyons, G. E., Moore, T., Brasic, N., Li, M., Roszkowski, J. J., and Nishimura, M. I. (2006). Influence of human CD8 on antigen recognition by T-cell receptor-transduced cells. Cancer Res 66, 11455-11461.

78. Nagai, K., Ochi, T., Fujiwara, H., An, J., Shirakata, T., Mineno, J., Kuzushima, K., Shiku, H., Melenhorst, J. J., Gostick, E., et al. (2012). Aurora kinase A-specific T-cell receptor gene transfer redirects T lymphocytes to display effective antileukemia reactivity. Blood 119, 368-376.

79. Panina-Bordignon, P., Tan, A., Termijtelen, A., Demotz, S., Corradin, G., and Lanzavecchia, A. (1989). Universally immunogenic T cell epitopes: promiscuous binding to human MHC class II and promiscuous recognition by T cells. Eur J Immunol 19, 2237-2242.

80. Vitiello, A., Marchesini, D., Furze, J., Sherman, L. A., and Chesnut, R. W. (1991). Analysis of the HLA-restricted influenza-specific cytotoxic T lymphocyte response in transgenic mice carrying a chimeric human-mouse class I major histocompatibility complex. J Exp Med 173, 1007-1015.

81. Yachi, P. P., Ampudia, J., Zal, T., and Gascoigne, N. R. J. (2006). Altered peptide ligands induce delayed CD8-T cell receptor interaction—a role for CD8 in distinguishing antigen quality. Immunity 25, 203-211.

82. Pushko P, Parker M, Ludwig G V, Davis N L, Johnston R E, Smith J F. Replicon-helper systems from attenuated Venezuelan equine encephalitis virus: expression of heterologous genes in vitro and immunization against heterologous pathogens in vivo. Virology. 1997 Dec. 22; 239(2):389-401.

83. Strauss, J H and E G Strauss. The alphaviruses: gene expression, replication, and evolution. Microbiol Rev. 1994 September; 58(3): 491-562.

84. Rhême C, Ehrengruber M U, Grandgirard D. Alphaviral cytotoxicity and its implication in vector development. Exp Physiol. 2005 January; 90(1):45-52. Epub 2004 Nov. 12.

85. Riley, Michael K. II, and Wilfred Vermerris. Recent Advances in Nanomaterials for Gene Delivery—A Review. Nanomaterials 2017, 7(5), 94.

86. Frolov I, Hardy R, Rice C M. Cis-acting RNA elements at the 5' end of Sindbis virus genome RNA regulate minus- and plus-strand RNA synthesis. RNA. 2001 November; 7(11):1638-51.

87. Jose J, Snyder J E, Kuhn R J. A structural and functional perspective of alphavirus replication and assembly. Future Microbiol. 2009 September; 4(7):837-56.

88. Bo Li and C. olin N. Dewey. RSEM: accurate transcript quantification from RNA-Seq data with or without a referenfe genome. *BMC Bioinformatics,* 12:323, August 2011

89. Hillary Pearson, Tariq Daouda, Diana Paola Granados, Chantal Durette, Eric Bonneil, Mathieu Courcelles, Anja Rodenbrock, Jean-Philippe Laverdure, Caroline Côté, Sylvie Mader, Sébastien Lemieux, Pierre Thibault, and Claude Perreault. MHC class I-associated peptides derive from selective regions of the human genome. The Journal of Clinical Investigation, 2016, 90. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.

91. Mommen G P., Marino, F., Meiring H D., Poelen, M C., van Gaans-van den Brink, J A., Mohammed S., Heck A J., and van Els C A. Sampling From the Proteome to the Human Leukocyte Antigen-DR (HLA-DR) Ligandome Proceeds Via High Specificity. Mol Cell Proteomics 15(4): 1412-1423, April 2016.

92. Sebastian Kreiter, Mathias Vormehr, Niels van de Roemer, Mustafa Diken, Martin Löwer, Jan Diekmann, Sebastian Boegel, Barbara Schrörs, Fulvia Vascotto, John C. Castle, Arbel D. Tadmor, Stephen P. Schoenberger, Christoph Huber, Özlem Türeci, and Ugur Sahin. Mutant MHC class II epitopes drive therapeutic immune responses to caner. Nature 520, 692-696, April 2015.

93. Tran E., Turcotte S., Gros A., Robbins P. F., Lu Y. C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T cells in a patient with epithelial cancer. Science 344(6184) 641-645, May 2014.

94. Andreatta M., Karosiene E., Rasmussen M., Stryhn A., Buus S., Nielsen M. Accurate pan-specific prediction of peptide-MHC class II binding affinity with improved binding core identification. Immunogenetics 67(11-12) 641-650, November 2015.

95. Nielsen, M., Lund, O. NN-align. An artificial neural network-based alignment algorithm for MHC class II peptide binding prediction. *BMC Bioinformatics* 10:296, September 2009.

96. Nielsen, M., Lundegaard, C., Lund, O. Prediction of MHC class II binding affinity using SMM-align, a novel stabilization matrix alignment method. *BMC Bioinformatics* 8:238, July 2007.

97. Zhang, J., et al. PEAKS DB: de novo sequencing assisted database search for sensitive and accurate peptide identification. Molecular & Cellular Proteomics. 11(4):1-8. Jan. 2, 2012.

98. Jensen, Kamilla Kjaergaard, et al. "Improved Methods for Prediting Peptide Binding Affinity to MHC Class II Molecules." Immunology, 2018, doi:10.1111/imm.12889.

99. Carter, S. L., Cibulskis, K., Helman, E., McKenna, A., Shen, H., Zack, T., Laird, P. W., Onofrio, R. C., Winckler, W., Weir, B. A., et al. (2012). Absolute quantification of somatic DNA alterations in human cancer. *Nat. Biotechnol.* 30, 413-421

100. McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele-Specific HLA Loss and Immune Escape in Lung Cancer Evolution. Cell 171, 1259-1271.e11.

101. Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. *Nat. Biotechnol.* 33, 1152-1158.

102. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

103. Van Loo, P., Nordgard, S. H., Lingjærde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.

104. MacLean, B., Tomazela, D. M., Shulman, N., Chambers, M., Finney, G. L., Frewen, B., Kern, R., Tabb, D. L., Liebler, D. C., MacCoss, M. J., (2010). Skyline: an open source document editor for creating and analyzing targeted proteomics experiments. Bioinformatics 26(7),966-8.

What is claimed is:

1. A method for treating a subject with cancer, the method comprising administering to the subject an immunotherapy comprising an antigen-based vaccine to the subject, wherein the antigen-based vaccine comprises an antigen expression system, comprising:

the antigen expression system, wherein the antigen expression system comprises one or more vectors, the one or more vectors comprising:

(a) a vector backbone, wherein the backbone comprises:

(i) at least one promoter nucleotide sequence, and (ii) at least one polyadenylation (poly(A)) sequence; and (b) a cassette, wherein the cassette comprises an antigen-encoding nucleic acid sequence encoding the amino acid sequence of SEQ ID NO: 65.

2. The method of claim 1, wherein the vector backbone comprises either:

a chimpanzee adenovirus vector, or a self-amplifying RNA (samRNA) vector.

3. The method of claim 2, wherein the samRNA vector comprises the sequence of SEQ ID NO:6.

4. The method of claim 3, wherein the cassette is inserted at position 7544 of the sequence of SEQ ID NO:6.

5. The method of claim 2, wherein the chimpanzee adenovirus vector is a ChAdV68 vector comprising:

the sequence of SEQ ID NO:1;

the sequence of SEQ ID NO:1, except that the sequence is fully deleted or functionally deleted in at least one gene selected from the group consisting of the chimpanzee adenovirus E1A, E1B, E2A, E2B, E3, E4, L1, L2, L3, L4, and L5 genes of the sequence of SEQ ID NO:1;

a gene or regulatory sequence obtained from the sequence of SEQ ID NO:1;

a partially deleted E4 gene comprising a deleted or partially-deleted E4orf2 region and a deleted or partially-deleted E4orf3 region;

at least nucleotides 2 to 36,518 of the sequence of SEQ ID NO:1 and further comprising: (1) an E1 deletion of at least nucleotides 577 to 3403 of the sequence of SEQ ID NO:1, (2) an E3 deletion of at least nucleotides 27,125 to 31,825 of the sequence of SEQ ID NO:1, and (3) a partial deletion of at least nucleotides 34,916 to 35,642 of the sequence of SEQ ID NO:1;

the sequence of SEQ ID NO:68;

one or more deletions between base pair number 577 and 3403 or between base pair 456 and 3014; or one or more deletions between base pair number 3957 and 10346, base pair number 21787 and 23370, and base pair number 33486 and 36193 of the sequence of SEQ ID NO:1.

6. The method of claim 2, wherein the chimpanzee adenovirus vector is a ChAdV68 vector comprising a partially deleted E4 gene with reference to the adenovirus genome, wherein the partially deleted E4 gene comprises a partially-deleted E4orf2 region, a deleted E4orf3 region, and a partially-deleted E4orf4 region.

7. The method of claim 5, wherein the cassette is inserted in the ChAdV68 vector at any one of the deleted E1 regions, any one of the deleted E3 regions, or any one of the deleted ChAdV68 regions that allows incorporation of the cassette.

8. The method of claim 1, wherein the method further comprises administering to the subject a second antigen expression system.

9. An antigen-encoding cassette, or a polypeptide encoded by the cassette, wherein the antigen-encoding cassette comprises an antigen-encoding nucleic acid sequence encoding the amino acid sequence of SEQ ID NO: 65.

10. The method of claim 2, wherein the chimpanzee adenovirus vector is a ChAdV68 vector comprising at least nucleotides 2 to 36,518 of the sequence of SEQ ID NO:1 and further comprising: (1) an E1 deletion of nucleotides 577 to 3403 of the sequence of SEQ ID NO:1, (2) an E3 deletion of nucleotides 27,125 to 31,825 of the sequence of SEQ ID NO: 1, and (3) a partial E4 deletion of nucleotides 34,916 to 35,642 of the sequence of SEQ ID NO:1; wherein the antigen cassette is inserted within the E1 deletion.

11. The method of claim 2, wherein the samRNA vector is a Venezuelan equine encephalitis virus vector.

12. The method of claim 8, wherein the second antigen expression system is different from the antigen expression system of claim 1.

13. The method of claim 6, wherein the partially-deleted E4orf2 region, the deleted E4orf3 region, and the partially-deleted E4orf4 region is a deletion of nucleotides 34,916 to 35,642 of the sequence of SEQ ID NO:1.

14. An antigen-based vaccine comprising:

an antigen expression system, wherein the antigen expression system comprises one or more vectors, the one or more vectors comprising:

(a) a vector backbone, wherein the backbone comprises:

(i) at least one promoter nucleotide sequence, and (ii) at least one polyadenylation (poly(A)) sequence; and (b) a cassette, wherein the cassette comprises an antigen-encoding nucleic acid sequence encoding the amino acid sequence of SEQ ID NO: 65.

15. The composition of claim 14, wherein the vector backbone comprises either:

a chimpanzee adenovirus vector, or a self-amplifying RNA (samRNA) vector.

16. The composition of claim 15, wherein the samRNA vector is a Venezuelan equine encephalitis virus vector.

17. The composition of claim 15, wherein the samRNA vector comprises the sequence of SEQ ID NO:6.

18. The composition of claim 17, wherein the cassette is inserted at position 7544 of the sequence of SEQ ID NO:6.

19. The composition of claim 14, wherein the chimpanzee adenovirus vector is a ChAdV68 vector comprising:

the sequence of SEQ ID NO:1;

the sequence of SEQ ID NO:1, except that the sequence is fully deleted or functionally deleted in at least one gene selected from the group consisting of the chimpanzee adenovirus E1A, E1B, E2A, E2B, E3, E4, L1, L2, L3, L4, and L5 genes of the sequence of SEQ ID NO:1;

a gene or regulatory sequence obtained from the sequence of SEQ ID NO:1;

a partially deleted E4 gene comprising a deleted or partially-deleted E4orf2 region and a deleted or partially-deleted E4orf3 region;

at least nucleotides 2 to 36,518 of the sequence of SEQ ID NO:1 and further comprising: (1) an E1 deletion of at least nucleotides 577 to 3403 of the sequence of SEQ ID NO:1, (2) an E3 deletion of at least nucleotides 27,125 to 31,825 of the sequence of SEQ ID NO:1, and (3) a partial deletion of at least nucleotides 34,916 to 35,642 of the sequence of SEQ ID NO:1;

the sequence of SEQ ID NO:68;

one or more deletions between base pair number 577 and 3403 or between base pair 456 and 3014; or one or more deletions between base pair number 3957 and 10346, base pair number 21787 and 23370, and base pair number 33486 and 36193 of the sequence of SEQ ID NO:1.

20. The composition of claim 19, wherein the cassette is inserted in the ChAdV68 vector at any one of the deleted E1 regions, any one of the deleted E3 regions, or any one of the deleted ChAdV68 regions that allows incorporation of the cassette.

21. The composition of claim 15, wherein the chimpanzee adenovirus vector is a ChAdV68 vector comprising a partially deleted E4 gene with reference to the adenovirus genome, wherein the partially deleted E4 gene comprises a partially-deleted E4orf2 region, a deleted E4orf3 region, and a partially-deleted E4orf4 region.

22. The composition of claim 21, wherein the partially-deleted E4orf2 region, the deleted E4orf3 region, and the partially-deleted E4orf4 region is a deletion of nucleotides 34,916 to 35,642 of the sequence of SEQ ID NO:1.

23. The composition of claim 15, wherein the chimpanzee adenovirus vector is a ChAdV68 vector comprising at least nucleotides 2 to 36,518 of the sequence of SEQ ID NO:1 and further comprising: (1) an E1 deletion of nucleotides 577 to 3403 of the sequence of SEQ ID NO:1, (2) an E3 deletion of nucleotides 27,125 to 31,825 of the sequence of SEQ ID NO:1, and (3) a partial E4 deletion of nucleotides 34,916 to 35,642 of the sequence of SEQ ID NO:1; wherein the antigen cassette is inserted within the E1 deletion.

* * * * *

SEQUENCE LISTING

<160> NUMBER OF SEQ ID NOS: 92

<210> SEQ ID NO 1
<211> LENGTH: 36519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
ccatcttcaa taatatacct caaacttttt gtgcgcgtta atatgcaaat gaggcgtttg     60
aatttgggga ggaagggcgg tgattggtcg agggatgagc gaccgttagg ggcggggcga    120
gtgacgtttt gatgacgtgg ttgcgaggag gagccagttt gcaagttctc gtgggaaaag    180
tgacgtcaaa cgaggtgtgg tttgaacacg gaaatactca attttcccgc gctctctgac    240
aggaaatgag gtgtttctgg gcggatgcaa gtgaaaacgg gccattttcg cgcgaaaact    300
gaatgaggaa gtgaaaatct gagtaatttc gcgtttatgg cagggaggag tatttgccga    360
gggccgagta gactttgacc gattacgtgg gggtttcgat taccgtgttt ttcacctaaa    420
tttccgcgta cggtgtcaaa gtccggtgtt tttacgtagg tgtcagctga tcgccagggt    480
atttaaacct gcgctctcca gtcaagaggc cactcttgag tgccagcgag aagagttttc    540
tcctccgcgc cgcgagtcag atctacactt tgaaagatga ggcacctgag agacctgccc    600
gatgagaaaa tcatcatcgc ttccgggaac gagattctgg aactggtggt aaatgccatg    660
atgggcgacg accctccgga gcccccccacc ccatttgaga caccttcgct gcacgatttg    720
tatgatctgg aggtggatgt gcccgaggac gatcccaatg aggaggcggt aaatgatttt    780
tttagcgatg ccgcgctgct agctgccgag gaggcttcga gctctagctc agacagcgac    840
tcttcactgc ataccccctag acccggcaga ggtgagaaaa agatccccga gcttaaaggg    900
gaagagatgg acttgcgctg ctatgaggaa tgcttgcccc cgagcgatga tgaggacgag    960
caggcgatcc agaacgcagc gagccaggga gtgcaagccg ccagcgagag ctttgcgctg   1020
gactgcccgc ctctgcccgg acacggctgt aagtcttgtg aatttcatcg catgaatact   1080
ggagataaag ctgtgttgtg tgcactttgc tatatgagag cttacaacca ttgtgtttac   1140
agtaagtgtg attaagttga actttagagg gaggcagaga gcagggtgac tgggcgatga   1200
ctggtttatt tatgtatata tgttctttat ataggtcccg tctctgacgc agatgatgag   1260
acccccacta caaagtccac ttcgtcaccc ccagaaattg gcacatctcc acctgagaat   1320
attgttagac cagttcctgt tagagccact gggaggagag cagctgtgga atgtttggat   1380
gacttgctac agggtggggt tgaacctttg gacttgtgta cccggaaacg ccccaggcac   1440
taagtgccac acatgtgtgt ttacttgagg tgatgtcagt atttataggg tgtggagtgc   1500
aataaaaaat gtgttgactt taagtgcgtg gtttatgact caggggtggg gactgtgagt   1560
atataagcag gtgcagacct gtgtggttag ctcagagcgg catggagatt tggacggtct   1620
tggaagactt tcacaagact agacagctgc tagagaacgc ctcgaacgga gtctcttacc   1680
tgtggagatt ctgcttcggt ggcgacctag ctaggctagt ctacagggcc aaacaggatt   1740
atagtgaaca atttgaggtt attttgagag agtgttctgg tctttttgac gctcttaact   1800
tgggccatca gtctcacttt aaccagagga tttcgagagc ccttgatttt actactcctg   1860
gcagaaccac tgcagcagta gcctttttttg cttttattct tgacaaatgg agtcaagaaa   1920
cccatttcag cagggattac cagctggatt tcttagcagt agctttgtgg agaacatgga   1980
```

-continued

```
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tgggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca agccctggcc   3060
cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggagggaagc atgccaggtt   3300
ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga gggaggggta ttcagccctt atctgacggg   3540
gcgtctcccc tcctgggcgg gagtgcgtca gaatgtgatg ggatccacgg tggacggccg   3600
gcccgtgcag cccgcgaact cttcaaccct gacctatgca accctgagct cttcgtcgtt   3660
ggacgcagct gccgccgcag ctgctgcatc tgccgccagc gccgtgcgcg gaatggccat   3720
gggcgccggc tactacggca ctctggtggc caactcgagt tccaccaata atcccgccag   3780
cctgaacgag gagaagctgt tgctgctgat ggcccagctc gaggccttga cccagcgcct   3840
gggcgagctg acccagcagg tggctcagct gcaggagcag acgcgggccg cggttgccac   3900
ggtgaaatcc aaataaaaaa tgaatcaata aataaacgga gacggttgtt gattttaaca   3960
cagagtctga atctttattt gatttttcgc gcgcggtagg ccctggacca ccggtctcga   4020
tcattgagca cccggtggat cttttccagg acccggtaga ggtgggcttg gatgttgagg   4080
tacatgggca tgagcccgtc ccgggggtgg aggtagctcc attgcagggc ctcgtgctcg   4140
ggggtggtgt tgtaaatcac ccagtcatag caggggcgca gggcatggtg ttgcacaata   4200
tctttgagga ggagactgat ggccacgggc agccctttgg tgtaggtgtt tacaaatctg   4260
ttgagctggg agggatgcat gcgggggggag atgaggtgca tcttggcctg gatcttgaga   4320
ttggcgatgt taccgcccag atcccgcctg ggttcatgt tgtgcaggac caccagcacg   4380
```

gtgtatccgg tgcacttggg gaatttatca tgcaacttgg aagggaaggc gtgaaagaat 4440
ttggcgacgc ctttgtgccc gcccaggttt tccatgcact catccatgat gatggcgatg 4500
ggcccgtggg cggcggcctg ggcaaagacg tttcgggggt cggacacatc atagttgtgg 4560
tcctgggtga ggtcatcata ggccatttta atgaatttgg ggcggagggt gccggactgg 4620
gggacaaagg taccctcgat cccgggggcg tagttcccct cacagatctg catctcccag 4680
gctttgagct cggagggggg gatcatgtcc acctgcgggg cgataaagaa cacggtttcc 4740
ggggcggggg agatgagctg ggccgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctcgcgcac gtgcatgttc 4920
tcgcgcacca gttccgccag gaggcgctct ccccccaggg ataggagctc ctggagcgag 4980
gcgaagtttt tcagcggctt gagtccgtcg gccatgggca ttttggagag ggtttgttgc 5040
aagagttcca ggcggtccca gagctcggtg atgtgctcta cggcatctcg atccagcaga 5100
cctcctcgtt tcgcgggttg ggacggctgc gggagtaggg caccagacga tgggcgtcca 5160
gcgcagccag ggtccggtcc ttccagggtc gcagcgtccg cgtcagggtg gtctccgtca 5220
cggtgaaggg gtgcgcgccg ggctgggcgc ttgcgagggt gcgcttcagg ctcatccggc 5280
tggtcgaaaa ccgctcccga tcggcgccct gcgcgtcggc caggtagcaa ttgaccatga 5340
gttcgtagtt gagcgcctcg gccgcgtggc ctttggcgcg gagcttacct ttggaagtct 5400
gcccgcaggc gggacagagg agggacttga gggcgtagag cttgggggcg aggaagacgg 5460
actcgggggc gtaggcgtcc gcgccgcagt gggcgcagac ggtctcgcac tccacgagcc 5520
aggtgaggtc gggctggtcg gggtcaaaaa ccagtttccc gccgttcttt ttgatgcgtt 5580
tcttaccttt ggtctccatg agctcgtgtc cccgctgggt gacaaagagg ctgtccgtgt 5640
ccccgtagac cgactttatg ggccggtcct cgagcggtgt gccgcggtcc tcctcgtaga 5700
ggaaccccgc ccactccgag acgaaagccc gggtccaggc cagcacgaag gaggccacgt 5760
gggacgggta gcggtcgttg tccaccagcg ggtccacctt ttccagggta tgcaaacaca 5820
tgtcccccte gtccacatcc aggaaggtga ttggcttgta agtgtaggcc acgtgaccgg 5880
gggtcccggc cggggggggta taaaagggtg cgggtccctg ctcgtcctca ctgtcttccg 5940
gatcgctgtc caggagcgcc agctgttggg gtaggtattc cctctcgaag gcgggcatga 6000
cctcggcact caggttgtca gtttctagaa acgaggagga tttgatattg acggtgccgg 6060
cggagatgcc tttcaagagc ccctcgtcca tctggtcaga aaagacgatc tttttgttgt 6120
cgagcttggt ggcgaaggag ccgtagaggg cgttggagag gagcttggcg atggagcgca 6180
tggtctggtt tttttccttg tcggcgcgct ccttggcggc gatgttgagc tgcacgtact 6240
cgcgcgccac gcacttccat tcggggaaga cggtggtcag ctcgtcgggc acgattctga 6300
cctgccagcc ccgattatgc agggtgatga ggtccacact ggtggccacc tcgccgcgca 6360
ggggctcatt agtccagcag aggcgtccgc ccttgcgcga gcagaagggg ggcagggggt 6420
ccagcatgac ctcgtcgggg gggtcggcat cgatggtgaa gatgccgggc aggaggtcgg 6480
ggtcaaagta gctgatggaa gtggccagat cgtccagggc agcttgccat tcgcgcacgg 6540
ccagcgcgcg ctcgtaggga ctgaggggcg tgccccaggg catgggatgg gtaagcgcgg 6600
aggcgtacat gccgcagatg tcgtagacgt agaggggctc ctcgaggatg ccgatgtagg 6660
tggggtagca gcgccccccg cggatgctgg cgcgcacgta gtcatacagc tcgtgcgagg 6720

-continued

```
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agcccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg gggcacctcg gcccggttgt   7380
tgatgacctg ggcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtcccccg tttcttcttg ggcggctggg gcgacggggg cggtgcctct tccatggtta   8460
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgcgg gcgcgcatga ccacctgggc   8940
gaggttgagc tccacgtggc gcgtgaagac cgcgtagttg cagaggcgct ggtagaggta   9000
gttgagcgtg gtggcgatgt gctcggtgac gaagaaatac atgatccagc ggcggagcgg   9060
catctcgctg acgtcgccca gcgcctccaa acgttccatg gcctcgtaaa agtccacggc   9120
```

```
gaagttgaaa aactgggagt tgcgcgccga gacggtcaac tcctcctcca gaagacggat   9180
gagctcggcg atggtggcgc gcacctcgcg ctcgaaggcc cccgggagtt cctccacttc   9240
ctcttcttcc tcctccacta acatctcttc tacttcctcc tcaggcggca gtggtggcgg   9300
gggagggggc ctgcgtcgcc ggcggcgcac gggcagacgg tcgatgaagc gctcgatggt   9360
ctcgccgcgc cggcgtcgca tggtctcggt gacggcgcgc ccgtcctcgc ggggccgcag   9420
cgtgaagacg ccgccgcgca tctccaggtg gccggggggg tccccgttgg gcagggagag   9480
ggcgctgacg atgcatctta tcaattgccc cgtagggact ccgcgcaagg acctgagcgt   9540
ctcgagatcc acgggatctg aaaaccgctg aacgaaggct tcgagccagt cgcagtcgca   9600
aggtaggctg agcacggttt cttctggcgg gtcatgttgg ttgggagcgg ggcgggcgat   9660
gctgctggtg atgaagttga aataggcggt tctgagacgg cggatggtgg cgaggagcac   9720
caggtctttg ggcccggctt gctggatgcg cagacggtcg gccatgcccc aggcgtggtc   9780
ctgacacctg gccaggtcct tgtagtagtc ctgcatgagc cgctccacgg gcacctcctc   9840
ctcgcccgcg cggccgtgca tgcgcgtgag cccgaagccg cgctggggct ggacgagcgc   9900
caggtcggcg acgacgcgct cggcgaggat ggcttgctgg atctgggtga gggtggtctg   9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
```

-continued

```
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gaggggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
ttcctgatgc aggagggggc cacccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
```

```
tctctgttgt tgttgtatct agtatgatga ggcgtgcgta cccggagggt cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcgg ccagctgaaa accatcatgc acaccaacat gcccaacgtg aacgagttca  14280
tgtacagcaa caagttcaag gcgcgggtga tggtctcccg caagaccccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
agttcgacac taggaacttc aggctgggct gggaccccgt gaccgagctg gtcatgcccg  14580
ggtgtacac caacgaggct ttccatcccg atattgtctt gctgcccggc tgcggggtgg  14640
acttcaccga gagccgcctc agcaacctgc tgggcattcg caagaggcag cccttccagg  14700
aaggcttcca gatcatgtac gaggatctgg aggggggcaa catcccccgcg ctcctggatg  14760
tcgacgccta tgagaaaagc aaggaggatg cagcagctga agcaactgca gccgtagcta  14820
ccgcctctac cgaggtcagg ggcgataatt ttgcaagcgc cgcagcagtg gcagcggccg  14880
aggcggctga aaccgaaagt aagatagtca ttcagccggt ggagaaggat agcaagaaca  14940
ggagctacaa cgtactaccg gacaagataa acaccgccta ccgcagctgg tacctagcct  15000
acaactatgg cgaccccgag aagggcgtgc gctcctggac gctgctcacc acctcggacg  15060
tcacctgcgg cgtggagcaa gtctactggt cgctgcccga catgatgcaa gacccggtca  15120
ccttccgctc cacgcgtcaa gttagcaact acccggtggt gggcgccgag ctcctgcccg  15180
tctactccaa gagcttcttc aacgagcagg ccgtctactc gcagcagctg cgcgccttca  15240
cctcgcttac gcacgtcttc aaccgcttcc ccgagaacca gatcctcgtc cgcccgcccg  15300
cgcccaccat taccaccgtc agtgaaaacg ttcctgctct cacagatcac gggaccctgc  15360
cgctgcgcag cagtatccgg ggagtccagc gcgtgaccgt tactgacgcc agacgccgca  15420
cctgccccta cgtctacaag gccctgggca tagtcgcgcc gcgcgtcctc tcgagccgca  15480
ccttctaaat gtccattctc atctcgccca gtaataacac cggttggggc ctgcgcgcgc  15540
ccagcaagat gtacggaggc gctcgccaac gctccacgca acaccccgtg cgcgtgcgcg  15600
ggcacttccg cgctccctgg ggcgccctca agggccgcgt gcggtcgcgc accaccgtcg  15660
acgacgtgat cgaccaggtg gtggccgacg cgcgcaacta cacccccgcc gccgcgcccg  15720
tctccaccgt ggacgccgtc atcgacagcg tggtggccga cgcgcgccgg tacgcccgcg  15780
ccaagagccg gcggcggcgc atcgcccggc ggcaccggag cacccccgcc atgcgcgcgg  15840
cgcgagcctt gctgcgcagg gccaggcgca cgggacgcag ggccatgctc agggcggcca  15900
gacgcgcggc ttcaggcgcc agcgccggca ggacccggag acgcgcggcc acggcggcgg  15960
cagcggccat cgccagcatg tcccgcccgc ggcgagggaa cgtgtactgg gtgcgcgacg  16020
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
```

-continued

```
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgccgctgca accacccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt gggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgaccccgc cccgatgcgg aggagacgct gctgacgcac acggacgagc cgccccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc accccatcga tgctgcccca gtgggcgtac atgcacatcg  18360
ccggacagga cgcttcggag tacctgagtc cgggtctggt gcagtttgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
```

tggccagcac ctactttgac atccgcggcg tgctggatcg gggccctagc ttcaaaccct 18660
actccggcac cgcctacaac agtctggccc ccaagggagc acccaacact tgtcagtgga 18720
catataaagc cgatggtgaa actgccacag aaaaaaccta tacatatgga aatgcacccg 18780
tgcagggcat taacatcaca aaagatggta ttcaacttgg aactgacacc gatgatcagc 18840
caatctacgc agataaaacc tatcagcctg aacctcaagt gggtgatgct gaatggcatg 18900
acatcactgg tactgatgaa aagtatggag gcagagctct taagcctgat accaaaatga 18960
agccttgtta tggttctttt gccaagccta ctaataaaga aggaggtcag gcaaatgtga 19020
aaacaggaac aggcactact aaagaatatg acatagacat ggctttcttt gacaacagaa 19080
gtgcggctgc tgctggccta gctccagaaa ttgttttgta tactgaaaat gtggatttgg 19140
aaactccaga tacccatatt gtatacaaag caggcacaga tgacagcagc tcttctatta 19200
atttgggtca gcaagccatg cccaacagac ctaactacat tggtttcaga gacaacttta 19260
tcgggctcat gtactacaac agcactggca atatgggggt gctggccggt caggcttctc 19320
agctgaatgc tgtggttgac ttgcaagaca gaaacaccga gctgtcctac cagctcttgc 19380
ttgactctct gggtgacaga acccggtatt tcagtatgtg gaatcaggcg gtggacagct 19440
atgatcctga tgtgcgcatt attgaaaatc atggtgtgga ggatgaactt cccaactatt 19500
gtttccctct ggatgctgtt ggcagaacag atacttatca gggaattaag gctaatggaa 19560
ctgatcaaac cacatggacc aaagatgaca gtgtcaatga tgctaatgag ataggcaagg 19620
gtaatccatt cgccatggaa atcaacatcc aagccaacct gtggaggaac ttcctctacg 19680
ccaacgtggc cctgtacctg cccgactctt acaagtacac gccggccaat gttaccctgc 19740
ccaccaacac caacacctac gattacatga acggccgggt ggtggcgccc tcgctggtgg 19800
actcctacat caacatcggg gcgcgctggt cgctggatcc catggacaac gtgaacccct 19860
tcaaccacca ccgcaatgcg gggctgcgct accgctccat gctcctgggc aacgggcgct 19920
acgtgccctt ccacatccag gtgccccaga aatttttcgc catcaagagc ctcctgctcc 19980
tgcccgggtc ctacacctac gagtggaact tccgcaagga cgtcaacatg atcctgcaga 20040
gctccctcgg caacgacctg cgcacggacg gggcctccat ctccttcacc agcatcaacc 20100
tctacgccac cttcttcccc atggcgcaca acacggcctc cacgctcgag gccatgctgc 20160
gcaacgacac caacgaccag tccttcaacg actacctctc ggcggccaac atgctctacc 20220
ccatcccggc caacgccacc aacgtgccca tctccatccc ctcgcgcaac tgggccgcct 20280
tccgcggctg gtccttcacg cgtctcaaga ccaaggagac gccctcgctg ggctccgggt 20340
tcgaccccta cttcgtctac tcgggctcca tcccctacct cgacggcacc ttctacctca 20400
accacacctt caagaaggtc tccatcacct tcgactcctc cgtcagctgg cccggcaacg 20460
accggctcct gacgcccaac gagttcgaaa tcaagcgcac cgtcgacggc gagggctaca 20520
acgtggccca gtgcaacatg accaaggact ggttcctggt ccagatgctg gcccactaca 20580
acatcggcta ccagggcttc tacgtgcccg agggctacaa ggaccgcatg tactccttct 20640
tccgcaactt ccagcccatg agccgccagg tggtggacga ggtcaactac aaggactacc 20700
aggccgtcac cctggcctac cagcacaaca actcgggctt cgtcggctac ctcgcgccca 20760
ccatgcgcca gggccagccc taccccgcca actaccccta cccgctcatc ggcaagagcg 20820
ccgtcaccag cgtcacccag aaaaagttcc tctgcgacag ggtcatgtgg cgcatcccct 20880
tctccagcaa cttcatgtcc atgggcgcgc tcaccgacct cggccagaac atgctctatg 20940

```
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccc gaccgcccca tggacaagaa ccccaccatg aacttgctga cgggggtgcc  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccatacccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg gggtgcgct cccggcggcg  23340
```

ctctgactga cttcctccgc ggccggccat tgtgttctcc tagggaggaa caacaagcat 23400
ggagactcag ccatcgccaa cctcgccatc tgccccacc gccgacgaga agcagcagca 23460
gcagaatgaa agcttaaccg ccccgccgcc cagccccgcc acctccgacg cggccgtccc 23520
agacatgcaa gagatggagg aatccatcga gattgacctg ggctatgtga cgcccgcgga 23580
gcacgaggag gagctggcag tgcgcttttc acaagaagag atacaccaag aacagccaga 23640
gcaggaagca gagaatgagc agagtcaggc tgggctcgag catgacggcg actacctcca 23700
cctgagcggg ggggaggacg cgctcatcaa gcatctggcc cggcaggcca ccatcgtcaa 23760
ggatgcgctg ctcgaccgca ccgaggtgcc cctcagcgtg gaggagctca gccgcgccta 23820
cgagttgaac ctcttctcgc cgcgcgtgcc ccccaagcgc cagcccaatg gcacctgcga 23880
gcccaacccg cgcctcaact tctacccggt cttcgcggtg cccgaggccc tggccaccta 23940
ccacatcttt ttcaagaacc aaaagatccc cgtctcctgc cgcgccaacc gcacccgcgc 24000
cgacgccctt ttcaacctgg gtcccggcgc ccgcctacct gatatcgcct ccttggaaga 24060
ggttcccaag atcttcgagg gtctgggcag cgacgagact cgggccgcga acgctctgca 24120
aggagaagga ggagagcatg agcaccacag cgccctggtc gagttggaag gcgacaacgc 24180
gcggctggcg gtgctcaaac gcacggtcga gctgacccat ttcgcctacc cggctctgaa 24240
cctgcccccc aaagtcatga gcgcggtcat ggaccaggtg ctcatcaagc gcgcgtcgcc 24300
catctccgag gacgagggca tgcaagactc cgaggagggc aagcccgtgg tcagcgacga 24360
gcagctggcc cggtggctgg gtcctaatgc tagtccccag agtttggaag agcggcgcaa 24420
actcatgatg gccgtggtcc tggtgaccgt ggagctggag tgcctgcgcc gcttcttcgc 24480
cgacgcggag accctgcgca aggtcgagga gaacctgcac tacctcttca ggcacgggtt 24540
cgtgcgccag gcctgcaaga tctccaacgt ggagctgacc aacctggtct cctacatggg 24600
catcttgcac gagaaccgcc tggggcagaa cgtgctgcac accaccctgc gcggggaggc 24660
ccggcgcgac tacatccgcg actgcgtcta cctctacctc tgccacacct ggcagacggg 24720
catgggcgtg tggcagcagt gtctggagga gcagaacctg aaagagctct gcaagctcct 24780
gcagaagaac ctcaagggtc tgtggaccgg gttcgacgag cgcaccaccg cctcggacct 24840
ggccgacctc attttccccg agcgcctcag gctgacgctg cgcaacggcc tgcccgactt 24900
tatgagccaa agcatgttgc aaaactttcg ctctttcatc ctcgaacgct ccggaatcct 24960
gcccgccacc tgctccgcgc tgccctcgga cttcgtgccg ctgaccttcc gcgagtgccc 25020
cccgccgctg tggagccact gctacctgct gcgcctggcc aactacctgg cctaccactc 25080
ggacgtgatc gaggacgtca gcggcgaggg cctgctcgag tgccactgcc gctgcaacct 25140
ctgcacgccg caccgctccc tggcctgcaa cccccagctg ctgagcgaga cccagatcat 25200
cggcaccttc gagttgcaag ggcccagcga aggcgagggt tcagccgcca agggggtct 25260
gaaactcacc ccggggctgt ggacctcggc ctacttgcgc aagttcgtgc ccgaggacta 25320
ccatcccttc gagatcaggt tctacgagga ccaatcccat ccgcccaagg ccgagctgtc 25380
ggcctgcgtc atcacccagg gggcgatcct ggcccaattg caagccatcc agaaatcccg 25440
ccaagaattc ttgctgaaaa agggccgcgg ggtctacctc gacccccaga ccggtgagga 25500
gctcaacccc ggcttccccc aggatgcccc gaggaaacaa gaagctgaaa gtggagctgc 25560
cgcccgtgga ggatttggag gaagactggg agaacagcag tcaggcagag gaggaggaga 25620
tggaggaaga ctgggacagc actcaggcag aggaggacag cctgcaagac agtctggagg 25680

-continued

```
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
```

-continued

```
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aatttttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt ttttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgtgggcccc atctagcagt cccactgcta gtaccaatga gcagactact  30360
gaatttttgt ccactgtcga gagccacacc acagctacct ccagtgcctt ctctagcacc  30420
```

gccaatctct cctcgctttc ctctacacca atcagtcccg ctactactcc tagccccgct 30480
cctcttccca ctcccctgaa gcaaacagac ggcggcatgc aatggcagat caccctgctc 30540
attgtgatcg ggttggtcat cctggccgtg ttgctctact acatcttctg ccgccgcatt 30600
cccaacgcgc accgcaagcc ggtctacaag cccatcattg tcgggcagcc ggagccgctt 30660
caggtggaag gggtctaag gaatcttctc ttctctttta cagtatggtg attgaactat 30720
gattcctaga caattcttga tcactattct tatctgcctc ctccaagtct gtgccaccct 30780
cgctctggtg gccaacgcca gtccagactg tattgggccc ttcgcctcct acgtgctctt 30840
tgccttcacc acctgcatct gctgctgtag catagtctgc ctgcttatca ccttcttcca 30900
gttcattgac tggatctttg tgcgcatcgc ctacctgcgc caccaccccc agtaccgcga 30960
ccagcgagtg gcgcggctgc tcaggctcct ctgataagca tgcgggctct gctacttctc 31020
gcgcttctgc tgttagtgct cccccgtccc gtcgaccccc ggtcccccac ccagtccccc 31080
gaggaggtcc gcaaatgcaa attccaagaa ccctggaaat tcctcaaatg ctaccgccaa 31140
aaatcagaca tgcatcccag ctggatcatg atcattggga tcgtgaacat tctggcctgc 31200
accctcatct cctttgtgat ttacccctgc tttgactttg gttggaactc gccagaggcg 31260
ctctatctcc cgcctgaacc tgacacacca ccacagcaac ctcaggcaca cgcactacca 31320
ccactacagc ctaggccaca atacatgccc atattagact atgaggccga gccacagcga 31380
cccatgctcc ccgctattag ttacttcaat ctaaccggcg gagatgactg acccactggc 31440
caacaacaac gtcaacgacc ttctcctgga catggacggc cgcgcctcgg agcagcgact 31500
cgcccaactt cgcattcgcc agcagcagga gagagccgtc aaggagctgc aggatgcggt 31560
ggccatccac cagtgcaaga gaggcatctt ctgcctggtg aaacaggcca agatctccta 31620
cgaggtcact ccaaacgacc atcgcctctc ctacgagctc ctgcagcagc gccagaagtt 31680
cacctgcctg gtcggagtca accccatcgt catcacccag cagtctggcg ataccaaggg 31740
gtgcatccac tgctcctgcg actcccccga ctgcgtccac actctgatca agaccctctg 31800
cggcctccgc gacctcctcc ccatgaacta atcacccct tatccagtga aataaagatc 31860
atattgatga tgattttaca gaaataaaaa ataatcattt gatttgaaat aaagatacaa 31920
tcatattgat gatttgagtt taacaaaaaa ataaagaatc acttacttga aatctgatac 31980
caggtctctg tccatgtttt ctgccaacac cacttcactc ccctcttccc agctctggta 32040
ctgcaggccc cggcgggctg caaacttcct ccacacgctg aaggggatgt caaattcctc 32100
ctgtccctca atcttcattt tatcttctat cagatgtcca aaaagcgcgt ccgggtggat 32160
gatgacttcg accccgtcta cccctacgat gcagacaacg caccgaccgt gcccttcatc 32220 aacccccccct tcgtctcttc agatggattc caagagaagc ccctgggggt gttgtccctg 32280
cgactggccg accccgtcac caccaagaac ggggaaatca ccctcaagct gggagagggg 32340
gtggacctcg attcctcggg aaaactcatc tccaacacgg ccaccaaggc cgccgcccct 32400
ctcagttttt ccaacaacac catttccctt aacatggatc accccttta cactaaagat 32460 ggaaaattat ccttacaagt ttctccacca ttaaatatac tgagaacaag cattctaaac 32520
acactagctt taggttttgg atcaggttta ggactccgtg gctctgcctt ggcagtacag 32580
ttagtctctc cacttacatt tgatactgat ggaaacataa agcttacctt agacagaggt 32640
ttgcatgtta caacaggaga tgcaattgaa agcaacataa gctgggctaa aggtttaaaa 32700
tttgaagatg gagccatagc aaccaacatt ggaaatgggt tagagtttgg aagcagtagt 32760
acagaaacag gtgttgatga tgcttaccca atccaagtta aacttggatc tggccttagc 32820

```
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtatagg   33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg gggctaactc ttataccttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
```

```
tgttacactc ctgcaccatc cccagataat tttcattttt ccagccttga atgattcgaa  35220

ctagttcctg aggtaaatcc aagccagcca tgataaagag ctcgcgcaga gcgccctcca  35280

ccggcattct taagcacacc ctcataattc caagatattc tgctcctggt tcacctgcag  35340

cagattgaca agcggaatat caaaatctct gccgcgatcc ctgagctcct ccctcagcaa  35400

taactgtaag tactctttca tatcctctcc gaaattttta gccataggac caccaggaat  35460

aagattaggg caagccacag tacagataaa ccgaagtcct ccccagtgag cattgccaaa  35520

tgcaagactg ctataagcat gctggctaga cccggtgata tcttccagat aactggacag  35580

aaaatcgccc aggcaatttt taagaaaatc aacaaaagaa aaatcctcca ggtggacgtt  35640

tagagcctcg ggaacaacga tgaagtaaat gcaagcggtg cgttccagca tggttagtta  35700

gctgatctgt agaaaaaaca aaaatgaaca ttaaaccatg ctagcctggc gaacaggtgg  35760

gtaaatcgtt ctctccagca ccaggcaggc cacggggtct ccggcgcgac cctcgtaaaa  35820

attgtcgcta tgattgaaaa ccatcacaga gagacgttcc cggtggccgg cgtgaatgat  35880

tcgacaagat gaatacaccc ccggaacatt ggcgtccgcg agtgaaaaaa agcgcccgag  35940

gaagcaataa ggcactacaa tgctcagtct caagtccagc aaagcgatgc catgcggatg  36000

aagcacaaaa ttctcaggtg cgtacaaaat gtaattactc ccctcctgca caggcagcaa  36060

agcccccgat ccctccaggt acacatacaa agcctcagcg tccatagctt accgagcagc  36120

agcacacaac aggcgcaaga gtcagagaaa ggctgagctc taacctgtcc acccgctctc  36180

tgctcaatat atagcccaga tctacactga cgtaaaggcc aaagtctaaa aatacccgcc  36240

aaataatcac acacgcccag cacacgccca gaaaccggtg acacactcaa aaaaatacgc  36300

gcacttcctc aaacgcccaa aactgccgtc atttccgggt tcccacgcta cgtcatcaaa  36360

acacgacttt caaattccgt cgaccgttaa aaacgtcacc cgccccgccc ctaacggtcg  36420

cccgtctctc agccaatcag cgccccgcat ccccaaattc aaacacctca tttgcatatt  36480

aacgcgcaca aaaagtttga ggtatattat tgatgatgg                         36519
```

<210> SEQ ID NO 2
<211> LENGTH: 31588
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ccatcttcaa taatatacct caaacttttt gtgcgcgtta atatgcaaat gaggcgtttg     60

aatttgggga ggaagggcgg tgattggtcg agggatgagc gaccgttagg ggcggggcga    120

gtgacgtttt gatgacgtgg ttgcgaggag gagccagttt gcaagttctc gtgggaaaag    180

tgacgtcaaa cgaggtgtgg tttgaacacg gaaatactca attttcccgc gctctctgac    240

aggaaatgag gtgtttctgg gcggatgcaa gtgaaaacgg gccattttcg cgcgaaaact    300

gaatgaggaa gtgaaaatct gagtaatttc gcgtttatgg cagggaggag tatttgccga    360

gggccgagta gactttgacc gattacgtgg gggtttcgat taccgtgttt ttcacctaaa    420

tttccgcgta cggtgtcaaa gtccggtgtt tttacgtagg tgtcagctga tcgccagggt    480

atttaaacct gcgctctcca gtcaagaggc cactcttgag tgccagcgag aagagttttc    540

tcctccgcgc cgcgagtcag atctacactt tgaaagtagg gataacaggg taatgacatt    600

gattattgac tagttgttaa tagtaatcaa ttacggggtc attagttcat agcccatata    660
```

-continued

```
tggagttccg cgttacataa cttacggtaa atggcccgcc tggctgaccg cccaacgacc     720
cccgcccatt gacgtcaata atgacgtatg ttcccatagt aacgccaata gggactttcc     780
attgacgtca atgggtggag tatttacggt aaactgccca cttggcagta catcaagtgt     840
atcatatgcc aagtccgccc cctattgacg tcaatgacgg taaatggccc gcctggcatt     900
atgcccagta catgacctta cgggactttc ctacttggca gtacatctac gtattagtca     960
tcgctattac catggtgatg cggttttggc agtacaccaa tgggcgtgga tagcggtttg    1020
actcacgggg atttccaagt ctccacccca ttgacgtcaa tgggagtttg ttttggcacc    1080
aaaatcaacg ggactttcca aaatgtcgta ataaccccgc cccgttgacg caaatgggcg    1140
gtaggcgtgt acggtgggag gtctatataa gcagagctcg tttagtgaac cgtcagatcg    1200
cctggaacgc catccacgct gttttgacct ccatagaaga cagcgatcgc gccaccatgg    1260
ccgggatgtt ccaggcactg tccgaaggct gcacacccta tgatattaac cagatgctga    1320
atgtcctggg agaccaccag gtctctggcc tggagcagct ggagagcatc atcaacttcg    1380
agaagctgac cgagtggaca agctccaatg tgatgcctat cctgtcccca ctgaccaagg    1440
gcatcctggg cttcgtgttt accctgacag tgccttctga gcggggcctg tcttgcatca    1500
gcgaggcaga cgcaaccaca ccagagtccg ccaatctggg cgaggagatc ctgtctcagc    1560
tgtacctgtg gccccgggtg acatatcact ccccttctta cgcctatcac cagttcgagc    1620
ggagagccaa gtacaagaga cacttcccag gctttggcca gtctctgctg ttcggctacc    1680
ccgtgtacgt gttcggcgat tgcgtgcagg gcgactggga tgccatccgg tttagatact    1740
gcgcaccacc tggatatgca ctgctgaggt gtaacgacac caattattcc gccctgctgg    1800
cagtgggcgc cctggagggc cctcgcaatc aggattggct gggcgtgcca aggcagctgg    1860
tgacacgcat gcaggccatc cagaacgcag gcctgtgcac cctggtggca atgctggagg    1920
agacaatctt ctggctgcag gcctttctga tggccctgac cgacagcggc cccaagacaa    1980
acatcatcgt ggattcccag tacgtgatgg gcatctccaa gccttctttc caggagtttg    2040
tggactggga gaacgtgagc ccagagctga attccaccga tcagccattc tggcaggcag    2100
gaatcctggc aaggaacctg gtgcctatgg tggccacagt gcagggccag aatctgaagt    2160
accagggcca gagcctggtc atcagcgcct ccatcatcgt gtttaacctg ctggagctgg    2220
agggcgacta tcgggacgat ggcaacgtgt gggtgcacac cccactgagc cccagaacac    2280
tgaacgcctg ggtgaaggcc gtggaggaga agaagggcat cccagtgcac ctggagctgg    2340
cctccatgac caatatggag ctgatgtcta gcatcgtgca ccagcaggtg aggacatacg    2400
gacccgtgtt catgtgcctg ggaggcctgc tgaccatggt ggcaggagcc gtgtggctga    2460
cagtgcgggt gctggagctg ttcagagccg cccagctggc caacgatgtg gtgctgcaga    2520
tcatggagct gtgcggagca gcctttcgcc aggtgtgcca caccacagtg ccatggccca    2580
atgcctccct gacccccaag tggaacaatg agacaacaca gcctcagatc gccaactgta    2640
gcgtgtacga cttcttcgtg tggctgcact actatagcgt gagggatacc ctgtggcccc    2700
gcgtgacata ccacatgaat aagtacgcct atcacatgct ggagaggcgc gccaagtata    2760
agagaggccc tggcccaggc gcaaagtttg tggcagcatg gaccctgaag gccgccgccg    2820
gccccggccc cggccagtat atcaaggcta acagtaagtt cattggaatc acagagctgg    2880
gacccggacc tggataatga gtttaaactc ccatttaaat gtgagggtta atgcttcgag    2940
cagacatgat aagatacatt gatgagtttg gacaaaccac aactagaatg cagtgaaaaa    3000
aatgctttat ttgtgaaatt tgtgatgcta ttgctttatt tgtaaccatt ataagctgca    3060
```

```
ataaacaagt taacaacaac aattgcattc attttatgtt tcaggttcag gggagatgt   3120
gggaggtttt ttaaagcaag taaaacctct acaaatgtgg taaaataact ataacggtcc   3180
taaggtagcg agtgagtagt gttctggggc gggggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat ttttcgcgcg   3780
cggtaggccc tggaccaccg gtctcgatca ttgagcaccc ggtggatctt ttccaggacc   3840
cggtagaggt gggcttggat gttgaggtac atgggcatga gcccgtcccg ggggtggagg   3900
tagctccatt gcagggcctc gtgctcgggg gtggtgttgt aaatcaccca gtcatagcag   3960
gggcgcaggg catggtgttg cacaatatct ttgaggagga gactgatggc cacgggcagc   4020
cctttggtgt aggtgtttac aaatctgttg agctgggagg gatgcatgcg gggggagatg   4080
aggtgcatct tggcctggat cttgagattg gcgatgttac cgcccagatc ccgcctgggg   4140
ttcatgttgt gcaggaccac cagcacggtg tatccggtgc acttggggaa tttatcatgc   4200
aacttggaag ggaaggcgtg aaagaatttg gcgacgcctt tgtgcccgcc caggttttcc   4260
atgcactcat ccatgatgat ggcgatgggc ccgtgggcgg cggcctgggc aaagacgttt   4320
cgggggtcgg acacatcata gttgtggtcc tgggtgaggt catcataggc cattttaatg   4380
aatttggggc ggagggtgcc ggactggggg acaaaggtac cctcgatccc gggggcgtag   4440
ttcccctcac agatctgcat ctcccaggct ttgagctcgg aggggggat catgtccacc   4500
tgcggggcga taaagaacac ggtttccggg gcgggggaga tgagctgggc cgaaagcaag   4560
ttccggagca gctgggactt gccgcagccg gtggggccgt agatgacccc gatgaccggc   4620
tgcaggtggt agttgaggga gagacagctg ccgtcctccc ggaggagggg ggccacctcg   4680
ttcatcatct cgcgcacgtg catgttctcg cgcaccagtt ccgccaggag gcgctctccc   4740
cccagggata ggagctcctg gagcgaggcg aagtttttca gcggcttgag tccgtcggcc   4800
atgggcattt tggagagggt ttgttgcaag agttccaggc ggtcccagag ctcggtgatg   4860
tgctctacgg catctcgatc cagcagacct cctcgtttcg cgggttggga cggctgcggg   4920
agtagggcac cagacgatgg gcgtccagcg cagccagggt ccggtccttc cagggtcgca   4980
gcgtccgcgt cagggtggtc tccgtcacgg tgaaggggtg cgcgccgggc tgggcgcttg   5040
cgagggtgcg cttcaggctc atccggctgg tcgaaaaccg ctcccgatcg gcgccctgcg   5100
cgtcggccag gtagcaattg accatgagtt cgtagttgag cgcctcggcc gcgtggcctt   5160
tggcgcggag cttacctttg gaagtctgcc cgcaggcggg acagaggagg gacttgaggg   5220
cgtagagctt gggggcgagg aagacggact cgggggcgta ggcgtccgcg ccgcagtggg   5280
cgcagacggt ctcgcactcc acgagccagg tgaggtcggg ctggtcgggg tcaaaaacca   5340
gtttcccgcc gttctttttg atgcgtttct tacctttggt ctccatgagc tcgtgtcccc   5400
```

-continued

```
gctgggtgac aaagaggctg tccgtgtccc cgtagaccga ctttatgggc cggtcctcga   5460
gcggtgtgcc gcggtcctcc tcgtagagga accccgccca ctccgagacg aaagcccggg   5520
tccaggccag cacgaaggag gccacgtggg acgggtagcg gtcgttgtcc accagcgggt   5580
ccaccttttc cagggtatgc aaacacatgt ccccctcgtc cacatccagg aaggtgattg   5640
gcttgtaagt gtaggccacg tgaccggggg tcccggccgg gggggtataa aagggtgcgg   5700
gtccctgctc gtcctcactg tcttccggat cgctgtccag gagcgccagc tgttggggta   5760
ggtattccct ctcgaaggcg ggcatgacct cggcactcag gttgtcagtt tctagaaacg   5820
aggaggattt gatattgacg gtgccggcgg agatgccttt caagagcccc tcgtccatct   5880
ggtcagaaaa gacgatcttt ttgttgtcga gcttggtggc gaaggagccg tagagggcgt   5940
tggagaggag cttggcgatg gagcgcatgg tctggttttt ttccttgtcg gcgcgctcct   6000
tggcggcgat gttgagctgc acgtactcgc gcgccacgca cttccattcg gggaagacgg   6060
tggtcagctc gtcgggcacg attctgacct gccagccccg attatgcagg gtgatgaggt   6120
ccacactggt ggccacctcg ccgcgcaggg gctcattagt ccagcagagg cgtccgccct   6180
tgcgcgagca gaagggggc agggggtcca gcatgacctc gtcgggggg tcggcatcga   6240
tggtgaagat gccgggcagg aggtcggggt caaagtagct gatggaagtg gccagatcgt   6300
ccagggcagc ttgccattcg cgcacggcca gcgcgcgctc gtagggactg aggggcgtgc   6360
cccagggcat gggatgggta agcgcggagg cgtacatgcc gcagatgtcg tagacgtaga   6420
ggggctcctc gaggatgccg atgtaggtgg ggtagcagcg ccccccgcgg atgctggcgc   6480
gcacgtagtc atacagctcg tgcgaggggg cgaggagccc cgggcccagg ttggtgcgac   6540
tgggcttttc ggcgcggtag acgatctggc ggaaaatggc atgcgagttg gaggagatgg   6600
tgggcctttg gaagatgttg aagtgggcgt ggggcagtcc gaccgagtcg cggatgaagt   6660
gggcgtagga gtcttgcagc ttggcgacga gctcggcggt gactaggacg tccagagcgc   6720
agtagtcgag ggtctcctgg atgatgtcat acttgagctg tcccttttgt ttccacagct   6780
cgcggttgag aaggaactct tcgcggtcct tccagtactc ttcgaggggg aacccgtcct   6840
gatctgcacg gtaagagcct agcatgtaga actggttgac ggccttgtag gcgcagcagc   6900
ccttctccac ggggagggcg taggcctggg cggccttgcg cagggaggtg tgcgtgaggg   6960
cgaaagtgtc cctgaccatg accttgagga actggtgctt gaagtcgata tcgtcgcagc   7020
ccccctgctc ccagagctgg aagtccgtgc gcttcttgta ggcggggttg ggcaaagcga   7080
aagtaacatc gttgaagagg atcttgcccg cgcggggcat aaagttgcga gtgatgcgga   7140
aaggttgggg cacctcggcc cggttgttga tgacctgggc ggcgagcacg atctcgtcga   7200
agccgttgat gttgtggccc acgatgtaga gttccacgaa tcgcggacgg cccttgacgt   7260
ggggcagttt cttgagctcc tcgtaggtga gctcgtcggg gtcgctgagc ccgtgctgct   7320
cgagcgccca gtcggcgaga tgggggttgg cgcggaggaa ggaagtccag agatccacgg   7380
ccagggcggt ttgcagacgg tcccggtact gacggaactg ctgcccgacg gccatttttt   7440
cgggggtgac gcagtagaag gtgcgggggt ccccgtgcca gcgatcccat ttgagctgga   7500
gggcgagatc gagggcgagc tcgacgagcc ggtcgtcccc ggagagtttc atgaccagca   7560
tgaaggggac gagctgcttg ccgaaggacc ccatccaggt gtaggtttcc acatcgtagg   7620
tgaggaagag cctttcggtg cgaggatgcg agccgatggg gaagaactgg atctcctgcc   7680
accaattgga ggaatggctg ttgatgtgat ggaagtagaa atgccgacgg cgcgccgaac   7740
actcgtgctt gtgtttatac aagcggccac agtgctcgca acgctgcacg ggatgcacgt   7800
```

-continued

```
gctgcacgag ctgtacctga gttcctttga cgaggaattt cagtgggaag tggagtcgtg   7860
gcgcctgcat ctcgtgctgt actacgtcgt ggtggtcggc ctggccctct tctgcctcga   7920
tggtggtcat gctgacgagc ccgcgcggga ggcaggtcca gacctcggcg cgagcgggtc   7980
ggagagcgag gacgagggcg cgcaggccgg agctgtccag ggtcctgaga cgctgcggag   8040
tcaggtcagt gggcagcggc ggcgcgcggt tgacttgcag gagtttttcc agggcgcgcg   8100
ggaggtccag atggtacttg atctccaccg cgccattggt ggcgacgtcg atggcttgca   8160
gggtcccgtg cccctggggt gtgaccaccg tcccccgttt cttcttgggc ggctggggcg   8220
acgggggcgg tgcctcttcc atggttagaa gcggcggcga ggacgcgcgc cgggcggcag   8280
gggcggctcg gggcccggag gcaggggcgg caggggcacg tcggcgccgc gcgcgggtag   8340
gttctggtac tgcgcccgga gaagactggc gtgagcgacg acgcgacggt tgacgtcctg   8400
gatctgacgc ctctgggtga aggccacggg acccgtgagt ttgaacctga aagagagttc   8460
gacagaatca atctcggtat cgttgacggc ggcctgccgc aggatctctt gcacgtcgcc   8520
cgagttgtcc tggtaggcga tctcggtcat gaactgctcg atctcctcct cttgaaggtc   8580
tccgcggccg gcgcgctcca cggtggccgc gaggtcgttg gagatgcggc ccatgagctg   8640
cgagaaggcg ttcatgcccg cctcgttcca gacgcggctg tagaccacga cgccctcggg   8700
atcgcgggcg cgcatgacca cctgggcgag gttgagctcc acgtggcgcg tgaagaccgc   8760
gtagttgcag aggcgctggt agaggtagtt gagcgtggtg gcgatgtgct cggtgacgaa   8820
gaaatacatg atccagcggc ggagcggcat ctcgctgacg tcgcccagcg cctccaaacg   8880
ttccatggcc tcgtaaaagt ccacggcgaa gttgaaaaac tgggagttgc gcgccgagac   8940
ggtcaactcc tcctccagaa gacggatgag ctcggcgatg gtggcgcgca cctcgcgctc   9000
gaaggccccc gggagttcct ccacttcctc ttcttcctcc tccactaaca tctcttctac   9060
ttcctcctca ggcggcagtg gtggcggggg agggggcctg cgtcgccggc ggcgcacggg   9120
cagacggtcg atgaagcgct cgatggtctc gccgcgccgg cgtcgcatgg tctcggtgac   9180
ggcgcgcccg tcctcgcggg gccgcagcgt gaagacgccg ccgcgcatct ccaggtggcc   9240
gggggggtcc ccgttgggca gggagagggc gctgacgatg catcttatca attgccccgt   9300
agggactccg cgcaaggacc tgagcgtctc gagatccacg ggatctgaaa accgctgaac   9360
gaaggcttcg agccagtcgc agtcgcaagg taggctgagc acggtttctt ctggcgggtc   9420
atgttggttg ggagcggggc gggcgatgct gctggtgatg aagttgaaat aggcggttct   9480
gagacggcgg atggtggcga ggagcaccag gtctttgggc ccggcttgct ggatgcgcag   9540
acggtcggcc atgccccagg cgtggtcctg acacctggcc aggtccttgt agtagtcctg   9600
catgagccgc tccacgggca cctcctcctc gcccgcgcgg ccgtgcatgc gcgtgagccc   9660
gaagccgcgc tggggctgga cgagcgccag gtcggcgacg acgcgctcgg cgaggatggc   9720
ttgctggatc tgggtgaggg tggtctggaa gtcatcaaag tcgacgaagc ggtggtaggc   9780
tccggtgttg atggtgtagg agcagttggc catgacggac cagttgacgg tctggtggcc   9840
cggacgcacg agctcgtggt acttgaggcg cgagtaggcg cgcgtgtcga agatgtagtc   9900
gttgcaggtg cgcaccaggt actggtagcc gatgaggaag tgcggcggcg gctggcggta   9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
```

ggtctggccc gtgaggcgcg cgcagtcgtg gatgctctat acgggcaaaa acgaaagcgg 10200
tcagcggctc gactccgtgg cctggaggct aagcgaacgg gttgggctgc gcgtgtaccc 10260
cggttcgaat ctcgaatcag gctggagccg cagctaacgt ggtattggca ctcccgtctc 10320
gacccaagcc tgcaccaacc ctccaggata cggaggcggg tcgttttgca acttttttt 10380
ggaggccgga tgagactagt aagcgcggaa agcggccgac cgcgatggct cgctgccgta 10440
gtctggagaa gaatcgccag ggttgcgttg cggtgtgccc cggttcgagg ccggccggat 10500
tccgcggcta acgagggcgt ggctgccccg tcgtttccaa gaccccatag ccagccgact 10560
tctccagtta cggagcgagc cctcttttg ttttgtttgt tttgccaga tgcatcccgt 10620
actgcggcag atgcgccccc accaccctcc accgcaacaa cagccccctc cacagccggc 10680
gcttctgccc ccgccccagc agcaacttcc agccacgacc gccgcggccg ccgtgagcgg 10740
ggctggacag agttatgatc accagctggc cttggaagag ggcgaggggc tggcgcgcct 10800
gggggcgtcg tcgccggagc ggcacccgcg cgtgcagatg aaaagggacg ctcgcgaggc 10860
ctacgtgccc aagcagaacc tgttcagaga caggagcggc gaggagcccg aggagatgcg 10920
cgcggcccgg ttccacgcgg ggcgggagct gcggcgcggc ctggaccgaa agagggtgct 10980
gagggacgag gatttcgagg cggacgagct gacggggatc agccccgcgc gcgcgcacgt 11040
ggccgcggcc aacctggtca cggcgtacga gcagaccgtg aaggaggaga gcaacttcca 11100
aaaatccttc aacaaccacg tgcgcaccct gatcgcgcgc gaggaggtga ccctgggcct 11160
gatgcacctg tgggacctgc tggaggccat cgtgcagaac cccaccagca agccgctgac 11220
ggcgcagctg ttcctggtgg tgcagcatag tcgggacaac gaagcgttca gggaggcgct 11280
gctgaatatc accgagcccg agggccgctg gctcctggac ctggtgaaca ttctgcagag 11340
catcgtggtg caggagcgcg ggctgccgct gtccgagaag ctggcggcca tcaacttctc 11400
ggtgctgagt ttgggcaagt actacgctag gaagatctac aagaccccgt acgtgcccat 11460
agacaaggag gtgaagatcg acgggtttta catgcgcatg accctgaaag tgctgaccct 11520
gagcgacgat ctgggggtgt accgcaacga caggatgcac cgtgcggtga gcgccagcag 11580
gcggcgcgag ctgagcgacc aggagctgat gcatagtctg cagcgggccc tgaccggggc 11640
cgggaccgag ggggagagct actttgacat gggcgcggac ctgcactggc agcccagccg 11700
ccgggccttg gaggcggcgg caggacccta cgtagaagag gtggacgatg aggtggacga 11760
ggagggcgag tacctggaag actgatggcg cgaccgtatt tttgctagat gcaacaacaa 11820
cagccacctc ctgatcccgc gatgcgggcg gcgctgcaga gccagccgtc cggcattaac 11880
tcctcggacg attggaccca ggccatgcaa cgcatcatgg cgctgacgac ccgcaacccc 11940
gaagccttta gacagcagcc ccaggccaac cggctctcgg ccatcctgga ggccgtggtg 12000
ccctcgcgct ccaaccccac gcacgagaag gtcctggcca tcgtgaacgc gctggtggag 12060
aacaaggcca tccgcggcga cgaggccggc ctggtgtaca acgcgctgct ggagcgcgtg 12120
gcccgctaca acagcaccaa cgtgcagacc aacctggacc gcatggtgac cgacgtgcgc 12180
gaggccgtgg cccagcgcga gcggttccac cgcgagtcca acctgggatc catggtggcg 12240
ctgaacgcct tcctcagcac ccagcccgcc aacgtgcccc ggggccagga ggactacacc 12300
aacttcatca gcgccctgcg cctgatggtg accgaggtgc cccagagcga ggtgtaccag 12360
tccgggccgg actacttctt ccagaccagt cgccagggct tgcagaccgt gaacctgagc 12420
caggctttca agaacttgca gggcctgtgg ggcgtgcagg ccccggtcgg ggaccgcgcg 12480
acggtgtcga gcctgctgac gccgaactcg cgcctgctgc tgctgctggt ggccccccttc 12540 acggacagcg gcagcatcaa ccgcaactcg tacctgggct acctgattaa cctgtaccgc 12600
gaggccatcg gccaggcgca cgtggacgag cagacctacc aggagatcac ccacgtgagc 12660
cgcgccctgg gccaggacga cccgggcaac ctggaagcca ccctgaactt tttgctgacc 12720
aaccggtcgc agaagatccc gccccagtac gcgctcagca ccgaggagga gcgcatcctg 12780
cgttacgtgc agcagagcgt gggcctgttc ctgatgcagg agggggccac ccccagcgcc 12840
gcgctcgaca tgaccgcgcg caacatggag cccagcatgt acgccagcaa ccgcccgttc 12900
atcaataaac tgatggacta cttgcatcgg gcggccgcca tgaactctga ctatttcacc 12960
aacgccatcc tgaatcccca ctggctcccg ccgccggggt tctacacggg cgagtacgac 13020
atgcccgacc ccaatgacgg gttcctgtgg gacgatgtgg acagcagcgt gttctccccc 13080
cgaccgggtg ctaacgagcg ccccttgtgg aagaaggaag gcagcgaccg acgcccgtcc 13140
tcggcgctgt ccggccgcga gggtgctgcc gcggcggtgc ccgaggccgc cagtcctttc 13200
ccgagcttgc ccttctcgct gaacagtatc cgcagcagcg agctgggcag gatcacgcgc 13260
ccgcgcttgc tgggcgaaga ggagtacttg aatgactcgc tgttgagacc cgagcgggag 13320
aagaacttcc ccaataacgg gatagaaagc ctggtggaca agatgagccg ctggaagacg 13380
tatgcgcagg agcacaggga cgatccccgg gcgtcgcagg gggccacgag ccggggcagc 13440
gccgcccgta aacgccggtg gcacgacagg cagcggggac agatgtggga cgatgaggac 13500
tccgccgacg acagcagcgt gttggacttg ggtgggagtg gtaacccgtt cgctcacctg 13560
cgcccccgta tcgggcgcat gatgtaagag aaaccgaaaa taaatgatac tcaccaaggc 13620
catggcgacc agcgtgcgtt cgtttcttct ctgttgttgt tgtatctagt atgatgaggc 13680
gtgcgtaccc ggagggtcct cctccctcgt acgagagcgt gatgcagcag gcgatggcgg 13740
cggcggcgat gcagcccccg ctggaggctc cttacgtgcc cccgcggtac ctggcgccta 13800
cggaggggcg gaacagcatt cgttactcgg agctggcacc cttgtacgat accacccggt 13860
tgtacctggt ggacaacaag tcggcggaca tcgcctcgct gaactaccag aacgaccaca 13920
gcaacttcct gaccaccgtg gtgcagaaca atgacttcac ccccacggag gccagcaccc 13980
agaccatcaa ctttgacgag cgctcgcggt ggggcggcca gctgaaaacc atcatgcaca 14040
ccaacatgcc caacgtgaac gagttcatgt acagcaacaa gttcaaggcg cgggtgatgg 14100
tctcccgcaa gacccccaat ggggtgacag tgacagagga ttatgatggt agtcaggatg 14160
agctgaagta tgaatgggtg gaatttgagc tgcccgaagg caacttctcg gtgaccatga 14220
ccatcgacct gatgaacaac gccatcatcg acaattactt ggcggtgggg cggcagaacg 14280
gggtgctgga gagcgacatc ggcgtgaagt tcgacactag gaacttcagg ctgggctggg 14340
accccgtgac cgagctggtc atgcccgggg tgtacaccaa cgaggctttc catcccgata 14400
ttgtcttgct gcccggctgc ggggtggact tcaccgagag ccgcctcagc aacctgctgg 14460
gcattcgcaa gaggcagccc ttccaggaag gcttccagat catgtacgag gatctggagg 14520
ggggcaacat ccccgcgctc ctggatgtcg acgcctatga gaaaagcaag gaggatgcag 14580
cagctgaagc aactgcagcc gtagctaccg cctctaccga ggtcaggggc gataattttg 14640
caagcgccgc agcagtggca gcggccgagg cggctgaaac cgaaagtaag atagtcattc 14700
agccggtgga gaaggatagc aagaacagga gctacaacgt actaccggac aagataaaca 14760
ccgcctaccg cagctggtac ctagcctaca actatggcga ccccgagaag ggcgtgcgct 14820
cctggacgct gctcaccacc tcggacgtca cctgcggcgt ggagcaagtc tactggtcgc 14880
tgcccgacat gatgcaagac ccggtcacct tccgctccac gcgtcaagtt agcaactacc 14940
cggtggtggg cgccgagctc ctgcccgtct actccaagag cttcttcaac gagcaggccg 15000
tctactcgca gcagctgcgc gccttcacct cgcttacgca cgtcttcaac cgcttccccg 15060
agaaccagat cctcgtccgc ccgcccgcgc ccaccattac caccgtcagt gaaaacgttc 15120
ctgctctcac agatcacggg accctgccgc tgcgcagcag tatccgggga gtccagcgcg 15180
tgaccgttac tgacgccaga cgccgcacct gcccctacgt ctacaaggcc ctgggcatag 15240
tcgcgccgcg cgtcctctcg agccgcacct tctaaatgtc cattctcatc tcgcccagta 15300
ataacaccgg ttggggcctg cgcgcgccca gcaagatgta cggaggcgct cgccaacgct 15360
ccacgcaaca ccccgtgcgc gtgcgcgggc acttccgcgc tccctggggc gccctcaagg 15420
gccgcgtgcg gtcgcgcacc accgtcgacg acgtgatcga ccaggtggtg gccgacgcgc 15480
gcaactacac ccccgccgcc gcgcccgtct ccaccgtgga cgccgtcatc gacagcgtgg 15540
tggccgacgc gcgccggtac gcccgcgcca agagccggcg gcggcgcatc gcccggcggc 15600
accggagcac ccccgccatg cgcgcggcgc gagccttgct gcgcagggcc aggcgcacgg 15660
gacgcagggc catgctcagg gcggccagac gcgcggcttc aggcgccagc gccggcagga 15720
cccggagacg cgcggccacg gcggcggcag cggccatcgc cagcatgtcc cgcccgcggc 15780
gagggaacgt gtactgggtg cgcgacgccg ccaccggtgt gcgcgtgccc gtgcgcaccc 15840
gcccccctcg cacttgaaga tgttcacttc gcgatgttga tgtgtcccag cggcgaggag 15900
gatgtccaag cgcaaattca aggaagagat gctccaggtc atcgcgcctg agatctacgg 15960
ccctgcggtg gtgaaggagg aaagaaagcc ccgcaaaatc aagcgggtca aaaaggacaa 16020
aaaggaagaa gaaagtgatg tggacggatt ggtggagttt gtgcgcgagt tcgccccccg 16080
gcggcgcgtg cagtggcgcg ggcggaaggt gcaaccggtg ctgagacccg gcaccaccgt 16140
ggtcttcacg cccggcgagc gctccggcac cgcttccaag cgctcctacg acgaggtgta 16200
cggggatgat gatattctgg agcaggcggc cgagcgcctg ggcgagtttg cttacggcaa 16260
gcgcagccgt tccgcaccga aggaagaggc ggtgtccatc ccgctggacc acggcaaccc 16320
cacgccgagc ctcaagcccg tgaccttgca gcaggtgctg ccgaccgcgg cgccgcgccg 16380
ggggttcaag cgcgagggcg aggatctgta ccccaccatg cagctgatgg tgcccaagcg 16440
ccagaagctg gaagacgtgc tggagaccat gaaggtggac ccggacgtgc agcccgaggt 16500
caaggtgcgg cccatcaagc aggtggcccc gggcctgggc gtgcagaccg tggacatcaa 16560
gattcccacg gagcccatgg aaacgcagac cgagcccatg atcaagccca gcaccagcac 16620
catggaggtg cagacggatc cctggatgcc atcggctcct agtcgaagac cccggcgcaa 16680
gtacggcgcg gccagcctgc tgatgcccaa ctacgcgctg catccttcca tcatccccac 16740
gccgggctac cgcggcacgc gcttctaccg cggtcatacc agcagccgcc gccgcaagac 16800
caccactcgc cgccgccgtc gccgcaccgc cgctgcaacc acccctgccg ccctggtgcg 16860
gagagtgtac cgccgcggcc gcgcacctct gaccctgccg cgcgcgcgct accacccgag 16920
catcgccatt taaactttcg cctgctttgc agatcaatgg ccctcacatg ccgccttcgc 16980
gttcccatta cgggctaccg aggaagaaaa ccgcgccgta gaaggctggc ggggaacggg 17040
atgcgtcgcc accaccaccg gcggcggcgc gccatcagca agcggttggg gggaggcttc 17100
ctgcccgcgc tgatccccat catcgccgcg gcgatcgggg cgatccccgg cattgcttcc 17160
gtggcggtgc aggcctctca gcgccactga gacacacttg gaaacatctt gtaataaacc 17220
aatggactct gacgctcctg gtcctgtgat gtgttttcgt agacagatgg aagacatcaa 17280

```
tttttcgtcc ctggctccgc gacacggcac gcggccgttc atgggcacct ggagcgacat  17340
cggcaccagc caactgaacg ggggcgcctt caattggagc agtctctgga gcgggcttaa  17400
gaatttcggg tccacgctta aaacctatgg cagcaaggcg tggaacagca ccacagggca  17460
ggcgctgagg gataagctga aagagcagaa cttccagcag aaggtggtcg atgggctcgc  17520
ctcgggcatc aacggggtgg tggacctggc caaccaggcc gtgcagcggc agatcaacag  17580
ccgcctggac ccggtgccgc ccgccggctc cgtggagatg ccgcaggtgg aggaggagct  17640
gcctcccctg gacaagcggg gcgagaagcg accccgcccc gatgcggagg agacgctgct  17700
gacgcacacg gacgagccgc ccccgtacga ggaggcggtg aaactgggtc tgcccaccac  17760
gcggcccatc gcgcccctgg ccaccggggt gctgaaaccc gaaaagcccg cgaccctgga  17820
cttgcctcct ccccagcctt cccgcccctc tacagtggct aagcccctgc cgccggtggc  17880
cgtggcccgc gcgcgacccg gggcaccgc ccgccctcat gcgaactggc agagcactct  17940
gaacagcatc gtgggtctgg gagtgcagag tgtgaagcgc cgccgctgct attaaaccta  18000
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
```

-continued

```
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
ttttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg accccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc acccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc cccgcacaag ctggcctgcg ccatcgtcaa  21060
cacggccggc cgcgagaccg gggcgagca ctggctggcc ttcgcctgga acccgcgctc  21120
gaacacctgc tacctcttcg acccttcgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
```

atcgcagtgc aggggggatca gcatcatctg ggcctggtcg gcgttcatcc ccgggtacat 22080
ggccttcatg aaagcctcca attgcctgaa cgcctgctgg gccttggctc cctcggtgaa 22140
gaagaccccg caggacttgc tagagaactg gttggtggcg cacccggcgt cgtgcacgca 22200
gcagcgcgcg tcgttgttgg ccagctgcac cacgctgcgc ccccagcggt tctgggtgat 22260
cttggcccgg tcggggttct ccttcagcgc gcgctgcccg ttctcgctcg ccacatccat 22320
ctcgatcatg tgctccttct ggatcatggt ggtcccgtgc aggcaccgca gcttgccctc 22380
ggcctcggtg cacccgtgca gccacagcgc gcacccggtg cactcccagt tcttgtgggc 22440
gatctgggaa tgcgcgtgca cgaagccctg caggaagcgg cccatcatgg tggtcagggt 22500
cttgttgcta gtgaaggtca gcggaatgcc gcggtgctcc tcgttgatgt acaggtggca 22560
gatgcggcgg tacacctcgc cctgctcggg catcagctgg aagttggctt tcaggtcggt 22620
ctccacgcgg tagcggtcca tcagcatagt catgatttcc ataccettct cccaggccga 22680
gacgatgggc aggctcatag ggttcttcac catcatctta gcgctagcag ccgcggccag 22740
ggggtcgctc tcgtccaggg tctcaaagct ccgcttgccg tccttctcgg tgatccgcac 22800
cggggggtag ctgaagccca cggccgccag ctcctcctcg gcctgtcttt cgtcctcgct 22860
gtcctggctg acgtcctgca ggaccacatg cttggtcttg cggggtttct tcttgggcgg 22920
cagcggcggc ggagatgttg gagatggcga gggggagcgc gagttctcgc tcaccactac 22980
tatctcttcc tcttcttggt ccgaggccac gcggcggtag gtatgtctct tcgggggcag 23040
aggcggaggc gacgggctct cgccgccgcg acttggcgga tggctggcag agccccttcc 23100
gcgttcgggg gtgcgctccc ggcggcgctc tgactgactt cctccgcggc cggccattgt 23160
gttctcctag ggaggaacaa caagcatgga gactcagcca tcgccaacct cgccatctgc 23220
ccccaccgcc gacgagaagc agcagcagca gaatgaaagc ttaaccgccc cgccgcccag 23280
ccccgccacc tccgacgcgg ccgtcccaga catgcaagag atggaggaat ccatcgagat 23340
tgacctgggc tatgtgacgc ccgcggagca cgaggaggag ctggcagtgc gcttttcaca 23400
agaagagata caccaagaac agccagagca ggaagcagag aatgagcaga gtcaggctgg 23460
gctcgagcat gacggcgact acctccacct gagcgggggg gaggacgcgc tcatcaagca 23520
tctggcccgg caggccacca tcgtcaagga tgcgctgctc gaccgcaccg aggtgcccct 23580
cagcgtggag gagctcagcc gcgcctacga gttgaacctc ttctcgccgc gcgtgccccc 23640
caagcgccag cccaatggca cctgcgagcc caacccgcgc ctcaacttct acccggtctt 23700
cgcggtgccc gaggccctgg ccacctacca catctttttc aagaaccaaa agatccccgt 23760
ctcctgccgc gccaaccgca cccgcgccga cgcccttttc aacctgggtc ccggcgcccg 23820
cctacctgat atcgcctcct tggaagaggt tcccaagatc ttcgagggtc tgggcagcga 23880
cgagactcgg gccgcgaacg ctctgcaagg agaaggagga gagcatgagc accacagcgc 23940
cctggtcgag ttggaaggcg acaacgcgcg gctggcggtg ctcaaacgca cggtcgagct 24000
gacccatttc gcctacccgg ctctgaacct gccccccaaa gtcatgagcg cggtcatgga 24060
ccaggtgctc atcaagcgcg cgtcgcccat ctccgaggac gagggcatgc aagactccga 24120
ggagggcaag cccgtggtca gcgacgagca gctggcccgg tggctgggtc ctaatgctag 24180
tccccagagt ttggaagagc ggcgcaaact catgatggcc gtggtcctgg tgaccgtgga 24240
gctggagtgc ctgcgccgct tcttcgccga cgcggagacc ctgcgcaagg tcgaggagaa 24300
cctgcactac ctcttcaggc acgggttcgt gcgccaggcc tgcaagatct ccaacgtgga 24360

-continued

```
gctgaccaac ctggtctcct acatgggcat cttgcacgag aaccgcctgg ggcagaacgt  24420
gctgcacacc accctgcgcg gggaggcccg gcgcgactac atccgcgact gcgtctacct  24480
ctacctctgc cacacctggc agacgggcat gggcgtgtgg cagcagtgtc tggaggagca  24540
gaacctgaaa gagctctgca agctcctgca gaagaacctc aagggtctgt ggaccgggtt  24600
cgacgagcgc accaccgcct cggacctggc cgacctcatt ttccccgagc gcctcaggct  24660
gacgctgcgc aacggcctgc ccgactttat gagccaaagc atgttgcaaa actttcgctc  24720
tttcatcctc gaacgctccg gaatcctgcc cgccacctgc tccgcgctgc cctcggactt  24780
cgtgccgctg accttccgcg agtgcccccc gccgctgtgg agccactgct acctgctgcg  24840
cctggccaac tacctggcct accactcgga cgtgatcgag gacgtcagcg gcgagggcct  24900
gctcgagtgc cactgccgct gcaacctctg cacgccgcac cgctccctgg cctgcaaccc  24960
ccagctgctg agcgagaccc agatcatcgg caccttcgag ttgcaagggc ccagcgaagg  25020
cgagggttca gccgccaagg ggggtctgaa actcaccccg gggctgtgga cctcggccta  25080
cttgcgcaag ttcgtgcccg aggactacca tcccttcgag atcaggttct acgaggacca  25140
atcccatccg cccaaggccg agctgtcggc ctgcgtcatc acccaggggg cgatcctggc  25200
ccaattgcaa gccatccaga aatcccgcca agaattcttg ctgaaaaagg gccgcggggt  25260
ctacctcgac ccccagaccg gtgaggagct caaccccggc ttcccccagg atgccccgag  25320
gaaacaagaa gctgaaagtg gagctgccgc ccgtggagga tttggaggaa gactgggaga  25380
acagcagtca ggcagaggag gaggagatgg aggaagactg ggacagcact caggcagagg  25440
aggacagcct gcaagacagt ctggaggaag acgaggagga ggcagaggag gaggtggaag  25500
aagcagccgc cgccagaccg tcgtcctcgg cgggggagaa agcaagcagc acggatacca  25560
tctccgctcc gggtcggggt cccgctcgac cacacagtag atgggacgag accggacgat  25620
tcccgaaccc caccacccag accggtaaga aggagcggca gggatacaag tcctggcggg  25680
ggcacaaaaa cgccatcgtc tcctgcttgc aggcctgcgg gggcaacatc tccttcaccc  25740
ggcgctacct gctcttccac cgcggggtga actttccccg caacatcttg cattactacc  25800
gtcacctcca cagcccctac tacttccaag aagaggcagc agcagcagaa aaagaccagc  25860
agaaaaccag cagctagaaa atccacagcg gcggcagcag gtggactgag gatcgcggcg  25920
aacgagccgg cgcaaacccg ggagctgagg aaccggatct ttcccaccct ctatgccatc  25980
ttccagcaga gtcgggggca ggagcaggaa ctgaaagtca agaaccgttc tctgcgctcg  26040
ctcacccgca gttgtctgta tcacaagagc gaagaccaac ttcagcgcac tctcgaggac  26100
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
```

```
ccgctcgggt ggcatcggca ctctccagtt cgtggaggag ttcactccct cggtctactt  26820
caaccccttc tccggctccc ccggccacta cccggacgag ttcatcccga acttcgacgc  26880
catcagcgag tcggtggacg gctacgattg aaactaatca cccccttatc cagtgaaata  26940
aagatcatat tgatgatgat tttacagaaa taaaaaataa tcatttgatt tgaaataaag  27000
atacaatcat attgatgatt tgagtttaac aaaaaaataa agaatcactt acttgaaatc  27060
tgataccagg tctctgtcca tgttttctgc caacaccact tcactcccct cttcccagct  27120
ctggtactgc aggccccggc gggctgcaaa cttcctccac acgctgaagg ggatgtcaaa  27180
ttcctcctgt ccctcaatct tcattttatc ttctatcaga tgtccaaaaa gcgcgtccgg  27240
gtggatgatg acttcgaccc cgtctacccc tacgatgcag acaacgcacc gaccgtgccc  27300
ttcatcaacc cccccttcgt ctcttcagat ggattccaag agaagcccct gggggtgttg  27360
tccctgcgac tggccgaccc cgtcaccacc aagaacgggg aaatcaccct caagctggga  27420
gagggggtgg acctcgattc ctcgggaaaa ctcatctcca acacggccac caaggccgcc  27480
gcccctctca gtttttccaa caacaccatt tcccttaaca tggatcaccc cttttacact  27540
aaagatggaa aattatcctt acaagtttct ccaccattaa atatactgag aacaagcatt  27600
ctaaacacac tagctttagg ttttggatca ggtttaggac tccgtggctc tgccttggca  27660
gtacagttag tctctccact tacatttgat actgatggaa acataaagct taccttagac  27720
agaggtttgc atgttacaac aggagatgca attgaaagca acataagctg ggctaaaggt  27780
ttaaaatttg aagatggagc catagcaacc aacattggaa atgggttaga gtttggaagc  27840
agtagtacag aaacaggtgt tgatgatgct tacccaatcc aagttaaact tggatctggc  27900
cttagctttg acagtacagg agccataatg gctggtaaca aagaagacga taaactcact  27960
ttgtggacaa cacctgatcc atcaccaaac tgtcaaatac tcgcagaaaa tgatgcaaaa  28020
ctaacacttt gcttgactaa atgtggtagt caaatactgg ccactgtgtc agtcttagtt  28080
gtaggaagtg gaaacctaaa ccccattact ggcaccgtaa gcagtgctca ggtgtttcta  28140
cgttttgatg caaacggtgt tcttttaaca gaacattcta cactaaaaaa atactggggg  28200
tataggcagg gagatagcat agatggcact ccatatacca atgctgtagg attcatgccc  28260
aatttaaaag cttatccaaa gtcacaaagt tctactacta aaaataatat agtagggcaa  28320
gtatacatga atggagatgt ttcaaaacct atgcttctca ctataaccct caatggtact  28380
gatgacagca acagtacata ttcaatgtca ttttcataca cctggactaa tggaagctat  28440
gttggagcaa catttggggc taactcttat accttctcat acatcgccca agaatgaaca  28500
ctgtatccca ccctgcatgc caacccttcc caccccactc tgtggaacaa actctgaaac  28560
acaaaataaa ataaagttca agtgttttat tgattcaaca gttttacagg attcgagcag  28620
ttatttttcc tccaccctcc caggacatgg aatacaccac cctctccccc cgcacagcct  28680
tgaacatctg aatgccattg gtgatggaca tgcttttggt ctccacgttc cacacagttt  28740
cagagcgagc cagtctcggg tcggtcaggg agatgaaacc ctccgggcac tcccgcatct  28800
gcacctcaca gctcaacagc tgaggattgt cctcggtggt cgggatcacg gttatctgga  28860
agaagcagaa gagcggcggt gggaatcata gtccgcgaac gggatcggcc ggtggtgtcg  28920
catcaggccc cgcagcagtc gctgccgccg ccgctccgtc aagctgctgc tcagggggtc  28980
cgggtccagg gactccctca gcatgatgcc cacggccctc agcatcagtc gtctggtgcg  29040
gcgggcgcag cagcgcatgc ggatctcgct caggtcgctg cagtacgtgc aacacagaac  29100
```

-continued

```
caccaggttg ttcaacagtc catagttcaa cacgctccag ccgaaactca tcgcgggaag  29160
gatgctaccc acgtggccgt cgtaccagat cctcaggtaa atcaagtggt gccccctcca  29220
gaacacgctg cccacgtaca tgatctcctt gggcatgtgg cggttcacca cctcccggta  29280
ccacatcacc ctctggttga acatgcagcc ccggatgatc ctgcggaacc acagggccag  29340
caccgccccg cccgccatgc agcgaagaga ccccgggtcc cggcaatggc aatggaggac  29400
ccaccgctcg tacccgtgga tcatctggga gctgaacaag tctatgttgg cacagcacag  29460
gcatatgctc atgcatctct tcagcactct caactcctcg gggtcaaaa ccatatccca  29520
gggcacgggg aactcttgca ggacagcgaa ccccgcagaa cagggcaatc ctcgcacaga  29580
acttacattg tgcatggaca gggtatcgca atcaggcagc accgggtgat cctccaccag  29640
agaagcgcgg gtctcggtct cctcacagcg tggtaagggg gccggccgat acgggtgatg  29700
gcgggacgcg gctgatcgtg ttcgcgaccg tgtcatgatg cagttgcttt cggacatttt  29760
cgtacttgct gtagcagaac ctggtccggg cgctgcacac cgatcgccgg cggcggtctc  29820
ggcgcttgga acgctcggtg ttgaaattgt aaaacagcca ctctctcaga ccgtgcagca  29880
gatctagggc ctcaggagtg atgaagatcc catcatgcct gatggctctg atcacatcga  29940
ccaccgtgga atgggccaga cccagccaga tgatgcaatt ttgttgggtt tcggtgacgg  30000
cgggggaggg aagaacagga agaaccatga ttaactttta atccaaacgg tctcggagta  30060
cttcaaaatg aagatcgcgg agatggcacc tctcgccccc gctgtgttgg tggaaaataa  30120
cagccaggtc aaaggtgata cggttctcga gatgttccac ggtggcttcc agcaaagcct  30180
ccacgcgcac atccagaaac aagacaatag cgaaagcggg agggttctct aattcctcaa  30240
tcatcatgtt acactcctgc accatcccca gataattttc atttttccag ccttgaatga  30300
ttcgaactag ttcctgaggt aaatccaagc cagccatgat aaagagctcg cgcagagcgc  30360
cctccaccgg cattcttaag cacaccctca taattccaag atattctgct cctggttcac  30420
ctgcagcaga ttgacaagcg gaatatcaaa atctctgccg cgatccctga gctcctccct  30480
cagcaataac tgtaagtact ctttcatatc ctctccgaaa tttttagcca taggaccacc  30540
aggaataaga ttagggcaag ccacagtaca gataaaccga agtcctcccc agtgagcatt  30600
gccaaatgca agactgctat aagcatgctg gctagacccg gtgatatctt ccagataact  30660
ggacagaaaa tcgcccaggc aatttttaag aaaatcaaca aaagaaaaat cctccaggtg  30720
gacgtttaga gcctcgggaa caacgatgaa gtaaatgcaa gcggtgcgtt ccagcatggt  30780
tagttagctg atctgtagaa aaaacaaaaa tgaacattaa accatgctag cctggcgaac  30840
aggtgggtaa atcgttctct ccagcaccag gcaggccacg gggtctccgg cgcgaccctc  30900
gtaaaaattg tcgctatgat tgaaaaccat cacagagaga cgttcccggt ggccggcgtg  30960
aatgattcga caagatgaat acacccccgg aacattggcg tccgcgagtg aaaaaaagcg  31020
cccgaggaag caataaggca ctacaatgct cagtctcaag tccagcaaag cgatgccatg  31080
cggatgaagc acaaaattct caggtgcgta caaaatgtaa ttactcccct cctgcacagg  31140
cagcaaagcc cccgatccct ccaggtacac atacaaagcc tcagcgtcca tagcttaccg  31200
agcagcagca cacaacaggc gcaagagtca gagaaaggct gagctctaac ctgtccaccc  31260
gctctctgct caatatatag cccagatcta cactgacgta aaggccaaag tctaaaaata  31320
cccgccaaat aatcacacac gcccagcaca cgcccagaaa ccggtgacac actcaaaaaa  31380
atacgcgcac ttcctcaaac gcccaaaact gccgtcattt ccgggttccc acgctacgtc  31440
atcaaaacac gactttcaaa ttccgtcgac cgttaaaaac gtcacccgcc ccgcccctaa  31500
```

cggtcgcccg tctctcagcc aatcagcgcc ccgcatcccc aaattcaaac acctcatttg 31560
catattaacg cgcacaaaaa gtttgagg 31588

<210> SEQ ID NO 3
<211> LENGTH: 11447
<212> TYPE: DNA
<213> ORGANISM: Venezuelan equine encephalitis virus

<400> SEQUENCE: 3
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgctggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980

-continued

```
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
```

-continued

```
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
```

-continued

```
acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga ccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gacatagtct agtccgccaa   7560

gatgttcccg ttccagccaa tgtatccgat gcagccaatg ccctatcgca acccgttcgc   7620

ggccccgcgc aggccctggt tccccagaac cgaccctttt ctggcgatgc aggtgcagga   7680

attaacccgc tcgatggcta acctgacgtt caagcaacgc cgggacgcgc cacctgaggg   7740

gccatccgct aagaaaccga agaaggaggc ctcgcaaaaa cagaaagggg gaggccaagg   7800

gaagaagaag aagaaccaag ggaagaagaa ggctaagaca gggccgccta atccgaaggc   7860

acagaatgga aacaagaaga agaccaacaa gaaaccaggc aagagacagc gcatggtcat   7920

gaaattggaa tctgacaaga cgttcccaat catgttggaa gggaagataa acggctacgc   7980

ttgtgtggtc ggagggaagt tattcaggcc gatgcatgtg gaaggcaaga tcgacaacga   8040

cgttctggcc gcgcttaaga cgaagaaagc atccaaatac gatcttgagt atgcagatgt   8100

gccacagaac atgcgggccg atacattcaa atacacccat gagaaacccc aaggctatta   8160

cagctggcat catggagcag tccaatatga aaatgggcgt ttcacggtgc cgaaaggagt   8220

tggggccaag ggagacagcg gacgacccat tctggataac cagggacggg tggtcgctat   8280

tgtgctggga ggtgtgaatg aaggatctag gacagccctt tcagtcgtca tgtggaacga   8340

gaagggagtt accgtgaagt atactccgga gaactgcgag caatggtcac tagtgaccac   8400

catgtgtctg ctcgccaatg tgacgttccc atgtgctcaa ccaccaattt gctacgacag   8460

aaaaccagca gagactttgg ccatgctcag cgttaacgtt gacaacccgg gctacgatga   8520

gctgctggaa gcagctgtta agtgccccgg aaggaaaagg agatccaccg aggagctgtt   8580

taaggagtat aagctaacgc gcccttacat ggccagatgc atcagatgtg cagttgggag   8640

ctgccatagt ccaatagcaa tcgaggcagt aaagagcgac gggcacgacg gttatgttag   8700

acttcagact tcctcgcagt atggcctgga ttcctccggc aacttaaagg gcaggaccat   8760

gcggtatgac atgcacggga ccattaaaga gataccacta catcaagtgt cactccatac   8820

atctcgcccg tgtcacattg tggatgggca cggttatttc ctgcttgcca ggtgcccggc   8880

aggggactcc atcaccatgg aatttaagaa agattccgtc acacactcct gctcggtgcc   8940

gtatgaagtg aaatttaatc ctgtaggcag agaactctat actcatcccc cagaacacgg   9000

agtagagcaa gcgtgccaag tctacgcaca tgatgcacag aacagaggag cttatgtcga   9060

gatgcacctc ccgggctcag aagtggacag cagtttggtt tccttgagcg gcagttcagt   9120
```

-continued

```
caccgtgaca cctcctgttg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttggatcacc tatggaacaa taaccaacag atgttctgga ttcaattgct   9900
gatccctctg gccgccttga tcgtagtgac tcgcctgctc aggtgcgtgt gctgtgtcgt   9960
gcctttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgatacct acagtgaact tggagtacgt  10140
cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tggggtcaaa ttaactgcag gtccgctttc  10500
cacagcttgg acaccctttg atcgcaaaat cgtgcagtat gccggggaga tctataatta  10560
tgattttcct gagtatgggg caggacaacc aggagcattt ggagatatac aatccagaac  10620
agtctcaagc tcagatctgt atgccaatac caacctagtg ctgcagagac ccaaagcagg  10680
agcgatccac gtgccataca ctcaggcacc ttcgggtttt gagcaatgga agaaagataa  10740
agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
gtgcgcagtc catgtgccat cagggactgc taccctaaaa gaagcagcag tcgagctaac  11040
cgagcaaggg tcggcgacta tccatttctc gaccgcaaat atccacccgg agttcaggct  11100
ccaaatatgc acatcatatg ttacgtgcaa aggtgattgt caccccccga aagaccatat  11160
tgtgacacac cctcagtatc acgcccaaac atttacagcc gcggtgtcaa aaaccgcgtg  11220
gacgtggtta acatccctgc tgggaggatc agccgtaatt attataattg gcttggtgct  11280
ggctactatt gtggccatgt acgtgctgac caaccagaaa cataattgaa tacagcagca  11340
attggcaagc tgcttacata gaactcgcgg cgattggcat gccgccttaa aatttttatt  11400
ttattttttc ttttcttttc cgaatcggat tttgttttta atatttc                11447
```

<210> SEQ ID NO 4
<211> LENGTH: 9577
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgctggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040

```
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
```

```
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
```

-continued tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gactctagaa tagtctttaa 7560
ttaagccacc atggcaggca tgtttcaggc gctgagcgaa ggctgcaccc cgtatgatat 7620
taaccagatg ctgaacgtgc tgggcgatca tcaggtctca ggccttgagc agcttgagag 7680
tataatcaac tttgaaaaac tgactgaatg gaccagttct aatgttatgc ctatcctgtc 7740
tcctctgaca aagggcatcc tgggcttcgt gtttaccctg accgtgcctt ctgagagagg 7800
acttagctgc attagcgaag cggatgcgac caccccggaa agcgcgaacc tgggcgaaga 7860
aattctgagc cagctgtatc tttggccaag ggtgacctac cattcccccta gttatgctta 7920
ccaccaattt gaaagacgag ccaaatataa aagacacttc cccggctttg gccagagcct 7980
gctgtttggc taccctgtgt acgtgttcgg cgattgcgtg cagggcgatt gggatgcgat 8040
tcgctttcgc tattgcgcgc cgccgggcta tgcgctgctg cgctgcaacg ataccaacta 8100
tagcgctctg ctggctgtgg gggccctaga aggacccagg aatcaggact ggcttggtgt 8160
cccaagacaa cttgtaactc ggatgcaggc tattcagaat gccggcctgt gtaccctggt 8220
ggccatgctg gaagagacaa tcttctggct gcaagcgttt ctgatggcgc tgaccgatag 8280
cggcccgaaa accaacatta ttgtggatag ccagtatgtg atgggcatta gcaaaccgag 8340
ctttcaggaa tttgtggatt gggaaaacgt gagcccggaa ctgaacagca ccgatcagcc 8400
gttttggcaa gccggaatcc tggccagaaa tctggtgcct atggtggcca cagtgcaggg 8460
ccagaacctg aagtaccagg gtcagtcact agtcatctct gcttctatca ttgtcttcaa 8520
cctgctggaa ctggaaggtg attatcgaga tgatggcaac gtgtgggtgc ataccccgct 8580
gagcccgcgc accctgaacg cgtgggtgaa agcggtggaa gaaaaaaaag gtattccagt 8640
tcacctagag ctggccagta tgaccaacat ggagctcatg agcagtattg tgcatcagca 8700
ggtcagaaca tacggccccg tgttcatgtg tctcggcgga ctgcttacaa tggtggctgg 8760
tgctgtgtgg ctgacagtgc gagtgctcga gctgttccgg gccgcgcagc tggccaacga 8820
cgtggtcctc cagatcatgg agctttgtgg tgcagcgttt cgccaggtgt gccataccac 8880
cgtgccgtgg ccgaacgcga gcctgacccc gaaatggaac aacgaaacca cccagcccca 8940
gatcgccaac tgcagcgtgt atgacttttt tgtgtggctc cattattatt ctgttcgaga 9000
cacactttgg ccaagggtga cctaccatat gaacaaatat gcgtatcata tgctggaaag 9060
acgagccaaa tataaaagag gaccaggacc tggcgctaaa tttgtggccg cctggacact 9120
gaaagccgct gctggtcctg gacctggcca gtacatcaag gccaacagca agttcatcgg 9180

-continued catcaccgaa ctcggacccg gaccaggctg atgattcgaa cggccgtatc acgcccaaac 9240
atttacagcc gcggtgtcaa aaaccgcgtg gacgtggtta acatccctgc tgggaggatc 9300
agccgtaatt attataattg gcttggtgct ggctactatt gtggccatgt acgtgctgac 9360
caaccagaaa cataattgaa tacagcagca attggcaagc tgcttacata gaactcgcgg 9420
cgattggcat gccgccttaa aatttttatt ttatttttc ttttctttc cgaatcggat 9480 tttgttttta atatttcaaa aaaaaaaaaa aaaaaaaaaa aaaaaaaaaa aaaaaaaaaa 9540
aaaaaaaaaa aaaaaaaaaa aaaaaaaaaa aaaaaaa 9577

<210> SEQ ID NO 5
<211> LENGTH: 11446
<212> TYPE: DNA
<213> ORGANISM: Venezuelan equine encephalitis virus

<400> SEQUENCE: 5
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680

-continued

```
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
```

```
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
```

-continued

```
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgttcccg ttccagccaa tgtatccgat gcagccaatg ccctatcgca acccgttcgc   7620
ggccccgcgc aggccctggt tccccagaac cgaccctttt ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
cagctggcat catggagcag tccaatatga aaatgggcgt ttcacggtgc cgaaaggagt   8220
tggggccaag ggagacagcg gacgacccat tctggataac cagggacggg tggtcgctat   8280
tgtgctggga ggtgtgaatg aaggatctag gacagccctt tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg gctacgatga   8520
gctgctggaa gcagctgtta agtgccccgg aaggaaaagg agatccaccg aggagctgtt   8580
taatgagtat aagctaacgc gcccttacat ggccagatgc atcagatgtg cagttgggag   8640
ctgccatagt ccaatagcaa tcgaggcagt aaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactctatac   8820
```

```
atctcgcccg tgtcacattg tggatgggca cggttatttc ctgcttgcca ggtgcccggc   8880
aggggactcc atcaccatgg aatttaagaa agattccgtc agacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
caccgtgaca cctcctgatg ggactagcgc cctggtggaa tgcgagtgtg gcggcacaaa   9180
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aaccttcggt ttcagatcag tgtcactgaa   9420
actgcaccct aagaatccca catatctaat cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttggatcacc tatggaacaa taaccaacag atgttctgga ttcaattgct   9900
gatccctctg gccgccttga tcgtagtgac tcgcctgctc aggtgcgtgt gctgtgtcgt   9960
gcctttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgatacct acagtgaact tggagtacgt  10140
cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tggggtcaaa ataactgcag gtccgctttc  10500
cacagcttgg acaccctttg atcgcaaaat cgtgcagtat gccggggaga tctataatta  10560
tgattttcct gagtatgggg caggacaacc aggagcattt ggagatatac aatccagaac  10620
agtctcaagc tctgatctgt atgccaatac caacctagtg ctgcagagac ccaaagcagg  10680
agcgatccac gtgccataca ctcaggcacc ttcgggtttt gagcaatgga agaaagataa  10740
agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
gtgcgcagtc catgtgccat cagggactgc taccctaaaa gaagcagcag tcgagctaac  11040
cgagcaaggg tcggcgacta tccatttctc gaccgcaaat atccacccgg agttcaggct  11100
ccaaatatgc acatcatatg ttacgtgcaa aggtgattgt cacccccga aagaccatat  11160
```

```
tgtgacacac cctcagtatc acgcccaaac atttacagcc gcggtgtcaa aaaccgcgtg  11220

gacgtggtta acatccctgc tgggaggatc agccgtaatt attataattg gcttggtgct  11280

ggctactatt gtggccatgt acgtgctgac caaccagaaa cataattgaa tacagcagca  11340

attggcaagc tgcttacata gaactcgcgg cgattggcat gccgccttaa aatttttatt  11400

ttatttttct tttcttttcc gaatcggatt ttgtttttaa tatttc                11446
```

<210> SEQ ID NO 6
<211> LENGTH: 7895
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaagccgatg   1620

tcgacttgat gttacaagag gctggggccg gctcagtgga gacacctcgt ggcttgataa   1680

aggttaccag ctacgctggc gaggacaaga tcggctctta cgctgtgctt tctccgcagg   1740
```

-continued

```
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
```

tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480

```
aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga cccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gacgtatcac gcccaaacat   7560

ttacagccgc ggtgtcaaaa accgcgtgga cgtggttaac atccctgctg ggaggatcag   7620

ccgtaattat tataattggc ttggtgctgg ctactattgt ggccatgtac gtgctgacca   7680

accagaaaca taattgaata cagcagcaat tggcaagctg cttacataga actcgcggcg   7740

attggcatgc cgccttaaaa tttttatttt atttttttctt ttcttttccg aatcggattt   7800

tgtttttaat atttcaaaaa aaaaaaaaaa aaaaaaaaaa aaaaaaaaaa aaaaaaaaaa   7860

aaaaaaaaaa aaaaaaaaaa aaaaaaaaaa aaaaa                              7895
```

<210> SEQ ID NO 7
<211> LENGTH: 7894
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600
```

-continued

```
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

-continued

```
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
```

-continued

```
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aacccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacgtatcac gcccaaacat   7560
ttacagccgc ggtgtcaaaa accgcgtgga cgtggttaac atccctgctg ggaggatcag   7620
ccgtaattat tataattggc ttggtgctgg ctactattgt ggccatgtac gtgctgacca   7680
accagaaaca taattgaata cagcagcaat tggcaagctg cttacataga actcgcggcg   7740
```

attggcatgc cgccttaaaa tttttatttt atttttcttt tcttttccga atcggatttt 7800
gtttttaata tttcaaaaaa aaaaaaaaaa aaaaaaaaaa aaaaaaaaaa aaaaaaaaaa 7860
aaaaaaaaaa aaaaaaaaaa aaaaaaaaaa aaaa 7894

<210> SEQ ID NO 8
<211> LENGTH: 7928
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
taatacgact cactatagga tgggcggcgc atgagagaag cccagaccaa ttacctaccc 60
aaaatggaga aagttcacgt tgacatcgag gaagacagcc cattcctcag agctttgcag 120
cggagcttcc cgcagtttga ggtagaagcc aagcaggtca ctgataatga ccatgctaat 180
gccagagcgt tttcgcatct ggcttcaaaa ctgatcgaaa cggaggtgga cccatccgac 240
acgatccttg acattggaag tgcgcccgcc cgcagaatgt attctaagca caagtatcat 300
tgtatctgtc cgatgagatg tgcggaagat ccggacagat tgtataagta tgcaactaag 360
ctgaagaaaa actgtaagga aataactgat aaggaattgg acaagaaaat gaaggagctc 420
gccgccgtca tgagcgaccc tgacctggaa actgagacta tgtgcctcca cgacgacgag 480
tcgtgtcgct acgaagggca agtcgctgtt taccaggatg tatacgcggt tgacggaccg 540
acaagtctct atcaccaagc caataaggga gttagagtcg cctactggat aggctttgac 600
accacccctt ttatgtttaa gaacttggct ggagcatatc catcatactc taccaactgg 660
gccgacgaaa ccgtgttaac ggctcgtaac ataggcctat gcagctctga cgttatggag 720
cggtcacgta gagggatgtc cattcttaga aagaagtatt tgaaaccatc caacaatgtt 780
ctattctctg ttggctcgac catctaccac gagaagaggg acttactgag gagctggcac 840
ctgccgtctg tatttcactt acgtggcaag caaaattaca catgtcggtg tgagactata 900
gttagttgcg acgggtacgt cgttaaaaga atagctatca gtccaggcct gtatgggaag 960
ccttcaggct atgctgctac gatgcaccgc gagggattct tgtgctgcaa agtgacagac 1020
acattgaacg gggagagggt ctcttttccc gtgtgcacgt atgtgccagc tacattgtgt 1080
gaccaaatga ctggcatact ggcaacagat gtcagtgcgg acgacgcgca aaaactgctg 1140
gttgggctca accagcgtat agtcgtcaac ggtcgcaccc agagaaacac caataccatg 1200
aaaaattacc ttttgcccgt agtggcccag gcatttgcta ggtgggcaaa ggaatataag 1260
gaagatcaag aagatgaaag gccactagga ctacgagata gacagttagt catggggtgt 1320
tgttgggctt ttagaaggca caagataaca tctatttata agcgcccgga tacccaaacc 1380
atcatcaaag tgaacagcga tttccactca ttcgtgctgc ccaggatagg cagtaacaca 1440
ttggagatcg ggctgagaac aagaatcagg aaaatgttag aggagcacaa ggagccgtca 1500
cctctcatta ccgccgagga cgtacaagaa gctaagtgcg cagccgatga ggctaaggag 1560
gtgcgtgaag ccgaggagtt gcgcgcagct ctaccacctt tggcagctga tgttgaggag 1620
cccactctgg aagccgatgt cgacttgatg ttacaagagg ctggggccgg ctcagtggag 1680
acacctcgtg gcttgataaa ggttaccagc tacgctggcg aggacaagat cggctcttac 1740
gctgtgcttt ctccgcaggc tgtactcaag agtgaaaaat tatcttgcat ccaccctctc 1800
gctgaacaag tcatagtgat aacacactct ggccgaaaag ggcgttatgc cgtggaacca 1860

```
taccatggta aagtagtggt gccagaggga catgcaatac ccgtccagga ctttcaagct   1920
ctgagtgaaa gtgccaccat tgtgtacaac gaacgtgagt tcgtaaacag gtacctgcac   1980
catattgcca cacatggagg agcgctgaac actgatgaag aatattacaa aactgtcaag   2040
cccagcgagc acgacggcga atacctgtac gacatcgaca ggaaacagtg cgtcaagaaa   2100
gaactagtca ctgggctagg gctcacaggc gagctggtgg atcctccctt ccatgaattc   2160
gcctacgaga gtctgagaac acgaccagcc gctccttacc aagtaccaac catagggtg    2220
tatggcgtgc caggatcagg caagtctggc atcattaaaa gcgcagtcac caaaaaagat   2280
ctagtggtga gcgccaagaa agaaaactgt gcagaaatta taagggacgt caagaaaatg   2340
aaagggctgg acgtcaatgc cagaactgtg gactcagtgc tcttgaatgg atgcaaacac   2400
cccgtagaga ccctgtatat tgacgaagct tttgcttgtc atgcaggtac tctcagagcg   2460
ctcatagcca ttataagacc taaaaaggca gtgctctgcg gggatcccaa acagtgcggt   2520
ttttttaaca tgatgtgcct gaaagtgcat tttaaccacg agatttgcac acaagtcttc   2580
cacaaaagca tctctcgccg ttgcactaaa tctgtgactt cggtcgtctc aaccttgttt   2640
tacgacaaaa aaatgagaac gacgaatccg aaagagacta agattgtgat tgacactacc   2700
ggcagtacca aacctaagca ggacgatctc attctcactt gtttcagagg gtgggtgaag   2760
cagttgcaaa tagattacaa aggcaacgaa ataatgacgg cagctgcctc tcaagggctg   2820
acccgtaaag gtgtgtatgc cgttcggtac aaggtgaatg aaaatcctct gtacgcaccc   2880
acctcagaac atgtgaacgt cctactgacc cgcacggagg accgcatcgt gtggaaaaca   2940
ctagccggcg acccatggat aaaaacactg actgccaagt accctgggaa tttcactgcc   3000
acgatagagg agtggcaagc agagcatgat gccatcatga ggcacatctt ggagagaccg   3060
gaccctaccg acgtcttcca gaataaggca aacgtgtgtt gggccaaggc tttagtgccg   3120
gtgctgaaga ccgctggcat agacatgacc actgaacaat ggaacactgt ggattatttt   3180
gaaacggaca aagctcactc agcagagata gtattgaacc aactatgcgt gaggttcttt   3240
ggactcgatc tggactccgg tctattttct gcacccactg ttccgttatc cattaggaat   3300
aatcactggg ataactcccc gtcgcctaac atgtacgggc tgaataaaga agtggtccgt   3360
cagctctctc gcaggtaccc acaactgcct cgggcagttg ccactggaag agtctatgac   3420
atgaacactg gtacactgcg caattatgat ccgcgcataa acctagtacc tgtaaacaga   3480
agactgcctc atgctttagt cctccaccat aatgaacacc cacagagtga cttttcttca   3540
ttcgtcagca aattgaaggg cagaactgtc ctggtggtcg gggaaaagtt gtccgtccca   3600
ggcaaaatgg ttgactggtt gtcagaccgg cctgaggcta ccttcagagc tcggctggat   3660
ttaggcatcc caggtgatgt gcccaaatat gacataaatat ttgttaatgt gaggacccca   3720
tataaatacc atcactatca gcagtgtgaa gaccatgcca ttaagcttag catgttgacc   3780
aagaaagctt gtctgcatct gaatcccggc ggaacctgtg tcagcatagg ttatggttac   3840
gctgacaggg ccagcgaaag catcattggt gctatagcgc ggcagttcaa gttttcccgg   3900
gtatgcaaac cgaaatcctc acttgaagag acggaagttc tgtttgtatt cattgggtac   3960
gatcgcaagg cccgtacgca caatccttac aagctttcat caaccttgac caacatttat   4020
acaggttcca gactccacga agccggatgt gcaccctcat atcatgtggt gcgaggggat   4080
attgccacgg ccaccgaagg agtgattata aatgctgcta acagcaaagg acaacctggc   4140
ggagggtgt gcggagcgct gtataagaaa ttcccggaaa gcttcgattt acagccgatc   4200
```

-continued

```
gaagtaggaa aagcgcgact ggtcaaaggt gcagctaaac atatcattca tgccgtagga   4260
ccaaacttca acaaagtttc ggaggttgaa ggtgacaaac agttggcaga ggcttatgag   4320
tccatcgcta agattgtcaa cgataacaat tacaagtcag tagcgattcc actgttgtcc   4380
accggcatct tttccgggaa caaagatcga ctaacccaat cattgaacca tttgctgaca   4440
gctttagaca ccactgatgc agatgtagcc atatactgca gggacaagaa atgggaaatg   4500
actctcaagg aagcagtggc taggagagaa gcagtggagg agatatgcat atccgacgac   4560
tcttcagtga cagaacctga tgcagagctg gtgagggtgc atccgaagag ttctttggct   4620
ggaaggaagg gctacagcac aagcgatggc aaaactttct catatttgga agggaccaag   4680
tttcaccagg cggccaagga tatagcagaa attaatgcca tgtggcccgt tgcaacggag   4740
gccaatgagc aggtatgcat gtatatcctc ggagaaagca tgagcagtat taggtcgaaa   4800
tgccccgtcg aagagtcgga agcctccaca ccacctagca cgctgccttg cttgtgcatc   4860
catgccatga ctccagaaag agtacagcgc ctaaaagcct cacgtccaga acaaattact   4920
gtgtgctcat cctttccatt gccgaagtat agaatcactg gtgtgcagaa gatccaatgc   4980
tcccagccta tattgttctc accgaaagtg cctgcgtata ttcatccaag gaagtatctc   5040
gtggaaacac caccggtaga cgagactccg gagccatcgg cagagaacca atccacagag   5100
gggacacctg aacaaccacc acttataacc gaggatgaga ccaggactag aacgcctgag   5160
ccgatcatca tcgaagagga agaagaggat agcataagtt tgctgtcaga tggcccgacc   5220
caccaggtgc tgcaagtcga ggcagacatt cacgggccgc cctctgtatc tagctcatcc   5280
tggtccattc ctcatgcatc cgactttgat gtggacagtt tatccatact tgacaccctg   5340
gagggagcta gcgtgaccag cggggcaacg tcagccgaga ctaactctta cttcgcaaag   5400
agtatggagt ttctggcgcg accggtgcct gcgcctcgaa cagtattcag gaaccctcca   5460
catcccgctc cgcgcacaag aacaccgtca cttgcaccca gcagggcctg ctcgagaacc   5520
agcctagttt ccaccccgcc aggcgtgaat agggtgatca ctagagagga gctcgaggcg   5580
cttaccccgt cacgcactcc tagcaggtcg gtctcgagaa ccagcctggt ctccaacccg   5640
ccaggcgtaa atagggtgat tacaagagag gagtttgagg cgttcgtagc acaacaacaa   5700
tgacggtttg atgcgggtgc atacatcttt tcctccgaca ccggtcaagg gcatttacaa   5760
caaaaatcag taaggcaaac ggtgctatcc gaagtggtgt tggagaggac cgaattggag   5820
atttcgtatg ccccgcgcct cgaccaagaa aaagaagaat tactacgcaa gaaattacag   5880
ttaaatccca cacctgctaa cagaagcaga taccagtcca ggaaggtgga gaacatgaaa   5940
gccataacag ctagacgtat tctgcaaggc ctagggcatt atttgaaggc agaaggaaaa   6000
gtggagtgct accgaaccct gcatcctgtt cctttgtatt catctagtgt gaaccgtgcc   6060
ttttcaagcc ccaaggtcgc agtggaagcc tgtaacgcca tgttgaaaga gaactttccg   6120
actgtggctt cttactgtat tattccagag tacgatgcct atttggacat ggttgacgga   6180
gcttcatgct gcttagacac tgccagtttt tgccctgcaa agctgcgcag ctttccaaag   6240
aaacactcct atttggaacc cacaatacga tcggcagtgc cttcagcgat ccagaacacg   6300
ctccagaacg tcctggcagc tgccacaaaa agaaattgca atgtcacgca aatgagagaa   6360
ttgcccgtat tggattcggc ggcctttaat gtggaatgct tcaagaaata tgcgtgtaat   6420
aatgaatatt gggaaacgtt taaagaaaac cccatcaggc ttactgaaga aaacgtggta   6480
aattacatta ccaaattaaa aggaccaaaa gctgctgctc tttttgcgaa gacacataat   6540
ttgaatatgt tgcaggacat accaatggac aggtttgtaa tggacttaaa gagagacgtg   6600
```

aaagtgactc caggaacaaa acatactgaa gaacggccca aggtacaggt gatccaggct 6660
gccgatccgc tagcaacagc gtatctgtgc ggaatccacc gagagctggt taggagatta 6720
aatgcggtcc tgcttccgaa cattcataca ctgtttgata tgtcggctga agactttgac 6780
gctattatag ccgagcactt ccagcctggg gattgtgttc tggaaactga catcgcgtcg 6840
tttgataaaa gtgaggacga cgccatggct ctgaccgcgt taatgattct ggaagactta 6900
ggtgtggacg cagagctgtt gacgctgatt gaggcggctt tcggcgaaat ttcatcaata 6960
catttgccca ctaaaactaa atttaaattc ggagccatga tgaaatctgg aatgttcctc 7020
acactgtttg tgaacacagt cattaacatt gtaatcgcaa gcagagtgtt gagagaacgg 7080
ctaaccggat caccatgtgc agcattcatt ggagatgaca atatcgtgaa aggagtcaaa 7140
tcggacaaat taatggcaga caggtgcgcc acctggttga atatggaagt caagattata 7200
gatgctgtgg tgggcgagaa agcgccttat ttctgtggag ggtttatttt gtgtgactcc 7260
gtgaccggca cagcgtgccg tgtggcagac cccctaaaaa ggctgtttaa gcttggcaaa 7320
cctctggcag cagacgatga acatgatgat gacaggagaa gggcattgca tgaagagtca 7380
acacgctgga accgagtggg tattctttca gagctgtgca aggcagtaga atcaaggtat 7440
gaaaccgtag gaacttccat catagttatg gccatgacta ctctagctag cagtgttaaa 7500
tcattcagct acctgagagg ggcccctata actctctacg gctaacctga atggactacg 7560
acgtatcacg cccaaacatt tacagccgcg gtgtcaaaaa ccgcgtggac gtggttaaca 7620
tccctgctgg gaggatcagc cgtaattatt ataattggct tggtgctggc tactattgtg 7680
gccatgtacg tgctgaccaa ccagaaacat aattgaatac agcagcaatt ggcaagctgc 7740
ttacatagaa ctcgcggcga ttggcatgcc gccttaaaat ttttatttta tttttctttt 7800
tcttttccga atcggatttt gtttttaata tttcaaaaaa aaaaaaaaaa aaaaaaaaaa 7860
aaaaaaaaaa aaaaaaaaaa aaaaaaaaaa aaaaaaaaaa aaaaaaaaaa aaaatacgta 7920
gtttaaac 7928

<210> SEQ ID NO 9
<211> LENGTH: 7927
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
taatacgact cactatagga taggcggcgc atgagagaag cccagaccaa ttacctaccc 60
aaaatggaga aagttcacgt tgacatcgag gaagacagcc cattcctcag agctttgcag 120
cggagcttcc cgcagtttga ggtagaagcc aagcaggtca ctgataatga ccatgctaat 180
gccagagcgt tttcgcatct ggcttcaaaa ctgatcgaaa cggaggtgga cccatccgac 240
acgatccttg acattggaag tgcgcccgcc cgcagaatgt attctaagca caagtatcat 300
tgtatctgtc cgatgagatg tgcggaagat ccggacagat tgtataagta tgcaactaag 360
ctgaagaaaa actgtaagga aataactgat aaggaattgg acaagaaaat gaaggagctc 420
gccgccgtca tgagcgaccc tgacctggaa actgagacta tgtgcctcca cgacgacgag 480
tcgtgtcgct acgaagggca agtcgctgtt taccaggatg tatacgcggt tgacggaccg 540
acaagtctct atcaccaagc caataaggga gttagagtcg cctactggat aggctttgac 600
accacccctt ttatgtttaa gaacttggct ggagcatatc catcatactc taccaactgg 660

-continued gccgacgaaa ccgtgttaac ggctcgtaac ataggcctat gcagctctga cgttatggag 720
cggtcacgta gagggatgtc cattcttaga aagaagtatt tgaaaccatc caacaatgtt 780
ctattctctg ttggctcgac catctaccac gagaagaggg acttactgag gagctggcac 840
ctgccgtctg tatttcactt acgtggcaag caaaattaca catgtcggtg tgagactata 900
gttagttgcg acgggtacgt cgttaaaaga atagctatca gtccaggcct gtatgggaag 960
ccttcaggct atgctgctac gatgcaccgc gagggattct tgtgctgcaa agtgacagac 1020
acattgaacg gggagagggt ctcttttccc gtgtgcacgt atgtgccagc tacattgtgt 1080
gaccaaatga ctggcatact ggcaacagat gtcagtgcgg acgacgcgca aaaactgctg 1140
gttgggctca accagcgtat agtcgtcaac ggtcgcaccc agagaaacac caataccatg 1200
aaaaattacc ttttgcccgt agtggcccag gcatttgcta ggtgggcaaa ggaatataag 1260
gaagatcaag aagatgaaag gccactagga ctacgagata gacagttagt catggggtgt 1320
tgttgggctt ttagaaggca caagataaca tctatttata agcgcccgga tacccaaacc 1380
atcatcaaag tgaacagcga tttccactca ttcgtgctgc ccaggatagg cagtaacaca 1440
ttggagatcg ggctgagaac aagaatcagg aaaatgttag aggagcacaa ggagccgtca 1500
cctctcatta ccgccgagga cgtacaagaa gctaagtgcg cagccgatga ggctaaggag 1560
gtgcgtgaag ccgaggagtt gcgcgcagct ctaccacctt tggcagctga tgttgaggag 1620
cccactctgg aagccgatgt cgacttgatg ttacaagagg ctggggccgg ctcagtggag 1680
acacctcgtg gcttgataaa ggttaccagc tacgatggcg aggacaagat cggctcttac 1740
gctgtgcttt ctccgcaggc tgtactcaag agtgaaaaat tatcttgcat ccaccctctc 1800
gctgaacaag tcatagtgat aacacactct ggccgaaaag ggcgttatgc cgtggaacca 1860
taccatggta aagtagtggt gccagaggga catgcaatac ccgtccagga ctttcaagct 1920
ctgagtgaaa gtgccaccat tgtgtacaac gaacgtgagt tcgtaaacag gtacctgcac 1980
catattgcca cacatggagg agcgctgaac actgatgaag aatattacaa aactgtcaag 2040
cccagcgagc acgacggcga atacctgtac gacatcgaca ggaaacagtg cgtcaagaaa 2100
gaactagtca ctgggctagg gctcacaggc gagctggtgg atcctccctt ccatgaattc 2160
gcctacgaga gtctgagaac acgaccagcc gctccttacc aagtaccaac catagggggtg 2220
tatggcgtgc caggatcagg caagtctggc atcattaaaa gcgcagtcac caaaaaagat 2280
ctagtggtga gcgccaagaa agaaaactgt gcagaaatta taagggacgt caagaaaatg 2340
aaagggctgg acgtcaatgc cagaactgtg gactcagtgc tcttgaatgg atgcaaacac 2400
cccgtagaga ccctgtatat tgacgaagct tttgcttgtc atgcaggtac tctcagagcg 2460
ctcatagcca ttataagacc taaaaaggca gtgctctgcg gggatcccaa acagtgcggt 2520
ttttttaaca tgatgtgcct gaaagtgcat tttaaccacg agatttgcac acaagtcttc 2580
cacaaaagca tctctcgccg ttgcactaaa tctgtgactt cggtcgtctc aaccttgttt 2640
tacgacaaaa aaatgagaac gacgaatccg aaagagacta agattgtgat tgacactacc 2700
ggcagtacca aacctaagca ggacgatctc attctcactt gtttcagagg gtgggtgaag 2760
cagttgcaaa tagattacaa aggcaacgaa ataatgacgg cagctgcctc tcaagggctg 2820
acccgtaaag gtgtgtatgc cgttcggtac aaggtgaatg aaaatcctct gtacgcaccc 2880
acctcagaac atgtgaacgt cctactgacc cgcacggagg accgcatcgt gtggaaaaca 2940
ctagccggcg acccatggat aaaaacactg actgccaagt accctgggaa tttcactgcc 3000

```
acgatagagg agtggcaagc agagcatgat gccatcatga ggcacatctt ggagagaccg   3060
gaccctaccg acgtcttcca gaataaggca aacgtgtgtt gggccaaggc tttagtgccg   3120
gtgctgaaga ccgctggcat agacatgacc actgaacaat ggaacactgt ggattatttt   3180
gaaacggaca aagctcactc agcagagata gtattgaacc aactatgcgt gaggttcttt   3240
ggactcgatc tggactccgg tctattttct gcacccactg ttccgttatc cattaggaat   3300
aatcactggg ataactcccc gtcgcctaac atgtacgggc tgaataaaga agtggtccgt   3360
cagctctctc gcaggtaccc acaactgcct cgggcagttg ccactggaag agtctatgac   3420
atgaacactg gtacactgcg caattatgat ccgcgcataa acctagtacc tgtaaacaga   3480
agactgcctc atgctttagt cctccaccat aatgaacacc cacagagtga cttttcttca   3540
ttcgtcagca aattgaaggg cagaactgtc ctggtggtcg gggaaaagtt gtccgtccca   3600
ggcaaaatgg ttgactggtt gtcagaccgg cctgaggcta ccttcagagc tcggctggat   3660
ttaggcatcc caggtgatgt gcccaaatat gacataatat ttgttaatgt gaggaccccca  3720
tataaatacc atcactatca gcagtgtgaa gaccatgcca ttaagcttag catgttgacc   3780
aagaaagctt gtctgcatct gaatcccggc ggaacctgtg tcagcatagg ttatggttac   3840
gctgacaggg ccagcgaaag catcattggt gctatagcgc ggcagttcaa gttttcccgg   3900
gtatgcaaac cgaaatcctc acttgaagag acggaagttc tgtttgtatt cattgggtac   3960
gatcgcaagg cccgtacgca caatccttac aagctttcat caaccttgac caacatttat   4020
acaggttcca gactccacga agccggatgt gcaccctcat atcatgtggt gcgaggggat   4080
attgccacgg ccaccgaagg agtgattata aatgctgcta acagcaaagg acaacctggc   4140
ggaggggtgt gcggagcgct gtataagaaa ttcccggaaa gcttcgattt acagccgatc   4200
gaagtaggaa aagcgcgact ggtcaaaggt gcagctaaac atatcattca tgccgtagga   4260
ccaaacttca acaaagtttc ggaggttgaa ggtgacaaac agttggcaga ggcttatgag   4320
tccatcgcta agattgtcaa cgataacaat tacaagtcag tagcgattcc actgttgtcc   4380
accggcatct tttccgggaa caaagatcga ctaacccaat cattgaacca tttgctgaca   4440
gctttagaca ccactgatgc agatgtagcc atatactgca gggacaagaa atgggaaatg   4500
actctcaagg aagcagtggc taggagagaa gcagtggagg agatatgcat atccgacgac   4560
tcttcagtga cagaacctga tgcagagctg gtgagggtgc atccgaagag ttctttggct   4620
ggaaggaagg gctacagcac aagcgatggc aaaactttct catatttgga agggaccaag   4680
tttcaccagg cggccaagga tatagcagaa attaatgcca tgtggcccgt tgcaacggag   4740
gccaatgagc aggtatgcat gtatatcctc ggagaaagca tgagcagtat taggtcgaaa   4800
tgccccgtcg aagagtcgga agcctccaca ccacctagca cgctgccttg cttgtgcatc   4860
catgccatga ctccagaaag agtacagcgc ctaaaagcct cacgtccaga acaaattact   4920
gtgtgctcat cctttccatt gccgaagtat agaatcactg gtgtgcagaa gatccaatgc   4980
tcccagccta tattgttctc accgaaagtg cctgcgtata ttcatccaag gaagtatctc   5040
gtggaaacac caccggtaga cgagactccg gagccatcgg cagagaacca atccacagag   5100
gggacacctg aacaaccacc acttataacc gaggatgaga ccaggactag aacgcctgag   5160
ccgatcatca tcgaagagga agaagaggat agcataagtt tgctgtcaga tggcccgacc   5220
caccaggtgc tgcaagtcga ggcagacatt cacgggccgc cctctgtatc tagctcatcc   5280
tggtccattc ctcatgcatc cgactttgat gtggacagtt tatccatact tgacaccctg   5340
gagggagcta gcgtgaccag cggggcaacg tcagccgaga ctaactctta cttcgcaaag   5400
```

```
agtatggagt ttctggcgcg accggtgcct gcgcctcgaa cagtattcag gaaccctcca   5460
catcccgctc cgcgcacaag aacaccgtca cttgcaccca gcagggcctg ctcgagaacc   5520
agcctagttt ccaccccgcc aggcgtgaat agggtgatca ctagagagga gctcgaggcg   5580
cttaccccgt cacgcactcc tagcaggtcg gtctcgagaa ccagcctggt ctccaacccg   5640
ccaggcgtaa atagggtgat tacaagagag gagtttgagg cgttcgtagc acaacaacaa   5700
tgacggtttg atgcgggtgc atacatcttt tcctccgaca ccggtcaagg gcatttacaa   5760
caaaaatcag taaggcaaac ggtgctatcc gaagtggtgt tggagaggac cgaattggag   5820
atttcgtatg ccccgcgcct cgaccaagaa aaagaagaat tactacgcaa gaaattacag   5880
ttaaatccca cacctgctaa cagaagcaga taccagtcca ggaaggtgga gaacatgaaa   5940
gccataacag ctagacgtat tctgcaaggc ctagggcatt atttgaaggc agaaggaaaa   6000
gtggagtgct accgaaccct gcatcctgtt cctttgtatt catctagtgt gaaccgtgcc   6060
ttttcaagcc ccaaggtcgc agtggaagcc tgtaacgcca tgttgaaaga gaactttccg   6120
actgtggctt cttactgtat tattccagag tacgatgcct atttggacat ggttgacgga   6180
gcttcatgct gcttagacac tgccagtttt tgccctgcaa agctgcgcag ctttccaaag   6240
aaacactcct atttggaacc cacaatacga tcggcagtgc cttcagcgat ccagaacacg   6300
ctccagaacg tcctggcagc tgccacaaaa agaaattgca atgtcacgca aatgagagaa   6360
ttgcccgtat tggattcggc ggcctttaat gtggaatgct tcaagaaata tgcgtgtaat   6420
aatgaatatt gggaaacgtt taaagaaaac cccatcaggc ttactgaaga aaacgtggta   6480
aattacatta ccaaattaaa aggaccaaaa gctgctgctc tttttgcgaa gacacataat   6540
ttgaatatgt tgcaggacat accaatggac aggtttgtaa tggacttaaa gagagacgtg   6600
aaagtgactc caggaacaaa acatactgaa gaacggccca aggtacaggt gatccaggct   6660
gccgatccgc tagcaacagc gtatctgtgc ggaatccacc gagagctggt taggagatta   6720
aatgcggtcc tgcttccgaa cattcataca ctgtttgata tgtcggctga agactttgac   6780
gctattatag ccgagcactt ccagcctggg gattgtgttc tggaaactga catcgcgtcg   6840
tttgataaaa gtgaggacga cgccatggct ctgaccgcgt taatgattct ggaagactta   6900
ggtgtggacg cagagctgtt gacgctgatt gaggcggctt tcggcgaaat ttcatcaata   6960
catttgccca ctaaaactaa atttaaattc ggagccatga tgaaatctgg aatgttcctc   7020
acactgtttg tgaacacagt cattaacatt gtaatcgcaa gcagagtgtt gagagaacgg   7080
ctaaccggat caccatgtgc agcattcatt ggagatgaca atatcgtgaa aggagtcaaa   7140
tcggacaaat taatggcaga caggtgcgcc acctggttga atatggaagt caagattata   7200
gatgctgtgg tgggcgagaa agcgccttat ttctgtggag ggtttatttt gtgtgactcc   7260
gtgaccggca cagcgtgccg tgtggcagac cccctaaaaa ggctgtttaa gcttggcaaa   7320
cctctggcag cagacgatga acatgatgat gacaggagaa gggcattgca tgaagagtca   7380
acacgctgga accgagtggg tattctttca gagctgtgca aggcagtaga atcaaggtat   7440
gaaaccgtag gaacttccat catagttatg gccatgacta ctctagctag cagtgttaaa   7500
tcattcagct acctgagagg ggcccctata actctctacg gctaacctga atggactacg   7560
acgtatcacg cccaaacatt tacagccgcg gtgtcaaaaa ccgcgtggac gtggttaaca   7620
tccctgctgg gaggatcagc cgtaattatt ataattggct tggtgctggc tactattgtg   7680
gccatgtacg tgctgaccaa ccagaaacat aattgaatac agcagcaatt ggcaagctgc   7740
```

```
ttacatagaa ctcgcggcga ttggcatgcc gccttaaaat ttttatttta tttttctttt   7800

cttttccgaa tcggattttg tttttaatat ttcaaaaaaa aaaaaaaaaa aaaaaaaaaa   7860

aaaaaaaaaa aaaaaaaaaa aaaaaaaaaa aaaaaaaaaa aaaaaaaaaa aaatacgtag   7920

tttaaac                                                             7927
```

<210> SEQ ID NO 10
<211> LENGTH: 36519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
ccatcttcaa taatatacct caaacttttt gtgcgcgtta atatgcaaat gaggcgtttg     60

aatttgggga ggaagggcgg tgattggtcg agggatgagc gaccgttagg ggcggggcga    120

gtgacgtttt gatgacgtgg ttgcgaggag gagccagttt gcaagttctc gtgggaaaag    180

tgacgtcaaa cgaggtgtgg tttgaacacg gaaatactca attttcccgc gctctctgac    240

aggaaatgag gtgtttctgg gcggatgcaa gtgaaaacgg gccattttcg cgcgaaaact    300

gaatgaggaa gtgaaaatct gagtaatttc gcgtttatgg cagggaggag tatttgccga    360

gggccgagta gactttgacc gattacgtgg gggtttcgat taccgtgttt ttcacctaaa    420

tttccgcgta cggtgtcaaa gtccggtgtt tttacgtagg tgtcagctga tcgccagggt    480

atttaaacct gcgctctcca gtcaagaggc cactcttgag tgccagcgag aagagttttc    540

tcctccgcgc cgcgagtcag atctacactt tgaaagatga ggcacctgag agacctgccc    600

gatgagaaaa tcatcatcgc ttccgggaac gagattctgg aactggtggt aaatgccatg    660

atgggcgacg accctccgga gcccccccacc ccatttgaga caccttcgct gcacgatttg    720

tatgatctgg aggtggatgt gcccgaggac gatcccaatg aggaggcggt aaatgatttt    780

tttagcgatg ccgcgctgct agctgccgag gaggcttcga gctctagctc agacagcgac    840

tcttcactgc ataccccctag acccggcaga ggtgagaaaa agatccccga gcttaaaggg    900

gaagagatgg acttgcgctg ctatgaggaa tgcttgcccc cgagcgatga tgaggacgag    960

caggcgatcc agaacgcagc gagccaggga gtgcaagccg ccagcgagag ctttgcgctg   1020

gactgcccgc ctctgcccgg acacggctgt aagtcttgtg aatttcatcg catgaatact   1080

ggagataaag ctgtgttgtg tgcactttgc tatatgagag cttacaacca ttgtgtttac   1140

agtaagtgtg attaagttga actttagagg gaggcagaga gcagggtgac tgggcgatga   1200

ctggtttatt tatgtatata tgttctttat ataggtcccg tctctgacgc agatgatgag   1260

acccccacta caaagtccac ttcgtcaccc ccagaaattg gcacatctcc acctgagaat   1320

attgttagac cagttcctgt tagagccact gggaggagag cagctgtgga atgtttggat   1380

gacttgctac agggtggggt tgaacctttg gacttgtgta cccggaaacg ccccaggcac   1440

taagtgccac acatgtgtgt ttacttgagg tgatgtcagt atttataggg tgtggagtgc   1500

aataaaaaat gtgttgactt taagtgcgtg gtttatgact caggggtggg gactgtgagt   1560

atataagcag gtgcagacct gtgtggttag ctcagagcgg catggagatt tggacggtct   1620

tggaagactt tcacaagact agacagctgc tagagaacgc ctcgaacgga gtctcttacc   1680

tgtggagatt ctgcttcggt ggcgacctag ctaggctagt ctacagggcc aaacaggatt   1740

atagtgaaca atttgaggtt attttgagag agtgttctgg tctttttgac gctcttaact   1800
```

```
tgggccatca gtctcacttt aaccagagga tttcgagagc ccttgatttt actactcctg   1860
gcagaaccac tgcagcagta gcctttttg cttttattct tgacaaatgg agtcaagaaa   1920
cccatttcag cagggattac cagctggatt tcttagcagt agctttgtgg agaacatgga   1980
agtgccagcg cctgaatgca atctccggct acttgccggt acagccgcta gacactctga   2040
ggatcctgaa tctccaggag agtcccaggg cacgccaacg tcgccagcag cagcagcagg   2100
aggaggatca agaagagaac ccgagagccg gcctggaccc tccggcggag gaggaggagt   2160
agctgacctg tttcctgaac tgcgccgggt gctgactagg tcttcgagtg gtcgggagag   2220
ggggattaag cgggagaggc atgatgagac taatcacaga actgaactga ctgtgggtct   2280
gatgagtcgc aagcgcccag aaacagtgtg gtggcatgag gtgcagtcga ctggcacaga   2340
tgaggtgtcg gtgatgcatg agaggttttc tctagaacaa gtcaagactt gttggttaga   2400
gcctgaggat gattgggagg tagccatcag gaattatgcc aagctggctc tgaggccaga   2460
caagaagtac aagattacta agctgataaa tatcagaaat gcctgctaca tctcagggaa   2520
tggggctgaa gtggagatct gtctccagga aagggtggct ttcagatgct gcatgatgaa   2580
tatgtacccg ggagtggtgg gcatggatgg ggttaccttt atgaacatga ggttcagggg   2640
agatgggtat aatggcacgg tctttatggc caataccaag ctgacagtcc atggctgctc   2700
cttctttggg tttaataaca cctgcatcga ggcctggggt caggtcggtg tgaggggctg   2760
cagtttttca gccaactgga tgggggtcgt gggcaggacc aagagtatgc tgtccgtgaa   2820
gaaatgcttg tttgagaggt gccacctggg ggtgatgagc gagggcgaag ccagaatccg   2880
ccactgcgcc tctaccgaga cgggctgctt tgtgctgtgc aagggcaatg ctaagatcaa   2940
gcataatatg atctgtggag cctcggacga gcgcggctac cagatgctga cctgcgccgg   3000
cgggaacagc catatgctgg ccaccgtaca tgtggcttcc catgctcgca agccctggcc   3060
cgagttcgag cacaatgtca tgaccaggtg caatatgcat ctggggtccc gccgaggcat   3120
gttcatgccc taccagtgca acctgaatta tgtgaaggtg ctgctggagc ccgatgccat   3180
gtccagagtg agcctgacgg gggtgtttga catgaatgtg gaggtgtgga agattctgag   3240
atatgatgaa tccaagacca ggtgccgagc ctgcgagtgc ggagggaagc atgccaggtt   3300
ccagcccgtg tgtgtggatg tgacggagga cctgcgaccc gatcatttgg tgttgccctg   3360
caccgggacg gagttcggtt ccagcgggga agaatctgac tagagtgagt agtgttctgg   3420
ggcgggggag gacctgcatg agggccagaa taactgaaat ctgtgctttt ctgtgtgttg   3480
cagcagcatg agcggaagcg gctcctttga gggaggggta ttcagccctt atctgacggg   3540
gcgtctcccc tcctgggcgg gagtgcgtca gaatgtgatg ggatccacgg tggacggccg   3600
gcccgtgcag cccgcgaact cttcaaccct gacctatgca accctgagct cttcgtcgtt   3660
ggacgcagct gccgccgcag ctgctgcatc tgccgccagc gccgtgcgcg gaatggccat   3720
gggcgccggc tactacggca ctctggtggc caactcgagt tccaccaata atcccgccag   3780
cctgaacgag gagaagctgt tgctgctgat ggcccagctc gaggccttga cccagcgcct   3840
gggcgagctg acccagcagg tggctcagct gcaggagcag acgcgggccg cggttgccac   3900
ggtgaaatcc aaataaaaaa tgaatcaata aataaacgga gacggttgtt gattttaaca   3960
cagagtctga atctttattt gatttttcgc gcgcggtagg ccctggacca ccggtctcga   4020
tcattgagca cccggtggat cttttccagg acccggtaga ggtgggcttg gatgttgagg   4080
tacatgggca tgagcccgtc ccgggggtgg aggtagctcc attgcagggc ctcgtgctcg   4140
ggggtggtgt tgtaaatcac ccagtcatag caggggcgca gggcatggtg ttgcacaata   4200
```

tctttgagga ggagactgat ggccacgggc agccctttgg tgtaggtgtt tacaaatctg 4260
ttgagctggg agggatgcat gcggggggag atgaggtgca tcttggcctg gatcttgaga 4320
ttggcgatgt taccgcccag atcccgcctg ggttcatgt tgtgcaggac caccagcacg 4380
gtgtatccgg tgcacttggg gaatttatca tgcaacttgg aagggaaggc gtgaaagaat 4440
ttggcgacgc ctttgtgccc gcccaggttt tccatgcact catccatgat gatggcgatg 4500
ggcccgtggg cggcggcctg ggcaaagacg tttcgggggt cggacacatc atagttgtgg 4560
tcctgggtga ggtcatcata ggccatttta atgaatttgg ggcggagggt gccggactgg 4620
gggacaaagg taccctcgat cccgggggcg tagttcccct cacagatctg catctcccag 4680
gctttgagct cggagggggg gatcatgtcc acctgcgggg cgataaagaa cacggtttcc 4740
ggggcggggg agatgagctg ggccgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctcgcgcac gtgcatgttc 4920
tcgcgcacca gttccgccag gaggcgctct ccccccaggg ataggagctc ctggagcgag 4980
gcgaagtttt tcagcggctt gagtccgtcg gccatgggca ttttggagag ggtttgttgc 5040
aagagttcca ggcggtccca gagctcggtg atgtgctcta cggcatctcg atccagcaga 5100
cctcctcgtt tcgcgggttg ggacggctgc gggagtaggg caccagacga tgggcgtcca 5160
gcgcagccag ggtccggtcc ttccagggtc gcagcgtccg cgtcagggtg gtctccgtca 5220
cggtgaaggg gtgcgcgccg ggctgggcgc ttgcgagggt gcgcttcagg ctcatccggc 5280
tggtcgaaaa ccgctcccga tcggcgccct gcgcgtcggc caggtagcaa ttgaccatga 5340
gttcgtagtt gagcgcctcg gccgcgtggc ctttggcgcg gagcttacct ttggaagtct 5400
gcccgcaggc gggacagagg agggacttga gggcgtagag cttgggggcg aggaagacgg 5460
actcgggggc gtaggcgtcc gcgccgcagt gggcgcagac ggtctcgcac tccacgagcc 5520
aggtgaggtc gggctggtcg gggtcaaaaa ccagtttccc gccgttcttt ttgatgcgtt 5580
tcttaccttt ggtctccatg agctcgtgtc cccgctgggt gacaaagagg ctgtccgtgt 5640
ccccgtagac cgactttatg ggccggtcct cgagcggtgt gccgcggtcc tcctcgtaga 5700
ggaaccccgc ccactccgag acgaaagccc gggtccaggc cagcacgaag gaggccacgt 5760
gggacgggta gcggtcgttg tccaccagcg ggtccacctt ttccagggta tgcaaacaca 5820
tgtcccctc gtccacatcc aggaaggtga ttggcttgta agtgtaggcc acgtgaccgg 5880
gggtcccggc cggggggta taaaagggtg cgggtccctg ctcgtcctca ctgtcttccg 5940
gatcgctgtc caggagcgcc agctgttggg gtaggtattc cctctcgaag gcgggcatga 6000
cctcggcact caggttgtca gtttctagaa acgaggagga tttgatattg acggtgccgg 6060
cggagatgcc tttcaagagc ccctcgtcca tctggtcaga aaagacgatc tttttgttgt 6120
cgagcttggt ggcgaaggag ccgtagaggg cgttggagag gagcttggcg atggagcgca 6180
tggtctggtt tttttccttg tcggcgcgct ccttggcggc gatgttgagc tgcacgtact 6240
cgcgcgccac gcacttccat tcggggaaga cggtggtcag ctcgtcgggc acgattctga 6300
cctgccagcc ccgattatgc agggtgatga ggtccacact ggtggccacc tcgccgcgca 6360
ggggctcatt agtccagcag aggcgtccgc ccttgcgcga gcagaagggg ggcagggggt 6420
ccagcatgac ctcgtcgggg gggtcggcat cgatggtgaa gatgccgggc aggaggtcgg 6480
ggtcaaagta gctgatggaa gtggccagat cgtccagggc agcttgccat tcgcgcacgg 6540

-continued

```
ccagcgcgcg ctcgtaggga ctgaggggcg tgccccaggg catgggatgg gtaagcgcgg   6600
aggcgtacat gccgcagatg tcgtagacgt agaggggctc ctcgaggatg ccgatgtagg   6660
tggggtagca gcgccccccg cggatgctgg cgcgcacgta gtcatacagc tcgtgcgagg   6720
gggcgaggag ccccgggccc aggttggtgc gactgggctt ttcggcgcgg tagacgatct   6780
ggcggaaaat ggcatgcgag ttggaggaga tggtgggcct ttggaagatg ttgaagtggg   6840
cgtggggcag tccgaccgag tcgcggatga agtgggcgta ggagtcttgc agcttggcga   6900
cgagctcggc ggtgactagg acgtccagag cgcagtagtc gagggtctcc tggatgatgt   6960
catacttgag ctgtcccttt tgtttccaca gctcgcggtt gagaaggaac tcttcgcggt   7020
ccttccagta ctcttcgagg gggaacccgt cctgatctgc acggtaagag cctagcatgt   7080
agaactggtt gacggccttg taggcgcagc agcccttctc cacggggagg gcgtaggcct   7140
gggcggcctt gcgcagggag gtgtgcgtga gggcgaaagt gtccctgacc atgaccttga   7200
ggaactggtg cttgaagtcg atatcgtcgc agcccccctg ctcccagagc tggaagtccg   7260
tgcgcttctt gtaggcgggg ttgggcaaag cgaaagtaac atcgttgaag aggatcttgc   7320
ccgcgcgggg cataaagttg cgagtgatgc ggaaaggttg ggcacctcg gcccggttgt   7380
tgatgacctg gcggcgagc acgatctcgt cgaagccgtt gatgttgtgg cccacgatgt   7440
agagttccac gaatcgcgga cggcccttga cgtggggcag tttcttgagc tcctcgtagg   7500
tgagctcgtc ggggtcgctg agcccgtgct gctcgagcgc ccagtcggcg agatgggggt   7560
tggcgcggag gaaggaagtc cagagatcca cggccagggc ggtttgcaga cggtcccggt   7620
actgacggaa ctgctgcccg acggccattt tttcgggggt gacgcagtag aaggtgcggg   7680
ggtccccgtg ccagcgatcc catttgagct ggagggcgag atcgagggcg agctcgacga   7740
gccggtcgtc cccggagagt ttcatgacca gcatgaaggg gacgagctgc ttgccgaagg   7800
accccatcca ggtgtaggtt tccacatcgt aggtgaggaa gagcctttcg gtgcgaggat   7860
gcgagccgat ggggaagaac tggatctcct gccaccaatt ggaggaatgg ctgttgatgt   7920
gatggaagta gaaatgccga cggcgcgccg aacactcgtg cttgtgttta tacaagcggc   7980
cacagtgctc gcaacgctgc acgggatgca cgtgctgcac gagctgtacc tgagttcctt   8040
tgacgaggaa tttcagtggg aagtggagtc gtggcgcctg catctcgtgc tgtactacgt   8100
cgtggtggtc ggcctggccc tcttctgcct cgatggtggt catgctgacg agcccgcgcg   8160
ggaggcaggt ccagacctcg gcgcgagcgg gtcggagagc gaggacgagg gcgcgcaggc   8220
cggagctgtc cagggtcctg agacgctgcg gagtcaggtc agtgggcagc ggcggcgcgc   8280
ggttgacttg caggagtttt tccagggcgc gcgggaggtc cagatggtac ttgatctcca   8340
ccgcgccatt ggtggcgacg tcgatggctt gcagggtccc gtgcccctgg ggtgtgacca   8400
ccgtcccccg tttcttcttg ggcggctggg gcgacggggg cggtgcctct tccatggtta   8460
gaagcggcgg cgaggacgcg cgccgggcgg caggggcggc tcggggcccg gaggcagggg   8520
cggcaggggc acgtcggcgc cgcgcgcggg taggttctgg tactgcgccc ggagaagact   8580
ggcgtgagcg acgacgcgac ggttgacgtc ctggatctga cgcctctggg tgaaggccac   8640
gggacccgtg agtttgaacc tgaaagagag ttcgacagaa tcaatctcgg tatcgttgac   8700
ggcggcctgc cgcaggatct cttgcacgtc gcccgagttg tcctggtagg cgatctcggt   8760
catgaactgc tcgatctcct cctcttgaag gtctccgcgg ccggcgcgct ccacggtggc   8820
cgcgaggtcg ttggagatgc ggcccatgag ctgcgagaag gcgttcatgc ccgcctcgtt   8880
ccagacgcgg ctgtagacca cgacgccctc gggatcgcgg gcgcgcatga ccacctgggc   8940
```

gaggttgagc tccacgtggc gcgtgaagac cgcgtagttg cagaggcgct ggtagaggta 9000
gttgagcgtg gtggcgatgt gctcggtgac gaagaaatac atgatccagc ggcggagcgg 9060
catctcgctg acgtcgccca gcgcctccaa acgttccatg gcctcgtaaa agtccacggc 9120
gaagttgaaa aactgggagt tgcgcgccga gacggtcaac tcctcctcca gaagacggat 9180
gagctcggcg atggtggcgc gcacctcgcg ctcgaaggcc cccgggagtt cctccacttc 9240
ctcttcttcc tcctccacta acatctcttc tacttcctcc tcaggcggca gtggtggcgg 9300
gggagggggc ctgcgtcgcc ggcggcgcac gggcagacgg tcgatgaagc gctcgatggt 9360
ctcgccgcgc cggcgtcgca tggtctcggt gacggcgcgc ccgtcctcgc ggggccgcag 9420
cgtgaagacg ccgccgcgca tctccaggtg gccgggggg tccccgttgg gcagggagag 9480
ggcgctgacg atgcatctta tcaattgccc cgtagggact ccgcgcaagg acctgagcgt 9540
ctcgagatcc acgggatctg aaaaccgctg aacgaaggct tcgagccagt cgcagtcgca 9600
aggtaggctg agcacggttt cttctggcgg gtcatgttgg ttgggagcgg ggcgggcgat 9660
gctgctggtg atgaagttga aataggcggt tctgagacgg cggatggtgg cgaggagcac 9720
caggtctttg ggcccggctt gctggatgcg cagacggtcg gccatgcccc aggcgtggtc 9780
ctgacacctg gccaggtcct tgtagtagtc ctgcatgagc cgctccacgg gcacctcctc 9840
ctcgcccgcg cggccgtgca tgcgcgtgag cccgaagccg cgctggggct ggacgagcgc 9900
caggtcggcg acgacgcgct cggcgaggat ggcttgctgg atctgggtga gggtggtctg 9960
gaagtcatca aagtcgacga agcggtggta ggctccggtg ttgatggtgt aggagcagtt 10020
ggccatgacg gaccagttga cggtctggtg gcccggacgc acgagctcgt ggtacttgag 10080
gcgcgagtag gcgcgcgtgt cgaagatgta gtcgttgcag gtgcgcacca ggtactggta 10140
gccgatgagg aagtgcggcg gcggctggcg gtagagcggc catcgctcgg tggcgggggc 10200
gccgggcgcg aggtcctcga gcatggtgcg gtggtagccg tagatgtacc tggacatcca 10260
ggtgatgccg gcggcggtgg tggaggcgcg cgggaactcg cggacgcggt tccagatgtt 10320
gcgcagcggc aggaagtagt tcatggtggg cacggtctgg cccgtgaggc gcgcgcagtc 10380
gtggatgctc tatacgggca aaaacgaaag cggtcagcgg ctcgactccg tggcctggag 10440
gctaagcgaa cgggttgggc tgcgcgtgta ccccggttcg aatctcgaat caggctggag 10500
ccgcagctaa cgtggtattg gcactcccgt ctcgacccaa gcctgcacca accctccagg 10560
atacggaggc gggtcgtttt gcaacttttt tttggaggcc ggatgagact agtaagcgcg 10620
gaaagcggcc gaccgcgatg gctcgctgcc gtagtctgga gaagaatcgc cagggttgcg 10680
ttgcggtgtg ccccggttcg aggccggccg gattccgcgg ctaacgaggg cgtggctgcc 10740
ccgtcgtttc caagacccca tagccagccg acttctccag ttacggagcg agcccctctt 10800
ttgttttgtt tgtttttgcc agatgcatcc cgtactgcgg cagatgcgcc cccaccaccc 10860
tccaccgcaa caacagcccc ctccacagcc ggcgcttctg cccccgcccc agcagcaact 10920
tccagccacg accgccgcgg ccgccgtgag cggggctgga cagagttatg atcaccagct 10980
ggccttggaa gagggcgagg ggctggcgcg cctgggggcg tcgtcgccgg agcggcaccc 11040
gcgcgtgcag atgaaaaggg acgctcgcga ggcctacgtg cccaagcaga acctgttcag 11100
agacaggagc ggcgaggagc ccgaggagat gcgcgcggcc cggttccacg cggggcggga 11160
gctgcggcgc ggcctggacc gaaagagggt gctgagggac gaggatttcg aggcggacga 11220
gctgacgggg atcagccccg cgcgcgcgca cgtggccgcg gccaacctgg tcacggcgta 11280

-continued

```
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
ttcctgatgc aggagggggc cacccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgcccettg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
```

aggcagcggg gacagatgtg ggacgatgag gactccgccg acgacagcag cgtgttggac 13740
ttgggtggga gtggtaaccc gttcgctcac ctgcgccccc gtatcgggcg catgatgtaa 13800
gagaaaccga aaataaatga tactcaccaa ggccatggcg accagcgtgc gttcgtttct 13860
tctctgttgt tgttgtatct agtatgatga ggcgtgcgta cccggagggt cctcctccct 13920
cgtacgagag cgtgatgcag caggcgatgg cggcggcggc gatgcagccc ccgctggagg 13980
ctccttacgt gcccccgcgg tacctggcgc ctacggaggg gcggaacagc attcgttact 14040
cggagctggc acccttgtac gataccaccc ggttgtacct ggtggacaac aagtcggcgg 14100
acatcgcctc gctgaactac cagaacgacc acagcaactt cctgaccacc gtggtgcaga 14160
acaatgactt cacccccacg gaggccagca cccagaccat caactttgac gagcgctcgc 14220
ggtggggcgg ccagctgaaa accatcatgc acaccaacat gcccaacgtg aacgagttca 14280
tgtacagcaa caagttcaag gcgcgggtga tggtctcccg caagaccccc aatggggtga 14340
cagtgacaga ggattatgat ggtagtcagg atgagctgaa gtatgaatgg gtggaatttg 14400
agctgcccga aggcaacttc tcggtgacca tgaccatcga cctgatgaac aacgccatca 14460
tcgacaatta cttggcggtg gggcggcaga acggggtgct ggagagcgac atcggcgtga 14520
agttcgacac taggaacttc aggctgggct gggaccccgt gaccgagctg gtcatgcccg 14580
gggtgtacac caacgaggct ttccatcccg atattgtctt gctgcccggc tgcggggtgg 14640
acttcaccga gagccgcctc agcaacctgc tgggcattcg caagaggcag cccttccagg 14700
aaggcttcca gatcatgtac gaggatctgg agggggcaa catccccgcg ctcctggatg 14760
tcgacgccta tgagaaaagc aaggaggatg cagcagctga agcaactgca gccgtagcta 14820
ccgcctctac cgaggtcagg ggcgataatt ttgcaagcgc cgcagcagtg gcagcggccg 14880
aggcggctga aaccgaaagt aagatagtca ttcagccggt ggagaaggat agcaagaaca 14940
ggagctacaa cgtactaccg gacaagataa acaccgccta ccgcagctgg tacctagcct 15000
acaactatgg cgaccccgag aagggcgtgc gctcctggac gctgctcacc acctcggacg 15060
tcacctgcgg cgtggagcaa gtctactggt cgctgcccga catgatgcaa gacccggtca 15120
ccttccgctc cacgcgtcaa gttagcaact acccggtggt gggcgccgag ctcctgcccg 15180
tctactccaa gagcttcttc aacgagcagg ccgtctactc gcagcagctg cgcgccttca 15240
cctcgcttac gcacgtcttc aaccgcttcc ccgagaacca gatcctcgtc cgcccgcccg 15300
cgcccaccat taccaccgtc agtgaaaacg ttcctgctct cacagatcac gggaccctgc 15360
cgctgcgcag cagtatccgg ggagtccagc gcgtgaccgt tactgacgcc agacgccgca 15420
cctgccccta cgtctacaag gccctgggca tagtcgcgcc gcgcgtcctc tcgagccgca 15480
ccttctaaat gtccattctc atctcgccca gtaataacac cggttggggc ctgcgcgcgc 15540
ccagcaagat gtacggaggc gctcgccaac gctccacgca acaccccgtg cgcgtgcgcg 15600
ggcacttccg cgctccctgg ggcgccctca agggccgcgt gcggtcgcgc accaccgtcg 15660
acgacgtgat cgaccaggtg gtggccgacg cgcgcaacta cacccccgcc gccgcgcccg 15720
tctccaccgt ggacgccgtc atcgacagcg tggtggccga cgcgcgccgg tacgcccgcg 15780
ccaagagccg gcggcggcgc atcgcccggc ggcaccggag cacccccgcc atgcgcgcgg 15840
cgcgagcctt gctgcgcagg gccaggcgca cgggacgcag ggccatgctc agggcggcca 15900
gacgcgcggc ttcaggcgcc agcgccggca ggacccggag acgcgcggcc acggcggcgg 15960
cagcggccat cgccagcatg tcccgcccgc ggcgagggaa cgtgtactgg gtgcgcgacg 16020

-continued

```
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgccgctgca accacccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt ggggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgaccccgc cccgatgcgg aggagacgct gctgacgcac acggacgagc cgcccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc accccatcga tgctgcccca gtgggcgtac atgcacatcg  18360
ccggacagga cgcttcggag tacctgagtc cgggtctggt gcagtttgcc cgcgccacag  18420
```

acacctactt cagtctgggg aacaagttta ggaaccccac ggtggcgccc acgcacgatg 18480
tgaccaccga ccgcagccag cggctgacgc tgcgcttcgt gcccgtggac cgcgaggaca 18540
acacctactc gtacaaagtg cgctacacgc tggccgtggg cgacaaccgc gtgctggaca 18600
tggccagcac ctactttgac atccgcggcg tgctggatcg gggccctagc ttcaaaccct 18660
actccggcac cgcctacaac agtctggccc ccaagggagc acccaacact tgtcagtgga 18720
catataaagc cgatggtgaa actgccacag aaaaaaccta tacatatgga aatgcacccg 18780
tgcagggcat taacatcaca aaagatggta ttcaacttgg aactgacacc gatgatcagc 18840
caatctacgc agataaaacc tatcagcctg aacctcaagt gggtgatgct gaatggcatg 18900
acatcactgg tactgatgaa aagtatggag gcagagctct taagcctgat accaaaatga 18960
agccttgtta tggttctttt gccaagccta ctaataaaga aggaggtcag gcaaatgtga 19020
aaacaggaac aggcactact aaagaatatg acatagacat ggctttcttt gacaacagaa 19080
gtgcggctgc tgctggccta gctccagaaa ttgttttgta tactgaaaat gtggatttgg 19140
aaactccaga tacccatatt gtatacaaag caggcacaga tgacagcagc tcttctatta 19200
atttgggtca gcaagccatg cccaacagac ctaactacat tggtttcaga gacaacttta 19260
tcgggctcat gtactacaac agcactggca atatgggggt gctggccggt caggcttctc 19320
agctgaatgc tgtggttgac ttgcaagaca gaaacaccga gctgtcctac cagctcttgc 19380
ttgactctct gggtgacaga acccggtatt tcagtatgtg gaatcaggcg gtggacagct 19440
atgatcctga tgtgcgcatt attgaaaatc atggtgtgga ggatgaactt cccaactatt 19500
gtttccctct ggatgctgtt ggcagaacag atacttatca gggaattaag gctaatggaa 19560
ctgatcaaac cacatggacc aaagatgaca gtgtcaatga tgctaatgag ataggcaagg 19620
gtaatccatt cgccatggaa atcaacatcc aagccaacct gtggaggaac ttcctctacg 19680
ccaacgtggc cctgtacctg cccgactctt acaagtacac gccggccaat gttaccctgc 19740
ccaccaacac caacacctac gattacatga acggccgggt ggtggcgccc tcgctggtgg 19800
actcctacat caacatcggg gcgcgctggt cgctggatcc catggacaac gtgaacccct 19860
tcaaccacca ccgcaatgcg gggctgcgct accgctccat gctcctgggc aacgggcgct 19920
acgtgccctt ccacatccag gtgccccaga aatttttcgc catcaagagc ctcctgctcc 19980
tgcccgggtc ctacacctac gagtggaact tccgcaagga cgtcaacatg atcctgcaga 20040
gctccctcgg caacgacctg cgcacggacg gggcctccat ctccttcacc agcatcaacc 20100
tctacgccac cttcttcccc atggcgcaca acacggcctc cacgctcgag gccatgctgc 20160
gcaacgacac caacgaccag tccttcaacg actacctctc ggcggccaac atgctctacc 20220
ccatccccgc caacgccacc aacgtgccca tctccatccc ctcgcgcaac tgggccgcct 20280
tccgcggctg gtccttcacg cgtctcaaga ccaaggagac gccctcgctg ggctccgggt 20340
tcgaccccta cttcgtctac tcgggctcca tcccctacct cgacggcacc ttctacctca 20400
accacacctt caagaaggtc tccatcacct tcgactcctc cgtcagctgg cccggcaacg 20460
accggctcct gacgcccaac gagttcgaaa tcaagcgcac cgtcgacggc gagggctaca 20520
acgtggccca gtgcaacatg accaaggact ggttcctggt ccagatgctg gcccactaca 20580
acatcggcta ccagggcttc tacgtgcccg agggctacaa ggaccgcatg tactccttct 20640
tccgcaactt ccagcccatg agccgccagg tggtggacga ggtcaactac aaggactacc 20700
aggccgtcac cctggcctac cagcacaaca actcgggctt cgtcggctac ctcgcgccca 20760

```
ccatgcgcca gggccagccc taccccgcca actacccta cccgctcatc ggcaagagcg  20820
ccgtcaccag cgtcacccag aaaaagttcc tctgcgacag ggtcatgtgg cgcatcccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccc gaccgcccca tggacaagaa ccccaccatg aacttgctga cgggggtgcc  21600
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
```

cgagggggag cgcgagttct cgctcaccac tactatctct tcctcttctt ggtccgaggc 23220
cacgcggcgg taggtatgtc tcttcggggg cagaggcgga ggcgacgggc tctcgccgcc 23280
gcgacttggc ggatggctgg cagagcccct tccgcgttcg ggggtgcgct cccggcggcg 23340
ctctgactga cttcctccgc ggccggccat tgtgttctcc tagggaggaa caacaagcat 23400
ggagactcag ccatcgccaa cctcgccatc tgccccccacc gccgacgaga agcagcagca 23460
gcagaatgaa agcttaaccg ccccgccgcc cagccccgcc acctccgacg cggccgtccc 23520
agacatgcaa gagatggagg aatccatcga gattgacctg ggctatgtga cgcccgcgga 23580
gcacgaggag gagctggcag tgcgcttttc acaagaagag atacaccaag aacagccaga 23640
gcaggaagca gagaatgagc agagtcaggc tgggctcgag catgacggcg actacctcca 23700
cctgagcggg ggggaggacg cgctcatcaa gcatctggcc cggcaggcca ccatcgtcaa 23760
ggatgcgctg ctcgaccgca ccgaggtgcc cctcagcgtg gaggagctca gccgcgccta 23820
cgagttgaac ctcttctcgc cgcgcgtgcc ccccaagcgc cagcccaatg gcacctgcga 23880
gcccaacccg cgcctcaact tctacccggt cttcgcggtg cccgaggccc tggccaccta 23940
ccacatcttt ttcaagaacc aaaagatccc cgtctcctgc cgcgccaacc gcacccgcgc 24000
cgacgccctt ttcaacctgg gtcccggcgc ccgcctacct gatatcgcct ccttggaaga 24060
ggttcccaag atcttcgagg gtctgggcag cgacgagact cgggccgcga acgctctgca 24120
aggagaagga ggagagcatg agcaccacag cgccctggtc gagttggaag gcgacaacgc 24180
gcggctggcg gtgctcaaac gcacggtcga gctgacccat ttcgcctacc cggctctgaa 24240
cctgcccccc aaagtcatga gcgcggtcat ggaccaggtg ctcatcaagc gcgcgtcgcc 24300
catctccgag gacgagggca tgcaagactc cgaggagggc aagcccgtgg tcagcgacga 24360
gcagctggcc cggtggctgg gtcctaatgc tagtccccag agtttggaag agcggcgcaa 24420
actcatgatg gccgtggtcc tggtgaccgt ggagctggag tgcctgcgcc gcttcttcgc 24480
cgacgcggag accctgcgca aggtcgagga gaacctgcac tacctcttca ggcacgggtt 24540
cgtgcgccag gcctgcaaga tctccaacgt ggagctgacc aacctggtct cctacatggg 24600
catcttgcac gagaaccgcc tggggcagaa cgtgctgcac accaccctgc gcggggaggc 24660
ccggcgcgac tacatccgcg actgcgtcta cctctacctc tgccacacct ggcagacggg 24720
catgggcgtg tggcagcagt gtctggagga gcagaacctg aaagagctct gcaagctcct 24780
gcagaagaac ctcaagggtc tgtggaccgg gttcgacgag cgcaccaccg cctcggacct 24840
ggccgacctc attttccccg agcgcctcag gctgacgctg cgcaacggcc tgcccgactt 24900
tatgagccaa agcatgttgc aaaactttcg ctctttcatc ctcgaacgct ccggaatcct 24960
gcccgccacc tgctccgcgc tgccctcgga cttcgtgccg ctgaccttcc gcgagtgccc 25020
cccgccgctg tggagccact gctacctgct gcgcctggcc aactacctgg cctaccactc 25080
ggacgtgatc gaggacgtca gcggcgaggg cctgctcgag tgccactgcc gctgcaacct 25140
ctgcacgccg caccgctccc tggcctgcaa cccccagctg ctgagcgaga cccagatcat 25200
cggcaccttc gagttgcaag ggcccagcga aggcgagggt tcagccgcca agggggggtct 25260
gaaactcacc ccggggctgt ggacctcggc ctacttgcgc aagttcgtgc ccgaggacta 25320
ccatcccttc gagatcaggt tctacgagga ccaatcccat ccgcccaagg ccgagctgtc 25380
ggcctgcgtc atcacccagg gggcgatcct ggcccaattg caagccatcc agaaatcccg 25440
ccaagaattc ttgctgaaaa agggccgcgg ggtctacctc gacccccaga ccggtgagga 25500

```
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
```

```
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aattttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgattttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
```

```
ttaaatcagc ctaccaccac tacagcagca gaggttgcca gctcgtctgg ggtccgagtg  30300
gcatttttga tgttggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaag gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
gaggaggtcc gcaaatgcaa attccaagaa ccctggaaat tcctcaaatg ctaccgccaa  31140
aaatcagaca tgcatcccag ctggatcatg atcattggga tcgtgaacat tctggcctgc  31200
accctcatct cctttgtgat ttacccctgc tttgactttg gttggaactc gccagaggcg  31260
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcacccccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
gatgacttcg accccgtcta cccctacgat gcagacaacg caccgaccgt gcccttcatc  32220
aacccccccct tcgtctcttc agatggattc caagagaagc ccctgggggt gttgtccctg  32280
cgactggccg accccgtcac caccaagaac ggggaaatca ccctcaagct gggagagggg  32340
gtggacctcg attcctcggg aaaactcatc tccaacacgg ccaccaaggc cgccgcccct  32400
ctcagttttt ccaacaacac catttccctt aacatggatc accccttttta cactaaagat  32460
ggaaaattat ccttacaagt ttctccacca ttaaatatac tgagaacaag cattctaaac  32520
acactagctt taggttttgg atcaggttta ggactccgtg gctctgcctt ggcagtacag  32580
ttagtctctc cacttacatt tgatactgat ggaaacataa agcttacctt agacagaggt  32640
```

-continued

```
ttgcatgtta caacaggaga tgcaattgaa agcaacataa gctgggctaa aggtttaaaa  32700
tttgaagatg gagccatagc aaccaacatt ggaaatgggt tagagtttgg aagcagtagt  32760
acagaaacag gtgttgatga tgcttaccca atccaagtta aacttggatc tggccttagc  32820
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtataggg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg ggctaactcc ttataccttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
```

-continued aatgaagatc gcggagatgg cacctctcgc ccccgctgtg ttggtggaaa ataacagcca 35040
ggtcaaaggt gatacggttc tcgagatgtt ccacggtggc ttccagcaaa gcctccacgc 35100
gcacatccag aaacaagaca atagcgaaag cgggagggtt ctctaattcc tcaatcatca 35160
tgttacactc ctgcaccatc cccagataat tttcattttt ccagccttga atgattcgaa 35220
ctagttcctg aggtaaatcc aagccagcca tgataaagag ctcgcgcaga gcgccctcca 35280
ccggcattct taagcacacc ctcataattc caagatattc tgctcctggt tcacctgcag 35340
cagattgaca agcggaatat caaaatctct gccgcgatcc ctgagctcct ccctcagcaa 35400
taactgtaag tactctttca tatcctctcc gaaattttta gccataggac caccaggaat 35460
aagattaggg caagccacag tacagataaa ccgaagtcct ccccagtgag cattgccaaa 35520
tgcaagactg ctataagcat gctggctaga cccggtgata tcttccagat aactggacag 35580
aaaatcgccc aggcaatttt taagaaaatc aacaaaagaa aaatcctcca ggtggacgtt 35640
tagagcctcg ggaacaacga tgaagtaaat gcaagcggtg cgttccagca tggttagtta 35700
gctgatctgt agaaaaaaca aaaatgaaca ttaaaccatg ctagcctggc gaacaggtgg 35760
gtaaatcgtt ctctccagca ccaggcaggc cacggggtct ccggcgcgac cctcgtaaaa 35820
attgtcgcta tgattgaaaa ccatcacaga gagacgttcc cggtggccgg cgtgaatgat 35880
tcgacaagat gaatacaccc ccggaacatt ggcgtccgcg agtgaaaaaa agcgcccgag 35940
gaagcaataa ggcactacaa tgctcagtct caagtccagc aaagcgatgc catgcggatg 36000
aagcacaaaa ttctcaggtg cgtacaaaat gtaattactc ccctcctgca caggcagcaa 36060
agcccccgat ccctccaggt acacatacaa agcctcagcg tccatagctt accgagcagc 36120
agcacacaac aggcgcaaga gtcagagaaa ggctgagctc taacctgtcc acccgctctc 36180
tgctcaatat atagcccaga tctacactga cgtaaaggcc aaagtctaaa aatacccgcc 36240
aaataatcac acacgcccag cacacgccca gaaaccggtg acacactcaa aaaaatacgc 36300
gcacttcctc aaacgcccaa aactgccgtc atttccgggt tcccacgcta cgtcatcaaa 36360
acacgacttt caaattccgt cgaccgttaa aaacgtcacc cgccccgccc ctaacggtcg 36420
cccgtctctc agccaatcag cgccccgcat ccccaaattc aaacacctca tttgcatatt 36480
aacgcgcaca aaaagtttga ggtatattat tgatgatgg 36519

<210> SEQ ID NO 11
<211> LENGTH: 31867
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480

-continued

```
atttaaacct gcgctctcca gtcaagaggc cactcttgag tgccagcgag aagagttttc    540
tcctccgcgc cgcgagtcag atctacactt tgaaagtagg gataacaggg taatgacatt    600
gattattgac tagttgttaa tagtaatcaa ttacggggtc attagttcat agcccatata    660
tggagttccg cgttacataa cttacggtaa atggcccgcc tggctgaccg cccaacgacc    720
cccgcccatt gacgtcaata atgacgtatg ttcccatagt aacgccaata gggactttcc    780
attgacgtca atgggtggag tatttacggt aaactgccca cttggcagta catcaagtgt    840
atcatatgcc aagtccgccc cctattgacg tcaatgacgg taaatggccc gcctggcatt    900
atgcccagta catgacctta cgggactttc ctacttggca gtacatctac gtattagtca    960
tcgctattac catggtgatg cggttttggc agtacaccaa tgggcgtgga tagcggtttg   1020
actcacgggg atttccaagt ctccacccca ttgacgtcaa tgggagtttg ttttggcacc   1080
aaaatcaacg ggactttcca aaatgtcgta ataaccccgc cccgttgacg caaatgggcg   1140
gtaggcgtgt acggtgggag gtctatataa gcagagctcg tttagtgaac cgtcagatcg   1200
cctggaacgc catccacgct gttttgacct ccatagaaga cagcgatcgc gccaccatgg   1260
tgagcaaggg cgaggagctg ttcaccgggg tggtgcccat cctggtcgag ctggacggcg   1320
acgtaaacgg ccacaagttc agcgtgtccg gcgagggcga gggcgatgcc acctacggca   1380
agctgaccct gaagttcatc tgcaccaccg gcaagctgcc cgtgccctgg cccaccctcg   1440
tgaccaccct gacctacggc gtgcagtgct tcagccgcta ccccgaccac atgaagcagc   1500
acgacttctt caagtccgcc atgcccgaag gctacgtcca ggagcgcacc atcttcttca   1560
aggacgacgg caactacaag acccgcgccg aggtgaagtt cgagggcgac accctggtga   1620
accgcatcga gctgaagggc atcgacttca aggaggacgg caacatcctg gggcacaagc   1680
tggagtacaa ctacaacagc cacaacgtct atatcatggc cgacaagcag aagaacggca   1740
tcaaggtgaa cttcaagatc cgccacaaca tcgaggacgg cagcgtgcag ctcgccgacc   1800
actaccagca gaacaccccc atcggcgacg gccccgtgct gctgcccgac aaccactacc   1860
tgagcaccca gtccgccctg agcaaagacc ccaacgagaa gcgcgatcac atggtcctgc   1920
tggagttcgt gaccgccgcc gggatcactc tcggcatgga cgagctttac aagtagtgag   1980
tttaaactcc catttaaatg tgagggttaa tgcttcgagc agacatgata agatacattg   2040
atgagtttgg acaaaccaca actagaatgc agtgaaaaaa atgctttatt tgtgaaattt   2100
gtgatgctat tgctttattt gtaaccatta taagctgcaa taaacaagtt aacaacaaca   2160
attgcattca ttttatgttt caggttcagg gggagatgtg ggaggttttt taaagcaagt   2220
aaaacctcta caaatgtggt aaaataacta taacggtcct aaggtagcga gtgagtagtg   2280
ttctggggcg gggggaggacc tgcatgaggg ccagaataac tgaaatctgt gcttttctgt   2340
gtgttgcagc agcatgagcg gaagcggctc ctttgaggga ggggtattca gcccttatct   2400
gacggggcgt ctcccctcct gggcgggagt gcgtcagaat gtgatgggat ccacggtgga   2460
cggccggccc gtgcagcccg cgaactcttc aaccctgacc tatgcaaccc tgagctcttc   2520
gtcgttggac gcagctgccg ccgcagctgc tgcatctgcc gccagcgccg tgcgcggaat   2580
ggccatgggc gccggctact acggcactct ggtggccaac tcgagttcca ccaataatcc   2640
cgccagcctg aacgaggaga agctgttgct gctgatggcc cagctcgagg ccttgaccca   2700
gcgcctgggc gagctgaccc agcaggtggc tcagctgcag gagcagacgc gggccgcggt   2760
tgccacggtg aaatccaaat aaaaaatgaa tcaataaata aacggagacg gttgttgatt   2820
ttaacacaga gtctgaatct ttatttgatt tttcgcgcgc ggtaggccct ggaccaccgg   2880
```

-continued

```
tctcgatcat tgagcacccg gtggatcttt tccaggaccc ggtagaggtg ggcttggatg   2940
ttgaggtaca tgggcatgag cccgtcccgg gggtggaggt agctccattg cagggcctcg   3000
tgctcggggg tggtgttgta aatcacccag tcatagcagg ggcgcagggc atggtgttgc   3060
acaatatctt tgaggaggag actgatggcc acgggcagcc ctttggtgta ggtgtttaca   3120
aatctgttga gctgggaggg atgcatgcgg ggggagatga ggtgcatctt ggcctggatc   3180
ttgagattgg cgatgttacc gcccagatcc cgcctggggt tcatgttgtg caggaccacc   3240
agcacggtgt atccggtgca cttggggaat ttatcatgca acttggaagg gaaggcgtga   3300
aagaatttgg cgacgccttt gtgcccgccc aggttttcca tgcactcatc catgatgatg   3360
gcgatgggcc cgtgggcggc ggcctgggca aagacgtttc gggggtcgga cacatcatag   3420
ttgtggtcct gggtgaggtc atcataggcc attttaatga atttggggcg gagggtgccg   3480
gactggggga caaaggtacc ctcgatcccg gggcgtagt tcccctcaca gatctgcatc   3540
tcccaggctt tgagctcgga ggggggatc atgtccacct gcggggcgat aaagaacacg   3600
gtttccgggg cgggggagat gagctgggcc gaaagcaagt tccggagcag ctgggacttg   3660
ccgcagccgg tggggccgta gatgaccccg atgaccggct gcaggtggta gttgagggag   3720
agacagctgc cgtcctcccg gaggaggggg gccacctcgt tcatcatctc gcgcacgtgc   3780
atgttctcgc gcaccagttc cgccaggagg cgctctcccc ccagggatag gagctcctgg   3840
agcgaggcga agtttttcag cggcttgagt ccgtcggcca tgggcatttt ggagagggtt   3900
tgttgcaaga gttccaggcg gtcccagagc tcggtgatgt gctctacggc atctcgatcc   3960
agcagacctc ctcgtttcgc gggttgggac ggctgcggga gtagggcacc agacgatggg   4020
cgtccagcgc agccagggtc cggtccttcc agggtcgcag cgtccgcgtc agggtggtct   4080
ccgtcacggt gaaggggtgc gcgccgggct gggcgcttgc gagggtgcgc ttcaggctca   4140
tccggctggt cgaaaaccgc tcccgatcgg cgccctgcgc gtcggccagg tagcaattga   4200
ccatgagttc gtagttgagc gcctcggccg cgtggccttt ggcgcggagc ttacctttgg   4260
aagtctgccc gcaggcggga cagaggaggg acttgagggc gtagagcttg ggggcgagga   4320
agacggactc gggggcgtag gcgtccgcgc cgcagtgggc gcagacggtc tcgcactcca   4380
cgagccaggt gaggtcgggc tggtcggggt caaaaaccag tttcccgccg ttcttttga    4440
tgcgtttctt acctttggtc tccatgagct cgtgtccccg ctgggtgaca aagaggctgt   4500
ccgtgtcccc gtagaccgac tttatgggcc ggtcctcgag cggtgtgccg cggtcctcct   4560
cgtagaggaa ccccgcccac tccgagacga aagcccgggt ccaggccagc acgaaggagg   4620
ccacgtggga cgggtagcgg tcgttgtcca ccagcgggtc caccttttcc agggtatgca   4680
aacacatgtc cccctcgtcc acatccagga aggtgattgg cttgtaagtg taggccacgt   4740
gaccgggggt cccggccggg ggggtataaa agggtgcggg tccctgctcg tcctcactgt   4800
cttccggatc gctgtccagg agcgccagct gttggggtag gtattccctc tcgaaggcgg   4860
gcatgacctc ggcactcagg ttgtcagttt ctagaaacga ggaggatttg atattgacgg   4920
tgccggcgga gatgcctttc aagagcccct cgtccatctg gtcagaaaag acgatctttt   4980
tgttgtcgag cttggtggcg aaggagccgt agagggcgtt ggagaggagc ttggcgatgg   5040
agcgcatggt ctggtttttt tccttgtcgg cgcgctcctt ggcggcgatg ttgagctgca   5100
cgtactcgcg cgccacgcac ttccattcgg ggaagacggt ggtcagctcg tcgggcacga   5160
ttctgacctg ccagccccga ttatgcaggg tgatgaggtc cacactggtg gccacctcgc   5220
```

```
cgcgcagggg ctcattagtc cagcagaggc gtccgccctt gcgcgagcag aagggggca   5280
gggggtccag catgacctcg tcggggggt cggcatcgat ggtgaagatg ccgggcagga   5340
ggtcggggtc aaagtagctg atggaagtgg ccagatcgtc cagggcagct tgccattcgc   5400
gcacggccag cgcgctctcg tagggactga ggggcgtgcc ccagggcatg ggatgggtaa   5460
gcgcggaggc gtacatgccg cagatgtcgt agacgtagag gggctcctcg aggatgccga   5520
tgtaggtggg gtagcagcgc cccccgcgga tgctggcgcg cacgtagtca tacagctcgt   5580
gcgagggggc gaggagcccc gggcccaggt tggtgcgact gggcttttcg gcgcggtaga   5640
cgatctggcg gaaaatggca tgcgagttgg aggagatggt gggcctttgg aagatgttga   5700
agtgggcgtg gggcagtccg accgagtcgc ggatgaagtg ggcgtaggag tcttgcagct   5760
tggcgacgag ctcggcggtg actaggacgt ccagagcgca gtagtcgagg gtctcctgga   5820
tgatgtcata cttgagctgt ccctttttgtt tccacagctc gcggttgaga aggaactctt   5880
cgcggtcctt ccagtactct tcgaggggga acccgtcctg atctgcacgg taagagccta   5940
gcatgtagaa ctggttgacg gccttgtagg cgcagcagcc cttctccacg ggagggcgt   6000
aggcctgggc ggccttgcgc agggaggtgt gcgtgagggc gaaagtgtcc ctgaccatga   6060
ccttgaggaa ctggtgcttg aagtcgatat cgtcgcagcc cccctgctcc cagagctgga   6120
agtccgtgcg cttcttgtag gcggggttgg gcaaagcgaa agtaacatcg ttgaagagga   6180
tcttgcccgc gcggggcata aagttgcgag tgatgcggaa aggttggggc acctcggccc   6240
ggttgttgat gacctgggcg gcgagcacga tctcgtcgaa gccgttgatg ttgtggccca   6300
cgatgtagag ttccacgaat cgcggacggc ccttgacgtg ggcagtttc ttgagctcct   6360
cgtaggtgag ctcgtcgggg tcgctgagcc cgtgctgctc gagcgcccag tcggcgagat   6420
gggggttggc gcggaggaag gaagtccaga gatccacggc cagggcggtt tgcagacggt   6480
cccggtactg acggaactgc tgcccgacgg ccattttttc gggggtgacg cagtagaagg   6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg ggcggctcgg ggcccggagg   7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
```

```
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggccccg ggagttcctc    8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
gagcaccagg tctttgggcc cggcttgctg gatgcgcaga cggtcggcca tgccccaggc   8640
gtggtcctga cacctggcca ggtccttgta gtagtcctgc atgagccgct ccacgggcac   8700
ctcctcctcg cccgcgcggc cgtgcatgcg cgtgagcccg aagccgcgct ggggctggac   8760
gagcgccagg tcggcgacga cgcgctcggc gaggatggct tgctggatct gggtgagggt   8820
ggtctggaag tcatcaaagt cgacgaagcg gtggtaggct ccggtgttga tggtgtagga   8880
gcagttggcc atgacggacc agttgacggt ctggtggccc ggacgcacga gctcgtggta   8940
cttgaggcgc gagtaggcgc gcgtgtcgaa gatgtagtcg ttgcaggtgc gcaccaggta   9000
ctggtagccg atgaggaagt gcggcggcgg ctggcggtag agcggccatc gctcggtggc   9060
gggggcgccg ggcgcgaggt cctcgagcat ggtgcggtgg tagccgtaga tgtacctgga   9120
catccaggtg atgccggcgg cggtggtgga ggcgcgcggg aactcgcgga cgcggttcca   9180
gatgttgcgc agcggcagga agtagttcat ggtgggcacg gtctggcccg tgaggcgcgc   9240
gcagtcgtgg atgctctata cggcaaaaa cgaaagcggt cagcggctcg actccgtggc    9300
ctggaggcta agcgaacggg ttgggctgcg cgtgtacccc ggttcgaatc tcgaatcagg   9360
ctggagccgc agctaacgtg gtattggcac tcccgtctcg acccaagcct gcaccaaccc   9420
tccaggatac ggaggcgggt cgttttgcaa cttttttttg gaggccggat gagactagta   9480
agcgcggaaa gcggccgacc gcgatggctc gctgccgtag tctggagaag aatcgccagg   9540
gttgcgttgc ggtgtgcccc ggttcgaggc cggccggatt ccgcggctaa cgagggcgtg   9600
gctgccccgt cgtttccaag accccatagc cagccgactt ctccagttac ggagcgagcc   9660
cctcttttgt tttgtttgtt tttgccagat gcatcccgta ctgcggcaga tgcgccccca   9720
ccaccctcca ccgcaacaac agccccctcc acagccggcg cttctgcccc cgccccagca   9780
gcaacttcca gccacgaccg ccgcggccgc cgtgagcggg gctggacaga gttatgatca   9840
ccagctggcc ttggaagagg gcgaggggct ggcgcgcctg gggcgtcgt cgccggagcg    9900
gcacccgcgc gtgcagatga aaagggacgc tcgcgaggcc tacgtgccca agcagaacct   9960
```

-continued

```
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gccccccttca cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctccccccc gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
```

```
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
atgtaagaga aaccgaaaat aaatgatact caccaaggcc atggcgacca gcgtgcgttc  12720
gtttcttctc tgttgttgtt gtatctagta tgatgaggcg tgcgtacccg gagggtcctc  12780
ctccctcgta cgagagcgtg atgcagcagg cgatggcggc ggcggcgatg cagcccccgc  12840
tggaggctcc ttacgtgccc ccgcggtacc tggcgcctac ggagggggcgg aacagcattc  12900
gttactcgga gctggcaccc ttgtacgata ccacccggtt gtacctggtg gacaacaagt  12960
cggcggacat cgcctcgctg aactaccaga acgaccacag caacttcctg accaccgtgg  13020
tgcagaacaa tgacttcacc cccacggagg ccagcaccca gaccatcaac tttgacgagc  13080
gctcgcggtg gggcggccag ctgaaaacca tcatgcacac caacatgccc aacgtgaacg  13140
agttcatgta cagcaacaag ttcaaggcgc gggtgatggt ctcccgcaag acccccaatg  13200
gggtgacagt gacagaggat tatgatggta gtcaggatga gctgaagtat gaatgggtgg  13260
aatttgagct gcccgaaggc aacttctcgg tgaccatgac catcgacctg atgaacaacg  13320
ccatcatcga caattacttg gcggtggggc ggcagaacgg ggtgctggag agcgacatcg  13380
gcgtgaagtt cgacactagg aacttcaggc tgggctggga ccccgtgacc gagctggtca  13440
tgcccggggt gtacaccaac gaggctttcc atcccgatat tgtcttgctg cccggctgcg  13500
gggtggactt caccgagagc cgcctcagca acctgctggg cattcgcaag aggcagccct  13560
tccaggaagg cttccagatc atgtacgagg atctggaggg gggcaacatc cccgcgctcc  13620
tggatgtcga cgcctatgag aaaagcaagg aggatgcagc agctgaagca actgcagccg  13680
tagctaccgc ctctaccgag gtcaggggcg ataattttgc aagcgccgca gcagtggcag  13740
cggccgaggc ggctgaaacc gaaagtaaga tagtcattca gccggtggag aaggatagca  13800
agaacaggag ctacaacgta ctaccggaca agataaacac cgcctaccgc agctggtacc  13860
tagcctacaa ctatggcgac cccgagaagg gcgtgcgctc ctggacgctg ctcaccacct  13920
cggacgtcac ctgcggcgtg gagcaagtct actggtcgct gcccgacatg atgcaagacc  13980
cggtcacctt ccgctccacg cgtcaagtta gcaactaccc ggtggtgggc gccgagctcc  14040
tgcccgtcta ctccaagagc ttcttcaacg agcaggccgt ctactcgcag cagctgcgcg  14100
ccttcacctc gcttacgcac gtcttcaacc gcttccccga gaaccagatc ctcgtccgcc  14160
cgcccgcgcc caccattacc accgtcagtg aaaacgttcc tgctctcaca gatcacggga  14220
ccctgccgct gcgcagcagt atccggggag tccagcgcgt gaccgttact gacgccagac  14280
gccgcacctg cccctacgtc tacaaggccc tgggcatagt cgcgccgcgc gtcctctcga  14340
gccgcacctt ctaaatgtcc attctcatct cgcccagtaa taacaccggt tggggcctgc  14400
gcgcgcccag caagatgtac ggaggcgctc gccaacgctc cacgcaacac cccgtgcgcg  14460
tgcgcgggca cttccgcgct ccctggggcg ccctcaaggg ccgcgtgcgg tcgcgcacca  14520
ccgtcgacga cgtgatcgac caggtggtgg ccgacgcgcg caactacacc cccgccgccg  14580
cgcccgtctc caccgtggac gccgtcatcg acagcgtggt ggccgacgcg cgccggtacg  14640
cccgcgccaa gagccggcgg cggcgcatcg cccggcggca ccggagcacc cccgccatgc  14700
```

-continued

```
gcgcggcgcg agccttgctg cgcagggcca ggcgcacggg acgcagggcc atgctcaggg  14760
cggccagacg cgcggcttca ggcgccagcg ccggcaggac ccggagacgc gcggccacgg  14820
cggcggcagc ggccatcgcc agcatgtccc gcccgcggcg agggaacgtg tactgggtgc  14880
gcgacgccgc caccggtgtg cgcgtgcccg tgcgcacccg ccccccctcgc acttgaagat  14940
gttcacttcg cgatgttgat gtgtcccagc ggcgaggagg atgtccaagc gcaaattcaa  15000
ggaagagatg ctccaggtca tcgcgcctga gatctacggc cctgcggtgg tgaaggagga  15060
aagaaagccc cgcaaaatca agcgggtcaa aaaggacaaa aaggaagaag aaagtgatgt  15120
ggacggattg gtggagtttg tgcgcgagtt cgcccccccgg cggcgcgtgc agtggcgcgg  15180
gcggaaggtg caaccggtgc tgagacccgg caccaccgtg gtcttcacgc ccggcgagcg  15240
ctccggcacc gcttccaagc gctcctacga cgaggtgtac ggggatgatg atattctgga  15300
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
ggagaccatg aaggtggacc cggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat ttttcgtccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
```

tctgtgtgtg tatgtattat gtcgccgccg ccgctgtcca ccagaaggag gagtgaagag 17160
gcgcgtcgcc gagttgcaag atggccaccc catcgatgct gccccagtgg gcgtacatgc 17220
acatcgccgg acaggacgct tcggagtacc tgagtccggg tctggtgcag tttgcccgcg 17280
ccacagacac ctacttcagt ctggggaaca agtttaggaa ccccacggtg gcgcccacgc 17340
acgatgtgac caccgaccgc agccagcggc tgacgctgcg cttcgtgccc gtggaccgcg 17400
aggacaacac ctactcgtac aaagtgcgct acacgctggc cgtgggcgac aaccgcgtgc 17460
tggacatggc cagcacctac tttgacatcc gcggcgtgct ggatcggggc cctagcttca 17520
aaccctactc cggcaccgcc tacaacagtc tggcccccaa gggagcaccc aacacttgtc 17580
agtggacata taaagccgat ggtgaaactg ccacagaaaa aacctataca tatggaaatg 17640
cacccgtgca gggcattaac atcacaaaag atggtattca acttggaact gacaccgatg 17700
atcagccaat ctacgcagat aaaacctatc agcctgaacc tcaagtgggt gatgctgaat 17760
ggcatgacat cactggtact gatgaaaagt atggaggcag agctcttaag cctgatacca 17820
aaatgaagcc ttgttatggt tcttttgcca agcctactaa taaagaagga ggtcaggcaa 17880
atgtgaaaac aggaacaggc actactaaag aatatgacat agacatggct ttctttgaca 17940
acagaagtgc ggctgctgct ggcctagctc cagaaattgt tttgtatact gaaaatgtgg 18000
atttggaaac tccagatacc catattgtat acaaagcagg cacagatgac agcagctctt 18060
ctattaattt gggtcagcaa gccatgccca acagacctaa ctacattggt ttcagagaca 18120
actttatcgg gctcatgtac tacaacagca ctggcaatat gggggtgctg gccggtcagg 18180
cttctcagct gaatgctgtg gttgacttgc aagacagaaa caccgagctg tcctaccagc 18240
tcttgcttga ctctctgggt gacagaaccc ggtatttcag tatgtggaat caggcggtgg 18300
acagctatga tcctgatgtg cgcattattg aaaatcatgg tgtggaggat gaacttccca 18360
actattgttt ccctctggat gctgttggca gaacagatac ttatcaggga attaaggcta 18420
atggaactga tcaaaccaca tggaccaaag atgacagtgt caatgatgct aatgagatag 18480
gcaagggtaa tccattcgcc atggaaatca acatccaagc caacctgtgg aggaacttcc 18540
tctacgccaa cgtggccctg tacctgcccg actcttacaa gtacacgccg gccaatgtta 18600
ccctgcccac caacaccaac acctacgatt acatgaacgg ccgggtggtg gcgccctcgc 18660
tggtggactc ctacatcaac atcggggcgc gctggtcgct ggatcccatg gacaacgtga 18720
accccttcaa ccaccaccgc aatgcggggc tgcgctaccg ctccatgctc ctgggcaacg 18780
ggcgctacgt gcccttccac atccaggtgc cccagaaatt tttcgccatc aagagcctcc 18840
tgctcctgcc cgggtcctac acctacgagt ggaacttccg caaggacgtc aacatgatcc 18900
tgcagagctc cctcggcaac gacctgcgca cggacggggc ctccatctcc ttcaccagca 18960
tcaacctcta cgccaccttc ttccccatgg cgcacaacac ggcctccacg ctcgaggcca 19020
tgctgcgcaa cgacaccaac gaccagtcct tcaacgacta cctctcggcg gccaacatgc 19080
tctaccccat cccggccaac gccaccaacg tgcccatctc catcccctcg cgcaactggg 19140
ccgccttccg cggctggtcc ttcacgcgtc tcaagaccaa ggagacgccc tcgctgggct 19200
ccgggttcga cccctacttc gtctactcgg gctccatccc ctacctcgac ggcaccttct 19260
acctcaacca caccttcaag aaggtctcca tcaccttcga ctcctccgtc agctggcccg 19320
gcaacgaccg gctcctgacg cccaacgagt tcgaaatcaa gcgcaccgtc gacggcgagg 19380
gctacaacgt ggcccagtgc aacatgacca aggactggtt cctggtccag atgctggccc 19440

```
actacaacat cggctaccag ggcttctacg tgcccgaggg ctacaaggac cgcatgtact  19500
ccttcttccg caacttccag cccatgagcc gccaggtggt ggacgaggtc aactacaagg  19560
actaccaggc cgtcaccctg gcctaccagc acaacaactc gggcttcgtc ggctacctcg  19620
cgcccaccat gcgccagggc cagccctacc ccgccaacta cccctacccg ctcatcggca  19680
agagcgccgt caccagcgtc acccagaaaa agttcctctg cgacagggtc atgtggcgca  19740
tccccttctc cagcaacttc atgtccatgg gcgcgctcac cgacctcggc cagaacatgc  19800
tctatgccaa ctccgcccac gcgctagaca tgaatttcga agtcgacccc atggatgagt  19860
ccacccttct ctatgttgtc ttcgaagtct tcgacgtcgt ccgagtgcac cagccccacc  19920
gcggcgtcat cgaggccgtc tacctgcgca ccccettctc ggccggtaac gccaccacct  19980
aagctcttgc ttcttgcaag ccatggccgc gggctccggc gagcaggagc tcagggccat  20040
catccgcgac ctgggctgcg ggccctactt cctgggcacc ttcgataagc gcttcccggg  20100
attcatggcc ccgcacaagc tggcctgcgc catcgtcaac acggccggcc gcgagaccgg  20160
gggcgagcac tggctggcct tcgcctggaa cccgcgctcg aacacctgct acctcttcga  20220
ccccttcggg ttctcggacg agcgcctcaa gcagatctac cagttcgagt acgagggcct  20280
gctgcgccgc agcgccctgg ccaccgagga ccgctgcgtc accctggaaa agtccaccca  20340
gaccgtgcag ggtccgcgct cggccgcctg cgggctcttc tgctgcatgt tcctgcacgc  20400
cttcgtgcac tggcccgacc gccccatgga caagaacccc accatgaact tgctgacggg  20460
ggtgcccaac ggcatgctcc agtcgcccca ggtggaaccc accctgcgcc gcaaccagga  20520
ggcgctctac cgcttcctca actcccactc cgcctacttt cgctcccacc gcgcgcgcat  20580
cgagaaggcc accgccttcg accgcatgaa tcaagacatg taaaccgtgt gtgtatgtta  20640
aatgtcttta ataaacagca ctttcatgtt acacatgcat ctgagatgat ttatttagaa  20700
atcgaaaggg ttctgccggg tctcggcatg gcccgcgggc agggacacgt tgcggaactg  20760
gtacttggcc agccacttga actcggggat cagcagtttg ggcagcgggg tgtcggggaa  20820
ggagtcggtc cacagcttcc gcgtcagttg cagggcgccc agcaggtcgg gcgcggagat  20880
cttgaaatcg cagttgggac ccgcgttctg cgcgcgggag ttgcggtaca cggggttgca  20940
gcactggaac accatcaggg ccgggtgctt cacgctcgcc agcaccgtcg cgtcggtgat  21000
gctctccacg tcgaggtcct cggcgttggc catcccgaag gggtcatct tgcaggtctg  21060
ccttcccatg gtgggcacgc acccgggctt gtggttgcaa tcgcagtgca gggggatcag  21120
catcatctgg gcctggtcgg cgttcatccc cgggtacatg gccttcatga aagcctccaa  21180
ttgcctgaac gcctgctggg ccttggctcc ctcggtgaag aagaccccgc aggacttgct  21240
agagaactgg ttggtggcgc acccggcgtc gtgcacgcag cagcgcgcgt cgttgttggc  21300
cagctgcacc acgctgcgcc cccagcggtt ctgggtgatc ttggcccggt cggggttctc  21360
cttcagcgcg cgctgcccgt tctcgctcgc cacatccatc tcgatcatgt gctccttctg  21420
gatcatggtg gtcccgtgca ggcaccgcag cttgccctcg gcctcggtgc acccgtgcag  21480
ccacagcgcg cacccggtgc actcccagtt cttgtgggcg atctgggaat gcgcgtgcac  21540
gaagccctgc aggaagcggc ccatcatggt ggtcagggtc ttgttgctag tgaaggtcag  21600
cggaatgccg cggtgctcct cgttgatgta caggtggcag atgcggcggt acacctcgcc  21660
ctgctcgggc atcagctgga agttggcttt caggtcggtc tccacgcggt agcggtccat  21720
cagcatagtc atgatttcca tacccttctc ccaggccgag acgatgggca ggctcatagg  21780
gttcttcacc atcatcttag cgctagcagc cgcggccagg gggtcgctct cgtccagggt  21840
```

ctcaaagctc cgcttgccgt ccttctcggt gatccgcacc ggggggtagc tgaagcccac 21900
ggccgccagc tcctcctcgg cctgtctttc gtcctcgctg tcctggctga cgtcctgcag 21960
gaccacatgc ttggtcttgc ggggtttctt cttgggcggc agcggcggcg gagatgttgg 22020
agatggcgag gggagcgcg agttctcgct caccactact atctcttcct cttcttggtc 22080
cgaggccacg cggcggtagg tatgtctctt cgggggcaga ggcggaggcg acgggctctc 22140
gccgccgcga cttggcggat ggctggcaga gccccttccg cgttcggggg tgcgctcccg 22200
gcggcgctct gactgacttc ctccgcggcc ggccattgtg ttctcctagg gaggaacaac 22260
aagcatggag actcagccat cgccaacctc gccatctgcc cccaccgccg acgagaagca 22320
gcagcagcag aatgaaagct taaccgcccc gccgcccagc cccgccacct ccgacgcggc 22380
cgtcccagac atgcaagaga tggaggaatc catcgagatt gacctgggct atgtgacgcc 22440
cgcggagcac gaggaggagc tggcagtgcg cttttcacaa gaagagatac accaagaaca 22500
gccagagcag gaagcagaga atgagcagag tcaggctggg ctcgagcatg acggcgacta 22560
cctccacctg agcggggggg aggacgcgct catcaagcat ctggcccggc aggccaccat 22620
cgtcaaggat gcgctgctcg accgcaccga ggtgcccctc agcgtggagg agctcagccg 22680
cgcctacgag ttgaacctct tctcgccgcg cgtgcccccc aagcgccagc ccaatggcac 22740
ctgcgagccc aacccgcgcc tcaacttcta cccggtcttc gcggtgcccg aggccctggc 22800
cacctaccac atctttttca agaaccaaaa gatccccgtc tcctgccgcg ccaaccgcac 22860
ccgcgccgac gccctttca acctgggtcc cggcgcccgc ctacctgata tcgcctcctt 22920
ggaagaggtt cccaagatct tcgagggtct gggcagcgac gagactcggg ccgcgaacgc 22980
tctgcaagga gaaggaggag agcatgagca ccacagcgcc ctggtcgagt tggaaggcga 23040
caacgcgcgg ctggcggtgc tcaaacgcac ggtcgagctg acccatttcg cctacccggc 23100
tctgaacctg ccccccaaag tcatgagcgc ggtcatggac caggtgctca tcaagcgcgc 23160
gtcgcccatc tccgaggacg agggcatgca agactccgag gagggcaagc ccgtggtcag 23220
cgacgagcag ctggcccggt ggctgggtcc taatgctagt ccccagagtt tggaagagcg 23280
gcgcaaactc atgatggccg tggtcctggt gaccgtggag ctggagtgcc tgcgccgctt 23340
cttcgccgac gcggagaccc tgcgcaaggt cgaggagaac ctgcactacc tcttcaggca 23400
cgggttcgtg cgccaggcct gcaagatctc caacgtggag ctgaccaacc tggtctccta 23460
catgggcatc ttgcacgaga accgcctggg gcagaacgtg ctgcacacca ccctgcgcgg 23520
ggaggcccgg cgcgactaca tccgcgactg cgtctacctc tacctctgcc acacctggca 23580
gacgggcatg ggcgtgtggc agcagtgtct ggaggagcag aacctgaaag agctctgcaa 23640
gctcctgcag aagaacctca agggtctgtg gaccgggttc gacgagcgca ccaccgcctc 23700
ggacctggcc gacctcattt tccccgagcg cctcaggctg acgctgcgca acggcctgcc 23760
cgactttatg agccaaagca tgttgcaaaa ctttcgctct ttcatcctcg aacgctccgg 23820
aatcctgccc gccacctgct ccgcgctgcc ctcggacttc gtgccgctga ccttccgcga 23880
gtgccccccg ccgctgtgga gccactgcta cctgctgcgc ctggccaact acctggccta 23940
ccactcggac gtgatcgagg acgtcagcgg cgagggcctg ctcgagtgcc actgccgctg 24000
caacctctgc acgccgcacc gctccctggc ctgcaacccc cagctgctga gcgagaccca 24060
gatcatcggc accttcgagt tgcaagggcc cagcgaaggc gagggttcag ccgccaaggg 24120
gggtctgaaa ctcaccccgg ggctgtggac ctcggcctac ttgcgcaagt tcgtgcccga 24180

```
ggactaccat cccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aaccccggct tcccccagga tgccccgagg aaacaagaag ctgaaagtgg  24420
agctgccgcc cgtggaggat ttggaggaag actgggagaa cagcagtcag gcagaggagg  24480
aggagatgga ggaagactgg gacagcactc aggcagagga ggacagcctg caagacagtc  24540
tggaggaaga cgaggaggag gcagaggagg aggtggaaga agcagccgcc gccagaccgt  24600
cgtcctcggc gggggagaaa gcaagcagca cggataccat ctccgctccg ggtcggggtc  24660
ccgctcgacc acacagtaga tgggacgaga ccggacgatt cccgaacccc accacccaga  24720
ccggtaagaa ggagcggcag ggatacaagt cctggcgggg gcacaaaaac gccatcgtct  24780
cctgcttgca ggcctgcggg ggcaacatct ccttcacccg gcgctacctg ctcttccacc  24840
gcggggtgaa ctttccccgc aacatcttgc attactaccg tcacctccac agcccctact  24900
acttccaaga agaggcagca gcagcagaaa aagaccagca gaaaaccagc agctagaaaa  24960
tccacagcgg cggcagcagg tggactgagg atcgcggcga acgagccggc gcaaacccgg  25020
gagctgagga accggatctt tcccaccctc tatgccatct tccagcagag tcgggggcag  25080
gagcaggaac tgaaagtcaa gaaccgttct ctgcgctcgc tcacccgcag ttgtctgtat  25140
cacaagagcg aagaccaact tcagcgcact ctcgaggacg ccgaggctct cttcaacaag  25200
tactgcgcgc tcactcttaa agagtagccc gcgcccgccc agtcgcagaa aaaggcggga  25260
attacgtcac ctgtgccctt cgccctagcc gcctccaccc atcatcatga gcaaagagat  25320
tcccacgcct tacatgtgga gctaccagcc ccagatgggc ctggccgccg gtgccgccca  25380
ggactactcc acccgcatga attggctcag cgccgggccc gcgatgatct cacgggtgaa  25440
tgacatccgc gcccaccgaa accagatact cctagaacag tcagcgctca ccgccacgcc  25500
ccgcaatcac ctcaatccgc gtaattggcc cgccgccctg gtgtaccagg aaattcccca  25560
gcccacgacc gtactacttc cgcgagacgc ccaggccgaa gtccagctga ctaactcagg  25620
tgtccagctg gcgggcggcg ccaccctgtg tcgtcaccgc cccgctcagg gtataaagcg  25680
gctggtgatc cggggcagag gcacacagct caacgacgag gtggtgagct cttcgctggg  25740
tctgcgacct gacggagtct tccaactcgc cggatcgggg agatcttcct tcacgcctcg  25800
tcaggccgtc ctgactttgg agagttcgtc ctcgcagccc cgctcgggtg gcatcggcac  25860
tctccagttc gtggaggagt tcactccctc ggtctacttc aacccccttct ccggctcccc  25920
cggccactac ccggacgagt tcatcccgaa cttcgacgcc atcagcgagt cggtggacgg  25980
ctacgattga atgtcccatg gtggcgcagc tgacctagct cggcttcgac acctggacca  26040
ctgccgccgc ttccgctgct tcgctcggga tctcgccgag tttgcctact ttgagctgcc  26100
cgaggagcac cctcagggcc cggcccacgg agtgcggatc gtcgtcgaag gggcctcga  26160
ctcccacctg cttcggatct tcagccagcg tccgatcctg gtcgagcgcg agcaaggaca  26220
gacccttctg actctgtact gcatctgcaa ccacccccggc ctgcatgaaa gtctttgttg  26280
tctgctgtgt actgagtata ataaaagctg agatcagcga ctactccgga cttccgtgtg  26340
ttcctgaatc catcaaccag tctttgttct tcaccgggaa cgagaccgag ctccagctcc  26400
agtgtaagcc ccacaagaag tacctcacct ggctgttcca gggctccccg atcgccgttg  26460
tcaaccactg cgacaacgac ggagtcctgc tgagcggccc tgccaacctt actttttcca  26520
cccgcagaag caagctccag ctcttccaac ccttcctccc cgggacctat cagtgcgtct  26580
```

cgggaccctg ccatcacacc ttccacctga tcccgaatac cacagcgtcg ctccccgcta 26640
ctaacaacca aactaacctc caccaacgcc accgtcgcga cggccacaat acatgcccat 26700
attagactat gaggccgagc cacagcgacc catgctcccc gctattagtt acttcaatct 26760
aaccggcgga gatgactgac ccactggcca acaacaacgt caacgacctt ctcctggaca 26820
tggacggccg cgcctcggag cagcgactcg cccaacttcg cattcgccag cagcaggaga 26880
gagccgtcaa ggagctgcag gatgcggtgg ccatccacca gtgcaagaga ggcatcttct 26940
gcctggtgaa acaggccaag atctcctacg aggtcactcc aaacgaccat cgcctctcct 27000
acgagctcct gcagcagcgc cagaagttca cctgcctggt cggagtcaac cccatcgtca 27060
tcacccagca gtctggcgat accaaggggt gcatccactg ctcctgcgac tcccccgact 27120
gcgtccacac tctgatcaag accctctgcg gcctccgcga cctcctcccc atgaactaat 27180
cacccccctta tccagtgaaa taaagatcat attgatgatg attttacaga aataaaaaat 27240
aatcatttga tttgaaataa agatacaatc atattgatga tttgagttta acaaaaaaat 27300
aaagaatcac ttacttgaaa tctgatacca ggtctctgtc catgttttct gccaacacca 27360
cttcactccc ctcttcccag ctctggtact gcaggccccg gcgggctgca aacttcctcc 27420
acacgctgaa ggggatgtca aattcctcct gtccctcaat cttcatttta tcttctatca 27480
gatgtccaaa aagcgcgtcc gggtggatga tgacttcgac cccgtctacc cctacgatgc 27540
agacaacgca ccgaccgtgc ccttcatcaa cccccccttc gtctcttcag atggattcca 27600
agagaagccc ctgggggtgt tgtccctgcg actggccgac cccgtcacca ccaagaacgg 27660
ggaaatcacc ctcaagctgg gagagggggt ggacctcgat tcctcgggaa aactcatctc 27720
caacacggcc accaaggccg ccgcccctct cagtttttcc aacaacacca tttcccttaa 27780
catggatcac cccttttaca ctaaagatgg aaaattatcc ttacaagttt ctccaccatt 27840
aaatatactg agaacaagca ttctaaacac actagcttta ggttttggat caggtttagg 27900
actccgtggc tctgccttgg cagtacagtt agtctctcca cttacatttg atactgatgg 27960
aaacataaag cttaccttag acagaggttt gcatgttaca acaggagatg caattgaaag 28020
caacataagc tgggctaaag gtttaaaatt tgaagatgga gccatagcaa ccaacattgg 28080
aaatgggtta gagtttggaa gcagtagtac agaaacaggt gttgatgatg cttacccaat 28140
ccaagttaaa cttggatctg gccttagctt tgacagtaca ggagccataa tggctggtaa 28200
caaagaagac gataaactca ctttgtggac aacacctgat ccatcaccaa actgtcaaat 28260
actcgcagaa aatgatgcaa aactaacact ttgcttgact aaatgtggta gtcaaatact 28320
ggccactgtg tcagtcttag ttgtaggaag tggaaaccta aaccccatta ctggcaccgt 28380
aagcagtgct caggtgtttc tacgttttga tgcaaacggt gttcttttaa cagaacattc 28440
tacactaaaa aaatactggg ggtataggca gggagatagc atagatggca ctccatatac 28500
caatgctgta ggattcatgc ccaatttaaa agcttatcca aagtcacaaa gttctactac 28560
taaaaataat atagtagggc aagtatacat gaatggagat gtttcaaaac ctatgcttct 28620
cactataacc ctcaatggta ctgatgacag caacagtaca tattcaatgt cattttcata 28680
cacctggact aatggaagct atgttggagc aacatttggg gctaactctt ataccttctc 28740
atacatcgcc caagaatgaa cactgtatcc caccctgcat gccaaccctt cccaccccac 28800
tctgtggaac aaactctgaa acacaaaata aaataaagtt caagtgtttt attgattcaa 28860
cagttttaca ggattcgagc agttattttt cctccaccct cccaggacat ggaatacacc 28920

```
accctctccc cccgcacagc cttgaacatc tgaatgccat tggtgatgga catgcttttg  28980
gtctccacgt tccacacagt ttcagagcga gccagtctcg ggtcggtcag ggagatgaaa  29040
ccctccgggc actcccgcat ctgcacctca cagctcaaca gctgaggatt gtcctcggtg  29100
gtcgggatca cggttatctg gaagaagcag aagagcggcg gtgggaatca tagtccgcga  29160
acgggatcgg ccggtggtgt cgcatcaggc cccgcagcag tcgctgccgc cgccgctccg  29220
tcaagctgct gctcaggggg tccgggtcca gggactccct cagcatgatg cccacggccc  29280
tcagcatcag tcgtctggtg cggcgggcgc agcagcgcat gcggatctcg ctcaggtcgc  29340
tgcagtacgt gcaacacaga accaccaggt tgttcaacag tccatagttc aacacgctcc  29400
agccgaaact catcgcggga aggatgctac ccacgtggcc gtcgtaccag atcctcaggt  29460
aaatcaagtg gtgccccctc cagaacacgc tgcccacgta catgatctcc ttgggcatgt  29520
ggcggttcac cacctcccgg taccacatca ccctctggtt gaacatgcag ccccggatga  29580
tcctgcggaa ccacagggcc agcaccgccc cgcccgccat gcagcgaaga gaccccgggt  29640
cccggcaatg gcaatggagg acccaccgct cgtacccgtg gatcatctgg gagctgaaca  29700
agtctatgtt ggcacagcac aggcatatgc tcatgcatct cttcagcact ctcaactcct  29760
cgggggtcaa aaccatatcc cagggcacgg ggaactcttg caggacagcg aaccccgcag  29820
aacagggcaa tcctcgcaca gaacttacat tgtgcatgga cagggtatcg caatcaggca  29880
gcaccgggtg atcctccacc agagaagcgc gggtctcggt ctcctcacag cgtggtaagg  29940
gggccggccg atacgggtga tggcgggacg cggctgatcg tgttcgcgac cgtgtcatga  30000
tgcagttgct ttcggacatt ttcgtacttg ctgtagcaga acctggtccg ggcgctgcac  30060
accgatcgcc ggcggcggtc tcggcgcttg gaacgctcgg tgttgaaatt gtaaaacagc  30120
cactctctca gaccgtgcag cagatctagg gcctcaggag tgatgaagat cccatcatgc  30180
ctgatggctc tgatcacatc gaccaccgtg gaatgggcca gacccagcca gatgatgcaa  30240
ttttgttggg tttcggtgac ggcgggggag ggaagaacag gaagaaccat gattaacttt  30300
taatccaaac ggtctcggag tacttcaaaa tgaagatcgc ggagatggca cctctcgccc  30360
ccgctgtgtt ggtggaaaat aacagccagg tcaaaggtga tacggttctc gagatgttcc  30420
acggtggctt ccagcaaagc ctccacgcgc acatccagaa acaagacaat agcgaaagcg  30480
ggagggttct ctaattcctc aatcatcatg ttacactcct gcaccatccc cagataattt  30540
tcatttttcc agccttgaat gattcgaact agttcgtgag gtaaatccaa gccagccatg  30600
ataaagagct cgcgcagagc gccctccacc ggcattctta agcacaccct cataattcca  30660
agatattctg ctcctggttc acctgcagca gattgacaag cggaatatca aaatctctgc  30720
cgcgatccct gagctcctcc ctcagcaata actgtaagta ctctttcata tcctctccga  30780
aatttttagc cataggacca ccaggaataa gattagggca agccacagta cagataaacc  30840
gaagtcctcc ccagtgagca ttgccaaatg caagactgct ataagcatgc tggctagacc  30900
cggtgatatc ttccagataa ctggacagaa aatcgcccag gcaattttta agaaaatcaa  30960
caaaagaaaa atcctccagg tggacgttta gagcctcggg aacaacgatg aagtaaatgc  31020
aagcggtgcg ttccagcatg gttagttagc tgatctgtag aaaaaacaaa aatgaacatt  31080
aaaccatgct agcctggcga acaggtgggt aaatcgttct ctccagcacc aggcaggcca  31140
cggggtctcc ggcgcgaccc tcgtaaaaat tgtcgctatg attgaaaacc atcacagaga  31200
gacgttcccg gtggccggcg tgaatgattc gacaagatga atacaccccc ggaacattgg  31260
cgtccgcgag tgaaaaaaag cgcccgagga agcaataagg cactacaatg ctcagtctca  31320
```

agtccagcaa agcgatgcca tgcggatgaa gcacaaaatt ctcaggtgcg tacaaaatgt 31380
aattactccc ctcctgcaca ggcagcaaag cccccgatcc ctccaggtac acatacaaag 31440
cctcagcgtc catagcttac cgagcagcag cacacaacag gcgcaagagt cagagaaagg 31500
ctgagctcta acctgtccac ccgctctctg ctcaatatat agcccagatc tacactgacg 31560
taaaggccaa agtctaaaaa tacccgccaa ataatcacac acgcccagca cacgcccaga 31620
aaccggtgac acactcaaaa aaatacgcgc acttcctcaa acgcccaaaa ctgccgtcat 31680
ttccgggttc ccacgctacg tcatcaaaac acgactttca aattccgtcg accgttaaaa 31740
acgtcacccg ccccgcccct aacggtcgcc cgtctctcag ccaatcagcg ccccgcatcc 31800
ccaaattcaa acacctcatt tgcatattaa cgcgcacaaa aagtttgagg tatattattg 31860
atgatgg 31867

<210> SEQ ID NO 12
<211> LENGTH: 32788
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12
ccatcttcaa taatatacct caaacttttt gtgcgcgtta atatgcaaat gaggcgtttg 60
aatttgggga ggaagggcgg tgattggtcg agggatgagc gaccgttagg ggcggggcga 120
gtgacgtttt gatgacgtgg ttgcgaggag gagccagttt gcaagttctc gtgggaaaag 180
tgacgtcaaa cgaggtgtgg tttgaacacg gaaatactca attttcccgc gctctctgac 240
aggaaatgag gtgtttctgg gcggatgcaa gtgaaaacgg gccattttcg cgcgaaaact 300
gaatgaggaa gtgaaaatct gagtaatttc gcgtttatgg cagggaggag tatttgccga 360
gggccgagta gactttgacc gattacgtgg gggtttcgat taccgtgttt ttcacctaaa 420
tttccgcgta cggtgtcaaa gtccggtgtt tttacgtagg tgtcagctga tcgccagggt 480
atttaaacct gcgctctcca gtcaagaggc cactcttgag tgccagcgag aagagttttc 540
tcctccgcgc cgcgagtcag atctacactt tgaaagtagg gataacaggg taatgacatt 600
gattattgac tagttgttaa tagtaatcaa ttacggggtc attagttcat agcccatata 660
tggagttccg cgttacataa cttacggtaa atggcccgcc tggctgaccg cccaacgacc 720
cccgcccatt gacgtcaata atgacgtatg ttcccatagt aacgccaata gggactttcc 780
attgacgtca atgggtggag tatttacggt aaactgccca cttggcagta catcaagtgt 840
atcatatgcc aagtccgccc cctattgacg tcaatgacgg taaatggccc gcctggcatt 900
atgcccagta catgacctta cgggactttc ctacttggca gtacatctac gtattagtca 960
tcgctattac catggtgatg cggttttggc agtacaccaa tgggcgtgga tagcggtttg 1020
actcacgggg atttccaagt ctccacccca ttgacgtcaa tgggagtttg ttttggcacc 1080
aaaatcaacg ggactttcca aaatgtcgta ataaccccgc cccgttgacg caaatgggcg 1140
gtaggcgtgt acggtgggag gtctatataa gcagagctcg tttagtgaac cgtcagatcg 1200
cctggaacgc catccacgct gttttgacct ccatagaaga cagcgatcgc gccaccatgg 1260
ccgggatgtt ccaggcactg tccgaaggct gcacacccta tgatattaac cagatgctga 1320
atgtcctggg agaccaccag gtctctggcc tggagcagct ggagagcatc atcaacttcg 1380
agaagctgac cgagtggaca agctccaatg tgatgcctat cctgtcccca ctgaccaagg 1440

```
gcatcctggg cttcgtgttt accctgacag tgccttctga gcggggcctg tcttgcatca   1500
gcgaggcaga cgcaaccaca ccagagtccg ccaatctggg cgaggagatc ctgtctcagc   1560
tgtacctgtg gccccgggtg acatatcact ccccttctta cgcctatcac cagttcgagc   1620
ggagagccaa gtacaagaga cacttcccag gctttggcca gtctctgctg ttcggctacc   1680
ccgtgtacgt gttcggcgat tgcgtgcagg gcgactggga tgccatccgg tttagatact   1740
gcgcaccacc tggatatgca ctgctgaggt gtaacgacac caattattcc gccctgctgg   1800
cagtgggcgc cctggagggc cctcgcaatc aggattggct gggcgtgcca aggcagctgg   1860
tgacacgcat gcaggccatc cagaacgcag gcctgtgcac cctggtggca atgctggagg   1920
agacaatctt ctggctgcag gcctttctga tggccctgac cgacagcggc cccaagacaa   1980
acatcatcgt ggattcccag tacgtgatgg gcatctccaa gccttctttc caggagtttg   2040
tggactggga gaacgtgagc ccagagctga attccaccga tcagccattc tggcaggcag   2100
gaatcctggc aaggaacctg gtgcctatgg tggccacagt gcagggccag aatctgaagt   2160
accagggcca gagcctggtc atcagcgcct ccatcatcgt gtttaacctg ctggagctgg   2220
agggcgacta tcgggacgat ggcaacgtgt gggtgcacac cccactgagc cccagaacac   2280
tgaacgcctg ggtgaaggcc gtggaggaga agaagggcat cccagtgcac ctggagctgg   2340
cctccatgac caatatggag ctgatgtcta gcatcgtgca ccagcaggtg aggacatacg   2400
gacccgtgtt catgtgcctg ggaggcctgc tgaccatggt ggcaggagcc gtgtggctga   2460
cagtgcgggt gctggagctg ttcagagccg cccagctggc caacgatgtg gtgctgcaga   2520
tcatggagct gtgcggagca gcctttcgcc aggtgtgcca caccacagtg ccatggccca   2580
atgcctccct gacccccaag tggaacaatg agacaacaca gcctcagatc gccaactgta   2640
gcgtgtacga cttcttcgtg tggctgcact actatagcgt gagggatacc ctgtggcccc   2700
gcgtgacata ccacatgaat aagtacgcct atcacatgct ggagaggcgc gccaagtata   2760
agagaggccc tggcccaggc gcaaagtttg tggcagcatg gaccctgaag gccgccgccg   2820
gccccggccc cggccagtat atcaaggcta acagtaagtt cattggaatc acagagctgg   2880
gacccggacc tggataatga gtttaaactc ccatttaaat gtgagggtta atgcttcgag   2940
cagacatgat aagatacatt gatgagtttg gacaaaccac aactagaatg cagtgaaaaa   3000
aatgctttat ttgtgaaatt tgtgatgcta ttgctttatt tgtaaccatt ataagctgca   3060
ataaacaagt taacaacaac aattgcattc attttatgtt tcaggttcag ggggagatgt   3120
gggaggtttt ttaaagcaag taaaacctct acaaatgtgg taaaataact ataacggtcc   3180
taaggtagcg agtgagtagt gttctggggc gggggaggac ctgcatgagg gccagaataa   3240
ctgaaatctg tgcttttctg tgtgttgcag cagcatgagc ggaagcggct cctttgaggg   3300
aggggtattc agcccttatc tgacggggcg tctcccctcc tgggcgggag tgcgtcagaa   3360
tgtgatggga tccacggtgg acggccggcc cgtgcagccc gcgaactctt caaccctgac   3420
ctatgcaacc ctgagctctt cgtcgttgga cgcagctgcc gccgcagctg ctgcatctgc   3480
cgccagcgcc gtgcgcggaa tggccatggg cgccggctac tacggcactc tggtggccaa   3540
ctcgagttcc accaataatc ccgccagcct gaacgaggag aagctgttgc tgctgatggc   3600
ccagctcgag gccttgaccc agcgcctggg cgagctgacc cagcaggtgg ctcagctgca   3660
ggagcagacg cgggccgcgg ttgccacggt gaaatccaaa taaaaaatga atcaataaat   3720
aaacggagac ggttgttgat tttaacacag agtctgaatc tttatttgat tttcgcgcg    3780
```

-continued

```
cggtaggccc tggaccaccg gtctcgatca ttgagcaccc ggtggatctt ttccaggacc   3840
cggtagaggt gggcttggat gttgaggtac atgggcatga gcccgtcccg ggggtggagg   3900
tagctccatt gcagggcctc gtgctcgggg gtggtgttgt aaatcaccca gtcatagcag   3960
gggcgcaggg catggtgttg cacaatatct ttgaggagga gactgatggc cacgggcagc   4020
cctttggtgt aggtgtttac aaatctgttg agctgggagg gatgcatgcg gggggagatg   4080
aggtgcatct tggcctggat cttgagattg gcgatgttac cgcccagatc ccgcctgggg   4140
ttcatgttgt gcaggaccac cagcacggtg tatccggtgc acttggggaa tttatcatgc   4200
aacttggaag ggaaggcgtg aaagaatttg gcgacgcctt tgtgcccgcc caggttttcc   4260
atgcactcat ccatgatgat ggcgatgggc ccgtgggcgg cggcctgggc aaagacgttt   4320
cgggggtcgg acacatcata gttgtggtcc tgggtgaggt catcataggc cattttaatg   4380
aatttggggc ggagggtgcc ggactggggg acaaaggtac cctcgatccc gggggcgtag   4440
ttcccctcac agatctgcat ctcccaggct ttgagctcgg aggggggat catgtccacc   4500
tgcggggcga taaagaacac ggtttccggg gcgggggaga tgagctgggc cgaaagcaag   4560
ttccggagca gctgggactt gccgcagccg gtggggccgt agatgacccc gatgaccggc   4620
tgcaggtggt agttgaggga gagacagctg ccgtcctccc ggaggagggg ggccacctcg   4680
ttcatcatct cgcgcacgtg catgttctcg cgcaccagtt ccgccaggag gcgctctccc   4740
cccagggata ggagctcctg gagcgaggcg aagtttttca gcggcttgag tccgtcggcc   4800
atgggcattt tggagagggt ttgttgcaag agttccaggc ggtcccagag ctcggtgatg   4860
tgctctacgg catctcgatc cagcagacct cctcgtttcg cgggttggga cggctgcggg   4920
agtagggcac cagacgatgg gcgtccagcg cagccagggt ccggtccttc cagggtcgca   4980
gcgtccgcgt cagggtggtc tccgtcacgg tgaaggggtg cgcgccgggc tgggcgcttg   5040
cgagggtgcg cttcaggctc atccggctgg tcgaaaaccg ctcccgatcg gcgccctgcg   5100
cgtcggccag gtagcaattg accatgagtt cgtagttgag cgcctcggcc gcgtggcctt   5160
tggcgcggag cttacctttg gaagtctgcc cgcaggcggg acagaggagg gacttgaggg   5220
cgtagagctt gggggcgagg aagacggact cgggggcgta ggcgtccgcg ccgcagtggg   5280
cgcagacggt ctcgcactcc acgagccagg tgaggtcggg ctggtcgggg tcaaaaacca   5340
gtttcccgcc gttctttttg atgcgtttct tacctttggt ctccatgagc tcgtgtcccc   5400
gctgggtgac aaagaggctg tccgtgtccc cgtagaccga ctttatgggc cggtcctcga   5460
gcggtgtgcc gcggtcctcc tcgtagagga accccgccca ctccgagacg aaagcccggg   5520
tccaggccag cacgaaggag gccacgtggg acgggtagcg gtcgttgtcc accagcgggt   5580
ccacctttc cagggtatgc aaacacatgt ccccctcgtc cacatccagg aaggtgattg   5640
gcttgtaagt gtaggccacg tgaccggggg tcccggccgg gggggtataa aagggtgcgg   5700
gtccctgctc gtcctcactg tcttccggat cgctgtccag gagcgccagc tgttggggta   5760
ggtattccct ctcgaaggcg ggcatgacct cggcactcag gttgtcagtt tctagaaacg   5820
aggaggattt gatattgacg gtgccggcgg agatgccttt caagagcccc tcgtccatct   5880
ggtcagaaaa gacgatcttt ttgttgtcga gcttggtggc gaaggagccg tagagggcgt   5940
tggagaggag cttggcgatg gagcgcatgg tctggttttt ttccttgtcg gcgcgctcct   6000
tggcggcgat gttgagctgc acgtactcgc gcgccacgca cttccattcg gggaagacgg   6060
tggtcagctc gtcgggcacg attctgacct gccagccccg attatgcagg gtgatgaggt   6120
ccacactggt ggccacctcg ccgcgcaggg gctcattagt ccagcagagg cgtccgccct   6180
```

tgcgcgagca gaaggggggc aggggggtcca gcatgacctc gtcgggggggg tcggcatcga 6240
tggtgaagat gccgggcagg aggtcggggt caaagtagct gatggaagtg gccagatcgt 6300
ccagggcagc ttgccattcg cgcacggcca gcgcgctctc gtagggactg aggggcgtgc 6360
cccagggcat gggatgggta agcgcggagg cgtacatgcc gcagatgtcg tagacgtaga 6420
ggggctcctc gaggatgccg atgtaggtgg ggtagcagcg ccccccgcgg atgctggcgc 6480
gcacgtagtc atacagctcg tgcgaggggg cgaggagccc cgggcccagg ttggtgcgac 6540
tgggcttttc ggcgcggtag acgatctggc ggaaaatggc atgcgagttg gaggagatgg 6600
tgggcctttg gaagatgttg aagtgggcgt ggggcagtcc gaccgagtcg cggatgaagt 6660
gggcgtagga gtcttgcagc ttggcgacga gctcggcggt gactaggacg tccagagcgc 6720
agtagtcgag ggtctcctgg atgatgtcat acttgagctg tcccttttgt ttccacagct 6780
cgcggttgag aaggaactct tcgcggtcct tccagtactc ttcgaggggg aacccgtcct 6840
gatctgcacg gtaagagcct agcatgtaga actggttgac ggccttgtag gcgcagcagc 6900
ccttctccac ggggagggcg taggcctggg cggccttgcg cagggaggtg tgcgtgaggg 6960
cgaaagtgtc cctgaccatg accttgagga actggtgctt gaagtcgata tcgtcgcagc 7020
ccccctgctc ccagagctgg aagtccgtgc gcttcttgta ggcggggttg ggcaaagcga 7080
aagtaacatc gttgaagagg atcttgcccg cgcggggcat aaagttgcga gtgatgcgga 7140
aaggttgggg cacctcggcc cggttgttga tgacctgggc ggcgagcacg atctcgtcga 7200
agccgttgat gttgtggccc acgatgtaga gttccacgaa tcgcggacgg cccttgacgt 7260
ggggcagttt cttgagctcc tcgtaggtga gctcgtcggg gtcgctgagc ccgtgctgct 7320
cgagcgccca gtcggcgaga tgggggttgg cgcggaggaa ggaagtccag agatccacgg 7380
ccagggcggt ttgcagacgg tcccggtact gacggaactg ctgcccgacg gccatttttt 7440
cgggggtgac gcagtagaag gtgcgggggt ccccgtgcca gcgatcccat ttgagctgga 7500
gggcgagatc gagggcgagc tcgacgagcc ggtcgtcccc ggagagtttc atgaccagca 7560
tgaaggggac gagctgcttg ccgaaggacc ccatccaggt gtaggtttcc acatcgtagg 7620
tgaggaagag cctttcggtg cgaggatgcg agccgatggg gaagaactgg atctcctgcc 7680
accaattgga ggaatggctg ttgatgtgat ggaagtagaa atgccgacgg cgcgccgaac 7740
actcgtgctt gtgtttatac aagcggccac agtgctcgca acgctgcacg ggatgcacgt 7800
gctgcacgag ctgtacctga gttcctttga cgaggaattt cagtgggaag tggagtcgtg 7860
gcgcctgcat ctcgtgctgt actacgtcgt ggtggtcggc ctggccctct tctgcctcga 7920
tggtggtcat gctgacgagc ccgcgcggga ggcaggtcca gacctcggcg cgagcgggtc 7980
ggagagcgag gacgagggcg cgcaggccgg agctgtccag ggtcctgaga cgctgcggag 8040
tcaggtcagt gggcagcggc ggcgcgcggt tgacttgcag gagtttttcc agggcgcgcg 8100
ggaggtccag atggtacttg atctccaccg cgccattggt ggcgacgtcg atggcttgca 8160
gggtcccgtg cccctggggt gtgaccaccg tcccccgttt cttcttgggc ggctggggcg 8220
acgggggcgg tgcctcttcc atggttagaa gcggcggcga ggacgcgcgc cgggcggcag 8280
gggcggctcg gggcccggag gcaggggcgg caggggcacg tcggcgccgc gcgcgggtag 8340
gttctggtac tgcgcccgga gaagactggc gtgagcgacg acgcgacggt tgacgtcctg 8400
gatctgacgc ctctgggtga aggccacggg acccgtgagt ttgaacctga aagagagttc 8460
gacagaatca atctcggtat cgttgacggc ggcctgccgc aggatctctt gcacgtcgcc 8520

```
cgagttgtcc tggtaggcga tctcggtcat gaactgctcg atctcctcct cttgaaggtc   8580
tccgcggccg gcgcgctcca cggtggccgc gaggtcgttg gagatgcggc ccatgagctg   8640
cgagaaggcg ttcatgcccg cctcgttcca gacgcggctg tagaccacga cgccctcggg   8700
atcgcgggcg cgcatgacca cctgggcgag gttgagctcc acgtggcgcg tgaagaccgc   8760
gtagttgcag aggcgctggt agaggtagtt gagcgtggtg gcgatgtgct cggtgacgaa   8820
gaaatacatg atccagcggc ggagcggcat ctcgctgacg tcgcccagcg cctccaaacg   8880
ttccatggcc tcgtaaaagt ccacggcgaa gttgaaaaac tgggagttgc gcgccgagac   8940
ggtcaactcc tcctccagaa gacggatgag ctcggcgatg gtggcgcgca cctcgcgctc   9000
gaaggccccc gggagttcct ccacttcctc ttcttcctcc tccactaaca tctcttctac   9060
ttcctcctca ggcggcagtg gtggcggggg agggggcctg cgtcgccggc ggcgcacggg   9120
cagacggtcg atgaagcgct cgatggtctc gccgcgccgg cgtcgcatgg tctcggtgac   9180
ggcgcgcccg tcctcgcggg gccgcagcgt gaagacgccg ccgcgcatct ccaggtggcc   9240
gggggggtcc ccgttgggca gggagagggc gctgacgatg catcttatca attgccccgt   9300
agggactccg cgcaaggacc tgagcgtctc gagatccacg ggatctgaaa accgctgaac   9360
gaaggcttcg agccagtcgc agtcgcaagg taggctgagc acggtttctt ctggcgggtc   9420
atgttggttg ggagcggggc gggcgatgct gctggtgatg aagttgaaat aggcggttct   9480
gagacggcgg atggtggcga ggagcaccag gtctttgggc ccggcttgct ggatgcgcag   9540
acggtcggcc atgccccagg cgtggtcctg acacctggcc aggtccttgt agtagtcctg   9600
catgagccgc tccacgggca cctcctcctc gcccgcgcgg ccgtgcatgc gcgtgagccc   9660
gaagccgcgc tggggctgga cgagcgccag gtcggcgacg acgcgctcgg cgaggatggc   9720
ttgctggatc tgggtgaggg tggtctggaa gtcatcaaag tcgacgaagc ggtggtaggc   9780
tccggtgttg atggtgtagg agcagttggc catgacggac cagttgacgg tctggtggcc   9840
cggacgcacg agctcgtggt acttgaggcg cgagtaggcg cgcgtgtcga agatgtagtc   9900
gttgcaggtg cgcaccaggt actggtagcc gatgaggaag tgcggcggcg gctggcggta   9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
ggtctggccc gtgaggcgcg cgcagtcgtg gatgctctat acgggcaaaa acgaaagcgg  10200
tcagcggctc gactccgtgg cctggaggct aagcgaacgg gttgggctgc gcgtgtaccc  10260
cggttcgaat ctcgaatcag gctggagccg cagctaacgt ggtattggca ctcccgtctc  10320
gacccaagcc tgcaccaacc ctccaggata cggaggcggg tcgttttgca acttttttt   10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc ccctcttttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
```

```
cgcggcccgg ttccacgcgg ggcgggagct gcggcgcggc ctggaccgaa agagggtgct  10980
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac cccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag ggggagagct actttgacat gggcgcggac ctgcactggc agcccagccg  11700
ccgggccttg gaggcggcgg caggacccta cgtagaagag gtggacgatg aggtggacga  11760
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggccccccttc  12540
acggacagcg gcagcatcaa ccgcaactcg tacctgggct acctgattaa cctgtaccgc  12600
gaggccatcg gccaggcgca cgtggacgag cagacctacc aggagatcac ccacgtgagc  12660
cgcgccctgg gccaggacga cccgggcaac ctggaagcca ccctgaactt tttgctgacc  12720
aaccggtcgc agaagatccc gccccagtac gcgctcagca ccgaggagga gcgcatcctg  12780
cgttacgtgc agcagagcgt gggcctgttc ctgatgcagg agggggccac ccccagcgcc  12840
gcgctcgaca tgaccgcgcg caacatggag cccagcatgt acgccagcaa ccgcccgttc  12900
atcaataaac tgatggacta cttgcatcgg gcggccgcca tgaactctga ctatttcacc  12960
aacgccatcc tgaatcccca ctggctcccg ccgccggggt tctacacggg cgagtacgac  13020
atgcccgacc ccaatgacgg gttcctgtgg gacgatgtgg acagcagcgt gttctccccc  13080
cgaccgggtg ctaacgagcg ccccttgtgg aagaaggaag gcagcgaccg acgcccgtcc  13140
tcggcgctgt ccggccgcga gggtgctgcc gcggcggtgc ccgaggccgc cagtcctttc  13200
ccgagcttgc ccttctcgct gaacagtatc cgcagcagcg agctgggcag gatcacgcgc  13260
```

```
ccgcgcttgc tgggcgaaga ggagtacttg aatgactcgc tgttgagacc cgagcgggag  13320
aagaacttcc ccaataacgg gatagaaagc ctggtggaca agatgagccg ctggaagacg  13380
tatgcgcagg agcacaggga cgatccccgg gcgtcgcagg gggccacgag ccggggcagc  13440
gccgcccgta aacgccggtg gcacgacagg cagcggggac agatgtggga cgatgaggac  13500
tccgccgacg acagcagcgt gttggacttg ggtgggagtg gtaacccgtt cgctcacctg  13560
cgccccgta tcgggcgcat gatgtaagag aaaccgaaaa taaatgatac tcaccaaggc  13620
catggcgacc agcgtgcgtt cgtttcttct ctgttgttgt tgtatctagt atgatgaggc  13680
gtgcgtaccc ggagggtcct cctccctcgt acgagagcgt gatgcagcag gcgatggcgg  13740
cggcggcgat gcagcccccg ctggaggctc cttacgtgcc cccgcggtac ctggcgccta  13800
cggaggggcg gaacagcatt cgttactcgg agctggcacc cttgtacgat accacccggt  13860
tgtacctggt ggacaacaag tcggcggaca tcgcctcgct gaactaccag aacgaccaca  13920
gcaacttcct gaccaccgtg gtgcagaaca atgacttcac ccccacggag gccagcaccc  13980
agaccatcaa ctttgacgag cgctcgcggt ggggcggcca gctgaaaacc atcatgcaca  14040
ccaacatgcc caacgtgaac gagttcatgt acagcaacaa gttcaaggcg cgggtgatgg  14100
tctcccgcaa gacccccaat ggggtgacag tgacagagga ttatgatggt agtcaggatg  14160
agctgaagta tgaatgggtg gaatttgagc tgcccgaagg caacttctcg gtgaccatga  14220
ccatcgacct gatgaacaac gccatcatcg acaattactt ggcggtgggg cggcagaacg  14280
gggtgctgga gagcgacatc ggcgtgaagt tcgacactag gaacttcagg ctgggctggg  14340
accccgtgac cgagctggtc atgcccgggg tgtacaccaa cgaggctttc catcccgata  14400
ttgtcttgct gcccggctgc ggggtggact tcaccgagag ccgcctcagc aacctgctgg  14460
gcattcgcaa gaggcagccc ttccaggaag gcttccagat catgtacgag gatctggagg  14520
ggggcaacat ccccgcgctc ctggatgtcg acgcctatga gaaaagcaag gaggatgcag  14580
cagctgaagc aactgcagcc gtagctaccg cctctaccga ggtcaggggc gataattttg  14640
caagcgccgc agcagtggca gcggccgagg cggctgaaac cgaaagtaag atagtcattc  14700
agccggtgga gaaggatagc aagaacagga gctacaacgt actaccggac aagataaaca  14760
ccgcctaccg cagctggtac ctagcctaca actatggcga ccccgagaag ggcgtgcgct  14820
cctggacgct gctcaccacc tcggacgtca cctgcggcgt ggagcaagtc tactggtcgc  14880
tgcccgacat gatgcaagac ccggtcacct tccgctccac gcgtcaagtt agcaactacc  14940
cggtggtggg cgccgagctc ctgcccgtct actccaagag cttcttcaac gagcaggccg  15000
tctactcgca gcagctgcgc gccttcacct cgcttacgca cgtcttcaac cgcttccccg  15060
agaaccagat cctcgtccgc ccgcccgcgc ccaccattac caccgtcagt gaaaacgttc  15120
ctgctctcac agatcacggg accctgccgc tgcgcagcag tatccgggga gtccagcgcg  15180
tgaccgttac tgacgccaga cgccgcacct gcccctacgt ctacaaggcc ctgggcatag  15240
tcgcgccgcg cgtcctctcg agccgcacct tctaaatgtc cattctcatc tcgcccagta  15300
ataacaccgg ttggggcctg cgcgcgccca gcaagatgta cggaggcgct cgccaacgct  15360
ccacgcaaca ccccgtgcgc gtgcgcgggc acttccgcgc tccctggggc gccctcaagg  15420
gccgcgtgcg gtcgcgcacc accgtcgacg acgtgatcga ccaggtggtg gccgacgcgc  15480
gcaactacac ccccgccgcc gcgcccgtct ccaccgtgga cgccgtcatc gacagcgtgg  15540
tggccgacgc gcgccggtac gcccgcgcca agagccggcg gcggcgcatc gcccggcggc  15600
accggagcac ccccgccatg cgcgcggcgc gagccttgct gcgcagggcc aggcgcacgg  15660
```

gacgcagggc catgctcagg gcggccagac gcgcggcttc aggcgccagc gccggcagga 15720
cccggagacg cgcggccacg gcggcggcag cggccatcgc cagcatgtcc cgcccgcggc 15780
gagggaacgt gtactgggtg cgcgacgccg ccaccggtgt gcgcgtgccc gtgcgcaccc 15840
gcccccctcg cacttgaaga tgttcacttc gcgatgttga tgtgtcccag cggcgaggag 15900
gatgtccaag cgcaaattca aggaagagat gctccaggtc atcgcgcctg agatctacgg 15960
ccctgcggtg gtgaaggagg aaagaaagcc ccgcaaaatc aagcgggtca aaaaggacaa 16020
aaaggaagaa gaaagtgatg tggacggatt ggtggagttt gtgcgcgagt tcgccccccg 16080
gcggcgcgtg cagtggcgcg ggcggaaggt gcaaccggtg ctgagacccg gcaccaccgt 16140
ggtcttcacg cccggcgagc gctccggcac cgcttccaag cgctcctacg acgaggtgta 16200
cggggatgat gatattctgg agcaggcggc cgagcgcctg ggcgagtttg cttacggcaa 16260
gcgcagccgt tccgcaccga aggaagaggc ggtgtccatc ccgctggacc acggcaaccc 16320
cacgccgagc ctcaagcccg tgaccttgca gcaggtgctg ccgaccgcgg cgccgcgccg 16380
ggggttcaag cgcgagggcg aggatctgta ccccaccatg cagctgatgg tgcccaagcg 16440
ccagaagctg gaagacgtgc tggagaccat gaaggtggac ccggacgtgc agcccgaggt 16500
caaggtgcgg cccatcaagc aggtggcccc gggcctgggc gtgcagaccg tggacatcaa 16560
gattcccacg gagcccatgg aaacgcagac cgagcccatg atcaagccca gcaccagcac 16620
catggaggtg cagacggatc cctggatgcc atcggctcct agtcgaagac cccggcgcaa 16680
gtacggcgcg gccagcctgc tgatgcccaa ctacgcgctg catccttcca tcatccccac 16740
gccgggctac cgcggcacgc gcttctaccg cggtcatacc agcagccgcc gccgcaagac 16800
caccactcgc cgccgccgtc gccgcaccgc cgctgcaacc acccctgccg ccctggtgcg 16860
gagagtgtac cgccgcggcc gcgcacctct gaccctgccg cgcgcgcgct accacccgag 16920
catcgccatt taaactttcg cctgctttgc agatcaatgg ccctcacatg ccgccttcgc 16980
gttcccatta cgggctaccg aggaagaaaa ccgcgccgta gaaggctggc ggggaacggg 17040
atgcgtcgcc accaccaccg gcggcggcgc gccatcagca agcggttggg gggaggcttc 17100
ctgcccgcgc tgatccccat catcgccgcg gcgatcgggg cgatccccgg cattgcttcc 17160
gtggcggtgc aggcctctca gcgccactga gacacacttg gaaacatctt gtaataaacc 17220
aatggactct gacgctcctg gtcctgtgat gtgttttcgt agacagatgg aagacatcaa 17280
tttttcgtcc ctggctccgc gacacggcac gcggccgttc atgggcacct ggagcgacat 17340
cggcaccagc caactgaacg gggcgccttt caattggagc agtctctgga gcgggcttaa 17400
gaatttcggg tccacgctta aacctatggg cagcaaggcg tggaacagca ccacagggca 17460
ggcgctgagg gataagctga aagagcagaa cttccagcag aaggtggtcg atgggctcgc 17520
ctcgggcatc aacggggtgg tggacctggc caaccaggcc gtgcagcggc agatcaacag 17580
ccgcctggac ccggtgccgc ccgccggctc cgtggagatg ccgcaggtgg aggaggagct 17640
gcctcccctg gacaagcggg gcgagaagcg accccgcccc gatgcggagg agacgctgct 17700
gacgcacacg gacgagccgc ccccgtacga ggaggcggtg aaactgggtc tgcccaccac 17760
gcggcccatc gcgcccctgg ccaccggggt gctgaaaccc gaaaagcccg cgaccctgga 17820
cttgcctcct ccccagcctt cccgcccctc tacagtggct aagcccctgc cgccggtggc 17880
cgtggcccgc gcgcgacccg gggcaccgc ccgccctcat gcgaactggc agagcactct 17940
gaacagcatc gtgggtctgg gagtgcagag tgtgaagcgc cgccgctgct attaaaccta 18000

```
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
ttttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg acccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
```

-continued

```
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc acccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc cccgcacaag ctggcctgcg ccatcgtcaa  21060
cacggccggc cgcgagaccg gggcgagca ctggctggcc ttcgcctgga acccgcgctc  21120
gaacacctgc tacctcttcg accccttcgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc ccccagcggt tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc atacccttct cccaggccga  22680
gacgatgggc aggctcatag ggttcttcac catcatctta gcgctagcag ccgcggccag  22740
```

ggggtcgctc tcgtccaggg tctcaaagct ccgcttgccg tccttctcgg tgatccgcac 22800
cggggggtag ctgaagccca cggccgccag ctcctcctcg gcctgtcttt cgtcctcgct 22860
gtcctggctg acgtcctgca ggaccacatg cttggtcttg cggggtttct tcttgggcgg 22920
cagcggcggc ggagatgttg gagatggcga gggggagcgc gagttctcgc tcaccactac 22980
tatctcttcc tcttcttggt ccgaggccac gcggcggtag gtatgtctct tcgggggcag 23040
aggcggaggc gacgggctct cgccgccgcg acttggcgga tggctggcag agccccttcc 23100
gcgttcgggg gtgcgctccc ggcggcgctc tgactgactt cctccgcggc cggccattgt 23160
gttctcctag ggaggaacaa caagcatgga gactcagcca tcgccaacct cgccatctgc 23220
ccccaccgcc gacgagaagc agcagcagca gaatgaaagc ttaaccgccc cgccgcccag 23280
ccccgccacc tccgacgcgg ccgtcccaga catgcaagag atggaggaat ccatcgagat 23340
tgacctgggc tatgtgacgc ccgcggagca cgaggaggag ctggcagtgc gcttttcaca 23400
agaagagata caccaagaac agccagagca ggaagcagag aatgagcaga gtcaggctgg 23460
gctcgagcat gacggcgact acctccacct gagcgggggg gaggacgcgc tcatcaagca 23520
tctggcccgg caggccacca tcgtcaagga tgcgctgctc gaccgcaccg aggtgcccct 23580
cagcgtggag gagctcagcc gcgcctacga gttgaacctc ttctcgccgc gcgtgccccc 23640
caagcgccag cccaatggca cctgcgagcc caacccgcgc ctcaacttct acccggtctt 23700
cgcggtgccc gaggccctgg ccacctacca catctttttc aagaaccaaa agatccccgt 23760
ctcctgccgc gccaaccgca cccgcgccga cgcccttttc aacctgggtc ccggcgcccg 23820
cctacctgat atcgcctcct tggaagaggt tcccaagatc ttcgagggtc tgggcagcga 23880
cgagactcgg gccgcgaacg ctctgcaagg agaaggagga gagcatgagc accacagcgc 23940
cctggtcgag ttggaaggcg acaacgcgcg gctggcggtg ctcaaacgca cggtcgagct 24000
gacccatttc gcctacccgg ctctgaacct gccccccaaa gtcatgagcg cggtcatgga 24060
ccaggtgctc atcaagcgcg cgtcgcccat ctccgaggac gagggcatgc aagactccga 24120
ggagggcaag cccgtggtca gcgacgagca gctggcccgg tggctgggtc ctaatgctag 24180
tccccagagt ttggaagagc ggcgcaaact catgatggcc gtggtcctgg tgaccgtgga 24240
gctggagtgc ctgcgccgct tcttcgccga cgcggagacc ctgcgcaagg tcgaggagaa 24300
cctgcactac ctcttcaggc acgggttcgt gcgccaggcc tgcaagatct ccaacgtgga 24360
gctgaccaac ctggtctcct acatgggcat cttgcacgag aaccgcctgg ggcagaacgt 24420
gctgcacacc accctgcgcg gggaggcccg gcgcgactac atccgcgact gcgtctacct 24480
ctacctctgc cacacctggc agacgggcat gggcgtgtgg cagcagtgtc tggaggagca 24540
gaacctgaaa gagctctgca agctcctgca gaagaacctc aagggtctgt ggaccgggtt 24600
cgacgagcgc accaccgcct cggacctggc cgacctcatt ttccccgagc gcctcaggct 24660
gacgctgcgc aacggcctgc ccgactttat gagccaaagc atgttgcaaa actttcgctc 24720
tttcatcctc gaacgctccg gaatcctgcc cgccacctgc tccgcgctgc cctcggactt 24780
cgtgccgctg accttccgcg agtgccccccc gccgctgtgg agccactgct acctgctgcg 24840
cctggccaac tacctggcct accactcgga cgtgatcgag gacgtcagcg gcgagggcct 24900
gctcgagtgc cactgccgct gcaacctctg cacgccgcac cgctccctgg cctgcaaccc 24960
ccagctgctg agcgagaccc agatcatcgg caccttcgag ttgcaagggc ccagcgaagg 25020
cgagggttca gccgccaagg ggggtctgaa actcaccccg ggctgtggga cctcggccta 25080
cttgcgcaag ttcgtgcccg aggactacca tcccttcgag atcaggttct acgaggacca 25140

-continued

```
atcccatccg cccaaggccg agctgtcggc ctgcgtcatc acccaggggg cgatcctggc  25200
ccaattgcaa gccatccaga aatcccgcca agaattcttg ctgaaaaagg gccgcggggt  25260
ctacctcgac ccccagaccg gtgaggagct caaccccggc ttcccccagg atgccccgag  25320
gaaacaagaa gctgaaagtg gagctgccgc ccgtggagga tttggaggaa gactgggaga  25380
acagcagtca ggcagaggag gaggagatgg aggaagactg ggacagcact caggcagagg  25440
aggacagcct gcaagacagt ctggaggaag acgaggagga ggcagaggag gaggtggaag  25500
aagcagccgc cgccagaccg tcgtcctcgg cgggggagaa agcaagcagc acggatacca  25560
tctccgctcc gggtcggggt cccgctcgac cacacagtag atgggacgag accggacgat  25620
tcccgaaccc caccacccag accggtaaga aggagcggca gggatacaag tcctggcggg  25680
ggcacaaaaa cgccatcgtc tcctgcttgc aggcctgcgg gggcaacatc tccttcaccc  25740
ggcgctacct gctcttccac cgcggggtga actttccccg caacatcttg cattactacc  25800
gtcacctcca cagcccctac tacttccaag aagaggcagc agcagcagaa aaagaccagc  25860
agaaaaccag cagctagaaa atccacagcg gcggcagcag gtggactgag gatcgcggcg  25920
aacgagccgg cgcaaacccg ggagctgagg aaccggatct ttcccaccct ctatgccatc  25980
ttccagcaga gtcgggggca ggagcaggaa ctgaaagtca agaaccgttc tctgcgctcg  26040
ctcacccgca gttgtctgta tcacaagagc gaagaccaac ttcagcgcac tctcgaggac  26100
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
ccgctcgggt ggcatcggca ctctccagtt cgtggaggag ttcactccct cggtctactt  26820
caaccccttc tccggctccc ccggccacta cccggacgag ttcatcccga acttcgacgc  26880
catcagcgag tcggtggacg gctacgattg aatgtcccat ggtggcgcag ctgacctagc  26940
tcggcttcga cacctggacc actgccgccg cttccgctgc ttcgctcggg atctcgccga  27000
gtttgcctac tttgagctgc ccgaggagca ccctcagggc ccggcccacg gagtgcggat  27060
cgtcgtcgaa gggggcctcg actcccacct gcttcggatc ttcagccagc gtccgatcct  27120
ggtcgagcgc gagcaaggac agacccttct gactctgtac tgcatctgca accacccccgg  27180
cctgcatgaa agtctttgtt gtctgctgtg tactgagtat aataaaagct gagatcagcg  27240
actactccgg acttccgtgt gttcctgaat ccatcaacca gtctttgttc ttcaccggga  27300
acgagaccga gctccagctc cagtgtaagc cccacaagaa gtacctcacc tggctgttcc  27360
agggctcccc gatcgccgtt gtcaaccact gcgacaacga cggagtcctg ctgagcggcc  27420
ctgccaacct tactttttcc acccgcagaa gcaagctcca gctcttccaa cccttcctcc  27480
```

-continued

```
ccgggaccta tcagtgcgtc tcgggaccct gccatcacac cttccacctg atcccgaata  27540
ccacagcgtc gctccccgct actaacaacc aaactaacct ccaccaacgc caccgtcgcg  27600
acggccacaa tacatgccca tattagacta tgaggccgag ccacagcgac ccatgctccc  27660
cgctattagt tacttcaatc taaccggcgg agatgactga cccactggcc aacaacaacg  27720
tcaacgacct tctcctggac atggacggcc gcgcctcgga gcagcgactc gcccaacttc  27780
gcattcgcca gcagcaggag agagccgtca aggagctgca ggatgcggtg gccatccacc  27840
agtgcaagag aggcatcttc tgcctggtga aacaggccaa gatctcctac gaggtcactc  27900
caaacgacca tcgcctctcc tacgagctcc tgcagcagcg ccagaagttc acctgcctgg  27960
tcggagtcaa ccccatcgtc atcacccagc agtctggcga taccaagggg tgcatccact  28020
gctcctgcga ctcccccgac tgcgtccaca ctctgatcaa gaccctctgc ggcctccgcg  28080
acctcctccc catgaactaa tcaccccctt atccagtgaa ataaagatca tattgatgat  28140
gattttacag aaataaaaaa taatcatttg atttgaaata aagatacaat catattgatg  28200
atttgagttt aacaaaaaaa taaagaatca cttacttgaa atctgatacc aggtctctgt  28260
ccatgttttc tgccaacacc acttcactcc cctcttccca gctctggtac tgcaggcccc  28320
ggcgggctgc aaacttcctc cacacgctga aggggatgtc aaattcctcc tgtccctcaa  28380
tcttcatttt atcttctatc agatgtccaa aaagcgcgtc cgggtggatg atgacttcga  28440
ccccgtctac ccctacgatg cagacaacgc accgaccgtg cccttcatca accccccctt  28500
cgtctcttca gatggattcc aagagaagcc cctgggggtg ttgtccctgc gactggccga  28560
ccccgtcacc accaagaacg gggaaatcac cctcaagctg ggagaggggg tggacctcga  28620
ttcctcggga aaactcatct ccaacacggc caccaaggcc gccgcccctc tcagtttttc  28680
caacaacacc atttccctta acatggatca ccccttttac actaaagatg gaaaattatc  28740
cttacaagtt tctccaccat taaatatact gagaacaagc attctaaaca cactagcttt  28800
aggttttgga tcaggtttag gactccgtgg ctctgccttg gcagtacagt tagtctctcc  28860
acttacattt gatactgatg gaaacataaa gcttacctta gacagaggtt tgcatgttac  28920
aacaggagat gcaattgaaa gcaacataag ctgggctaaa ggtttaaaat ttgaagatgg  28980
agccatagca accaacattg gaaatgggtt agagtttgga agcagtagta cagaaacagg  29040
tgttgatgat gcttacccaa tccaagttaa acttggatct ggccttagct ttgacagtac  29100
aggagccata atggctggta acaaagaaga cgataaactc actttgtgga caacacctga  29160
tccatcacca aactgtcaaa tactcgcaga aaatgatgca aaactaacac tttgcttgac  29220
taaatgtggt agtcaaatac tggccactgt gtcagtctta gttgtaggaa gtggaaacct  29280
aaaccccatt actggcaccg taagcagtgc tcaggtgttt ctacgttttg atgcaaacgg  29340
tgttctttta acagaacatt ctacactaaa aaaatactgg gggtataggc agggagatag  29400
catagatggc actccatata ccaatgctgt aggattcatg cccaatttaa aagcttatcc  29460
aaagtcacaa agttctacta ctaaaaataa tatagtaggg caagtataca tgaatggaga  29520
tgtttcaaaa cctatgcttc tcactataac cctcaatggt actgatgaca gcaacagtac  29580
atattcaatg tcattttcat acacctggac taatggaagc tatgttggag caacatttgg  29640
ggctaactct tataccttct catacatcgc ccaagaatga acactgtatc ccaccctgca  29700
tgccaaccct tcccacccca ctctgtggaa caaactctga aacacaaaat aaaataaagt  29760
tcaagtgttt tattgattca acagttttac aggattcgag cagttatttt tcctccaccc  29820
tcccaggaca tggaatacac caccctctcc ccccgcacag ccttgaacat ctgaatgcca  29880
```

ttggtgatgg acatgctttt ggtctccacg ttccacacag tttcagagcg agccagtctc 29940
gggtcggtca gggagatgaa accctccggg cactcccgca tctgcacctc acagctcaac 30000
agctgaggat tgtcctcggt ggtcgggatc acggttatct ggaagaagca gaagagcggc 30060
ggtgggaatc atagtccgcg aacgggatcg gccggtggtg tcgcatcagg ccccgcagca 30120
gtcgctgccg ccgccgctcc gtcaagctgc tgctcagggg gtccgggtcc agggactccc 30180
tcagcatgat gcccacggcc ctcagcatca gtcgtctggt gcggcgggcg cagcagcgca 30240
tgcggatctc gctcaggtcg ctgcagtacg tgcaacacag aaccaccagg ttgttcaaca 30300
gtccatagtt caacacgctc cagccgaaac tcatcgcggg aaggatgcta cccacgtggc 30360
cgtcgtacca gatcctcagg taaatcaagt ggtgcccccct ccagaacacg ctgcccacgt 30420
acatgatctc cttgggcatg tggcggttca ccacctcccg gtaccacatc accctctggt 30480
tgaacatgca gccccggatg atcctgcgga accacagggc cagcaccgcc ccgcccgcca 30540
tgcagcgaag agaccccggg tcccggcaat ggcaatggag gacccaccgc tcgtacccgt 30600
ggatcatctg ggagctgaac aagtctatgt tggcacagca caggcatatg ctcatgcatc 30660
tcttcagcac tctcaactcc tcgggggtca aaaccatatc ccagggcacg gggaactctt 30720
gcaggacagc gaaccccgca gaacagggca atcctcgcac agaacttaca ttgtgcatgg 30780
acagggtatc gcaatcaggc agcaccgggt gatcctccac cagagaagcg cgggtctcgg 30840
tctcctcaca gcgtggtaag ggggccggcc gatacgggtg atggcgggac gcggctgatc 30900
gtgttcgcga ccgtgtcatg atgcagttgc tttcggacat tttcgtactt gctgtagcag 30960
aacctggtcc gggcgctgca caccgatcgc cggcggcggt ctcggcgctt ggaacgctcg 31020
gtgttgaaat tgtaaaacag ccactctctc agaccgtgca gcagatctag ggcctcagga 31080
gtgatgaaga tcccatcatg cctgatggct ctgatcacat cgaccaccgt ggaatgggcc 31140
agacccagcc agatgatgca attttgttgg gtttcggtga cggcggggga gggaagaaca 31200
ggaagaacca tgattaactt ttaatccaaa cggtctcgga gtacttcaaa atgaagatcg 31260
cggagatggc acctctcgcc cccgctgtgt tggtggaaaa taacagccag gtcaaaggtg 31320
atacggttct cgagatgttc cacggtggct tccagcaaag cctccacgcg cacatccaga 31380
aacaagacaa tagcgaaagc gggagggttc tctaattcct caatcatcat gttacactcc 31440
tgcaccatcc ccagataatt ttcatttttc cagccttgaa tgattcgaac tagttcgtga 31500
ggtaaatcca agccagccat gataaagagc tcgcgcagag cgccctccac cggcattctt 31560
aagcacaccc tcataattcc aagatattct gctcctggtt cacctgcagc agattgacaa 31620
gcggaatatc aaaatctctg ccgcgatccc tgagctcctc cctcagcaat aactgtaagt 31680
actctttcat atcctctccg aaatttttag ccataggacc accaggaata agattagggc 31740
aagccacagt acagataaac cgaagtcctc cccagtgagc attgccaaat gcaagactgc 31800
tataagcatg ctggctagac ccggtgatat cttccagata actggacaga aaatcgccca 31860
ggcaattttt aagaaaatca acaaaagaaa aatcctccag gtggacgttt agagcctcgg 31920
gaacaacgat gaagtaaatg caagcggtgc gttccagcat ggttagttag ctgatctgta 31980
gaaaaaacaa aaatgaacat taaaccatgc tagcctggcg aacaggtggg taaatcgttc 32040
tctccagcac caggcaggcc acggggtctc cggcgcgacc ctcgtaaaaa ttgtcgctat 32100
gattgaaaac catcacagag agacgttccc ggtggccggc gtgaatgatt cgacaagatg 32160
aatacacccc cggaacattg gcgtccgcga gtgaaaaaaa gcgcccgagg aagcaataag 32220

```
gcactacaat gctcagtctc aagtccagca aagcgatgcc atgcggatga agcacaaaat  32280

tctcaggtgc gtacaaaatg taattactcc cctcctgcac aggcagcaaa gcccccgatc  32340

cctccaggta cacatacaaa gcctcagcgt ccatagctta ccgagcagca gcacacaaca  32400

ggcgcaagag tcagagaaag gctgagctct aacctgtcca cccgctctct gctcaatata  32460

tagcccagat ctacactgac gtaaaggcca aagtctaaaa atacccgcca aataatcaca  32520

cacgcccagc acacgcccag aaaccggtga cacactcaaa aaaatacgcg cacttcctca  32580

aacgcccaaa actgccgtca tttccgggtt cccacgctac gtcatcaaaa cacgactttc  32640

aaattccgtc gaccgttaaa aacgtcaccc gccccgcccc taacggtcgc ccgtctctca  32700

gccaatcagc gccccgcatc cccaaattca aacacctcat ttgcatatta acgcgcacaa  32760

aaagtttgag gtatattatt gatgatgg                                     32788
```

```
<210> SEQ ID NO 13
<211> LENGTH: 30684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

ccatcttcaa taatatacct caaacttttt gtgcgcgtta atatgcaaat gaggcgtttg     60

aatttgggga ggaagggcgg tgattggtcg agggatgagc gaccgttagg ggcggggcga    120

gtgacgtttt gatgacgtgg ttgcgaggag gagccagttt gcaagttctc gtgggaaaag    180

tgacgtcaaa cgaggtgtgg tttgaacacg gaaatactca attttcccgc gctctctgac    240

aggaaatgag gtgtttctgg gcggatgcaa gtgaaaacgg gccattttcg cgcgaaaact    300

gaatgaggaa gtgaaaatct gagtaatttc gcgtttatgg cagggaggag tatttgccga    360

gggccgagta gactttgacc gattacgtgg gggtttcgat taccgtgttt ttcacctaaa    420

tttccgcgta cggtgtcaaa gtccggtgtt tttacgtagg tgtcagctga tcgccagggt    480

atttaaacct gcgctctcca gtcaagaggc cactcttgag tgccagcgag aagagttttc    540

tcctccgcgc cgcgagtcag atctacactt tgaaagtagg gataacaggg taatgacatt    600

gattattgac tagttgttaa tagtaatcaa ttacggggtc attagttcat agcccatata    660

tggagttccg cgttacataa cttacggtaa atggcccgcc tggctgaccg cccaacgacc    720

cccgcccatt gacgtcaata atgacgtatg ttcccatagt aacgccaata gggactttcc    780

attgacgtca atgggtggag tatttacggt aaactgccca cttggcagta catcaagtgt    840

atcatatgcc aagtccgccc cctattgacg tcaatgacgg taaatggccc gcctggcatt    900

atgcccagta catgacctta cgggactttc ctacttggca gtacatctac gtattagtca    960

tcgctattac catggtgatg cggttttggc agtacaccaa tgggcgtgga tagcggtttg   1020

actcacgggg atttccaagt ctccacccca ttgacgtcaa tgggagtttg ttttggcacc   1080

aaaatcaacg ggactttcca aaatgtcgta ataaccccgc cccgttgacg caaatgggcg   1140

gtaggcgtgt acggtgggag gtctatataa gcagagctcg tttagtgaac cgtcagatcg   1200

cctggaacgc catccacgct gttttgacct ccatagaaga cagcgatcgc gccaccatgg   1260

tgagcaaggg cgaggagctg ttcaccgggg tggtgcccat cctggtcgag ctggacggcg   1320

acgtaaacgg ccacaagttc agcgtgtccg gcgagggcga gggcgatgcc acctacggca   1380

agctgaccct gaagttcatc tgcaccaccg gcaagctgcc cgtgccctgg cccaccctcg   1440
```

tgaccaccct gacctacggc gtgcagtgct tcagccgcta ccccgaccac atgaagcagc 1500
acgacttctt caagtccgcc atgcccgaag gctacgtcca ggagcgcacc atcttcttca 1560
aggacgacgg caactacaag acccgcgccg aggtgaagtt cgagggcgac accctggtga 1620
accgcatcga gctgaagggc atcgacttca aggaggacgg caacatcctg gggcacaagc 1680
tggagtacaa ctacaacagc cacaacgtct atatcatggc cgacaagcag aagaacggca 1740
tcaaggtgaa cttcaagatc cgccacaaca tcgaggacgg cagcgtgcag ctcgccgacc 1800
actaccagca gaacaccccc atcggcgacg gccccgtgct gctgcccgac aaccactacc 1860
tgagcaccca gtccgccctg agcaaagacc ccaacgagaa gcgcgatcac atggtcctgc 1920
tggagttcgt gaccgccgcc gggatcactc tcggcatgga cgagctttac aagtagtgag 1980
tttaaactcc catttaaatg tgagggttaa tgcttcgagc agacatgata agatacattg 2040
atgagtttgg acaaaccaca actagaatgc agtgaaaaaa atgctttatt tgtgaaattt 2100
gtgatgctat tgctttattt gtaaccatta taagctgcaa taaacaagtt aacaacaaca 2160
attgcattca ttttatgttt caggttcagg gggagatgtg ggaggttttt taaagcaagt 2220
aaaacctcta caaatgtggt aaaataacta taacggtcct aaggtagcga gtgagtagtg 2280
ttctggggcg gggaggacc tgcatgaggg ccagaataac tgaaatctgt gcttttctgt 2340
gtgttgcagc agcatgagcg gaagcggctc ctttgaggga ggggtattca gcccttatct 2400
gacggggcgt ctcccctcct gggcgggagt gcgtcagaat gtgatgggat ccacggtgga 2460
cggccggccc gtgcagcccg cgaactcttc aaccctgacc tatgcaaccc tgagctcttc 2520
gtcgttggac gcagctgccg ccgcagctgc tgcatctgcc gccagcgccg tgcgcggaat 2580
ggccatgggc gccggctact acggcactct ggtggccaac tcgagttcca ccaataatcc 2640
cgccagcctg aacgaggaga agctgttgct gctgatggcc cagctcgagg ccttgaccca 2700
gcgcctgggc gagctgaccc agcaggtggc tcagctgcag gagcagacgc gggccgcggt 2760
tgccacggtg aaatccaaat aaaaaatgaa tcaataaata aacggagacg gttgttgatt 2820
ttaacacaga gtctgaatct ttatttgatt tttcgcgcgc ggtaggccct ggaccaccgg 2880
tctcgatcat tgagcacccg gtggatcttt tccaggaccc ggtagaggtg ggcttggatg 2940
ttgaggtaca tgggcatgag cccgtcccgg gggtggaggt agctccattg cagggcctcg 3000
tgctcggggg tggtgttgta aatcacccag tcatagcagg ggcgcagggc atggtgttgc 3060
acaatatctt tgaggaggag actgatggcc acgggcagcc ctttggtgta ggtgtttaca 3120
aatctgttga gctgggaggg atgcatgcgg ggggagatga ggtgcatctt ggcctggatc 3180
ttgagattgg cgatgttacc gcccagatcc cgcctggggt tcatgttgtg caggaccacc 3240
agcacggtgt atccggtgca cttggggaat ttatcatgca acttggaagg gaaggcgtga 3300
aagaatttgg cgacgccttt gtgcccgccc aggttttcca tgcactcatc catgatgatg 3360
gcgatgggcc cgtgggcggc ggcctgggca aagacgtttc gggggtcgga cacatcatag 3420
ttgtggtcct gggtgaggtc atcataggcc attttaatga atttggggcg gagggtgccg 3480
gactggggga caaaggtacc ctcgatcccg gggggcgtagt tcccctcaca gatctgcatc 3540
tcccaggctt tgagctcgga ggggggggatc atgtccacct gcggggcgat aaagaacacg 3600
gtttccgggg cgggggagat gagctgggcc gaaagcaagt tccggagcag ctgggacttg 3660
ccgcagccgg tggggccgta gatgaccccg atgaccggct gcaggtggta gttgagggag 3720
agacagctgc cgtcctcccg gaggaggggg gccacctcgt tcatcatctc gcgcacgtgc 3780
atgttctcgc gcaccagttc cgccaggagg cgctctcccc ccagggatag gagctcctgg 3840

-continued agcgaggcga agtttttcag cggcttgagt ccgtcggcca tgggcatttt ggagagggtt 3900
tgttgcaaga gttccaggcg gtcccagagc tcggtgatgt gctctacggc atctcgatcc 3960
agcagacctc ctcgtttcgc gggttgggac ggctgcggga gtagggcacc agacgatggg 4020
cgtccagcgc agccagggtc cggtccttcc agggtcgcag cgtccgcgtc agggtggtct 4080
ccgtcacggt gaaggggtgc gcgccgggct gggcgcttgc gagggtgcgc ttcaggctca 4140
tccggctggt cgaaaaccgc tcccgatcgg cgccctgcgc gtcggccagg tagcaattga 4200
ccatgagttc gtagttgagc gcctcggccg cgtggccttt ggcgcggagc ttacctttgg 4260
aagtctgccc gcaggcggga cagaggaggg acttgagggc gtagagcttg ggggcgagga 4320
agacggactc gggggcgtag gcgtccgcgc cgcagtgggc gcagacggtc tcgcactcca 4380
cgagccaggt gaggtcgggc tggtcggggt caaaaaccag tttcccgccg ttctttttga 4440
tgcgtttctt acctttggtc tccatgagct cgtgtccccg ctgggtgaca aagaggctgt 4500
ccgtgtcccc gtagaccgac tttatgggcc ggtcctcgag cggtgtgccg cggtcctcct 4560
cgtagaggaa ccccgcccac tccgagacga aagcccgggt ccaggccagc acgaaggagg 4620
ccacgtggga cgggtagcgg tcgttgtcca ccagcgggtc caccttttcc agggtatgca 4680
aacacatgtc cccctcgtcc acatccagga aggtgattgg cttgtaagtg taggccacgt 4740
gaccgggggt cccggccggg ggggtataaa agggtgcggg tccctgctcg tcctcactgt 4800
cttccggatc gctgtccagg agcgccagct gttggggtag gtattccctc tcgaaggcgg 4860
gcatgacctc ggcactcagg ttgtcagttt ctagaaacga ggaggatttg atattgacgg 4920
tgccggcgga gatgcctttc aagagcccct cgtccatctg gtcagaaaag acgatctttt 4980
tgttgtcgag cttggtggcg aaggagccgt agagggcgtt ggagaggagc ttggcgatgg 5040
agcgcatggt ctggtttttt tccttgtcgg cgcgctcctt ggcggcgatg ttgagctgca 5100
cgtactcgcg cgccacgcac ttccattcgg ggaagacggt ggtcagctcg tcgggcacga 5160
ttctgacctg ccagccccga ttatgcaggg tgatgaggtc cacactggtg gccacctcgc 5220
cgcgcagggg ctcattagtc cagcagaggc gtccgccctt gcgcgagcag aaggggggca 5280
gggggtccag catgacctcg tcgggggggt cggcatcgat ggtgaagatg ccgggcagga 5340
ggtcggggtc aaagtagctg atggaagtgg ccagatcgtc cagggcagct tgccattcgc 5400
gcacggccag cgcgcgctcg tagggactga ggggcgtgcc ccagggcatg ggatgggtaa 5460
gcgcggaggc gtacatgccg cagatgtcgt agacgtagag gggctcctcg aggatgccga 5520
tgtaggtggg gtagcagcgc cccccgcgga tgctggcgcg cacgtagtca tacagctcgt 5580
gcgagggggc gaggagcccc gggcccaggt tggtgcgact gggcttttcg gcgcggtaga 5640
cgatctggcg gaaaatggca tgcgagttgg aggagatggt gggcctttgg aagatgttga 5700
agtgggcgtg gggcagtccg accgagtcgc ggatgaagtg ggcgtaggag tcttgcagct 5760
tggcgacgag ctcggcggtg actaggacgt ccagagcgca gtagtcgagg gtctcctgga 5820
tgatgtcata cttgagctgt ccctttttgtt tccacagctc gcggttgaga aggaactctt 5880
cgcggtcctt ccagtactct tcgagggggga acccgtcctg atctgcacgg taagagccta 5940
gcatgtagaa ctggttgacg gccttgtagg cgcagcagcc cttctccacg gggagggcgt 6000
aggcctgggc ggccttgcgc agggaggtgt gcgtgagggc gaaagtgtcc ctgaccatga 6060
ccttgaggaa ctggtgcttg aagtcgatat cgtcgcagcc cccctgctcc cagagctgga 6120
agtccgtgcg cttcttgtag gcggggttgg gcaaagcgaa agtaacatcg ttgaagagga 6180

-continued

```
tcttgcccgc gcggggcata aagttgcgag tgatgcggaa aggttggggc acctcggccc   6240
ggttgttgat gacctgggcg gcgagcacga tctcgtcgaa gccgttgatg ttgtggccca   6300
cgatgtagag ttccacgaat cgcggacggc ccttgacgtg gggcagtttc ttgagctcct   6360
cgtaggtgag ctcgtcgggg tcgctgagcc cgtgctgctc gagcgcccag tcggcgagat   6420
gggggttggc gcggaggaag gaagtccaga gatccacggc cagggcggtt tgcagacggt   6480
cccggtactg acggaactgc tgcccgacgg ccatttttc ggggggtgacg cagtagaagg   6540
tgcgggggtc cccgtgccag cgatcccatt tgagctggag ggcgagatcg agggcgagct   6600
cgacgagccg gtcgtccccg gagagtttca tgaccagcat gaaggggacg agctgcttgc   6660
cgaaggaccc catccaggtg taggtttcca catcgtaggt gaggaagagc ctttcggtgc   6720
gaggatgcga gccgatgggg aagaactgga tctcctgcca ccaattggag gaatggctgt   6780
tgatgtgatg gaagtagaaa tgccgacggc gcgccgaaca ctcgtgcttg tgtttataca   6840
agcggccaca gtgctcgcaa cgctgcacgg gatgcacgtg ctgcacgagc tgtacctgag   6900
ttcctttgac gaggaatttc agtgggaagt ggagtcgtgg cgcctgcatc tcgtgctgta   6960
ctacgtcgtg gtggtcggcc tggccctctt ctgcctcgat ggtggtcatg ctgacgagcc   7020
cgcgcgggag gcaggtccag acctcggcgc gagcgggtcg gagagcgagg acgagggcgc   7080
gcaggccgga gctgtccagg gtcctgagac gctgcggagt caggtcagtg ggcagcggcg   7140
gcgcgcggtt gacttgcagg agtttttcca gggcgcgcgg gaggtccaga tggtacttga   7200
tctccaccgc gccattggtg gcgacgtcga tggcttgcag ggtcccgtgc ccctggggtg   7260
tgaccaccgt cccccgtttc ttcttgggcg gctggggcga cgggggcggt gcctcttcca   7320
tggttagaag cggcggcgag gacgcgcgcc gggcggcagg ggcggctcgg ggcccggagg   7380
caggggcggc aggggcacgt cggcgccgcg cgcgggtagg ttctggtact gcgcccggag   7440
aagactggcg tgagcgacga cgcgacggtt gacgtcctgg atctgacgcc tctgggtgaa   7500
ggccacggga cccgtgagtt tgaacctgaa agagagttcg acagaatcaa tctcggtatc   7560
gttgacggcg gcctgccgca ggatctcttg cacgtcgccc gagttgtcct ggtaggcgat   7620
ctcggtcatg aactgctcga tctcctcctc ttgaaggtct ccgcggccgg cgcgctccac   7680
ggtggccgcg aggtcgttgg agatgcggcc catgagctgc gagaaggcgt tcatgcccgc   7740
ctcgttccag acgcggctgt agaccacgac gccctcggga tcgcgggcgc gcatgaccac   7800
ctgggcgagg ttgagctcca cgtggcgcgt gaagaccgcg tagttgcaga ggcgctggta   7860
gaggtagttg agcgtggtgg cgatgtgctc ggtgacgaag aaatacatga tccagcggcg   7920
gagcggcatc tcgctgacgt cgcccagcgc ctccaaacgt tccatggcct cgtaaaagtc   7980
cacggcgaag ttgaaaaact gggagttgcg cgccgagacg gtcaactcct cctccagaag   8040
acggatgagc tcggcgatgg tggcgcgcac ctcgcgctcg aaggcccccg ggagttcctc   8100
cacttcctct tcttcctcct ccactaacat ctcttctact tcctcctcag gcggcagtgg   8160
tggcggggga gggggcctgc gtcgccggcg gcgcacgggc agacggtcga tgaagcgctc   8220
gatggtctcg ccgcgccggc gtcgcatggt ctcggtgacg gcgcgcccgt cctcgcgggg   8280
ccgcagcgtg aagacgccgc cgcgcatctc caggtggccg ggggggtccc cgttgggcag   8340
ggagagggcg ctgacgatgc atcttatcaa ttgccccgta gggactccgc gcaaggacct   8400
gagcgtctcg agatccacgg gatctgaaaa ccgctgaacg aaggcttcga gccagtcgca   8460
gtcgcaaggt aggctgagca cggtttcttc tggcgggtca tgttggttgg gagcggggcg   8520
ggcgatgctg ctggtgatga agttgaaata ggcggttctg agacggcgga tggtggcgag   8580
```

gagcaccagg tctttgggcc cggcttgctg gatgcgcaga cggtcggcca tgccccaggc 8640
gtggtcctga cacctggcca ggtccttgta gtagtcctgc atgagccgct ccacgggcac 8700
ctcctcctcg cccgcgcggc cgtgcatgcg cgtgagcccg aagccgcgct ggggctggac 8760
gagcgccagg tcggcgacga cgcgctcggc gaggatggct tgctggatct gggtgagggt 8820
ggtctggaag tcatcaaagt cgacgaagcg gtggtaggct ccggtgttga tggtgtagga 8880
gcagttggcc atgacggacc agttgacggt ctggtggccc ggacgcacga gctcgtggta 8940
cttgaggcgc gagtaggcgc gcgtgtcgaa gatgtagtcg ttgcaggtgc gcaccaggta 9000
ctggtagccg atgaggaagt gcggcggcgg ctggcggtag agcggccatc gctcggtggc 9060
gggggcgccg ggcgcgaggt cctcgagcat ggtgcggtgg tagccgtaga tgtacctgga 9120
catccaggtg atgccggcgg cggtggtgga ggcgcgcggg aactcgcgga cgcggttcca 9180
gatgttgcgc agcggcagga agtagttcat ggtgggcacg gtctggcccg tgaggcgcgc 9240
gcagtcgtgg atgctctata cgggcaaaaa cgaaagcggt cagcggctcg actccgtggc 9300
ctggaggcta agcgaacggg ttgggctgcg cgtgtacccc ggttcgaatc tcgaatcagg 9360
ctggagccgc agctaacgtg gtattggcac tcccgtctcg acccaagcct gcaccaaccc 9420
tccaggatac ggaggcgggt cgttttgcaa cttttttttg gaggccggat gagactagta 9480
agcgcggaaa gcggccgacc gcgatggctc gctgccgtag tctggagaag aatcgccagg 9540
gttgcgttgc ggtgtgcccc ggttcgaggc cggccggatt ccgcggctaa cgagggcgtg 9600
gctgccccgt cgtttccaag accccatagc cagccgactt ctccagttac ggagcgagcc 9660
cctcttttgt tttgtttgtt tttgccagat gcatcccgta ctgcggcaga tgcgccccca 9720
ccaccctcca ccgcaacaac agccccctcc acagccggcg cttctgcccc cgccccagca 9780
gcaacttcca gccacgaccg ccgcggccgc cgtgagcggg gctggacaga gttatgatca 9840
ccagctggcc ttggaagagg gcgaggggct ggcgcgcctg gggcgtcgt cgccggagcg 9900
gcacccgcgc gtgcagatga aaagggacgc tcgcgaggcc tacgtgccca agcagaacct 9960
gttcagagac aggagcggcg aggagcccga ggagatgcgc gcggcccggt tccacgcggg 10020
gcgggagctg cggcgcggcc tggaccgaaa gagggtgctg agggacgagg atttcgaggc 10080
ggacgagctg acggggatca gccccgcgcg cgcgcacgtg gccgcggcca acctggtcac 10140
ggcgtacgag cagaccgtga aggaggagag caacttccaa aaatccttca acaaccacgt 10200
gcgcaccctg atcgcgcgcg aggaggtgac cctgggcctg atgcacctgt gggacctgct 10260
ggaggccatc gtgcagaacc ccaccagcaa gccgctgacg gcgcagctgt tcctggtggt 10320
gcagcatagt cgggacaacg aagcgttcag ggaggcgctg ctgaatatca ccgagcccga 10380
gggccgctgg ctcctggacc tggtgaacat tctgcagagc atcgtggtgc aggagcgcgg 10440
gctgccgctg tccgagaagc tggcggccat caacttctcg gtgctgagtt tgggcaagta 10500
ctacgctagg aagatctaca agaccccgta cgtgcccata gacaaggagg tgaagatcga 10560
cgggttttac atgcgcatga ccctgaaagt gctgaccctg agcgacgatc tgggggtgta 10620
ccgcaacgac aggatgcacc gtgcggtgag cgccagcagg cggcgcgagc tgagcgacca 10680
ggagctgatg catagtctgc agcgggccct gaccggggcc gggaccgagg gggagagcta 10740
ctttgacatg ggcgcggacc tgcactggca gcccagccgc cgggccttgg aggcggcggc 10800
aggaccctac gtagaagagg tggacgatga ggtggacgag gagggcgagt acctggaaga 10860
ctgatggcgc gaccgtattt ttgctagatg caacaacaac agccacctcc tgatcccgcg 10920

```
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gcccccttca cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctcccccc gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
atgtaagaga aaccgaaaat aaatgatact caccaaggcc atggcgacca gcgtgcgttc  12720
gtttcttctc tgttgttgtt gtatctagta tgatgaggcg tgcgtacccg gagggtcctc  12780
ctccctcgta cgagagcgtg atgcagcagg cgatggcggc ggcggcgatg cagcccccgc  12840
tggaggctcc ttacgtgccc ccgcggtacc tggcgcctac ggaggggcgg aacagcattc  12900
gttactcgga gctggcaccc ttgtacgata ccacccggtt gtacctggtg gacaacaagt  12960
cggcggacat cgcctcgctg aactaccaga acgaccacag caacttcctg accaccgtgg  13020
tgcagaacaa tgacttcacc cccacggagg ccagcaccca gaccatcaac tttgacgagc  13080
gctcgcggtg gggcggccag ctgaaaacca tcatgcacac caacatgccc aacgtgaacg  13140
agttcatgta cagcaacaag ttcaaggcgc gggtgatggt ctcccgcaag acccccaatg  13200
gggtgacagt gacagaggat tatgatggta gtcaggatga gctgaagtat gaatgggtgg  13260
aatttgagct gcccgaaggc aacttctcgg tgaccatgac catcgacctg atgaacaacg  13320
```

-continued ccatcatcga caattacttg gcggtggggc ggcagaacgg ggtgctggag agcgacatcg 13380
gcgtgaagtt cgacactagg aacttcaggc tgggctggga ccccgtgacc gagctggtca 13440
tgcccggggt gtacaccaac gaggctttcc atcccgatat tgtcttgctg cccggctgcg 13500
gggtggactt caccgagagc cgcctcagca acctgctggg cattcgcaag aggcagccct 13560
tccaggaagg cttccagatc atgtacgagg atctggaggg gggcaacatc cccgcgctcc 13620
tggatgtcga cgcctatgag aaaagcaagg aggatgcagc agctgaagca actgcagccg 13680
tagctaccgc ctctaccgag gtcaggggcg ataattttgc aagcgccgca gcagtggcag 13740
cggccgaggc ggctgaaacc gaaagtaaga tagtcattca gccggtggag aaggatagca 13800
agaacaggag ctacaacgta ctaccggaca agataaacac cgcctaccgc agctggtacc 13860
tagcctacaa ctatggcgac cccgagaagg gcgtgcgctc ctggacgctg ctcaccacct 13920
cggacgtcac ctgcggcgtg gagcaagtct actggtcgct gcccgacatg atgcaagacc 13980
cggtcacctt ccgctccacg cgtcaagtta gcaactaccc ggtggtgggc gccgagctcc 14040
tgcccgtcta ctccaagagc ttcttcaacg agcaggccgt ctactcgcag cagctgcgcg 14100
ccttcacctc gcttacgcac gtcttcaacc gcttccccga gaaccagatc ctcgtccgcc 14160
cgcccgcgcc caccattacc accgtcagtg aaaacgttcc tgctctcaca gatcacggga 14220
ccctgccgct gcgcagcagt atccggggag tccagcgcgt gaccgttact gacgccagac 14280
gccgcacctg cccctacgtc tacaaggccc tgggcatagt cgcgccgcgc gtcctctcga 14340
gccgcacctt ctaaatgtcc attctcatct cgcccagtaa taacaccggt tggggcctgc 14400
gcgcgcccag caagatgtac ggaggcgctc gccaacgctc cacgcaacac cccgtgcgcg 14460
tgcgcgggca cttccgcgct ccctggggcg ccctcaaggg ccgcgtgcgg tcgcgcacca 14520
ccgtcgacga cgtgatcgac caggtggtgg ccgacgcgcg caactacacc cccgccgccg 14580
cgcccgtctc caccgtggac gccgtcatcg acagcgtggt ggccgacgcg cgccggtacg 14640
cccgcgccaa gagccggcgg cggcgcatcg cccggcggca ccggagcacc cccgccatgc 14700
gcgcggcgcg agccttgctg cgcagggcca ggcgcacggg acgcagggcc atgctcaggg 14760
cggccagacg cgcggcttca ggcgccagcg ccggcaggac ccggagacgc gcggccacgg 14820
cggcggcagc ggccatcgcc agcatgtccc gcccgcggcg agggaacgtg tactgggtgc 14880
gcgacgccgc caccggtgtg cgcgtgcccg tgcgcacccg ccccccctcgc acttgaagat 14940
gttcacttcg cgatgttgat gtgtcccagc ggcgaggagg atgtccaagc gcaaattcaa 15000
ggaagagatg ctccaggtca tcgcgcctga gatctacggc cctgcggtgg tgaaggagga 15060
aagaaagccc cgcaaaatca agcgggtcaa aaaggacaaa aaggaagaag aaagtgatgt 15120
ggacggattg gtggagtttg tgcgcgagtt cgcccccccgg cggcgcgtgc agtggcgcgg 15180
gcggaaggtg caaccggtgc tgagacccgg caccaccgtg gtcttcacgc ccggcgagcg 15240
ctccggcacc gcttccaagc gctcctacga cgaggtgtac ggggatgatg atattctgga 15300
gcaggcggcc gagcgcctgg gcgagtttgc ttacggcaag cgcagccgtt ccgcaccgaa 15360
ggaagaggcg gtgtccatcc cgctggacca cggcaacccc acgccgagcc tcaagcccgt 15420
gaccttgcag caggtgctgc cgaccgcggc gccgcgccgg gggttcaagc gcgagggcga 15480
ggatctgtac cccaccatgc agctgatggt gcccaagcgc cagaagctgg aagacgtgct 15540
ggagaccatg aaggtggacc cggacgtgca gcccgaggtc aaggtgcggc ccatcaagca 15600
ggtggccccg ggcctgggcg tgcagaccgt ggacatcaag attcccacgg agcccatgga 15660

-continued

```
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat ttttcgtccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccacgc  17340
acgatgtgac caccgaccgc agccagcggc tgacgctgcg cttcgtgccc gtggaccgcg  17400
aggacaacac ctactcgtac aaagtgcgct acacgctggc cgtgggcgac aaccgcgtgc  17460
tggacatggc cagcacctac tttgacatcc gcggcgtgct ggatcggggc cctagcttca  17520
aaccctactc cggcaccgcc tacaacagtc tggcccccaa gggagcaccc aacacttgtc  17580
agtggacata taaagccgat ggtgaaactg ccacagaaaa aacctataca tatggaaatg  17640
cacccgtgca gggcattaac atcacaaaag atggtattca acttggaact gacaccgatg  17700
atcagccaat ctacgcagat aaaacctatc agcctgaacc tcaagtgggt gatgctgaat  17760
ggcatgacat cactggtact gatgaaaagt atggaggcag agctcttaag cctgatacca  17820
aaatgaagcc ttgttatggt tcttttgcca agcctactaa taaagaagga ggtcaggcaa  17880
atgtgaaaac aggaacaggc actactaaag aatatgacat agacatggct ttctttgaca  17940
acagaagtgc ggctgctgct ggcctagctc cagaaattgt tttgtatact gaaaatgtgg  18000
atttggaaac tccagatacc catattgtat acaaaagcag cacagatgac agcagctctt  18060
```

ctattaattt gggtcagcaa gccatgccca acagacctaa ctacattggt ttcagagaca 18120
actttatcgg gctcatgtac tacaacagca ctggcaatat gggggtgctg gccggtcagg 18180
cttctcagct gaatgctgtg gttgacttgc aagacagaaa caccgagctg tcctaccagc 18240
tcttgcttga ctctctgggt gacagaaccc ggtatttcag tatgtggaat caggcggtgg 18300
acagctatga tcctgatgtg cgcattattg aaaatcatgg tgtggaggat gaacttccca 18360
actattgttt ccctctggat gctgttggca gaacagatac ttatcaggga attaaggcta 18420
atggaactga tcaaaccaca tggaccaaag atgacagtgt caatgatgct aatgagatag 18480
gcaagggtaa tccattcgcc atggaaatca acatccaagc caacctgtgg aggaacttcc 18540
tctacgccaa cgtggccctg tacctgcccg actcttacaa gtacacgccg gccaatgtta 18600
ccctgcccac caacaccaac acctacgatt acatgaacgg ccgggtggtg gcgccctcgc 18660
tggtggactc ctacatcaac atcggggcgc gctggtcgct ggatcccatg gacaacgtga 18720
accccttcaa ccaccaccgc aatgcggggc tgcgctaccg ctccatgctc ctgggcaacg 18780
ggcgctacgt gcccttccac atccaggtgc cccagaaatt tttcgccatc aagagcctcc 18840
tgctcctgcc cgggtcctac acctacgagt ggaacttccg caaggacgtc aacatgatcc 18900
tgcagagctc cctcggcaac gacctgcgca cggacggggc ctccatctcc ttcaccagca 18960
tcaacctcta cgccaccttc ttccccatgg cgcacaacac ggcctccacg ctcgaggcca 19020
tgctgcgcaa cgacaccaac gaccagtcct tcaacgacta cctctcggcg gccaacatgc 19080
tctaccccat cccggccaac gccaccaacg tgcccatctc catcccctcg cgcaactggg 19140
ccgccttccg cggctggtcc ttcacgcgtc tcaagaccaa ggagacgccc tcgctgggct 19200
ccgggttcga cccctacttc gtctactcgg gctccatccc ctacctcgac ggcaccttct 19260
acctcaacca caccttcaag aaggtctcca tcaccttcga ctcctccgtc agctggcccg 19320
gcaacgaccg gctcctgacg cccaacgagt tcgaaatcaa gcgcaccgtc gacggcgagg 19380
gctacaacgt ggcccagtgc aacatgacca aggactggtt cctggtccag atgctggccc 19440
actacaacat cggctaccag ggcttctacg tgcccgaggg ctacaaggac cgcatgtact 19500
ccttcttccg caacttccag cccatgagcc gccaggtggt ggacgaggtc aactacaagg 19560
actaccaggc cgtcaccctg gcctaccagc acaacaactc gggcttcgtc ggctacctcg 19620
cgcccaccat gcgccagggc cagccctacc ccgccaacta cccctacccg ctcatcggca 19680
agagcgccgt caccagcgtc acccagaaaa agttcctctg cgacagggtc atgtggcgca 19740
tccccttctc cagcaacttc atgtccatgg gcgcgctcac cgacctcggc cagaacatgc 19800
tctatgccaa ctccgcccac gcgctagaca tgaatttcga agtcgacccc atggatgagt 19860
ccacccttct ctatgttgtc ttcgaagtct tcgacgtcgt ccgagtgcac cagccccacc 19920
gcggcgtcat cgaggccgtc tacctgcgca cccccttctc ggccggtaac gccaccacct 19980
aagctcttgc ttcttgcaag ccatggccgc gggctccggc gagcaggagc tcagggccat 20040
catccgcgac ctgggctgcg ggccctactt cctgggcacc ttcgataagc gcttcccggg 20100
attcatggcc ccgcacaagc tggcctgcgc catcgtcaac acggccggcc gcgagaccgg 20160
gggcgagcac tggctggcct tcgcctggaa cccgcgctcg aacacctgct acctcttcga 20220
ccccttcggg ttctcggacg agcgcctcaa gcagatctac cagttcgagt acgagggcct 20280
gctgcgccgc agcgccctgg ccaccgagga ccgctgcgtc accctggaaa agtccaccca 20340
gaccgtgcag ggtccgcgct cggccgcctg cgggctcttc tgctgcatgt tcctgcacgc 20400

```
cttcgtgcac tggcccgacc gccccatgga caagaacccc accatgaact tgctgacggg  20460
ggtgcccaac ggcatgctcc agtcgcccca ggtggaaccc accctgcgcc gcaaccagga  20520
ggcgctctac cgcttcctca actcccactc cgcctacttt cgctcccacc gcgcgcgcat  20580
cgagaaggcc accgccttcg accgcatgaa tcaagacatg taaaccgtgt gtgtatgtta  20640
aatgtcttta ataaacagca ctttcatgtt acacatgcat ctgagatgat ttatttagaa  20700
atcgaaaggg ttctgccggg tctcggcatg gcccgcgggc agggacacgt tgcggaactg  20760
gtacttggcc agccacttga actcggggat cagcagtttg ggcagcgggg tgtcggggaa  20820
ggagtcggtc cacagcttcc gcgtcagttg cagggcgccc agcaggtcgg gcgcggagat  20880
cttgaaatcg cagttgggac ccgcgttctg cgcgcgggag ttgcggtaca cggggttgca  20940
gcactggaac accatcaggg ccgggtgctt cacgctcgcc agcaccgtcg cgtcggtgat  21000
gctctccacg tcgaggtcct cggcgttggc catcccgaag gggtcatct tgcaggtctg  21060
ccttcccatg gtgggcacgc acccgggctt gtggttgcaa tcgcagtgca gggggatcag  21120
catcatctgg gcctggtcgg cgttcatccc cgggtacatg gccttcatga aagcctccaa  21180
ttgcctgaac gcctgctggg ccttggctcc ctcggtgaag aagaccccgc aggacttgct  21240
agagaactgg ttggtggcgc acccggcgtc gtgcacgcag cagcgcgcgt cgttgttggc  21300
cagctgcacc acgctgcgcc cccagcggtt ctgggtgatc ttggcccggt cggggttctc  21360
cttcagcgcg cgctgcccgt tctcgctcgc cacatccatc tcgatcatgt gctccttctg  21420
gatcatggtg gtcccgtgca ggcaccgcag cttgccctcg gcctcggtgc acccgtgcag  21480
ccacagcgcg cacccggtgc actcccagtt cttgtgggcg atctgggaat gcgcgtgcac  21540
gaagccctgc aggaagcggc ccatcatggt ggtcagggtc ttgttgctag tgaaggtcag  21600
cggaatgccg cggtgctcct cgttgatgta caggtggcag atgcggcggt acacctcgcc  21660
ctgctcgggc atcagctgga agttggcttt caggtcggtc tccacgcggt agcggtccat  21720
cagcatagtc atgatttcca tacccttctc ccaggccgag acgatgggca ggctcatagg  21780
gttcttcacc atcatcttag cgctagcagc cgcggccagg gggtcgctct cgtccagggt  21840
ctcaaagctc cgcttgccgt ccttctcggt gatccgcacc ggggggtagc tgaagcccac  21900
ggccgccagc tcctcctcgg cctgtctttc gtcctcgctg tcctggctga cgtcctgcag  21960
gaccacatgc ttggtcttgc ggggtttctt cttgggcggc agcggcggcg gagatgttgg  22020
agatggcgag ggggagcgcg agttctcgct caccactact atctcttcct cttcttggtc  22080
cgaggccacg cggcggtagg tatgtctctt cgggggcaga ggcggaggcg acgggctctc  22140
gccgccgcga cttggcggat ggctggcaga gccccttccg cgttcggggg tgcgctcccg  22200
gcggcgctct gactgacttc ctccgcggcc ggccattgtg ttctcctagg gaggaacaac  22260
aagcatggag actcagccat cgccaacctc gccatctgcc cccaccgccg acgagaagca  22320
gcagcagcag aatgaaagct taaccgcccc gccgcccagc cccgccacct ccgacgcggc  22380
cgtcccagac atgcaagaga tggaggaatc catcgagatt gacctgggct atgtgacgcc  22440
cgcggagcac gaggaggagc tggcagtgcg cttttcacaa gaagagatac accaagaaca  22500
gccagagcag gaagcagaga atgagcagag tcaggctggg ctcgagcatg acggcgacta  22560
cctccacctg agcggggggg aggacgcgct catcaagcat ctggcccggc aggccaccat  22620
cgtcaaggat gcgctgctcg accgcaccga ggtgcccctc agcgtggagg agctcagccg  22680
cgcctacgag ttgaacctct tctcgccgcg cgtgccccc aagcgccagc ccaatggcac  22740
ctgcgagccc aacccgcgcc tcaacttcta cccggtcttc gcggtgcccg aggccctggc  22800
```

cacctaccac atctttttca agaaccaaaa gatccccgtc tcctgccgcg ccaaccgcac 22860
ccgcgccgac gcccttttca acctgggtcc cggcgcccgc ctacctgata tcgcctcctt 22920
ggaagaggtt cccaagatct tcgagggtct gggcagcgac gagactcggg ccgcgaacgc 22980
tctgcaagga gaaggaggag agcatgagca ccacagcgcc ctggtcgagt tggaaggcga 23040
caacgcgcgg ctggcggtgc tcaaacgcac ggtcgagctg acccatttcg cctacccggc 23100
tctgaacctg ccccccaaag tcatgagcgc ggtcatggac caggtgctca tcaagcgcgc 23160
gtcgcccatc tccgaggacg agggcatgca agactccgag gagggcaagc ccgtggtcag 23220
cgacgagcag ctggcccggt ggctgggtcc taatgctagt ccccagagtt tggaagagcg 23280
gcgcaaactc atgatggccg tggtcctggt gaccgtggag ctggagtgcc tgcgccgctt 23340
cttcgccgac gcggagaccc tgcgcaaggt cgaggagaac ctgcactacc tcttcaggca 23400
cgggttcgtg cgccaggcct gcaagatctc caacgtggag ctgaccaacc tggtctccta 23460
catgggcatc ttgcacgaga accgcctggg gcagaacgtg ctgcacacca ccctgcgcgg 23520
ggaggcccgg cgcgactaca tccgcgactg cgtctacctc tacctctgcc acacctggca 23580
gacgggcatg ggcgtgtggc agcagtgtct ggaggagcag aacctgaaag agctctgcaa 23640
gctcctgcag aagaacctca agggtctgtg gaccgggttc gacgagcgca ccaccgcctc 23700
ggacctggcc gacctcattt tccccgagcg cctcaggctg acgctgcgca acggcctgcc 23760
cgactttatg agccaaagca tgttgcaaaa ctttcgctct ttcatcctcg aacgctccgg 23820
aatcctgccc gccacctgct ccgcgctgcc ctcggacttc gtgccgctga ccttccgcga 23880
gtgccccccg ccgctgtgga gccactgcta cctgctgcgc ctggccaact acctggccta 23940
ccactcggac gtgatcgagg acgtcagcgg cgagggcctg ctcgagtgcc actgccgctg 24000
caacctctgc acgccgcacc gctccctggc ctgcaacccc cagctgctga gcgagaccca 24060
gatcatcggc accttcgagt tgcaagggcc cagcgaaggc gagggttcag ccgccaaggg 24120
gggtctgaaa ctcaccccgg ggctgtggac ctcggcctac ttgcgcaagt tcgtgcccga 24180
ggactaccat cccttcgaga tcaggttcta cgaggaccaa tcccatccgc ccaaggccga 24240
gctgtcggcc tgcgtcatca cccagggggc gatcctggcc caattgcaag ccatccagaa 24300
atcccgccaa gaattcttgc tgaaaaaggg ccgcggggtc tacctcgacc cccagaccgg 24360
tgaggagctc aaccccggct tcccccagga tgccccgagg aaacaagaag ctgaaagtgg 24420
agctgccgcc cgtggaggat ttggaggaag actgggagaa cagcagtcag gcagaggagg 24480
aggagatgga ggaagactgg gacagcactc aggcagagga ggacagcctg caagacagtc 24540
tggaggaaga cgaggaggag gcagaggagg aggtggaaga agcagccgcc gccagaccgt 24600
cgtcctcggc gggggagaaa gcaagcagca cggataccat ctccgctccg ggtcggggtc 24660
ccgctcgacc acacagtaga tgggacgaga ccggacgatt cccgaacccc accacccaga 24720
ccggtaagaa ggagcggcag ggatacaagt cctggcgggg gcacaaaaac gccatcgtct 24780
cctgcttgca ggcctgcggg ggcaacatct ccttcacccg gcgctacctg ctcttccacc 24840
gcggggtgaa ctttccccgc aacatcttgc attactaccg tcacctccac agcccctact 24900
acttccaaga agaggcagca gcagcagaaa aagaccagca gaaaaccagc agctagaaaa 24960
tccacagcgg cggcagcagg tggactgagg atcgcggcga acgagccggc gcaaacccgg 25020
gagctgagga accggatctt tcccaccctc tatgccatct tccagcagag tcgggggcag 25080
gagcaggaac tgaaagtcaa gaaccgttct ctgcgctcgc tcacccgcag ttgtctgtat 25140

-continued

```
cacaagagcg aagaccaact tcagcgcact ctcgaggacg ccgaggctct cttcaacaag  25200
tactgcgcgc tcactcttaa agagtagccc gcgcccgccc agtcgcagaa aaaggcggga  25260
attacgtcac ctgtgccctt cgccctagcc gcctccaccc atcatcatga gcaaagagat  25320
tcccacgcct tacatgtgga gctaccagcc ccagatgggc ctggccgccg gtgccgccca  25380
ggactactcc acccgcatga attggctcag cgccgggccc gcgatgatct cacgggtgaa  25440
tgacatccgc gcccaccgaa accagatact cctagaacag tcagcgctca ccgccacgcc  25500
ccgcaatcac ctcaatccgc gtaattggcc cgccgccctg gtgtaccagg aaattcccca  25560
gcccacgacc gtactacttc cgcgagacgc ccaggccgaa gtccagctga ctaactcagg  25620
tgtccagctg gcgggcggcg ccaccctgtg tcgtcaccgc cccgctcagg gtataaagcg  25680
gctggtgatc cggggcagag gcacacagct caacgacgag gtggtgagct cttcgctggg  25740
tctgcgacct gacggagtct tccaactcgc cggatcgggg agatcttcct tcacgcctcg  25800
tcaggccgtc ctgactttgg agagttcgtc ctcgcagccc cgctcgggtg gcatcggcac  25860
tctccagttc gtggaggagt tcactccctc ggtctacttc aacccettct ccggctcccc  25920
cggccactac ccggacgagt tcatcccgaa cttcgacgcc atcagcgagt cggtggacgg  25980
ctacgattga aactaatcac cccettatcc agtgaaataa agatcatatt gatgatgatt  26040
ttacagaaat aaaaaataat catttgattt gaaataaaga tacaatcata ttgatgattt  26100
gagtttaaca aaaaaataaa gaatcactta cttgaaatct gataccaggt ctctgtccat  26160
gttttctgcc aacaccactt cactcccctc ttcccagctc tggtactgca ggccccggcg  26220
ggctgcaaac ttcctccaca cgctgaaggg gatgtcaaat tcctcctgtc cctcaatctt  26280
cattttatct tctatcagat gtccaaaaag cgcgtccggg tggatgatga cttcgacccc  26340
gtctacccct acgatgcaga caacgcaccg accgtgccct tcatcaaccc ccccttcgtc  26400
tcttcagatg gattccaaga gaagcccctg gggtgttgt ccctgcgact ggccgacccc  26460
gtcaccacca agaacgggga aatcaccctc aagctgggag agggggtgga cctcgattcc  26520
tcgggaaaac tcatctccaa cacggccacc aaggccgccg cccctctcag tttttccaac  26580
aacaccattt cccttaacat ggatcacccc ttttacacta aagatggaaa attatcctta  26640
caagtttctc caccattaaa tatactgaga acaagcattc taaacacact agctttaggt  26700
tttggatcag gtttaggact ccgtggctct gccttggcag tacagttagt ctctccactt  26760
acatttgata ctgatggaaa cataaagctt accttagaca gaggtttgca tgttacaaca  26820
ggagatgcaa ttgaaagcaa cataagctgg gctaaaggtt taaaatttga agatggagcc  26880
atagcaacca acattggaaa tgggttagag tttggaagca gtagtacaga aacaggtgtt  26940
gatgatgctt acccaatcca agttaaactt ggatctggcc ttagctttga cagtacagga  27000
gccataatgg ctggtaacaa agaagacgat aaactcactt tgtggacaac acctgatcca  27060
tcaccaaact gtcaaatact cgcagaaaat gatgcaaaac taacactttg cttgactaaa  27120
tgtggtagtc aaatactggc cactgtgtca gtcttagttg taggaagtgg aaacctaaac  27180
cccattactg gcaccgtaag cagtgctcag gtgtttctac gttttgatgc aaacggtgtt  27240
cttttaacag aacattctac actaaaaaaa tactgggggt ataggcaggg agatagcata  27300
gatggcactc catataccaa tgctgtagga ttcatgccca atttaaaagc ttatccaaag  27360
tcacaaagtt ctactactaa aaataatata gtagggcaag tatacatgaa tggagatgtt  27420
tcaaaaccta tgcttctcac tataaccctc aatggtactg atgacagcaa cagtacatat  27480
tcaatgtcat tttcatacac ctggactaat ggaagctatg ttggagcaac atttggggct  27540
```

aactcttata ccttctcata catcgcccaa gaatgaacac tgtatcccac cctgcatgcc 27600
aacccttccc accccactct gtggaacaaa ctctgaaaca caaaataaaa taaagttcaa 27660
gtgttttatt gattcaacag ttttacagga ttcgagcagt tatttttcct ccaccctccc 27720
aggacatgga atacaccacc ctctcccccc gcacagcctt gaacatctga atgccattgg 27780
tgatggacat gcttttggtc tccacgttcc acacagtttc agagcgagcc agtctcgggt 27840
cggtcaggga gatgaaaccc tccgggcact cccgcatctg cacctcacag ctcaacagct 27900
gaggattgtc ctcggtggtc gggatcacgg ttatctggaa gaagcagaag agcggcggtg 27960
ggaatcatag tccgcgaacg ggatcggccg gtggtgtcgc atcaggcccc gcagcagtcg 28020
ctgccgccgc cgctccgtca agctgctgct cagggggtcc gggtccaggg actccctcag 28080
catgatgccc acggccctca gcatcagtcg tctggtgcgg cgggcgcagc agcgcatgcg 28140
gatctcgctc aggtcgctgc agtacgtgca acacagaacc accaggttgt tcaacagtcc 28200
atagttcaac acgctccagc cgaaactcat cgcgggaagg atgctaccca cgtggccgtc 28260
gtaccagatc ctcaggtaaa tcaagtggtg ccccctccag aacacgctgc ccacgtacat 28320
gatctccttg ggcatgtggc ggttcaccac ctcccggtac cacatcaccc tctggttgaa 28380
catgcagccc cggatgatcc tgcggaacca cagggccagc accgccccgc ccgccatgca 28440
gcgaagagac cccgggtccc ggcaatggca atggaggacc caccgctcgt acccgtggat 28500
catctgggag ctgaacaagt ctatgttggc acagcacagg catatgctca tgcatctctt 28560
cagcactctc aactcctcgg gggtcaaaac catatcccag ggcacgggga actcttgcag 28620
gacagcgaac cccgcagaac agggcaatcc tcgcacagaa cttacattgt gcatggacag 28680
ggtatcgcaa tcaggcagca ccgggtgatc ctccaccaga gaagcgcggg tctcggtctc 28740
ctcacagcgt ggtaaggggg ccggccgata cgggtgatgg cgggacgcgg ctgatcgtgt 28800
tcgcgaccgt gtcatgatgc agttgctttc ggacattttc gtacttgctg tagcagaacc 28860
tggtccgggc gctgcacacc gatcgccggc ggcggtctcg gcgcttggaa cgctcggtgt 28920
tgaaattgta aaacagccac tctctcagac cgtgcagcag atctagggcc tcaggagtga 28980
tgaagatccc atcatgcctg atggctctga tcacatcgac caccgtggaa tgggccagac 29040
ccagccagat gatgcaattt tgttgggttt cggtgacggc gggggaggga agaacaggaa 29100
gaaccatgat taacttttaa tccaaacggt ctcggagtac ttcaaaatga agatcgcgga 29160
gatggcacct ctcgcccccg ctgtgttggt ggaaaataac agccaggtca aaggtgatac 29220
ggttctcgag atgttccacg gtggcttcca gcaaagcctc cacgcgcaca tccagaaaca 29280
agacaatagc gaaagcggga gggttctcta attcctcaat catcatgtta cactcctgca 29340
ccatccccag ataatttca tttttccagc cttgaatgat tcgaactagt tcctgaggta 29400
aatccaagcc agccatgata aagagctcgc gcagagcgcc ctccaccggc attcttaagc 29460
acaccctcat aattccaaga tattctgctc ctggttcacc tgcagcagat tgacaagcgg 29520
aatatcaaaa tctctgccgc gatccctgag ctcctccctc agcaataact gtaagtactc 29580
tttcatatcc tctccgaaat ttttagccat aggaccacca ggaataagat tagggcaagc 29640
cacagtacag ataaaccgaa gtcctcccca gtgagcattg ccaaatgcaa gactgctata 29700
agcatgctgg ctagacccgg tgatatcttc cagataactg gacagaaaat cgcccaggca 29760
atttttaaga aaatcaacaa aagaaaaatc ctccaggtgg acgtttagag cctcgggaac 29820
aacgatgaag taaatgcaag cggtgcgttc cagcatggtt agttagctga tctgtagaaa 29880

```
aaacaaaaat gaacattaaa ccatgctagc ctggcgaaca ggtgggtaaa tcgttctctc  29940

cagcaccagg caggccacgg ggtctccggc gcgaccctcg taaaaattgt cgctatgatt  30000

gaaaaccatc acagagagac gttcccggtg gccggcgtga atgattcgac aagatgaata  30060

cacccccgga acattggcgt ccgcgagtga aaaaaagcgc ccgaggaagc aataaggcac  30120

tacaatgctc agtctcaagt ccagcaaagc gatgccatgc ggatgaagca caaaattctc  30180

aggtgcgtac aaaatgtaat tactcccctc ctgcacaggc agcaaagccc ccgatccctc  30240

caggtacaca tacaaagcct cagcgtccat agcttaccga gcagcagcac acaacaggcg  30300

caagagtcag agaaaggctg agctctaacc tgtccacccg ctctctgctc aatatatagc  30360

ccagatctac actgacgtaa aggccaaagt ctaaaaatac ccgccaaata atcacacacg  30420

cccagcacac gcccagaaac cggtgacaca ctcaaaaaaa tacgcgcact tcctcaaacg  30480

cccaaaactg ccgtcatttc cgggttccca cgctacgtca tcaaaacacg actttcaaat  30540

tccgtcgacc gttaaaaacg tcacccgccc cgcccctaac ggtcgcccgt ctctcagcca  30600

atcagcgccc cgcatcccca aattcaaaca cctcatttgc atattaacgc gcacaaaaag  30660

tttgaggtat attattgatg atgg                                          30684
```

<210> SEQ ID NO 14
<211> LENGTH: 8602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200
```

-continued

```
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
```

```
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
```

```
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaaagtccg ccatatgagg ccaccatgca gatcttcgtg aagaccctga ccggcaagac   7620
catcacccta gaggtggagc ccagtgacac catcgagaac gtgaaggcca agatccagga   7680
taaagagggc atcccccctg accagcagag gctgatcttt gccggcaagc agctggaaga   7740
tggccgcacc ctctctgatt acaacatcca gaaggagtca accctgcacc tggtccttcg   7800
cctgagaggt ggcgctgctt acagtataat caactttgaa aaactggctg cttacggcat   7860
cctgggcttt gtgtttacac tggctgccta cctgctgttt ggctatcctg tgtacgtggc   7920
cgcttatgga ctgtgtaccc tggtggccat gctggctgct tacaatctgg tgcctatggt   7980
ggccacagtg gccgcctatt gtcttggcgg actgctgaca atggtggcag cctacagccc   8040
gagctatgcg tatcatcagt ttgcagccta cggcccagga ccaggcgcta aatttgtggc   8100
tgcctggaca ctgaaagccg ccgctggacc aggtcctgga cagtacatca aggccaacag   8160
caagttcatc ggcatcaccg aactcggccc aggaccaggc tatccctacg atgtgcctga   8220
ttacgcctga tagtgatgat tcgaacggcc gtatcacgcc caaacattta cagccgcggt   8280
gtcaaaaacc gcgtggacgt ggttaacatc cctgctggga ggatcagccg taattattat   8340
```

```
aattggcttg gtgctggcta ctattgtggc catgtacgtg ctgaccaacc agaaacataa   8400

ttgaatacag cagcaattgg caagctgctt acatagaact cgcggcgatt ggcatgccgc   8460

cttaaaattt ttattttatt ttttcttttc ttttccgaat cggattttgt ttttaatatt   8520

tcaaaaaaaa aaaaaaaaaa aaaaaaaaaa aaaaaaaaaa aaaaaaaaaa aaaaaaaaaa   8580

aaaaaaaaaa aaaaaaaaaa aa                                            8602


<210> SEQ ID NO 15
<211> LENGTH: 9595
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaagccgatg   1620

tcgacttgat gttacaagag gctggggccg gctcagtgga gacacctcgt ggcttgataa   1680

aggttaccag ctacgctggc gaggacaaga tcggctctta cgctgtgctt tctccgcagg   1740
```

ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480

-continued

```
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gactctagaa tagtctttaa   7560
ttaaagtccg ccatatgaga tggaagatgc caaaaacatt aagaagggcc cagcgccatt   7620
ctacccactc gaagacggga ccgccggcga gcagctgcac aaagccatga agcgctacgc   7680
cctggtgccc ggcaccatcg cctttaccga cgcacatatc gaggtggaca ttacctacgc   7740
cgagtacttc gagatgagcg ttcggctggc agaagctatg aagcgctatg ggctgaatac   7800
aaaccatcgg atcgtggtgt gcagcgagaa tagcttgcag ttcttcatgc ccgtgttggg   7860
tgccctgttc atcggtgtgg ctgtggcccc agctaacgac atctacaacg agcgcgagct   7920
gctgaacagc atgggcatca gccagcccac cgtcgtattc gtgagcaaga aagggctgca   7980
aaagatcctc aacgtgcaaa agaagctacc gatcatacaa aagatcatca tcatggatag   8040
caagaccgac taccagggct tccaaagcat gtacaccttc gtgacttccc atttgccacc   8100
cggcttcaac gagtacgact tcgtgcccga gagcttcgac cgggacaaaa ccatcgccct   8160
gatcatgaac agtagtggca gtaccggatt gcccaagggc gtagccctac cgcaccgcac   8220
cgcttgtgtc cgattcagtc atgcccgcga ccccatcttc ggcaaccaga tcatccccga   8280
caccgctatc ctcagcgtgg tgccatttca ccacggcttc ggcatgttca ccacgctggg   8340
ctacttgatc tgcggctttc gggtcgtgct catgtaccgc ttcgaggagg agctattctt   8400
gcgcagcttg caagactata agattcaatc tgccctgctg gtgcccacac tatttagctt   8460
cttcgctaag agcactctca tcgacaagta cgacctaagc aacttgcacg agatcgccag   8520
cggcggggcg ccgctcagca aggaggtagg tgaggccgtg gccaaacgct tccacctacc   8580
aggcatccgc cagggctacg gcctgacaga aacaaccagc gccattctga tcacccccga   8640
aggggacgac aagcctggcg cagtaggcaa ggtggtgccc ttcttcgagg ctaaggtggt   8700
ggacttggac accggtaaga cactgggtgt gaaccagcgc ggcgagctgt gcgtccgtgg   8760
ccccatgatc atgagcggct acgttaacaa ccccgaggct acaaacgctc tcatcgacaa   8820
```

```
ggacggctgg ctgcacagcg gcgacatcgc ctactgggac gaggacgagc acttcttcat   8880

cgtggaccgg ctgaagagcc tgatcaaata caagggctac caggtagccc cagccgaact   8940

ggagagcatc ctgctgcaac accccaacat cttcgacgcc ggggtcgccg gcctgcccga   9000

cgacgatgcc ggcgagctgc ccgccgcagt cgtcgtgctg gaacacggta aaaccatgac   9060

cgagaaggag atcgtggact atgtggccag ccaggttaca accgccaaga agctgcgcgg   9120

tggtgttgtg ttcgtggacg aggtgcctaa aggactgacc ggcaagttgg acgcccgcaa   9180

gatccgcgag attctcatta aggccaagaa gggcggcaag atcgccgtgt aattcgaacg   9240

gccgtatcac gcccaaacat ttacagccgc ggtgtcaaaa accgcgtgga cgtggttaac   9300

atccctgctg ggaggatcag ccgtaattat tataattggc ttggtgctgg ctactattgt   9360

ggccatgtac gtgctgacca accagaaaca taattgaata cagcagcaat tggcaagctg   9420

cttacataga actcgcggcg attggcatgc cgccttaaaa tttttatttt atttttcttt   9480

ttcttttccg aatcggattt tgtttttaat atttcaaaaa aaaaaaaaaa aaaaaaaaaa   9540

aaaaaaaaaa aaaaaaaaaa aaaaaaaaaa aaaaaaaaaa aaaaaaaaaa aaaaa        9595
```

<210> SEQ ID NO 16
<211> LENGTH: 139
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135
```

<210> SEQ ID NO 17
<211> LENGTH: 167
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
```

```
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165


<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Thr Phe Ser Ser Tyr Gly Met His
1               5                   10


<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Ile Trp Tyr Asp Gly Ser Asn Lys Tyr Tyr Ala Asp Ser Val
1               5                   10                  15


<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Pro Arg Gly Ala Thr Leu Tyr Tyr Tyr Tyr Tyr Gly Met Asp Val
1               5                   10                  15


<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 21

Arg Ala Ser Gln Ser Ile Asn Ser Tyr Leu Asp
1 5 10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ala Ala Ser Ser Leu Gln Ser
1 5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Gln Gln Tyr Tyr Ser Thr Pro Phe Thr
1 5

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Arg Val Ser Ser Ser
20 25 30

Tyr Leu Ala Trp Tyr Gln Gln Lys Pro Gly Gln Ala Pro Arg Leu Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Leu Pro
85 90 95

Trp Thr Phe Gly Gln Gly Thr Lys Val Glu Ile Lys
100 105

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Glu Val Gln Leu Val Glu Ser Gly Gly Gly Leu Val Gln Pro Gly Gly
1 5 10 15

-continued

```
Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120


<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Tyr Trp Met Ser
1               5


<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ile Lys Gln Asp Gly Ser Glu Lys Tyr Tyr Val Asp Ser Val Lys
1               5                   10                  15

Gly


<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gly Gly Trp Phe Gly Glu Leu Ala Phe Asp Tyr
1               5                   10


<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Arg Val Ser Ser Ser Tyr Leu Ala
1               5                   10
```

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Asp Ala Ser Ser Arg Ala Thr
1 5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gln Gln Tyr Gly Ser Leu Pro Trp Thr
1 5

<210> SEQ ID NO 32
<211> LENGTH: 2019
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
gcccgggcat ttaaatgcga tcgcatcgat tacgactcta gaatagtcta gtccgcaggc 60
caccatgcag atcttcgtga agaccctgac cggcaagacc atcaccctag aggtggagcc 120
cagtgacacc atcgagaacg tgaaggccaa gatccaggat aaagagggca tcccccctga 180
ccagcagagg ctgatctttg ccggcaagca gctggaagat ggccgcaccc tctctgatta 240
caacatccag aaggagtcaa ccctgcacct ggtccttcgc ctgagaggtg ccatgtttca 300
ggcgctgagc gaaggctgca ccccgtatga tattaaccag atgctgaacg tgctgggcga 360
tcatcaggtc tcaggccttg agcagcttga gagtataatc aactttgaaa aactgactga 420
atggaccagt tctaatgtta tgcctatcct gtctcctctg acaaagggca tcctgggctt 480
cgtgtttacc ctgaccgtgc cttctgagag aggacttagc tgcattagcg aagcggatgc 540
gaccaccccg gaaagcgcga acctgggcga agaaattctg agccagctgt atctttggcc 600
aagggtgacc taccattccc ctagttatgc ttaccaccaa tttgaaagac gagccaaata 660
taaaagacac ttccccggct ttggccagag cctgctgttt ggctaccctg tgtacgtgtt 720
cggcgattgc gtgcagggcg attgggatgc gattcgcttt cgctattgcg cgccgccggg 780
ctatgcgctg ctgcgctgca acgataccaa ctatagcgct ctgctggctg tgggggccct 840
agaaggaccc aggaatcagg actggcttgg tgtcccaaga caacttgtaa ctcggatgca 900
ggctattcag aatgccggcc tgtgtaccct ggtggccatg ctggaagaga caatcttctg 960
gctgcaagcg tttctgatgg cgctgaccga tagcggcccg aaaaccaaca ttattgtgga 1020
tagccagtat gtgatgggca ttagcaaacc gagctttcag gaatttgtgg attgggaaaa 1080
cgtgagcccg gaactgaaca gcaccgatca gccgttttgg caagccggaa tcctggccag 1140
aaatctggtg cctatggtgg ccacagtgca gggccagaac ctgaagtacc agggtcagtc 1200

```
actagtcatc tctgcttcta tcattgtctt caacctgctg gaactggaag gtgattatcg   1260

agatgatggc aacgtgtggg tgcatacccc gctgagcccg cgcaccctga acgcgtgggt   1320

gaaagcggtg gaagaaaaaa aaggtattcc agttcaccta gagctggcca gtatgaccaa   1380

catggagctc atgagcagta ttgtgcatca gcaggtcaga acatacggcc ccgtgttcat   1440

gtgtctcggc ggactgctta caatggtggc tggtgctgtg tggctgacag tgcgagtgct   1500

cgagctgttc cgggccgcgc agctggccaa cgacgtggtc ctccagatca tggagctttg   1560

tggtgcagcg tttcgccagg tgtgccatac caccgtgccg tggccgaacg cgagcctgac   1620

cccgaaatgg aacaacgaaa ccacccagcc ccagatcgcc aactgcagcg tgtatgactt   1680

ttttgtgtgg ctccattatt attctgttcg agacacactt tggccaaggg tgacctacca   1740

tatgaacaaa tatgcgtatc atatgctgga aagacgagcc aaatataaaa gaggaccagg   1800

acctggcgct aaatttgtgg ccgcctggac actgaaagcc gctgctggtc ctggacctgg   1860

ccagtacatc aaggccaaca gcaagttcat cggcatcacc gaactcggac ccggaccagg   1920

ctgatgattt cgaaatttaa ataagcttgc ggccgctagg gataacaggg taattatcac   1980

gcccaaacat ttacagccgc ggtgtcaaaa accgcgtgg                          2019
```

```
<210> SEQ ID NO 33
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Met Phe Gln Ala
65                  70                  75                  80

Leu Ser Glu Gly Cys Thr Pro Tyr Asp Ile Asn Gln Met Leu Asn Val
                85                  90                  95

Leu Gly Asp His Gln Val Ser Gly Leu Glu Gln Leu Glu Ser Ile Ile
            100                 105                 110

Asn Phe Glu Lys Leu Thr Glu Trp Thr Ser Ser Asn Val Met Pro Ile
        115                 120                 125

Leu Ser Pro Leu Thr Lys Gly Ile Leu Gly Phe Val Phe Thr Leu Thr
    130                 135                 140

Val Pro Ser Glu Arg Gly Leu Ser Cys Ile Ser Glu Ala Asp Ala Thr
145                 150                 155                 160

Thr Pro Glu Ser Ala Asn Leu Gly Glu Glu Ile Leu Ser Gln Leu Tyr
                165                 170                 175

Leu Trp Pro Arg Val Thr Tyr His Ser Pro Ser Tyr Ala Tyr His Gln
            180                 185                 190

Phe Glu Arg Arg Ala Lys Tyr Lys Arg His Phe Pro Gly Phe Gly Gln
        195                 200                 205
```

-continued

```
Ser Leu Leu Phe Gly Tyr Pro Val Tyr Val Phe Gly Asp Cys Val Gln
    210                 215                 220

Gly Asp Trp Asp Ala Ile Arg Phe Arg Tyr Cys Ala Pro Pro Gly Tyr
225                 230                 235                 240

Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615
```

<210> SEQ ID NO 34
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggccggga tgttccaggc actgtccgaa ggctgcacac cctatgatat taaccagatg 60
ctgaatgtcc tgggagacca ccaggtctct ggcctggagc agctggagag catcatcaac 120
ttcgagaagc tgaccgagtg gacaagctcc aatgtgatgc ctatcctgtc cccactgacc 180
aagggcatcc tgggcttcgt gtttaccctg acagtgcctt ctgagcgggg cctgtcttgc 240
atcagcgagg cagacgcaac cacaccagag tccgccaatc tgggcgagga gatcctgtct 300
cagctgtacc tgtggccccg ggtgacatat cactcccctt cttacgccta tcaccagttc 360
gagcggagag ccaagtacaa gagacacttc ccaggctttg gccagtctct gctgttcggc 420
taccccgtgt acgtgttcgg cgattgcgtg cagggcgact gggatgccat ccggtttaga 480
tactgcgcac cacctggata tgcactgctg aggtgtaacg acaccaatta ttccgccctg 540
ctggcagtgg gcgccctgga gggccctcgc aatcaggatt ggctgggcgt gccaaggcag 600
ctggtgacac gcatgcaggc catccagaac gcaggcctgt gcaccctggt ggcaatgctg 660
gaggagacaa tcttctggct gcaggccttt ctgatggccc tgaccgacag cggccccaag 720
acaaacatca tcgtggattc ccagtacgtg atgggcatct ccaagccttc tttccaggag 780
tttgtggact gggagaacgt gagcccagag ctgaattcca ccgatcagcc attctggcag 840
gcaggaatcc tggcaaggaa cctggtgcct atggtggcca cagtgcaggg ccagaatctg 900
aagtaccagg gccagagcct ggtcatcagc gcctccatca tcgtgtttaa cctgctggag 960
ctggagggcg actatcggga cgatggcaac gtgtgggtgc acaccccact gagccccaga 1020
acactgaacg cctgggtgaa ggccgtggag gagaagaagg gcatcccagt gcacctggag 1080
ctggcctcca tgaccaatat ggagctgatg tctagcatcg tgcaccagca ggtgaggaca 1140
tacggacccg tgttcatgtg cctgggaggc ctgctgacca tggtggcagg agccgtgtgg 1200
ctgacagtgc gggtgctgga gctgttcaga gccgcccagc tggccaacga tgtggtgctg 1260
cagatcatgg agctgtgcgg agcagccttt cgccaggtgt gccacaccac agtgccatgg 1320
cccaatgcct ccctgacccc caagtggaac aatgagacaa cacagcctca gatcgccaac 1380
tgtagcgtgt acgacttctt cgtgtggctg cactactata gcgtgaggga taccctgtgg 1440
ccccgcgtga cataccacat gaataagtac gcctatcaca tgctggagag gcgcgccaag 1500
tataagagag gccctggccc aggcgcaaag tttgtggcag catggaccct gaaggccgcc 1560
gccggccccg gccccggcca gtatatcaag gctaacagta agttcattgg aatcacagag 1620
ctgggacccg gacctgga 1638

<210> SEQ ID NO 35
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ala Gly Met Phe Gln Ala Leu Ser Glu Gly Cys Thr Pro Tyr Asp
1               5                   10                  15

-continued

```
Ile Asn Gln Met Leu Asn Val Leu Gly Asp His Gln Val Ser Gly Leu
            20                  25                  30

Glu Gln Leu Glu Ser Ile Ile Asn Phe Glu Lys Leu Thr Glu Trp Thr
        35                  40                  45

Ser Ser Asn Val Met Pro Ile Leu Ser Pro Leu Thr Lys Gly Ile Leu
    50                  55                  60

Gly Phe Val Phe Thr Leu Thr Val Pro Ser Glu Arg Gly Leu Ser Cys
65                  70                  75                  80

Ile Ser Glu Ala Asp Ala Thr Thr Pro Glu Ser Ala Asn Leu Gly Glu
                85                  90                  95

Glu Ile Leu Ser Gln Leu Tyr Leu Trp Pro Arg Val Thr Tyr His Ser
            100                 105                 110

Pro Ser Tyr Ala Tyr His Gln Phe Glu Arg Arg Ala Lys Tyr Lys Arg
        115                 120                 125

His Phe Pro Gly Phe Gly Gln Ser Leu Leu Phe Gly Tyr Pro Val Tyr
    130                 135                 140

Val Phe Gly Asp Cys Val Gln Gly Asp Trp Asp Ala Ile Arg Phe Arg
145                 150                 155                 160

Tyr Cys Ala Pro Pro Gly Tyr Ala Leu Leu Arg Cys Asn Asp Thr Asn
                165                 170                 175

Tyr Ser Ala Leu Leu Ala Val Gly Ala Leu Glu Gly Pro Arg Asn Gln
            180                 185                 190

Asp Trp Leu Gly Val Pro Arg Gln Leu Val Thr Arg Met Gln Ala Ile
        195                 200                 205

Gln Asn Ala Gly Leu Cys Thr Leu Val Ala Met Leu Glu Glu Thr Ile
    210                 215                 220

Phe Trp Leu Gln Ala Phe Leu Met Ala Leu Thr Asp Ser Gly Pro Lys
225                 230                 235                 240

Thr Asn Ile Ile Val Asp Ser Gln Tyr Val Met Gly Ile Ser Lys Pro
                245                 250                 255

Ser Phe Gln Glu Phe Val Asp Trp Glu Asn Val Ser Pro Glu Leu Asn
            260                 265                 270

Ser Thr Asp Gln Pro Phe Trp Gln Ala Gly Ile Leu Ala Arg Asn Leu
        275                 280                 285

Val Pro Met Val Ala Thr Val Gln Gly Gln Asn Leu Lys Tyr Gln Gly
    290                 295                 300

Gln Ser Leu Val Ile Ser Ala Ser Ile Ile Val Phe Asn Leu Leu Glu
305                 310                 315                 320

Leu Glu Gly Asp Tyr Arg Asp Asp Gly Asn Val Trp Val His Thr Pro
                325                 330                 335

Leu Ser Pro Arg Thr Leu Asn Ala Trp Val Lys Ala Val Glu Glu Lys
            340                 345                 350

Lys Gly Ile Pro Val His Leu Glu Leu Ala Ser Met Thr Asn Met Glu
        355                 360                 365

Leu Met Ser Ser Ile Val His Gln Gln Val Arg Thr Tyr Gly Pro Val
    370                 375                 380

Phe Met Cys Leu Gly Gly Leu Leu Thr Met Val Ala Gly Ala Val Trp
385                 390                 395                 400

Leu Thr Val Arg Val Leu Glu Leu Phe Arg Ala Ala Gln Leu Ala Asn
                405                 410                 415

Asp Val Val Leu Gln Ile Met Glu Leu Cys Gly Ala Ala Phe Arg Gln
            420                 425                 430
```

```
Val Cys His Thr Thr Val Pro Trp Pro Asn Ala Ser Leu Thr Pro Lys
        435                 440                 445

Trp Asn Asn Glu Thr Thr Gln Pro Gln Ile Ala Asn Cys Ser Val Tyr
    450                 455                 460

Asp Phe Phe Val Trp Leu His Tyr Tyr Ser Val Arg Asp Thr Leu Trp
465                 470                 475                 480

Pro Arg Val Thr Tyr His Met Asn Lys Tyr Ala Tyr His Met Leu Glu
                485                 490                 495

Arg Arg Ala Lys Tyr Lys Arg Gly Pro Gly Pro Gly Ala Lys Phe Val
            500                 505                 510

Ala Ala Trp Thr Leu Lys Ala Ala Ala Gly Pro Gly Pro Gly Gln Tyr
        515                 520                 525

Ile Lys Ala Asn Ser Lys Phe Ile Gly Ile Thr Glu Leu Gly Pro Gly
    530                 535                 540

Pro Gly
545


<210> SEQ ID NO 36
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

gcccgggcat ttaaatgcga tcgcatcgat tacgactcta gaatagtcta gtccgcaggc     60

caccatgcag atcttcgtga agaccctgac cggcaagacc atcaccctag aggtggagcc    120

cagtgacacc atcgagaacg tgaaggccaa gatccaggat aaagagggca tccccccctga    180

ccagcagagg ctgatctttg ccggcaagca gctggaagat ggccgcaccc tctctgatta    240

caacatccag aaggagtcaa ccctgcacct ggtccttcgc ctgagaggtg ccatgtttca    300

ggcgctgagc gaaggctgca ccccgtatga tattaaccag atgctgaacg tgctgggcga    360

tcatcagttt aagcacatca aagcctttga ccggacattt gctaacaacc caggtcccat    420

ggttgtgttt gccacacctg ggcctatcct gtctcctctg acaaagggca tcctgggctt    480

cgtgtttacc ctgaccgtgc cttctgagag aggacttagc tgcattagcg aagcggatgc    540

gaccaccccg gaaagcgcga acctgggcga agaaattctg agccagctgt atctttggcc    600

aagggtgacc taccattccc ctagttatgc ttaccaccaa tttgaaagac gagccaaata    660

taaaagacac ttccccggct ttggccagag cctgctgttt ggctaccctg tgtacgtgtt    720

cggcgattgc gtgcagggcg attgggatgc gattcgcttt cgctattgcg cgccgccggg    780

ctatgcgctg ctgcgctgca acgataccaa ctatagcgct ctgctggctg tgggggccct    840

agaaggaccc aggaatcagg actggcttgg tgtcccaaga caacttgtaa ctcggatgca    900

ggctattcag aatgccggcc tgtgtaccct ggtggccatg ctggaagaga caatcttctg    960

gctgcaagcg tttctgatgg cgctgaccga tagcggcccg aaaaccaaca ttattgtgga   1020

tagccagtat gtgatgggca ttagcaaacc gagctttcag gaatttgtgg attgggaaaa   1080

cgtgagcccg gaactgaaca gcaccgatca gccgttttgg caagccggaa tcctggccag   1140

aaatctggtg cctatggtgg ccacagtgca gggccagaac ctgaagtacc agggtcagtc   1200

actagtcatc tctgcttcta tcattgtctt caacctgctg gaactggaag gtgattatcg   1260

agatgatggc aacgtgtggg tgcataccc gctgagcccg cgcaccctga acgcgtgggt   1320
```

gaaagcggtg gaagaaaaaa aaggtattcc agttcaccta gagctggcca gtatgaccaa 1380
catggagctc atgagcagta ttgtgcatca gcaggtcaga acatacggcc ccgtgttcat 1440
gtgtctcggc ggactgctta caatggtggc tggtgctgtg tggctgacag tgcgagtgct 1500
cgagctgttc cgggccgcgc agctggccaa cgacgtggtc ctccagatca tggagctttg 1560
tggtgcagcg tttcgccagg tgtgccatac caccgtgccg tggccgaacg cgagcctgac 1620
cccgaaatgg aacaacgaaa ccacccagcc ccagatcgcc aactgcagcg tgtatgactt 1680
ttttgtgtgg ctccattatt attctgttcg agacacactt tggccaaggg tgacctacca 1740
tatgaacaaa tatgcgtatc atatgctgga aagacgagcc aaatataaaa gaggaccagg 1800
acctggcgct aaatttgtgg ccgcctggac actgaaagcc gctgctggtc ctggacctgg 1860
ccagtacatc aaggccaaca gcaagttcat cggcatcacc gaactcggac ccggaccagg 1920
ctgatgattt cgaaatttaa ataagcttgc ggccgctagg gataacaggg taattatcac 1980
gcccaaacat ttacagccgc ggtgtcaaaa accgcgtgg 2019

<210> SEQ ID NO 37
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Met Gln Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Gly Lys
35 40 45

Gln Leu Glu Asp Gly Arg Thr Leu Ser Asp Tyr Asn Ile Gln Lys Glu
50 55 60

Ser Thr Leu His Leu Val Leu Arg Leu Arg Gly Ala Met Phe Gln Ala
65 70 75 80

Leu Ser Glu Gly Cys Thr Pro Tyr Asp Ile Asn Gln Met Leu Asn Val
85 90 95

Leu Gly Asp His Gln Phe Lys His Ile Lys Ala Phe Asp Arg Thr Phe
100 105 110

Ala Asn Asn Pro Gly Pro Met Val Val Phe Ala Thr Pro Gly Pro Ile
115 120 125

Leu Ser Pro Leu Thr Lys Gly Ile Leu Gly Phe Val Phe Thr Leu Thr
130 135 140

Val Pro Ser Glu Arg Gly Leu Ser Cys Ile Ser Glu Ala Asp Ala Thr
145 150 155 160

Thr Pro Glu Ser Ala Asn Leu Gly Glu Glu Ile Leu Ser Gln Leu Tyr
165 170 175

Leu Trp Pro Arg Val Thr Tyr His Ser Pro Ser Tyr Ala Tyr His Gln
180 185 190

Phe Glu Arg Arg Ala Lys Tyr Lys Arg His Phe Pro Gly Phe Gly Gln
195 200 205

Ser Leu Leu Phe Gly Tyr Pro Val Tyr Val Phe Gly Asp Cys Val Gln
210 215 220

Gly Asp Trp Asp Ala Ile Arg Phe Arg Tyr Cys Ala Pro Pro Gly Tyr
225 230 235 240

```
Ala Leu Leu Arg Cys Asn Asp Thr Asn Tyr Ser Ala Leu Leu Ala Val
                245                 250                 255

Gly Ala Leu Glu Gly Pro Arg Asn Gln Asp Trp Leu Gly Val Pro Arg
            260                 265                 270

Gln Leu Val Thr Arg Met Gln Ala Ile Gln Asn Ala Gly Leu Cys Thr
        275                 280                 285

Leu Val Ala Met Leu Glu Glu Thr Ile Phe Trp Leu Gln Ala Phe Leu
    290                 295                 300

Met Ala Leu Thr Asp Ser Gly Pro Lys Thr Asn Ile Ile Val Asp Ser
305                 310                 315                 320

Gln Tyr Val Met Gly Ile Ser Lys Pro Ser Phe Gln Glu Phe Val Asp
                325                 330                 335

Trp Glu Asn Val Ser Pro Glu Leu Asn Ser Thr Asp Gln Pro Phe Trp
            340                 345                 350

Gln Ala Gly Ile Leu Ala Arg Asn Leu Val Pro Met Val Ala Thr Val
        355                 360                 365

Gln Gly Gln Asn Leu Lys Tyr Gln Gly Gln Ser Leu Val Ile Ser Ala
    370                 375                 380

Ser Ile Ile Val Phe Asn Leu Leu Glu Leu Glu Gly Asp Tyr Arg Asp
385                 390                 395                 400

Asp Gly Asn Val Trp Val His Thr Pro Leu Ser Pro Arg Thr Leu Asn
                405                 410                 415

Ala Trp Val Lys Ala Val Glu Glu Lys Lys Gly Ile Pro Val His Leu
            420                 425                 430

Glu Leu Ala Ser Met Thr Asn Met Glu Leu Met Ser Ser Ile Val His
        435                 440                 445

Gln Gln Val Arg Thr Tyr Gly Pro Val Phe Met Cys Leu Gly Gly Leu
    450                 455                 460

Leu Thr Met Val Ala Gly Ala Val Trp Leu Thr Val Arg Val Leu Glu
465                 470                 475                 480

Leu Phe Arg Ala Ala Gln Leu Ala Asn Asp Val Val Leu Gln Ile Met
                485                 490                 495

Glu Leu Cys Gly Ala Ala Phe Arg Gln Val Cys His Thr Thr Val Pro
            500                 505                 510

Trp Pro Asn Ala Ser Leu Thr Pro Lys Trp Asn Asn Glu Thr Thr Gln
        515                 520                 525

Pro Gln Ile Ala Asn Cys Ser Val Tyr Asp Phe Phe Val Trp Leu His
    530                 535                 540

Tyr Tyr Ser Val Arg Asp Thr Leu Trp Pro Arg Val Thr Tyr His Met
545                 550                 555                 560

Asn Lys Tyr Ala Tyr His Met Leu Glu Arg Arg Ala Lys Tyr Lys Arg
                565                 570                 575

Gly Pro Gly Pro Gly Ala Lys Phe Val Ala Ala Trp Thr Leu Lys Ala
            580                 585                 590

Ala Ala Gly Pro Gly Pro Gly Gln Tyr Ile Lys Ala Asn Ser Lys Phe
        595                 600                 605

Ile Gly Ile Thr Glu Leu Gly Pro Gly Pro Gly
    610                 615
```

<210> SEQ ID NO 38
<211> LENGTH: 228
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 38
atgcagatct tcgtgaagac cctgaccggc aagaccatca ccctagaggt ggagcccagt 60
gacaccatcg agaacgtgaa ggccaagatc caggataaag agggcatccc ccctgaccag 120
cagaggctga tctttgccgg caagcagctg gaagatggcc gcaccctctc tgattacaac 180
atccagaagg agtcaaccct gcacctggtc cttcgcctga gaggtggc 228

<210> SEQ ID NO 39
<211> LENGTH: 228
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
atgcagatct tcgtgaagac cctgaccggc aagaccatca ccctagaggt ggagcccagt 60
gacaccatcg agaacgtgaa ggccaagatc caggataaag agggcatccc ccctgaccag 120
cagaggctga tctttgccgg caagcagctg gaagatggcc gcaccctctc tgattacaac 180
atccagaagg agtcaaccct gcacctggtc cttcgcctga gaggtgcc 228

<210> SEQ ID NO 40
<211> LENGTH: 78
<212> TYPE: DNA
<213> ORGANISM: Homo sapiens

<400> SEQUENCE: 40
atggccgtca tggcgccccg aaccctcgtc ctgctactct cgggggctct ggccctgacc 60
cagacctggg cgggctct 78

<210> SEQ ID NO 41
<211> LENGTH: 201
<212> TYPE: DNA
<213> ORGANISM: Homo sapiens

<400> SEQUENCE: 41
ccgtcttccc agcccaccat ccccatcgtg ggcatcattg ctggcctggt tctctttgga 60
gctgtgatca ctggagctgt ggtcgctgct gtgatgtgga ggaggaagag ctcagataga 120
aaaggaggga gctactctca ggctgcaagc agtgacagtg cccagggctc tgatgtgtct 180
ctcacagctt gtaaagtgtg a 201

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
atggagaccg atacactgct gctgtgggtg ctgctcctgt gggtgccagg aagcacaggc 60

<210> SEQ ID NO 43
<211> LENGTH: 3178
<212> TYPE: DNA
<213> ORGANISM: Homo sapiens

<400> SEQUENCE: 43

```
ggcaccgatt cggggcctgc ccggacttcg ccgcacgctg cagaacctcg cccagcgccc     60
accatgcccc ggcagctcag cgcggcggcc gcgctcttcg cgtccctggc cgtaattttg    120
cacgatggca gtcaaatgag agcaaaagca tttccagaaa ccagagatta ttctcaacct    180
actgcagcag caacagtaca ggacataaaa aaacctgtcc agcaaccagc taagcaagca    240
cctcaccaaa ctttagcagc aagattcatg gatggtcata tcacctttca aacagcggcc    300
acagtaaaaa ttccaacaac taccccagca actacaaaaa acactgcaac caccagccca    360
attacctaca ccctggtcac aacccaggcc acacccaaca actcacacac agctcctcca    420
gttactgaag ttacagtcgg ccctagctta gccccttatt cactgccacc caccatcacc    480
ccaccagctc atacagctgg aaccagttca tcaaccgtca gccacacaac tgggaacacc    540
actcaaccca gtaaccagac caccccttcca gcaactttat cgatagcact gcacaaaagc    600
acaaccggtc agaagcctga tcaacccacc catgccccag gaacaacggc agctgcccac    660
aataccaccc gcacagctgc acctgcctcc acggttcctg ggcccaccct tgcacctcag    720
ccatcgtcag tcaagactgg aatttatcag gttctaaacg gaagcagact ctgtataaaa    780
gcagagatgg ggatacagct gattgttcaa gacaaggagt cggttttttc acctcggaga    840
tacttcaaca tcgaccccaa cgcaacgcaa gcctctggga actgtggcac ccgaaaatcc    900
aaccttctgt tgaattttca gggcggattt gtgaatctca catttaccaa ggatgaagaa    960
tcatattata tcagtgaagt gggagcctat ttgaccgtct cagatccaga gacagtttac   1020
caaggaatca aacatgcggt ggtgatgttc cagacagcag tcgggcattc cttcaagtgc   1080
gtgagtgaac agagcctcca gttgtcagcc cacctgcagg tgaaaacaac cgatgtccaa   1140
cttcaagcct ttgattttga agatgaccac tttggaaatg tggatgagtg ctcgtctgac   1200
tacacaattg tgcttcctgt gattggggcc atcgtggttg gtctctgcct tatgggtatg   1260
ggtgtctata aaatccgcct aaggtgtcaa tcatctggat accagagaat ctaattgttg   1320
cccgggggga atgaaaataa tggaatttag agaactcttt catcccttcc aggatggatg   1380
ttgggaaatt ccctcagagt gtgggtcctt caaacaatgt aaaccaccat cttctattca   1440
aatgaagtga gtcatgtgtg atttaagttc aggcagcaca tcaatttcta aatacttttt   1500
gtttatttta tgaaagatat agtgagctgt ttattttcta gtttccttta gaatatttta   1560
gccactcaaa gtcaacattt gagatatgtt gaattaacat aatatatgta aagtagaata   1620
agccttcaaa ttataaacca agggtcaatt gtaactaata ctactgtgtg tgcattgaag   1680
attttatttt acccttgatc ttaacaaagc ctttgctttg ttatcaaatg gactttcagt   1740
gcttttacta tctgtgtttt atggtttcat gtaacataca tattcctggt gtagcactta   1800
actccttttc cactttaaat ttgtttttgt tttttgagac ggagtttcac tcttgtcacc   1860
caggctggag tacagtggca cgatctcggc ttatggcaac ctccgcctcc cgggttcaag   1920
tgattctcct gcttcagctt cccgagtagc tgggattaca ggcacacact accacgcctg   1980
gctaattttt gtatttttat tatagacggg tttcaccatg ttggccagac tggtcttgaa   2040
ctcttgacct caggtgatcc acccacctca gcctcccaaa gtgctgggat tacaggcatg   2100
agccattgcg cccggcctta aatgtttttt ttaatcatca aaaagaacaa catatctcag   2160
gttgtctaag tgtttttatg taaaaccaac aaaaagaaca aatcagctta tatttttat    2220
cttgatgact cctgctccag aattgctaga ctaagaatta ggtggctaca gatggtagaa   2280
ctaaacaata agcaagagac aataataatg gcccttaatt attaacaaag tgccagagtc   2340
```

```
taggctaagc actttatcta tatctcattt cattctcaca acttataagt gaatgagtaa   2400

actgagactt aagggaactg aatcacttaa atgtcacctg gctaactgat ggcagagcca   2460

gagcttgaat tcatgttggt ctgacatcaa ggtctttggt cttctcccta caccaagtta   2520

cctacaagaa caatgacacc acactctgcc tgaaggctca cacctcatac cagcatacgc   2580

tcaccttaca gggaaatggg tttatccagg atcatgagac attagggtag atgaaaggag   2640

agctttgcag ataacaaaat agcctatcct taataaatcc tccactctct ggaaggagac   2700

tgaggggctt tgtaaaacat tagtcagttg ctcattttta tgggattgct tagctgggct   2760

gtaaagatga aggcatcaaa taaactcaaa gtatttttaa attttttga taatagagaa   2820

acttcgctaa ccaactgttc tttcttgagt gtatagcccc atcttgtggt aacttgctgc   2880

ttctgcactt catatccata tttcctattg ttcactttat tctgtagagc agcctgccaa   2940

gaattttatt tctgctgttt tttttgctgc taaagaaagg aactaagtca ggatgttaac   3000

agaaaagtcc acataaccct agaattctta gtcaaggaat aattcaagtc agcctagaga   3060

ccatgttgac tttcctcatg tgtttcctta tgactcagta agttggcaag gtcctgactt   3120

tagtcttaat aaaacattga attgtagtaa aggtttttgc aataaaaact tactttgg     3178
```

<210> SEQ ID NO 44
<211> LENGTH: 1858
<212> TYPE: DNA
<213> ORGANISM: Mus sp.

<400> SEQUENCE: 44

```
attccggagg tgaaaaacaa tggcacaacg tgtataatgg ccagcttctc tgcctccttt     60

ctgaccacct acgagactgc gaatggttct cagatcgtga acatttccct gccagcctct    120

gcagaagtac tgaaaaatgg cagttcttgt ggtaaagaaa atgtttctga ccccagcctc    180

acaattactt ttggaagagg atatttactg acactcaact tcacaaaaaa tacaacacgt    240

tacagtgtcc agcatatgta ttttacatat aacttgtcag atacagaaca ttttcccaat    300

gccatcagca aagagatcta caccatggat tccacaactg acatcaaggc agacatcaac    360

aaagcatacc ggtgtgtcag tgatatccgg gtctacatga agaatgtgac cgttgtgctc    420

cgggatgcca ctatccaggc ctacctgtcg agtggcaact tcagcaagga agagacacac    480

tgcacacagg atggaccttc cccaaccact gggccaccca gcccctcacc accacttgtg    540

cccacaaacc ccactgtatc caagtacaat gttactggta acaacggaac ctgcctgctg    600

gcctctatgg cactgcaact gaatatcacc tacctgaaaa aggacaacaa gacggtgacc    660

agagcgttca acatcagccc aaatgacaca tctagtggga gttgcggtat caacttggtg    720

accctgaaag tggagaacaa gaacagagcc ctggaattgc agtttgggat gaatgccagc    780

tctagcctgt ttttcttgca aggagtgcgc ttgaatatga ctcttcctga tgccctagtg    840

cccacattca gcatctccaa ccattcactg aaagctcttc aggccactgt gggaaactca    900

tacaagtgca acactgagga acacatcttt gtcagcaaga tgctctccct caatgtcttc    960

agtgtgcagg tccaggcttt caaggtggac agtgacaggt ttgggtctgt ggaagagtgt   1020

gttcaggatg gtaacaacat gttgatcccc attgctgtgg gcggtgccct ggcagggctg   1080

atcctcatcg tcctcattgc ctacctcatt ggcaggaaga ggagtcacgc cggctatcag   1140

accatctagc ctggtgggca ggtgcaccag agatgcacag ggcctgttc tcacatcccc   1200

aagcttagat aggtgtggaa gggaggcaca ctttctggca aactgtttta aaatctgctt   1260
```

```
tatcaaatgt gaagttcatc ttgcaacatt tactatgcac aaaggaataa ctattgaaat   1320

gacggtgtta attttgctaa ctgggttaaa tattgatgag aaggctccac tgatttgact   1380

tttaagactt ggtgtttggt tcttcattct tttactcaga tttaagccta tcaaagggat   1440

actctggtcc agaccttggc ctggcaaggg tggctgatgg ttaggctgca cacacttaag   1500

aagcaacggg agcagggaag gcttgcacac aggcacgcac agggtcaacc tctggacact   1560

tggcttgggc tacctggcct tggggggggct gaactctggc atctggctgg gtacacaccc   1620

ccccaatttc tgtgctctgc cacccgtgag ctgccacttt cctaaataga aaatggcatt   1680

atttttattt acttttttgt aaagtgattt ccagtcttgt gttggcgttc agggtggccc   1740

tgtctctgca ctgtgtacaa taatagattc acactgctga cgtgtcttgc agcgtaggtg   1800

ggttgtacac tgggcatcag ctcacgtaat gcattgcctg taacgatgct aataaaaa     1858
```

```
<210> SEQ ID NO 45
<211> LENGTH: 2339
<212> TYPE: DNA
<213> ORGANISM: Homo sapiens

<400> SEQUENCE: 45

ggcccaaccg ccgcccgcgc ccccgctctc cgcaccgtac ccggccgcct cgcgccatgg     60

cggcccccgg cagcgcccgg cgacccctgc tgctgctact gctgttgctg ctgctcggcc    120

tcatgcattg tgcgtcagca gcaatgttta tggtgaaaaa tggcaacggg accgcgtgca    180

taatggccaa cttctctgct gccttctcag tgaactacga caccaagagt ggccctaaga    240

acatgacctt tgacctgcca tcagatgcca cagtggtgct caaccgcagc tcctgtggaa    300

aagagaacac ttctgacccc agtctcgtga ttgcttttgg aagaggacat acactcactc    360

tcaatttcac gagaaatgca acacgttaca gcgtccagct catgagtttt gtttataact    420

tgtcagacac acaccttttc cccaatgcga gctccaaaga aatcaagact gtggaatcta    480

taactgacat cagggcagat atagataaaa aatacagatg tgttagtggc acccaggtcc    540

acatgaacaa cgtgaccgta acgctccatg atgccaccat ccaggcgtac ctttccaaca    600

gcagcttcag caggggagag acacgctgtg aacaagacag gccttcccca accacagcgc    660

cccctgcgcc acccagcccc tcgccctcac ccgtgcccaa gagcccctct gtggacaagt    720

acaacgtgag cggcaccaac gggacctgcc tgctggccag catggggctg cagctgaacc    780

tcacctatga gaggaaggac aacacgacgg tgacaaggct tctcaacatc aaccccaaca    840

agacctcggc cagcgggagc tgcggcgccc acctggtgac tctggagctg cacagcgagg    900

gcaccaccgt cctgctcttc cagttcggga tgaatgcaag ttctagccgg tttttcctac    960

aaggaatcca gttgaataca attcttcctg acgccagaga ccctgccttt aaagctgcca   1020

acggctccct gcgagcgctg caggccacag tcggcaattc ctacaagtgc aacgcggagg   1080

agcacgtccg tgtcacgaag gcgttttcag tcaatatatt caaagtgtgg gtccaggctt   1140

tcaaggtgga aggtggccag tttggctctg tggaggagtg tctgctggac gagaacagca   1200

tgctgatccc catcgctgtg ggtggtgccc tggcggggct ggtcctcatc gtcctcatcg   1260

cctacctcgt cggcaggaag aggagtcacg caggctacca gactatctag cctggtgcac   1320

gcaggcacag cagctgcagg ggcctctgtt cctttctctg ggcttagggt cctgtcgaag   1380

gggaggcaca ctttctggca aacgtttctc aaatctgctt catccaatgt gaagttcatc   1440

ttgcagcatt tactatgcac aacagagtaa ctatcgaaat gacggtgtta attttgctaa   1500

ctgggttaaa tattttgcta actggttaaa cattaatatt taccaaagta ggattttgag   1560
```

ggtgggggtg ctctctctga gggggtgggg gtgccgctgt ctctgagggg tgggggtgcc 1620
gctgtctctg aggggtgggg gtgccgctct ctctgagggg gtgggggtgc cgctttctct 1680
gagggggtgg gggtgccgct ctctctgagg gggtgggggt gctgctctct ccgaggggtg 1740
gaatgccgct gtctctgagg ggtgggggtg ccgctctaaa ttggctccat atcatttgag 1800
tttagggttc tggtgtttgg tttcttcatt ctttactgca ctcagattta agccttacaa 1860
agggaaagcc tctggccgtc acacgtagga cgcatgaagg tcactcgtgg tgaggctgac 1920
atgctcacac attacaacag tagagaggga aaatcctaag acagaggaac tccagagatg 1980
agtgtctgga gcgcttcagt tcagctttaa aggccaggac gggccacacg tggctggcgg 2040
cctcgttcca gtggcggcac gtccttgggc gtctctaatg tctgcagctc aagggctggc 2100 actttttaa atataaaaat gggtgttatt tttattttt tttgtaaagt gatttttggt 2160
cttctgttga cattcggggt gatcctgttc tgcgctgtgt acaatgtgag atcggtgcgt 2220
tctcctgatg ttttgccgtg gcttggggat tgtacacggg accagctcac gtaatgcatt 2280
gcctgtaaca atgtaataaa aagcctcttt cttttaaaaa aaaaaaaaaa aaaaaaaaa 2339

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
cagtacatca aggccaacag caagttcatc ggcatcaccg aactc 45

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gln Tyr Ile Lys Ala Asn Ser Lys Phe Ile Gly Ile Thr Glu Leu
1 5 10 15

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gctaaatttg tggctgcctg gacactgaaa gccgccgct 39

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Ala Lys Phe Val Ala Ala Trp Thr Leu Lys Ala Ala Ala

-continued 1 5 10

<210> SEQ ID NO 50
<211> LENGTH: 593
<212> TYPE: DNA
<213> ORGANISM: Woodchuck hepatitis virus

<400> SEQUENCE: 50
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tgt 593

<210> SEQ ID NO 51
<211> LENGTH: 589
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
tctccccccc cccctctcc ctcccccccc cctaacgtta ctggccgaag ccgcttggaa 60
taaggccggt gtgcgtttgt ctatatgtta ttttccacca tattgccgtc ttttggcaat 120
gtgagggccc ggaaacctgg ccctgtcttc ttgacgagca ttcctagggg tctttcccct 180
ctcgccaaag gaatgcaagg tctgttgaat gtcgtgaagg aagcagttcc tctggaagct 240
tcttgaagac aaacaacgtc tgtagcgacc ctttgcaggc agcggaaccc cccacctggc 300
gacaggtgcc tctgcggcca aaagccacgt gtataagata cacctgcaaa ggcggcacaa 360
ccccagtgcc acgttgtgag ttggatagtt gtggaaagag tcaaatggct ctcctcaagc 420
gtattcaaca aggggctgaa ggatgcccag aaggtacccc attgtatggg atctgatctg 480
gggcctcggt gcacatgctt tacatgtgtt tagtcgaggt taaaaaaacg tctaggcccc 540
ccgaaccacg gggacgtggt tttcctttga aaaacacgat gataatatg 589

<210> SEQ ID NO 52
<211> LENGTH: 720
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtag 720

<210> SEQ ID NO 53
<211> LENGTH: 1563
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
atgctgctgc tgctgctgct gctgggcctg aggctacagc tctccctggg catcatccca 60
gttgaggagg agaacccgga cttctggaac cgcgaggcag ccgaggccct gggtgccgcc 120
aagaagctgc agcctgcaca gacagccgcc aagaacctca tcatcttcct gggcgatggg 180
atgggggtgt ctacggtgac agctgccagg atcctaaaag ggcagaagaa ggacaaactg 240
gggcctgaga taccccctggc catggaccgc ttcccatatg tggctctgtc caagacatac 300
aatgtagaca aacatgtgcc agacagtgga gccacagcca cggcctacct gtgcggggtc 360
aagggcaact tccagaccat tggcttgagt gcagccgccc gctttaacca gtgcaacacg 420
acacgcggca acgaggtcat ctccgtgatg aatcgggcca agaaagcagg gaagtcagtg 480
ggagtggtaa ccaccacacg agtgcagcac gcctcgccag ccggcaccta cgcccacacg 540
gtgaaccgca actggtactc ggacgccgac gtgcctgcct cggcccgcca ggaggggtgc 600
caggacatcg ctacgcagct catctccaac atggacattg acgtgatcct aggtggaggc 660
cgaaagtaca tgtttcgcat gggaacccca gaccctgagt acccagatga ctacagccaa 720
ggtgggacca ggctggacgg gaagaatctg gtgcaggaat ggctggcgaa gcgccagggt 780
gcccggtatg tgtggaaccg cactgagctc atgcaggctt ccctggaccc gtctgtgacc 840
catctcatgg gtctctttga gcctggagac atgaaatacg agatccaccg agactccaca 900
ctggacccct ccctgatgga gatgacagag gctgccctgc gcctgctgag caggaacccc 960
cgcggcttct tcctcttcgt ggagggtggt cgcatcgacc atggtcatca tgaaagcagg 1020
gcttaccggg cactgactga gacgatcatg ttcgacgacg ccattgagag ggcgggccag 1080
ctcaccagcg aggaggacac gctgagcctc gtcactgccg accactccca cgtcttctcc 1140
ttcggaggct accccctgcg agggagctcc atcttcgggc tggcccctgg caaggcccgg 1200
gacaggaagg cctacacggt cctcctatac ggaaacggtc caggctatgt gctcaaggac 1260
ggcgcccggc cggatgttac cgagagcgag agcgggagcc ccgagtatcg gcagcagtca 1320
gcagtgcccc tggacgaaga gacccacgca ggcgaggacg tggcggtgtt cgcgcgcggc 1380
ccgcaggcgc acctggttca cggcgtgcag gagcagacct tcatagcgca cgtcatggcc 1440
ttcgccgcct gcctggagcc ctacaccgcc tgcgacctgg cgcccccccgc cggcaccacc 1500 gacgccgcgc acccgggtta ctctagagtc ggggcggccg gccgcttcga gcagacatga 1560

```
taa                                                              1563


<210> SEQ ID NO 54
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

atggaagatg ccaaaaacat taagaagggc ccagcgccat tctacccact cgaagacggg     60

accgccggcg agcagctgca caaagccatg aagcgctacg ccctggtgcc cggcaccatc    120

gcctttaccg acgcacatat cgaggtggac attacctacg ccgagtactt cgagatgagc    180

gttcggctgg cagaagctat gaagcgctat gggctgaata caaaccatcg gatcgtggtg    240

tgcagcgaga atagcttgca gttcttcatg cccgtgttgg gtgccctgtt catcggtgtg    300

gctgtggccc cagctaacga catctacaac gagcgcgagc tgctgaacag catgggcatc    360

agccagccca ccgtcgtatt cgtgagcaag aaagggctgc aaaagatcct caacgtgcaa    420

aagaagctac cgatcataca aaagatcatc atcatggata gcaagaccga ctaccagggc    480

ttccaaagca tgtacacctt cgtgacttcc catttgccac ccggcttcaa cgagtacgac    540

ttcgtgcccg agagcttcga ccgggacaaa accatcgccc tgatcatgaa cagtagtggc    600

agtaccggat tgcccaaggg cgtagcccta ccgcaccgca ccgcttgtgt ccgattcagt    660

catgcccgcg accccatctt cggcaaccag atcatccccg acaccgctat cctcagcgtg    720

gtgccatttc accacggctt cggcatgttc accacgctgg gctacttgat ctgcggcttt    780

cgggtcgtgc tcatgtaccg cttcgaggag gagctattct tgcgcagctt gcaagactat    840

aagattcaat ctgccctgct ggtgcccaca ctatttagct tcttcgctaa gagcactctc    900

atcgacaagt acgacctaag caacttgcac gagatcgcca gcggcggggc gccgctcagc    960

aaggaggtag gtgaggccgt ggccaaacgc ttccacctac caggcatccg ccagggctac   1020

ggcctgacag aaacaaccag cgccattctg atcacccccg aaggggacga caagcctggc   1080

gcagtaggca aggtggtgcc cttcttcgag gctaaggtgg tggacttgga caccggtaag   1140

acactgggtg tgaaccagcg cggcgagctg tgcgtccgtg gccccatgat catgagcggc   1200

tacgttaaca accccgaggc tacaaacgct ctcatcgaca aggacggctg gctgcacagc   1260

ggcgacatcg cctactggga cgaggacgag cacttcttca tcgtggaccg gctgaagagc   1320

ctgatcaaat acaagggcta ccaggtagcc ccagccgaac tggagagcat cctgctgcaa   1380

caccccaaca tcttcgacgc cggggtcgcc ggcctgcccg acgacgatgc cggcgagctg   1440

cccgccgcag tcgtcgtgct ggaacacggt aaaaccatga ccgagaagga gatcgtggac   1500

tatgtggcca gccaggttac aaccgccaag aagctgcgcg gtggtgttgt gttcgtggac   1560

gaggtgccta aaggactgac cggcaagttg gacgcccgca agatccgcga gattctcatt   1620

aaggccaaga agggcggcaa gatcgccgtg taa                                1653


<210> SEQ ID NO 55
<211> LENGTH: 66
<212> TYPE: DNA
<213> ORGANISM: Foot-and-mouth disease virus

<400> SEQUENCE: 55

gtaaagcaaa cactgaactt tgaccttctc aagttggctg gagacgttga gtccaatcct     60
```

```
gggccc                                                                 66


<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Pro Gly Pro Gly
1               5


<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Thr Glu Tyr Lys Leu Val Val Val Gly Ala Cys Gly Val Gly Lys
1               5                   10                  15

Ser Ala Leu Thr Ile Gln Leu Ile Gln
            20                  25


<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Thr Glu Tyr Lys Leu Val Val Val Gly Ala Asp Gly Val Gly Lys
1               5                   10                  15

Ser Ala Leu Thr Ile Gln Leu Ile Gln
            20                  25


<210> SEQ ID NO 59
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Thr Glu Tyr Lys Leu Val Val Val Gly Ala Val Gly Val Gly Lys
1               5                   10                  15

Ser Ala Leu Thr Ile Gln Leu Ile Gln
            20                  25


<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Glu Thr Cys Leu Leu Asp Ile Leu Asp Thr Ala Gly His Glu Glu Tyr
1               5                   10                  15

Ser Ala Met Arg Asp Gln Tyr Met Arg
            20                  25


<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Arg Val Glu Tyr Leu Asp Asp Arg Asn Thr Phe Leu His Ser Val
1               5                   10                  15

Val Val Pro Tyr Glu Pro Pro Glu Val
            20                  25


<210> SEQ ID NO 62
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Ser Gly Thr Ala Lys Ser Val Thr Cys Thr Tyr Tyr Pro Ala Leu
1               5                   10                  15

Asn Lys Met Phe Cys Gln Leu Ala Lys
            20                  25


<210> SEQ ID NO 63
<211> LENGTH: 543
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Thr Glu Tyr Lys Leu Val Val Val Gly Ala Gly Asp Val Gly Lys
1               5                   10                  15

Ser Ala Leu Thr Ile Gln Leu Ile Gln Glu Thr Cys Leu Leu Asp Ile
            20                  25                  30

Leu Asp Thr Ala Gly Lys Glu Glu Tyr Ser Ala Met Arg Asp Gln Tyr
        35                  40                  45

Met Arg Met Cys Asn Ser Ser Cys Met Gly Gly Met Asn Arg Met Pro
    50                  55                  60

Ile Leu Thr Ile Ile Thr Leu Glu Asp Ser Ser Ser Gly Ile His Ser
65                  70                  75                  80

Gly Ala Thr Thr Thr Ala Pro Pro Leu Ser Gly Lys Gly Asn Pro Glu
                85                  90                  95

Glu Glu Asp Val Ser Gly Ile His Ser Gly Ala Thr Thr Thr Ala Pro
            100                 105                 110

Phe Leu Ser Gly Lys Gly Asn Pro Glu Glu Glu Asp Val Glu Ile Leu
        115                 120                 125

Asp Glu Ala Tyr Val Met Ala Tyr Val Met Ala Gly Val Gly Ser Pro
    130                 135                 140

Tyr Val Ser Arg Leu Leu Met Thr Glu Tyr Lys Leu Val Val Val Gly
```

-continued

```
145                 150                 155                 160

Ala Asp Gly Val Gly Lys Ser Ala Leu Thr Ile Gln Leu Ile Gln Glu
                165                 170                 175

Thr Cys Leu Leu Asp Ile Leu Asp Thr Ala Gly Arg Glu Glu Tyr Ser
            180                 185                 190

Ala Met Arg Asp Gln Tyr Met Arg Ser Tyr Leu Asp Ser Gly Ile His
        195                 200                 205

Ser Gly Ala Thr Ala Thr Ala Pro Ser Leu Ser Gly Lys Gly Asn Pro
    210                 215                 220

Glu Lys Ser Val Thr Cys Thr Tyr Ser Pro Ala Leu Asn Asn Met Phe
225                 230                 235                 240

Cys Gln Leu Ala Lys Thr Cys Pro Val Gln Met Thr Glu Tyr Lys Leu
                245                 250                 255

Val Val Val Gly Ala Ala Gly Val Gly Lys Ser Ala Leu Thr Ile Gln
            260                 265                 270

Leu Ile Gln Glu Thr Cys Leu Leu Asp Ile Leu Asp Thr Ala Gly Leu
        275                 280                 285

Glu Glu Tyr Ser Ala Met Arg Asp Gln Tyr Met Arg Leu Arg Val Glu
    290                 295                 300

Tyr Leu Asp Asp Arg Asn Thr Phe Leu His Ser Val Val Val Pro Tyr
305                 310                 315                 320

Glu Pro Pro Glu Val Asp Gly Gln Ile Thr Val Gly Gln Arg Ile Gly
                325                 330                 335

Ser Val Ser Phe Gly Thr Val Tyr Lys Gly Lys Trp His Gly Met Thr
            340                 345                 350

Glu Tyr Lys Leu Val Val Val Gly Ala Val Gly Val Gly Lys Ser Ala
        355                 360                 365

Leu Thr Ile Gln Leu Ile Gln Glu Thr Cys Leu Leu Asp Ile Leu Asp
    370                 375                 380

Thr Ala Gly His Glu Glu Tyr Ser Ala Met Arg Asp Gln Tyr Met Arg
385                 390                 395                 400

Trp Gln Gln Gln Ser Tyr Leu Asp Ser Gly Ile His Phe Gly Ala Thr
                405                 410                 415

Thr Thr Ala Pro Ser Leu Ser Gly Lys His Ser Gly Thr Ala Lys Ser
            420                 425                 430

Val Thr Cys Thr Tyr Tyr Pro Ala Leu Asn Lys Met Phe Cys Gln Leu
        435                 440                 445

Ala Lys Lys Ser Val Thr Cys Thr Tyr Ser Pro Ala Leu Asn Glu Met
    450                 455                 460

Phe Cys Gln Leu Ala Lys Thr Cys Pro Val Gln Met Thr Glu Tyr Lys
465                 470                 475                 480

Leu Val Val Val Gly Ala Cys Gly Val Gly Lys Ser Ala Leu Thr Ile
                485                 490                 495

Gln Leu Ile Gln Gly Pro Gly Pro Gly Ala Lys Phe Val Ala Ala Trp
            500                 505                 510

Thr Leu Lys Ala Ala Ala Gly Pro Gly Pro Gly Gln Tyr Ile Lys Ala
        515                 520                 525

Asn Ser Lys Phe Ile Gly Ile Thr Glu Leu Gly Pro Gly Pro Gly
    530                 535                 540
```

<210> SEQ ID NO 64
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Met Thr Glu Tyr Lys Leu Val Val Val Gly Ala Cys Gly Val Gly Lys
1               5                   10                  15

Ser Ala Leu Thr Ile Gln Leu Ile Gln Glu Thr Cys Leu Leu Asp Ile
            20                  25                  30

Leu Asp Thr Ala Gly His Glu Glu Tyr Ser Ala Met Arg Asp Gln Tyr
        35                  40                  45

Met Arg Met Thr Glu Tyr Lys Leu Val Val Val Gly Ala Gly Asp Val
    50                  55                  60

Gly Lys Ser Ala Leu Thr Ile Gln Leu Ile Gln Glu Thr Cys Leu Leu
65                  70                  75                  80

Asp Ile Leu Asp Thr Ala Gly Arg Glu Glu Tyr Ser Ala Met Arg Asp
                85                  90                  95

Gln Tyr Met Arg Met Thr Glu Tyr Lys Leu Val Val Val Gly Ala Asp
            100                 105                 110

Gly Val Gly Lys Ser Ala Leu Thr Ile Gln Leu Ile Gln Glu Thr Cys
        115                 120                 125

Leu Leu Asp Ile Leu Asp Thr Ala Gly Leu Glu Glu Tyr Ser Ala Met
    130                 135                 140

Arg Asp Gln Tyr Met Arg Met Thr Glu Tyr Lys Leu Val Val Val Gly
145                 150                 155                 160

Ala Val Gly Val Gly Lys Ser Ala Leu Thr Ile Gln Leu Ile Gln Glu
                165                 170                 175

Thr Cys Leu Leu Asp Ile Leu Asp Thr Ala Gly Lys Glu Glu Tyr Ser
            180                 185                 190

Ala Met Arg Asp Gln Tyr Met Arg Met Thr Glu Tyr Lys Leu Val Val
        195                 200                 205

Val Gly Ala Cys Gly Val Gly Lys Ser Ala Leu Thr Ile Gln Leu Ile
    210                 215                 220

Gln Glu Thr Cys Leu Leu Asp Ile Leu Asp Thr Ala Gly Lys Glu Glu
225                 230                 235                 240

Tyr Ser Ala Met Arg Asp Gln Tyr Met Arg Met Thr Glu Tyr Lys Leu
                245                 250                 255

Val Val Val Gly Ala Gly Asp Val Gly Lys Ser Ala Leu Thr Ile Gln
            260                 265                 270

Leu Ile Gln Glu Thr Cys Leu Leu Asp Ile Leu Asp Thr Ala Gly His
        275                 280                 285

Glu Glu Tyr Ser Ala Met Arg Asp Gln Tyr Met Arg Met Thr Glu Tyr
    290                 295                 300

Lys Leu Val Val Val Gly Ala Val Gly Val Gly Lys Ser Ala Leu Thr
305                 310                 315                 320

Ile Gln Leu Ile Gln Glu Thr Cys Leu Leu Asp Ile Leu Asp Thr Ala
                325                 330                 335

Gly Arg Glu Glu Tyr Ser Ala Met Arg Asp Gln Tyr Met Arg Met Thr
            340                 345                 350

Glu Tyr Lys Leu Val Val Val Gly Ala Asp Gly Val Gly Lys Ser Ala
        355                 360                 365

Leu Thr Ile Gln Leu Ile Gln Glu Thr Cys Leu Leu Asp Ile Leu Asp
    370                 375                 380

Thr Ala Gly Leu Glu Glu Tyr Ser Ala Met Arg Asp Gln Tyr Met Arg
```

-continued

```
385                 390                 395                 400

Gly Pro Gly Pro Gly Ala Lys Phe Val Ala Ala Trp Thr Leu Lys Ala
                405                 410                 415

Ala Ala Gly Pro Gly Pro Gly Gln Tyr Ile Lys Ala Asn Ser Lys Phe
            420                 425                 430

Ile Gly Ile Thr Glu Leu Gly Pro Gly Pro Gly
        435                 440


<210> SEQ ID NO 65
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Thr Glu Tyr Lys Leu Val Val Val Gly Ala Cys Gly Val Gly Lys
1               5                   10                  15

Ser Ala Leu Thr Ile Gln Leu Ile Gln Met Thr Glu Tyr Lys Leu Val
            20                  25                  30

Val Val Gly Ala Asp Gly Val Gly Lys Ser Ala Leu Thr Ile Gln Leu
        35                  40                  45

Ile Gln Glu Thr Cys Leu Leu Asp Ile Leu Asp Thr Ala Gly His Glu
    50                  55                  60

Glu Tyr Ser Ala Met Arg Asp Gln Tyr Met Arg Met Thr Glu Tyr Lys
65                  70                  75                  80

Leu Val Val Val Gly Ala Asp Gly Val Gly Lys Ser Ala Leu Thr Ile
                85                  90                  95

Gln Leu Ile Gln Met Thr Glu Tyr Lys Leu Val Val Val Gly Ala Val
            100                 105                 110

Gly Val Gly Lys Ser Ala Leu Thr Ile Gln Leu Ile Gln Met Thr Glu
        115                 120                 125

Tyr Lys Leu Val Val Val Gly Ala Cys Gly Val Gly Lys Ser Ala Leu
    130                 135                 140

Thr Ile Gln Leu Ile Gln Glu Thr Cys Leu Leu Asp Ile Leu Asp Thr
145                 150                 155                 160

Ala Gly His Glu Glu Tyr Ser Ala Met Arg Asp Gln Tyr Met Arg Met
                165                 170                 175

Thr Glu Tyr Lys Leu Val Val Val Gly Ala Asp Gly Val Gly Lys Ser
            180                 185                 190

Ala Leu Thr Ile Gln Leu Ile Gln Met Thr Glu Tyr Lys Leu Val Val
        195                 200                 205

Val Gly Ala Val Gly Val Gly Lys Ser Ala Leu Thr Ile Gln Leu Ile
    210                 215                 220

Gln Met Thr Glu Tyr Lys Leu Val Val Val Gly Ala Cys Gly Val Gly
225                 230                 235                 240

Lys Ser Ala Leu Thr Ile Gln Leu Ile Gln Glu Thr Cys Leu Leu Asp
                245                 250                 255

Ile Leu Asp Thr Ala Gly His Glu Glu Tyr Ser Ala Met Arg Asp Gln
            260                 265                 270

Tyr Met Arg Met Thr Glu Tyr Lys Leu Val Val Val Gly Ala Asp Gly
        275                 280                 285

Val Gly Lys Ser Ala Leu Thr Ile Gln Leu Ile Gln Met Thr Glu Tyr
    290                 295                 300
```

Lys Leu Val Val Val Gly Ala Val Gly Val Gly Lys Ser Ala Leu Thr
305 310 315 320

Ile Gln Leu Ile Gln Glu Thr Cys Leu Leu Asp Ile Leu Asp Thr Ala
325 330 335

Gly His Glu Glu Tyr Ser Ala Met Arg Asp Gln Tyr Met Arg Met Thr
340 345 350

Glu Tyr Lys Leu Val Val Val Gly Ala Val Gly Val Gly Lys Ser Ala
355 360 365

Leu Thr Ile Gln Leu Ile Gln Met Thr Glu Tyr Lys Leu Val Val Val
370 375 380

Gly Ala Cys Gly Val Gly Lys Ser Ala Leu Thr Ile Gln Leu Ile Gln
385 390 395 400

Gly Pro Gly Pro Gly Ala Lys Phe Val Ala Ala Trp Thr Leu Lys Ala
405 410 415

Ala Ala Gly Pro Gly Pro Gly Gln Tyr Ile Lys Ala Asn Ser Lys Phe
420 425 430

Ile Gly Ile Thr Glu Leu Gly Pro Gly Pro Gly
435 440

<210> SEQ ID NO 66
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Met Thr Glu Tyr Lys Leu Val Val Val Gly Ala Cys Gly Val Gly Lys
1 5 10 15

Ser Ala Leu Thr Ile Gln Leu Ile Gln Met Thr Glu Tyr Lys Leu Val
20 25 30

Val Val Gly Ala Asp Gly Val Gly Lys Ser Ala Leu Thr Ile Gln Leu
35 40 45

Ile Gln Glu Thr Cys Leu Leu Asp Ile Leu Asp Thr Ala Gly His Glu
50 55 60

Glu Tyr Ser Ala Met Arg Asp Gln Tyr Met Arg Met Thr Glu Tyr Lys
65 70 75 80

Leu Val Val Val Gly Ala Val Gly Val Gly Lys Ser Ala Leu Thr Ile
85 90 95

Gln Leu Ile Gln Gly Pro Gly Pro Gly Ala Lys Phe Val Ala Ala Trp
100 105 110

Thr Leu Lys Ala Ala Ala Gly Pro Gly Pro Gly Gln Tyr Ile Lys Ala
115 120 125

Asn Ser Lys Phe Ile Gly Ile Thr Glu Leu Gly Pro Gly Pro Gly
130 135 140

<210> SEQ ID NO 67
<211> LENGTH: 168
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Met Thr Glu Tyr Lys Leu Val Val Val Gly Ala Cys Gly Val Gly Lys
1 5 10 15

```
Ser Ala Leu Thr Ile Gln Leu Ile Gln Met Thr Glu Tyr Lys Leu Val
            20                  25                  30

Val Val Gly Ala Asp Gly Val Gly Lys Ser Ala Leu Thr Ile Gln Leu
        35                  40                  45

Ile Gln Glu Thr Cys Leu Leu Asp Ile Leu Asp Thr Ala Gly His Glu
    50                  55                  60

Glu Tyr Ser Ala Met Arg Asp Gln Tyr Met Arg Met Thr Glu Tyr Lys
65                  70                  75                  80

Leu Val Val Val Gly Ala Val Gly Val Gly Lys Ser Ala Leu Thr Ile
                85                  90                  95

Gln Leu Ile Gln Leu Arg Val Glu Tyr Leu Asp Asp Arg Asn Thr Phe
            100                 105                 110

Leu His Ser Val Val Val Pro Tyr Glu Pro Pro Glu Val Gly Pro Gly
        115                 120                 125

Pro Gly Ala Lys Phe Val Ala Ala Trp Thr Leu Lys Ala Ala Ala Gly
    130                 135                 140

Pro Gly Pro Gly Gln Tyr Ile Lys Ala Asn Ser Lys Phe Ile Gly Ile
145                 150                 155                 160

Thr Glu Leu Gly Pro Gly Pro Gly
                165


<210> SEQ ID NO 68
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Thr Glu Tyr Lys Leu Val Val Val Gly Ala Cys Gly Val Gly Lys
1               5                   10                  15

Ser Ala Leu Thr Ile Gln Leu Ile Gln Met Thr Glu Tyr Lys Leu Val
            20                  25                  30

Val Val Gly Ala Asp Gly Val Gly Lys Ser Ala Leu Thr Ile Gln Leu
        35                  40                  45

Ile Gln Glu Thr Cys Leu Leu Asp Ile Leu Asp Thr Ala Gly His Glu
    50                  55                  60

Glu Tyr Ser Ala Met Arg Asp Gln Tyr Met Arg Met Thr Glu Tyr Lys
65                  70                  75                  80

Leu Val Val Val Gly Ala Val Gly Val Gly Lys Ser Ala Leu Thr Ile
                85                  90                  95

Gln Leu Ile Gln His Ser Gly Thr Ala Lys Ser Val Thr Cys Thr Tyr
            100                 105                 110

Tyr Pro Ala Leu Asn Lys Met Phe Cys Gln Leu Ala Lys Gly Pro Gly
        115                 120                 125

Pro Gly Ala Lys Phe Val Ala Ala Trp Thr Leu Lys Ala Ala Ala Gly
    130                 135                 140

Pro Gly Pro Gly Gln Tyr Ile Lys Ala Asn Ser Lys Phe Ile Gly Ile
145                 150                 155                 160

Thr Glu Leu Gly Pro Gly Pro Gly
                165


<210> SEQ ID NO 69
<211> LENGTH: 1647
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 69

```
atggctggca tgaccgagta caaacttgtg gtggttggtg ctggagacgt ggggaaaagc     60
gccctgacaa ttcagcttat tcaggaaact tgcttattag acatattaga tactgccgga    120
aaagaagagt attctgctat gagagatcag tacatgcgga tgtgcaacag cagctgcatg    180
ggcggcatga accgcatgcc catcttgact attatcaccc tggaggattc ctccagtgga    240
atacattcgg gagccaccac cactgctcct cccctgtcag gtaagggaaa tcctgaagaa    300
gaagatgtta gcggcattca ttccggtgct acgacaactg caccatttct gtctggtaaa    360
ggtaatccag aggaggagga tgtggaaatt ctggatgagg cctacgtcat ggcctatgtg    420
atggctggcg ttggaagccc atacgtgagt agactgctga tgacagaata taaattagtg    480
gtagtaggag cagatggggt aggaaagagt gccttaacaa tccaactcat tcaggagacc    540
tgtttgttgg atattctgga tacagctggc cgggaagagt attcggcaat gagggaccaa    600
tatatgcgat cttacctcga cagcggaatc cactccggtg ccactgcaac agcgccgagc    660
ctgagtggta aggggaaccc tgagaagtca gtaacgtgta catacagccc tgctttaaac    720
aacatgtttt gccaacttgc aaaaacatgt cctgtacaga tgacagagta taaacttgta    780
gtggtggggg cagctggtgt aggtaaaagt gcacttacca tccagctgat tcaagagaca    840
tgtctgttag acatcttgga cacagccggg ctcgaggaat atagcgccat gagagaccag    900
tacatgcgac tgcgcgtgga gtatctggat gacaggaaca ccttcctgca ttctgttgtg    960
gtgccctatg agcccccgga ggtggatgga cagatcacag tgggccagag aattggcagc   1020
gtgtccttcg ggactgtgta caagggcaag tggcacggaa tgacggaata taagctggtg   1080
gtggtaggag cagtaggtgt cggtaaatca gccctcacca ttcagcttat acaggagact   1140
tgtttgctgg acatcctaga cactgctggc catgaggagt actccgccat gcgcgatcaa   1200
tacatgaggt ggcagcagca gagctacctg gactcaggga tccactttgg agctaccaca   1260
actgcgccat cactaagtgg gaaacacagc ggcaccgcca aatctgtcac gtgtacttac   1320
tacccagcct tgaacaagat gttctgtcaa ttagcaaaga aaagtgtcac ctgcacatat   1380
tcaccggcac tgaatgagat gttctgccag ctggctaaga cctgtcctgt gcagatgact   1440
gagtacaaac tggtcgttgt gggggcctgt ggggttggga agagcgctct gaccatccag   1500
ctcatccagg gacccggacc aggcgccaaa tttgttgctg cttggacact gaaagctgct   1560
gctgggcccg gaccaggcca gtacatcaag gccaactcta agtttatcgg catcaccgaa   1620
ttgggacctg gacccggcta gtagtga                                       1647
```

<210> SEQ ID NO 70
<211> LENGTH: 1341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70

```
atggctggca tgactgaata caaattagtt gtcgtcggtg catgcggggt aggcaagtcg     60
gccttaacga tacaacttat tcaagagaca tgtctactgg atatccttga cactgccggt    120
cacgaagaat atagtgcaat gagggaccag tacatgcgta tgacggaata taagttagta    180
```

```
gtagttggcg caggcgacgt agggaaatcc gctctaacta tccaactaat tcaagaaacg    240
tgcctactag atatattaga cacagcggga cgtgaggagt atagcgccat gcgtgaccag    300
tatatgcgga tgaccgagta taagctagtc gtagtcggcg cggatggggt tggtaagagc    360
gccttgacca tccagctcat acaagaaact tgccttctgg acatcctaga caccgcgggt    420
ctcgaagagt acagtgcgat gagagatcag tacatgagga tgacagaata caagctcgtt    480
gttgttggtg cggtcggtgt tggaaagagt gcgctaacca ttcagcttat ccaggaaacc    540
tgtctgttag acatcttaga taccgcaggt aaagaggaat attcggccat gagggatcaa    600
tatatgcgaa tgacagagta taaattggta gtggtagggg cttgcggagt ggggaaaagc    660
gcattgacta tacaattgat tcaggaaaca tgcctattgg acatactcga cacggccggg    720
aaagaagagt attccgcgat gcgagatcaa tacatgcgca tgaccgaata taaacttgtc    780
gttgtcggag cgggtgatgt aggtaaatcg gcgctcacaa tccaattaat ccaagagacg    840
tgcttgctag acattctgga tacagctggg cacgaggagt actcagctat gcgcgatcag    900
tatatgagga tgactgagta caagttggtc gtcgtaggag cggttggtgt cggaaaatct    960
gcgttgacaa ttcaactgat acaagagact tgtttgttag atattctcga tactgcgggt   1020
cgggaagaat actcggctat gagagaccaa tatatgagaa tgacggagta caaactcgta   1080
gttgtaggtg cggacggtgt aggaaagtct gcgcttacga ttcagttgat acaggagacc   1140
tgtttgctcg atatcttgga tacggcgggt ttggaggaat acagcgcaat gcgggaccaa   1200
tacatgagag gacccggacc aggcgccaaa tttgttgctg cttggacact gaaagctgct   1260
gctgggcccg gaccaggcca gtacatcaag gccaactcta agtttatcgg catcaccgaa   1320
ttgggacctg gacccggcta g                                             1341
```

<210> SEQ ID NO 71
<211> LENGTH: 1341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71

```
atggctggca tgaccgagta taaactagta gttgtgggag cgtgtggtgt aggcaagtcg     60
gcacttacaa ttcagttgat acaaatgacg gaatataagc tcgtagtagt cggagcagac    120
ggcgtgggga aatcagcgtt gactatccag ttaatacagg aaacttgcct attagacatc    180
ttggatacgg caggtcatga ggaatattcc gctatgagag atcagtatat gcgcatgacg    240
gagtataagc ttgtggttgt cggggccgac ggggtaggta agtcagcgct cacgatacaa    300
ttaattcaaa tgaccgaata caagttggtc gtggtggggg cagttggggt cggtaaatcc    360
gcgttaacga tccaacttat ccaaatgaca gaatataaac tcgttgttgt aggtgcatgt    420
ggcgtaggaa aaagcgcatt gaccatccag ctaattcagg agacgtgtct ccttgatatc    480
ctagacacgg cggggcacga agaatactcg gctatgcgcg accagtacat gagaatgacg    540
gaatacaaac ttgttgtcgt gggtgcggat ggagtaggga aaagtgctct aacaatacaa    600
ctcattcaga tgacagagta caaattggta gtcgtcggtg cggtaggagt tgggaagtct    660
gcactaacta ttcagctcat acagatgacc gagtacaagc tggtggtggt aggcgcttgc    720
ggtgtgggta agagtgcatt aaccatacag cttatacaag agacatgtct gctagatata    780
ttagataccg ccgggcatga agagtactct gccatgcgag accaatacat gcgtatgaca    840
```

-continued

```
gagtataaat tagtagtggt tggggcggac ggtgttggca agagcgcctt aactatacag    900

ttgatccaga tgacggagta caaactggtc gtcgttggtg cagtgggagt gggaaaatct    960

gcgctgacga ttcaactaat ccaagaaaca tgtttacttg acatcctcga cactgcgggt   1020

cacgaggagt attcggcgat gcgtgatcaa tatatgagga tgactgagta taagttagtc   1080

gtagttggag cggtcggtgt cggaaagtcc gcgctaacca ttcaattgat tcaaatgact   1140

gaatacaagc tagtggtagt aggagcatgc ggcgtcggca aatcggcttt aacaatccaa   1200

ctgatacagg gacccggacc aggcgccaaa tttgttgctg cttggacact gaaagctgct   1260

gctgggcccg gaccaggcca gtacatcaag gccaactcta agtttatcgg catcaccgaa   1320

ttgggacctg gacccggcta g                                             1341
```

<210> SEQ ID NO 72
<211> LENGTH: 441
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
atggctggca tgaccgagta taaactagta gttgtgggag cgtgtggtgt aggcaagtcg     60

gcacttacaa ttcagttgat acaaatgacg gaatataagc tcgtagtagt cggagcagac    120

ggcgtgggga aatcagcgtt gactatccag ttaatacagg aaacttgcct attagacatc    180

ttggatacgg caggtcatga ggaatattcc gctatgagag atcagtatat gcgcatgacc    240

gaatacaagt tggtcgtggt gggggcagtt ggggtcggta aatccgcgtt aacgatccaa    300

cttatccaag gacccggacc aggcgccaaa tttgttgctg cttggacact gaaagctgct    360

gctgggcccg gaccaggcca gtacatcaag gccaactcta agtttatcgg catcaccgaa    420

ttgggacctg gacccggcta g                                              441
```

<210> SEQ ID NO 73
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
atggctggca tgaccgagta taaactagta gttgtgggag cgtgtggtgt aggcaagtcg     60

gcacttacaa ttcagttgat acaaatgacg gaatataagc tcgtagtagt cggagcagac    120

ggcgtgggga aatcagcgtt gactatccag ttaatacagg aaacttgcct attagacatc    180

ttggatacgg caggtcatga ggaatattcc gctatgagag atcagtatat gcgcatgacc    240

gaatacaagt tggtcgtggt gggggcagtt ggggtcggta aatccgcgtt aacgatccaa    300

cttatccaac tgcgcgtgga gtatctggat gacaggaaca ccttcctgca ttctgttgtg    360

gtgccctatg agcccccgga ggtgggaccc ggaccaggcg ccaaatttgt tgctgcttgg    420

acactgaaag ctgctgctgg gcccggacca ggccagtaca tcaaggccaa ctctaagttt    480

atcggcatca ccgaattggg acctggaccc ggctag                             516
```

<210> SEQ ID NO 74
<211> LENGTH: 516
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 74
atggctggca tgaccgagta taaactagta gttgtgggag cgtgtggtgt aggcaagtcg 60
gcacttacaa ttcagttgat acaaatgacg gaatataagc tcgtagtagt cggagcagac 120
ggcgtgggga aatcagcgtt gactatccag ttaatacagg aaacttgcct attagacatc 180
ttggatacgg caggtcatga ggaatattcc gctatgagag atcagtatat gcgcatgacc 240
gaatacaagt tggtcgtggt gggggcagtt ggggtcggta aatccgcgtt aacgatccaa 300
cttatccaac acagcggcac cgccaaatct gtcacgtgta cttactaccc agccttgaac 360
aagatgttct gtcaattagc aaagggaccc ggaccaggcg ccaaatttgt tgctgcttgg 420
acactgaaag ctgctgctgg gcccggacca ggccagtaca tcaaggccaa ctctaagttt 480
atcggcatca ccgaattggg acctggaccc ggctag 516

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Val Val Val Gly Ala Cys Gly Val Gly Lys
1 5 10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Lys Leu Val Val Val Gly Ala Cys Gly Val
1 5 10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Val Val Gly Ala Asp Gly Val Gly Lys
1 5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Val Val Val Gly Ala Asp Gly Val Gly Lys
1 5 10

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Val Val Gly Ala Val Gly Val Gly Lys
1 5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Ala Val Gly Val Gly Lys Ser Ala Leu
1 5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Val Val Val Gly Ala Val Gly Val Gly Lys
1 5 10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Ile Leu Asp Thr Ala Gly His Glu Glu Tyr
1 5 10

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
tccctatcag tgatagaga 19

<210> SEQ ID NO 84
<211> LENGTH: 189
<212> TYPE: PRT
<213> ORGANISM: Homo sapiens

<400> SEQUENCE: 84

Met Thr Glu Tyr Lys Leu Val Val Val Gly Ala Gly Gly Val Gly Lys

-continued

```
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 85
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Val Thr Asn Thr Glu Met Phe Val Thr Ala Pro Asp Asn Leu Gly Tyr
1               5                   10                  15

Met Tyr Glu Val Gln Trp Pro Gly Gln Thr Gln Pro Gln Ile Ala Asn
            20                  25                  30

Cys Ser Val Tyr Asp Phe Phe Val Trp Leu His Tyr Tyr Ser Val Arg
        35                  40                  45

Asp Thr Val Thr Asn Thr Glu Met Phe Val Thr Ala Pro Asp Asn Leu
    50                  55                  60

Gly Tyr Met Tyr Glu Val Gln Trp Pro Gly Gln Thr Gln Pro Gln Ile
65                  70                  75                  80

Ala Asn Cys Ser Val Tyr Asp Phe Phe Val Trp Leu His Tyr Tyr Ser
                85                  90                  95

Val Arg Asp Thr
            100
```

<210> SEQ ID NO 86
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

```
Val Thr Asn Thr Glu Met Phe Val Thr Ala Pro Asp Asn Leu Gly Tyr
```

1 5 10 15

Met Tyr Glu Val Gln Trp Pro Gly Gln
20 25

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Thr Gln Pro Gln Ile Ala Asn Cys Ser Val Tyr Asp Phe Phe Val Trp
1 5 10 15

Leu His Tyr Tyr Ser Val Arg Asp Thr
20 25

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Tyr Val Tyr Val Ala Asp Val Ala Ala Lys
1 5 10

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
taatacgact cactata 17

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Lys Leu Val Val Val Gly Ala Val Gly Val
1 5 10

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Val Val Val Gly Ala Val Gly Gly Lys
1 5

<210> SEQ ID NO 92

-continued

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Ile Ile Asn Phe Glu Lys Leu
1               5
```